United States Patent
Thelen et al.

(10) Patent No.: US 11,802,286 B2
(45) Date of Patent: Oct. 31, 2023

(54) INCREASING PLANT OIL CONTENT BY IMPROVING ACTIVITY OF ACETYL-COA CARBOXYLASE

(71) Applicant: The Curators of the University of Missouri, Columbia, MO (US)

(72) Inventors: Jay J. Thelen, Columbia, MO (US); Matthew Salie, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 70 days.

(21) Appl. No.: 16/315,140

(22) PCT Filed: Jul. 6, 2017

(86) PCT No.: PCT/US2017/040851
§ 371 (c)(1),
(2) Date: Jan. 3, 2019

(87) PCT Pub. No.: WO2018/009626
PCT Pub. Date: Jan. 11, 2018

(65) Prior Publication Data
US 2019/0211348 A1 Jul. 11, 2019

Related U.S. Application Data

(60) Provisional application No. 62/359,635, filed on Jul. 7, 2016.

(51) Int. Cl.
*C12N 15/52* (2006.01)
*C12N 15/82* (2006.01)
*C12N 9/12* (2006.01)

(52) U.S. Cl.
CPC ......... *C12N 15/52* (2013.01); *C12N 15/8247* (2013.01); *C12N 9/12* (2013.01); *C12N 15/8234* (2013.01); *C12Y 207/11027* (2013.01)

(58) Field of Classification Search
CPC ................ C12N 15/8247; C12N 15/52; C12Y 207/11027
See application file for complete search history.

(56) References Cited

U.S. PATENT DOCUMENTS

| | | | |
|---|---|---|---|
| 2003/0110533 A1* | 6/2003 | Cahoon | C12N 9/93 800/281 |
| 2004/0093638 A1 | 5/2004 | Sasaki et al. | |
| 2012/0102600 A1* | 4/2012 | Nadolska-Orczyk | C12N 15/8261 800/294 |
| 2013/0096032 A1 | 4/2013 | Bush et al. | |
| 2014/0230091 A1* | 8/2014 | Shanklin | C12N 9/93 800/281 |
| 2018/0251775 A1* | 9/2018 | Thelen | C07K 14/415 |

FOREIGN PATENT DOCUMENTS

| | | | | |
|---|---|---|---|---|
| WO | WO 1994/023027 A2 | 10/1994 | | |
| WO | WO98/05758 | * | 2/1998 | ............... C12N 9/10 |
| WO | WO 1998/05758 A1 | 2/1998 | | |
| WO | WO-9805758 A1 | * | 2/1998 | ......... C12N 15/8241 |
| WO | WO 2017/039834 A1 | 3/2017 | | |

OTHER PUBLICATIONS

Sasaki et al (Review. Plant Acetyl-CoA Carboxylase: Structure, Biosynthesis, Regulation, and Gene Manipulation for Plant Breeding. Biosci. Biotechnol. Biochem., 68 (6), 1175-1184, 2004) (Year: 2004).*
Friedberg (Automated protein function prediction—the genomic challenge. Brief. Bioinformatics. 7:225-242, 2006) (Year: 2006).*
Wang et al (From Protein Sequence to Protein Function via Multi-Label Linear Discriminant Analysis. IEEE/ACM Transactions on Computational Biology and Bioinformatics, vol. 14, No. 3, 503-513, 2017) (Year: 2017).*
Andre, C., et al., "Feedback Regulation of Plastidic Acetyl-CoA Carboxylase by 18:1-acyl Carrier Protein in *Brassica napus*," Proceedings of the National Academy of Sciences of the United States of America 109(25):10107-10112 (2012).
Baud, S., et al., "WRINKLED1 Specifies the Regulatory Action of Leafy COTYLEDON2 Towards Fatty Acid Metabolism During Seed Maturation in *Arabidopsis*," The Plant Journal 50(5):825-838 (2007).
Chen, M., et al., "System Analysis of an *Arabidopsis* Mutant Altered in de Novo Fatty Acid Synthesis Reveals Diverse Changes in Seed Composition and Metabolism," Plant Physiology 150(1):27-41 (2009).
Feria Bourrelier, A.B., et al., "Chloroplast Acetyl-CoA Carboxylase Activity is 2-oxoglutarate-Regulated by Interaction of PII With the Biotin Carboxyl Carrier Subunit," Proceedings of the National Academy of Sciences of the United States of America 107(1):502-507 (2010).
Fukuda, N., et al., "Expression of the Genes Coding for Plastidic Acetyl-CoA Carboxylase Subunits Is Regulated by a Location-Sensitive Transcription Factor Binding Site," Plant Molecular Biology 82(4-5):473-483 (2013).
Hunter, S.C., and Ohlrogge, J.B., "Regulation of Spinach Chloroplast Acetyl-CoA Carboxylase," Archives of Biochemistry and Biophysics 359(2):170-178, 1998.
International Search Report and Opinion regarding International Application No. PCT/US16/41386, dated Dec. 1, 2016.

(Continued)

*Primary Examiner* — Charles Logsdon
*Assistant Examiner* — Wayne Zhong
(74) *Attorney, Agent, or Firm* — DENTONS US LLP

(57) ABSTRACT

The present invention provides a method and means to change fatty acid and ultimately triacylglycerol production in plants and algae. Methods of the invention comprise the step of altering the activity levels of the committed step for de novo fatty acid biosynthesis, acetyl-CoA carboxylases (ACCase). More specifically, methods of the invention directly enhance the activity of ACCase by overexpression of α-CT or a catalytic portion thereof.

8 Claims, 17 Drawing Sheets

Specification includes a Sequence Listing.

(56) References Cited

OTHER PUBLICATIONS

International Preliminary Report on Patentability regarding International Application No. PCT/US2017/040851, dated Jul. 30, 2018.
International Search Report and Written Opinion regarding International Application No. PCT/US2017/040851, dated Dec. 29, 2017.
Kozaki, A., et al., "Thiol-Disulfide Exchange Between Nuclear-Encoded and Chloroplast-Encoded Subunits of Pea Acetyl-CoA Carboxylase," The Journal of Biological Chemistry 276(43):39919-39925, 2001.
Li, L., et al., "PlantOrDB: a Genome-Wide Ortholog Database for Land Plants and Green Algae," BMC Plant Biology, vol. 15:161, 2015.
Lu and Kang, "Generation of Transgenic Plants of a Potential Oilseed Crop Camelina sativa by Agrobacterium-Mediated Transformation," Plant Cell Reports 27(2):273-278 (2008).
Sasaki, Y., and Nagano, Y., "Plant Acetyl-CoA Carboxylase: Structure, Biosynthesis, Regulation, and Gene Manipulation for Plant Breeding," Bioscience, Biotechnology and Biochemistry 68(6):1175-1184 (2004).
Sasaki, Y., et al., "Link Between Light and Fatty Acid Synthesis: Thioredoxin-Linked Reductive Activation of Plastidic Acetyl-CoA Carboxylase," Proceedings of the National Academy of Sciences of the United States of America 94(20):11096-11101, (1997).
Thelen, J.J., and Ohlrogge, J.B., "Both Antisense and Sense Expression of Biotin Carboxyl Carrier Protein Isoform 2 Inactivates the Plastid Acetyl-Coenzyme A Carboxylase in *Arabidopsis thaliana*," The Plant Journal 32 (4):419-431, Nov. 2002.
GenBank Accession No. AF164510, dated Jul. 1, 2000.
GenBank Accession No. AF164511, dated Jul. 1, 2000.
GenBank Accession No. AF165158, dated Aug. 1, 2000.
GenBank Accession No. AF165159, dated Aug. 1, 2000.
GenBank Accession No. NM_001248305, dated Oct. 18, 2018.
GenBank Accession No. NM_001249264, dated Mar. 2, 2017.
GenBank Accession No. NP_001319767, dated Feb. 14, 2019.
GenBank Accession No. NM_001339770, dated Feb. 14, 2019.
GenBank Accession No. U34392, dated Jul. 16, 1996.
GenBank Accession No. U40979, dated Jul. 16, 1996.
GenBank Accession No. AF092443, dated Jul. 26, 2016.
GenBank Accession No. NM_115471, dated Feb. 14, 2019.
GenBank Accession No. NP_567035, dated Feb. 14, 2019.

* cited by examiner

| NAME | ACCESSION | SEQUENCE |
|---|---|---|
| BCCP1 SENSE | AT5G16390 | 5'-CATATGTCAGCTGAAGGAAAGGAGAAAAACTCATTG-3' |
| BCCP1 ANTI-SENSE | | 5'-GGATCCCTACGGTTGAACCACAAACAGAGGAG-3' |
| BCCP2 SENSE | AT5G15530 | 5'-CATATGGAATTTATGGCTAAAGTCTCTGGTCTT-3' |
| BCCP2 ANTI-SENSE | | 5'-GGATCCTCAAGGTGCGATGACAAAAGAG-3' |
| BADC1 SENSE | AT3G56130 | 5'-GAATTCGCTAAGGCCGCTAAATCTTCGAC-3' |
| BADC1 ANTI-SENSE | | 5'-CTCGAGTCACTGGATGTTGATGTCGTG-3' |
| BADC2 SENSE | AT1G52670 | 5'-CATATGACGACTCTGCGATCTGTGAAAGCT-3' |
| BADC2 ANTI-SENSE | | 5'-GGATCCTTACTGAAGCTTCTTGATGCCAGGA-3' |
| BADC3 SENSE | AT3G15690 | 5'-CATATGGCTGTCCAAGTGTCTACTGTCCC-3' |
| BADC3 ANTI-SENSE | | 5'-GGATCCTTACTGAAGCTTCTTGATCCCAGGG-3' |
| apo-BCCP1 MUTANT SENSE | AT5G16390 | 5'-GCATTGTTGAAGCCATGAGGTTAATGAATGAAATA-3' |
| apo-BCCP1 MUTANT ANTI-SENSE | | 5'-TATTTCATTCATTAACCTCATGGCTTCAACAATGC-3' |

FIG. 2A

| NAME | PREDICTED TARGET PEPTIDE LENGTH |
|---|---|
| BCCP1 | 82 |
| BCCP2 | 87 |
| BADC1 | 56 |
| BADC2 | 47 |
| BADC3 | 54 |

FIG. 2B

| PROTEIN NAME | BCCP2 | BADC1 | BADC2 | BADC3 |
|---|---|---|---|---|
| BCCP1 | 51.0% | 24.4 | 27.3 | 29.3 |
| BCCP2 |  | 25.2 | 26.0 | 28.1 |
| BADC1 |  |  | 34.2 | 41.7 |
| BADC2 |  |  |  | 61.6 |

FIG. 4

| | | | |
|---|---|---|---|
| BCCP1 | QKGQVLCIVE | AMKL | MNEIESDHTGTVVDIVAEDGKPVSLDTPLFVVQP-------- |
| BCCP2 | QKGQIVCIIE | AMKL | MNEIEAEKSGTIMELLAEDGKPVSVDTPLFVIAP-------- |
| BADC1 | KEGQVIGYLH | QLGT | ELPVTSDVAGEVLKLLSDDGDSVGYGDPLVAVLPSFHDINIQ- |
| BADC2 | KEGQVLCYIE | QLGG | QIPVESDVSGEIVKILREDGEPVGYNDALITVLPSFPGIKKLQ |
| BADC3 | KEGQILCYIE | QLGG | QFPIESDVTGEVVKILREDGEPVGYNDALISILPSFPGIKKLQ |

FIG. 5

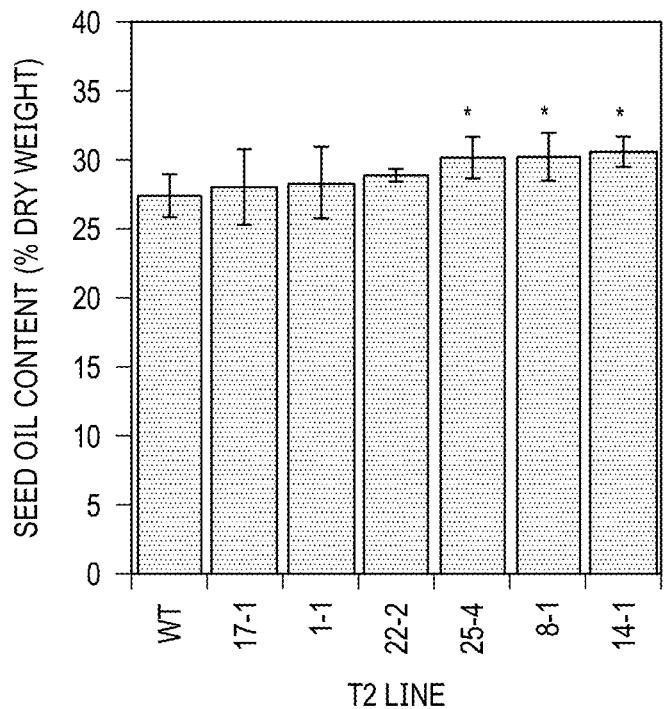
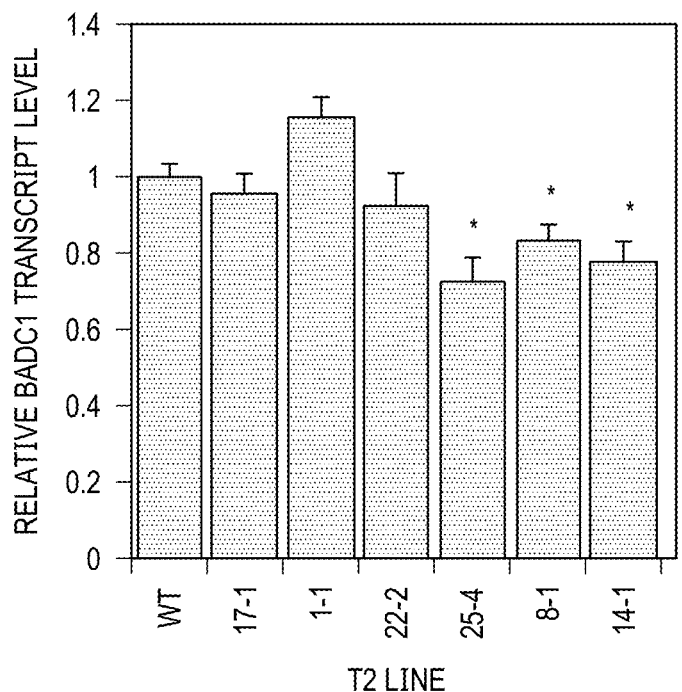

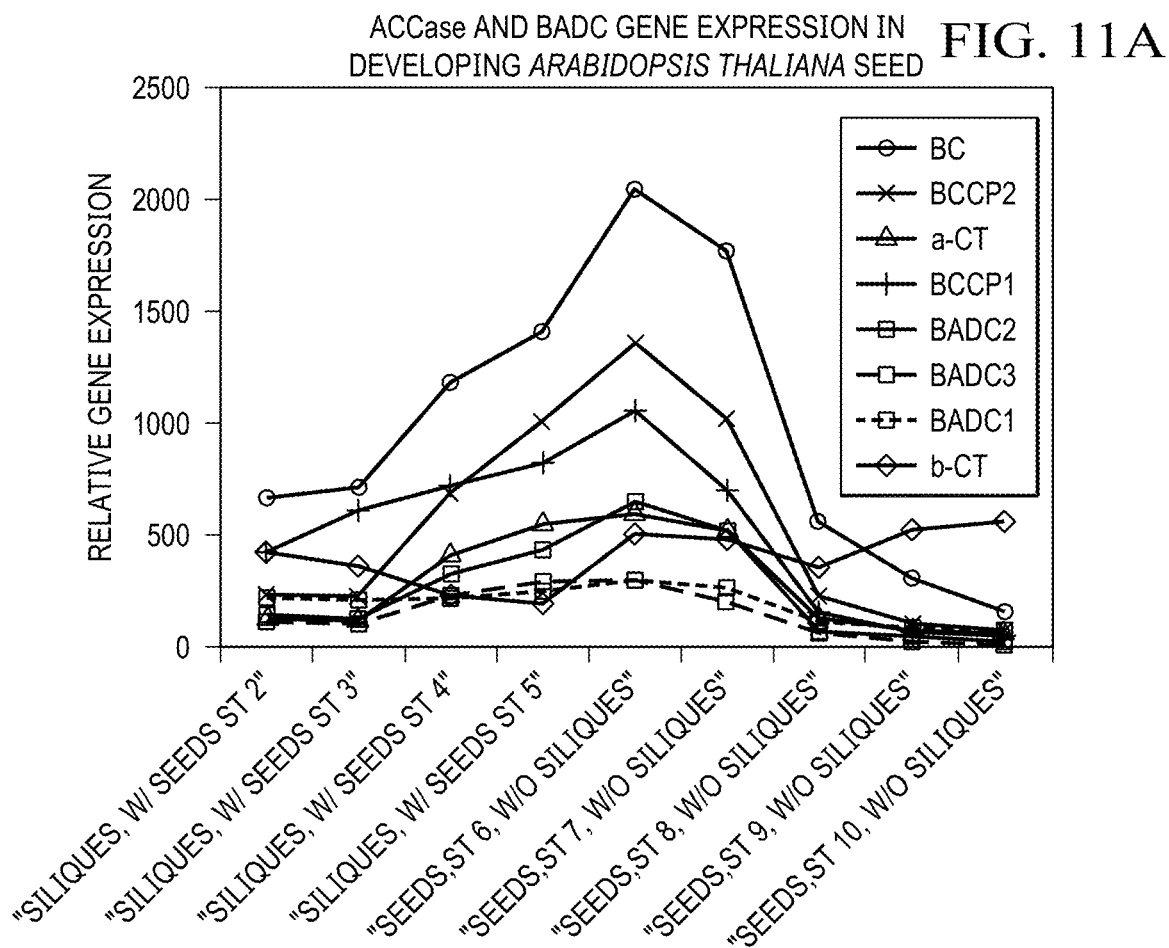

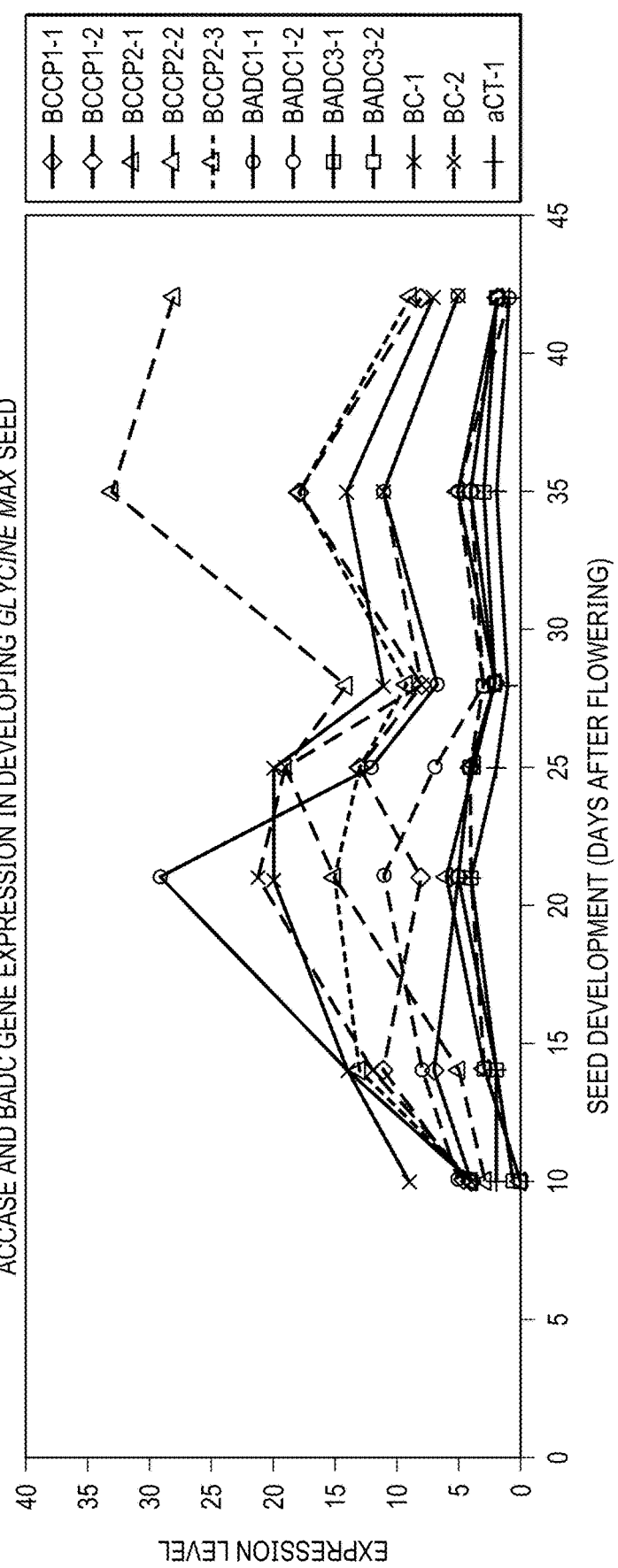

| μM BADC1 | % ACTIVITY | StDev |
|---|---|---|
| 1.25 | 0.96 | 0.05 |
| 6.25 | 0.80 | 0.03 |
| 8.75 | 0.79 | 0.03 |
| 15 | 0.73 | 0.07 |

FIG. 12

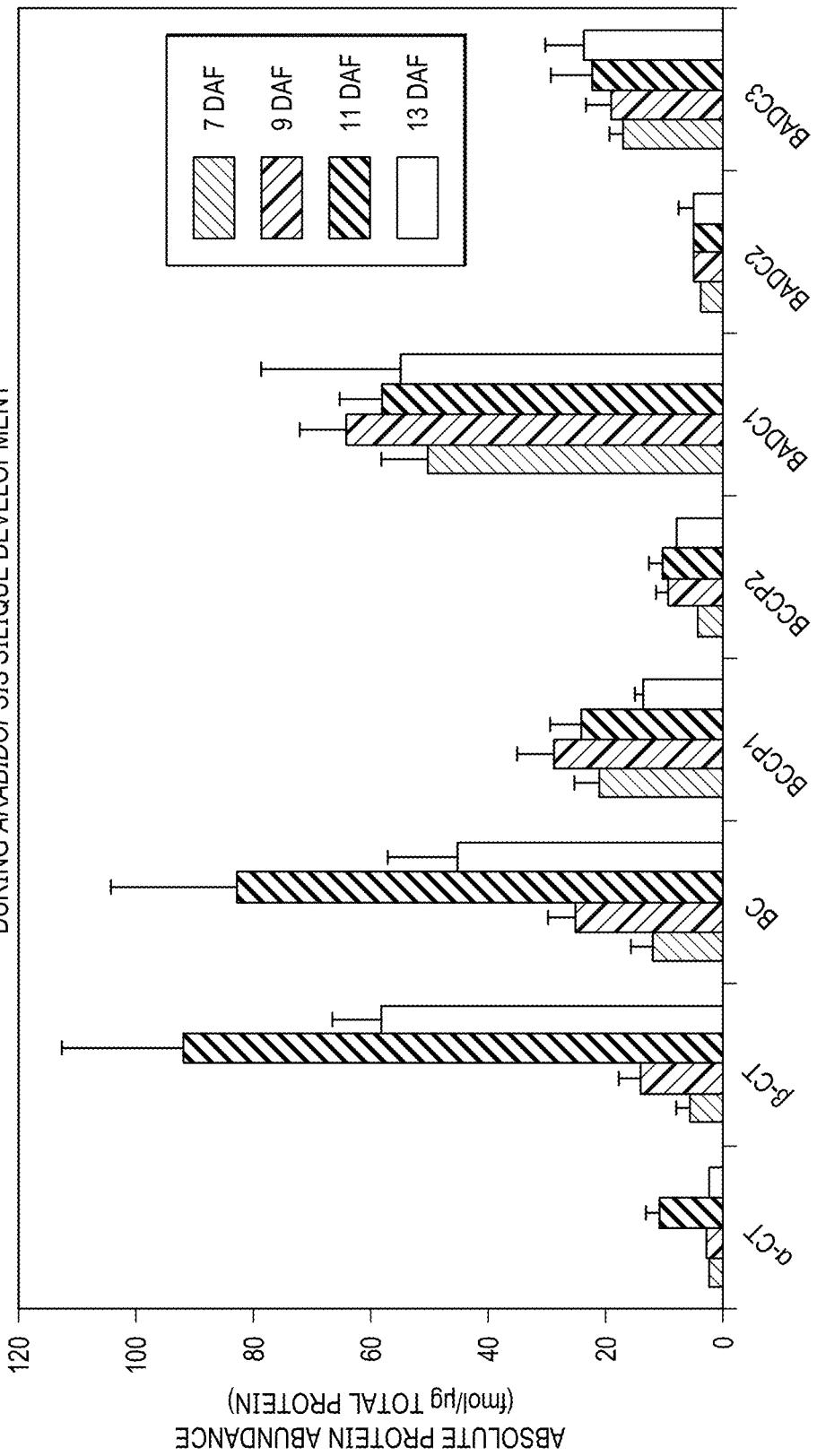

SEQUENCE LISTING

```
<160> NUMBER OF SEQ ID NOS: 180

<210> SEQ ID NO 1
<211> LENGTH: 281
<212> TYPE: PRT
<213> ORGANISM: Arabidopsis thaliana

<400> SEQUENCE: 1
```

```
Met Ala Ser Ser Ala Leu Gly Ser Leu His Gln Thr Leu Gly Ser
1               5                   10                  15

Ala Ile Asn Ser Gln Ser Glu Val His Ser Leu Ser Gly Asn Trp Ser
            20                  25                  30

Ala Ser Gly Asn Ser Cys Val Pro Arg Trp Arg Leu Ser Asn Arg Asn
        35                  40                  45

Ser Asn Tyr Arg Leu Val Leu Arg Ala Lys Ala Lys Ser Ser Thr
    50                  55                  60

Thr Thr Ile Ser Asp Gly Ser Ser Asp Ala Ser Val Ser Asp Gly Lys
65                  70                  75                  80

Lys Thr Val Arg Arg Ile Thr Phe Pro Lys Glu Val Glu Ala Leu Val
                85                  90                  95

His Glu Met Cys Asp Glu Thr Glu Val Ala Val Leu Gln Leu Lys Val
                100                 105                 110

Gly Asp Phe Glu Met Asn Leu Lys Arg Lys Ile Gly Ala Ala Thr Asn
            115                 120                 125

Pro Ile Pro Val Ala Asp Ile Ser Pro Thr Val Ala Pro Pro Ile Pro
130                 135                 140

Ser Glu Pro Met Asn Lys Ser Ala Ser Ser Ala Pro Ser Pro Ser Gln
145                 150                 155                 160

Ala Lys Pro Ser Ser Glu Lys Val Ser Pro Phe Lys Asn Thr Ser Tyr
                165                 170                 175

Gly Lys Pro Ala Lys Leu Ala Ala Leu Glu Ala Ser Gly Ser Thr Asn
            180                 185                 190

Tyr Val Leu Val Thr Ser Pro Ala Val Gly Lys Phe Gln Arg Ser Arg
        195                 200                 205

Thr Val Lys Gly Lys Lys Gln Ser Pro Ser Cys Lys Glu Gly Asp Ala
210                 215                 220

Ile Lys Glu Gly Gln Val Ile Gly Tyr Leu His Gln Leu Gly Thr Glu
225                 230                 235                 240

Leu Pro Val Thr Ser Asp Val Ala Gly Glu Val Leu Lys Leu Leu Ser
                245                 250                 255

Asp Asp Gly Asp Ser Val Gly Tyr Gly Asp Pro Leu Val Ala Val Leu
            260                 265                 270

Pro Ser Phe His Asp Ile Asn Ile Gln
        275                 280

<210> SEQ ID NO 2
<211> LENGTH: 2613
<212> TYPE: DNA
<213> ORGANISM: Arabidopsis thaliana

<400> SEQUENCE: 2
acggaccgta gtgtagtagt agatgcggcg gacggagtta ccaaagaaga aggccgctca    60
aaataattaa atttgttcaa ccgtcatctt cttcaactga tcttagctca actaacacac   120
tctttcttct tggcgtcaat tcaatcaacc aaaacctttt tctcctatct agctcacgct   180
ttcttcttct tccaatggcg tcttctgcag ctctcggatc tctccatcgt gagtctcttg   240
ctctctcact ctctgcgttt tactattct gttgatttca tgaggatagg aaaactagaa    300
atggaggacc atgagtaaaa tttcggaaat gaaaggcata gattggagct atccgttagt   360
gacgttgttg cttcttagag tgtaatttag cgacttaatt aagtttcaat ctcggatctt   420
gtgtgtctaa tttgtatcaa gagatgtttc agctagaaaa agtgaatttt atttgttcca   480
```

```
ttttacagag actttagggt cagccattaa ttcacagagt gaggttcact cgctttctgg    540
aaactggtct gcctctggta attcatgtgt gccacggtgg agattatcca acaggaacag    600
caactacagg ctcgtgttac gtgctaaggc cgctaaatct tcgacaacaa ccataagtga    660
tggtgagttt atcttccaca attcttcttc atgttcattt tgctggttaa tgccttttt     720 tactatcagg cttgtctcat cactttgcta atacgatcca ttggccaaag atggtattaa    780
tctgttttgc tcttaaagga actggaactg aaattcttag tctcgtttgc tcttaaagga    840
actagaaatg taactgtaag cctcggtctt ttaccagctg tcttggaacc aggagataca    900
gtgatgtgat attggaacat ttttctttta tttcctatga cttttgctta tttttggctt    960
tgcaggttca tctgatgcta gtgtgtcaga cgggaagaaa acagttcgac ggataacttt   1020
cccgaaagaa gtggaggttt cttccttgcc tttcatgggt cttagatatt aggttcttta   1080
atttataagt ttggtaggtg atgatatgac gatttcctca aatatgcact ttctagatcg   1140
tcaggatttt ggatgcataa cttcaggcaa tctactctta aattttaa tcatgacgta     1200 tggatgtacc tttctttata tgttgttaga tgaaatgttg caggcactgg ttcacgagat   1260
gtgtgatgaa actgaggttg ctgtgctgca acttaaggca agtctctctg ccattagttt   1320
taacttcatt attattatta tttgtaaact ttctttgagg ctactacaaa gacgagtgca   1380
ttttactcaa ccaacaatat ggggctaaat atcactgatt tgagataata aatgtaggt    1440 tccaacaatt agactcttct gaagctttct tttgctacag gttggagatt cgagatgaa    1500 cctaaaacgg aagattggag cagccacaaa ccccattccc gtggcggata tatctccaac   1560
tgtagcgcct cctattcctt ctgaacctat gaataaatct gcttcttcgg ctcctagccc   1620
atctcaagca aagccttcct ctgagaaagt gtctccattt aagaatacat catatgggaa   1680
accagcaaag ttggctgctt tggaggcatc tggatccacc aactatgtgt tagtcacatc   1740
tcccgcagta tgagatccat ttcctaatta gtggttgctt tcatatccct taatttctct   1800
gcagttttct tgtttgattt gatcttgttt cttctcttac caaaaggtgg gcaagtttca   1860
gaggagcaga actgtaaaag gaaagaaaca atctcctagc tgcaaagagg taaacgactc   1920
taaattcttt tgcatctctt agaacaaaag aacagaaata agatcaaaga gctaagtgaa   1980
aaaaactcct tagggtgatg caataaagga aggccaagtt attggatact tacatcagtt   2040
gggaacagaa cttccagtga cggtaatatc ttaactaata tatccatctc ttcttttgaaa  2100 ctatctaatc agactcatcg atcttgctat ttgtcgagca gtcagatgta gctggagaag   2160
tccttaagct tctttcagat gacggaggta aacatttgag tattcaaacc gtttcattta   2220
gtatgaacat tcagaaatta tataagtgaa ttgatatgaa ctcatgcttc gtgtgcaaac   2280
agactccgta ggttatggag atcctctggt tgcagtcttg ccatctttcc acgacatcaa   2340
catccagtga tgatggtttc ttcagcccaa ttccatagca aatgaatagt ctttcatccg   2400
gagactgtac tattcatctt ctcctgtgtt tgttcaatga agatttgtaa tctgtttagt   2460
tgcaaagagt ctactttgat cttgctctca tcatttgtca cgtaatgtgg attttctgca   2520
ccagagaaaa aaaacaattg tggaattttt atagaaatga cgtggctatc ttatcttctc   2580
cgatcatcaa ataaaatcaa ggctcaaaaa ttc                                 2613
```

<210> SEQ ID NO 3
<211> LENGTH: 274
<212> TYPE: PRT
<213> ORGANISM: Arabidopsis thaliana

<400> SEQUENCE: 3

```
Met Asn Ser Cys Ser Leu Gly Ala Pro Lys Val Arg Ile Phe Ala Thr
 1               5                  10                  15

Asn Phe Ser Arg Leu Arg Cys Gly Asn Leu Leu Ile Pro Asn Asn Gln
            20                  25                  30

Arg Leu Phe Val Asp Gln Ser Pro Met Lys Tyr Leu Ser Leu Arg Thr
        35                  40                  45

Thr Leu Arg Ser Val Lys Ala Ile Gln Leu Ser Thr Val Pro Pro Ala
 50                  55                  60

Glu Thr Glu Ala Ile Ala Asp Val Lys Asp Ser Asp Glu Thr Lys Ser
 65                  70                  75                  80

Thr Val Val Asn Thr His Leu Met Pro Lys Ser Glu Val Glu Ala
                85                  90                  95

Leu Ile Ser Glu Ile Thr Asp Ser Ser Ser Ile Ala Glu Phe Glu Leu
                100                 105                 110

Lys Leu Gly Gly Phe Arg Leu Tyr Val Ala Arg Lys Leu Thr Asp Glu
            115                 120                 125

Ser Ser Pro Pro Pro Gln Gln Ile Gln Pro Val Val Ala Ala Ser Ala
130                 135                 140

Thr Pro Glu Gly Val His Thr Asn Gly Ser Ala Thr Ser Ser Ser Leu
145                 150                 155                 160

Ala Ile Thr Lys Thr Ser Ser Ser Ala Asp Arg Pro Gln Thr Leu
                165                 170                 175

Ala Asn Lys Ala Ala Asp Gln Gly Leu Val Ile Leu Gln Ser Pro Thr
            180                 185                 190

Val Gly Tyr Phe Arg Arg Ser Lys Thr Ile Lys Gly Lys Arg Thr Pro
            195                 200                 205

Thr Ile Cys Lys Glu Lys Asp Ile Val Lys Glu Gly Gln Val Leu Cys
            210                 215                 220

Tyr Ile Glu Gln Leu Gly Gly Gln Ile Pro Val Glu Ser Asp Val Ser
225                 230                 235                 240

Gly Glu Ile Val Lys Ile Leu Arg Glu Asp Gly Pro Val Gly Tyr
                245                 250                 255

Asn Asp Ala Leu Ile Thr Val Leu Pro Ser Phe Pro Gly Ile Lys Lys
            260                 265                 270

Leu Gln
```

<210> SEQ ID NO 4
<211> LENGTH: 2631
<212> TYPE: DNA
<213> ORGANISM: Arabidopsis thaliana

<400> SEQUENCE: 4

```
atcaaattcg atttcatcgt cgtcactcgt caatcgccaa atcaacaaaa tcgtcttcct    60
cgttcgtatc gttcactcag ctttttttccc atcttcttct tcgcatcaca tattcttcat   120
tactaatata tctcctactc cagtcttcct ccatgaattc tgtaagtttt ctctatcttg   180
ttgcctcatg aatgattttg ttgttctcgt gaatccttgt tttaatctgt tcttcgttga   240
tactcaaatg ggtttgaaca agaagagtta ttttttgcaat gtgattagtg ttgatgcatc   300
ttcgtttcaa gataatgcgt ttaaagcttg tactttataa tgctattgtt tctctacttg   360
tttcaagact atgacttgca atgataaatt atacattgaa acatgtatag gtcaaggtaa   420
aagggatcta tggaggagtg ttgataactt tttgattctg tttcaggtag cttaggagct   480
cctaaagtta gaatttttgc aacaaatttc agtagattaa gatgtggaaa cttgctgata   540
```

-continued

```
ccgaacaatc aaagactatt tgttgaccaa agccctatga agtatctgag tctgagaacg    600
actctgcgat ctgtgaaagc tatccaattg tctactgtcc cacctgcaga aacagaaggt    660
atatagtaat ctgtctgtgt atttctgttt cacttgattg tgttttactg tttgtcataa    720
aatcctttag acaatgttca gatttgtggc ttatgaagtg gtatcgtttg cttgttttct    780
tctttaacat tcttcactac agctattgca gacgtaaaag attctgacga gaccaaatca    840
actgttgtga atactcacct catgcccaag tcctccgagg taggtgttac tttcctgttt    900
aacctctcat attcaagacc aagtatgatg cacaactgtt ataaaccttt aggggtttca    960
atttgggatt gttttgagaa atcacaaaag ttagaaagtt gcatttcagt gcaatagcac   1020
gatactgtgg ttctttgtta ttatgatgct agagaaggaa gaatgtgtga cctcgttgag   1080
ctagcttaga catgagctat gtcaaatcta atcattatgt tacattttca tcttctaggt   1140
ggaagcactc atcagcgaaa tcaccgattc ctcatccatt gcagagtttg aactcaaagt   1200
aagccccact tctgatttct gaactcataa ctatgttatt tattgttgct cagatcattt   1260
acttgtctct gctaagtttt ttcataaaat cgtgtctatg atagaagtag ttttactatt   1320
gacttaagtt tcatcttaac catggtttat tgtgaaagta aaccatggtt ggtttagctt   1380
ttctggtttg gtcaatgtcc ttatatagcg tctgagagat atgtgagagt tttatcgagt   1440
atttggtgag taatctaggg gagtgggagg agctccatta atcaaattcc tcaaggtctt   1500
gtaattctcg attgataagc tatgaaatat cagtttctat aagcaaatcg tatcagtcta   1560
ataattctgg tttctcccat ttgcatattt ctaatagctg ggaggtttcc gcctgtatgt   1620
agcaaggaaa ttaactgacg aaagtagtcc accacctcag caaattcagc ctgtggttgc   1680
tgcaagcgca actcctgagg gggttcacac taatggctca gctacttctt cgtcattggc   1740
tatcacaaaa acatcatctt cttcggcaga cagaccacaa acactcgcta acaaagctgc   1800
tgatcagggt ttagtgattc tccaatctcc aacggttaga gactagatca tttctttgaa   1860
actgacatga aatgattaaa attcatgatc tctcaactgg atggataatt atttgttgca   1920
ggtcggttat ttcaggagat ccaagaccat aaaagggaaa cgcactccta caatctgtaa   1980
agaggtactt cttctcctat gttttgaaca agtctttcaa aatatccatc ttcaaggagc   2040
atttggaatc tctcaattga ttatatattt gcttttggtt attctacaga aagacatagt   2100
gaaagaaggt caagttctat gctacattga acagctcggt ggccaaatcc cagttgaggt   2160
aacaatcgta atccctttcg gtttctttac ttttttttgc tttctcagtc ttcttattgt   2220
gttctttctt tcagtctgat gtttccggag agattgtcaa aatactccgc gaagatggcg   2280
gtaagaccct atttgctata tgtctttgaa tcggtactca tatagctatc aattctctct   2340
actgactttt gttttttttct tcttctgttt tgtgattcgg cagagcctgt aggatacaac   2400
gatgctctca tcacagtact tccctcattt cctggcatca agaagcttca gtaagaactg   2460
attttggctt aattgtgttt gtgctttgtg tattttgctt cttagttttt ctccacatag   2520
acaaaaataa gctctactcc aaaaaatctt tgtccgtacc attcctttg ttttaccaaa   2580
atttaattga aactttttg tttaccactg atattagaac atttcattct t             2631
```

<210> SEQ ID NO 5
<211> LENGTH: 263
<212> TYPE: PRT
<213> ORGANISM: Arabidopsis thaliana

<400> SEQUENCE: 5

```
Met Ala Ser Cys Ser Leu Gly Val Pro Lys Ile Lys Ile Ser Ala Val
1               5                   10                  15

Asp Leu Ser Arg Val Arg Ser Gly Ser Leu Leu Ile Pro Tyr Asn Gln
            20                  25                  30

Arg Ser Leu Leu Arg Gln Arg Pro Val Lys Tyr Leu Ser Leu Lys Thr
        35                  40                  45

Thr Phe Gly Ser Val Lys Ala Val Gln Val Ser Thr Val Pro Thr Ala
    50                  55                  60

Glu Thr Ser Ala Thr Ile Glu Val Lys Asp Ser Lys Glu Ile Lys Ser
65                  70                  75                  80

Ser Arg Leu Asn Ala Gln Leu Val Pro Lys Pro Ser Glu Val Glu Ala
                85                  90                  95

Leu Val Thr Glu Ile Cys Asp Ser Ser Ser Ile Ala Glu Phe Glu Leu
            100                 105                 110

Lys Leu Gly Gly Phe Arg Leu Tyr Val Ala Arg Asn Ile Ala Asp Asn
        115                 120                 125

Ser Ser Leu Gln Pro Pro Thr Pro Ala Val Thr Ala Ser Asn Ala
    130                 135                 140

Thr Thr Glu Ser Pro Glu Ser Asn Gly Ser Ala Ser Ser Thr Ser Leu
145                 150                 155                 160

Ala Ile Ser Lys Pro Ala Ser Ser Ala Ala Asp Gln Gly Leu Met Ile
                165                 170                 175

Leu Gln Ser Pro Lys Val Gly Phe Phe Arg Arg Ser Lys Thr Ile Lys
            180                 185                 190

Gly Lys Arg Leu Pro Ser Ser Cys Lys Glu Lys Asp Gln Val Lys Glu
        195                 200                 205

Gly Gln Ile Leu Cys Tyr Ile Glu Gln Leu Gly Gly Gln Phe Pro Ile
    210                 215                 220

Glu Ser Asp Val Thr Gly Glu Val Val Lys Ile Leu Arg Glu Asp Gly
225                 230                 235                 240

Glu Pro Val Gly Tyr Asn Asp Ala Leu Ile Ser Ile Leu Pro Ser Phe
                245                 250                 255

Pro Gly Ile Lys Lys Leu Gln
            260

<210> SEQ ID NO 6
<211> LENGTH: 2698
<212> TYPE: DNA
<213> ORGANISM: Arabidopsis thaliana

<400> SEQUENCE: 6
accactctgg ttgtatcgaa cgagcgaaac ccaaccaacg acgagcgttc acctcaaata    60
ttttgatttg atcaaatcat ctccacactc gccaaatcgt tgtgtcctcg ttcatatcgt   120
tatcgtatca gctcaaaaat ctcaatctct cttccttaca ttcttctgtt tctcgaatcc   180
ttgtctccct ccatggcttc ctgtaagttt ctctacctgt ctcttgttgt cttgcttgtt   240
ccagttttct tgggatcgta cactaaattg ggtttgtgtt tcctcattca aatttgaatg   300
ctttcgtagt tttctgctct catagaatca tattcatcga aaggttgtaa ctttggggat   360
tctgtttatt gagtgatagg aaaactcaga aagggactta actttgaaca attaggttga   420
ttttggtata aattagagat ctaaagttga agaatttgtc ttcagtatct gtttcaatgg   480
agatgagatt caagttactt catttgatat tgaattgcca agctaatcta attgatgagt   540
ttggcagtga taagttaatt tcataatttg tatctcttaa tatgaattac tcgacaacat   600
```

```
tacttaatct ttcactgttg agtatacgtg gagatcggtt aacgtgagtt tattctaaga    660
cattatattt tgaattactt aaaactttct ggagctatct tggattgagt gtataagatt    720
tgcttatgct caattttaaa aagtgaggga tcatattgaa gataagtgct tatttagtct    780 ttcttttga ctctgtcttg ttttggctga tttcccatat tgagaccttg gcgtatgacg     840
tatgttacag gtagcctagg agttcctaaa attaaaatct cggcagtaga ccttagtaga    900
gtaagatctg gaagcttact gataccatac aatcaaagat cattgcttcg acaaaggcca    960
gtgaagtact tgagtctgaa gacaacattt ggatctgtga aagctgtcca agtgtctact   1020
gtcccaactg cagaaacatc aggtacactt atctctatat gttttcttaa cttgaatatg   1080
ctcattttta ccgattttac tatcgatatg ttttgcacat cgagtgtgtt cacatgtggg   1140
ctgatgtgtt cctagaaagt ctcttttagt tttcctttaa tgctttctga tttattcttg   1200
ttatcaacag ctactataga agtaaaagat tctaaagaga tcaagtcatc tcgattaaac   1260
gctcagcttg ttcccaagcc ttctgaggtg ggttttgatt ttccatttaa tgttagaatg   1320
tcaatttaag aactctggtt cttctccctt attgtcaaat ggaagagaag aaatgtgttg   1380
tcttgaggat taagtggaga attcacttgt tgcctgcaca ataaaaccat ttgagtctgt   1440
ttttttaatt ggatgcattc aatatgtttt cttttcgat cttttaggtg gaagcccttg    1500
taactgaaat atgcgattct tcatcaattg cagagtttga actgaaagta aggctctact   1560
caattgaatt gttgtcatgt tattgctctt ttgcagagtc atctcagcta gttttgaa    1620 taggattctt atctaataat ttcggcctct ttcatttgca cattctaata gctgggggt    1680 ttccgactat atgtagcaag gaacatagct gacaatagta gtctacaacc tccgccaact   1740
cctgctgtga ctgcttcaaa tgcaactacc gagagtcctg agtcgaatgg atcagcttcc   1800
tctacttcac tggctatctc aaaaccagca tcgtcagccg ctgatcaggg tttgatgatt   1860
ctccaatctc caaaagtaag agaccacaca actcaaaggc aaaatgtcat atactctgtt   1920
ggaaaatgct atattttata gtttcaatca gaaagttgat cccaatctaa atggtgtgta   1980
atatgtgcag gtagggttct tcaggagatc caaaaccata aagggtaaac gcctgccttc   2040
gtcttgtaaa gaggtataac caatcttctt gaacagaaga gagtgtttga tttcatgggg   2100
gaaaccactg actaatctct tatttgctct tgtttaatct gacagaaaga ccaagtgaaa   2160
gaaggtcaaa ttctgtgcta cattgaacaa ctcggtggcc aatttccaat cgaggttaga   2220
taatattcca ttttaattcc tgatttagta attactatca cttgcttcaa ccaactcagt   2280
taaattgctt ctctgtttat cgatcaatct tctagtctga tgttaccggc gaggtagtca   2340
agatactccg agaagatgga ggcaagtctc tcgtcttctt taacctttct tcgttttct   2400 taaaacctcg gtgtaatgat ttttcttatc gttttctcat tcggaacaga gcctgtagga   2460
tacaatgatg ctctcatctc catccttcca tccttccctg ggatcaagaa gcttcagtaa   2520
aaccaaattc gagctggttt tgagttatga cactgtgcct tgtgtatgct ttagataaa    2580 gaaacttcat tcatatttgt atttgtcttt tgcttgtatg aaagttcttc tttaagactc   2640
ttttattctg tatgcttttt cttatatata aaaacattat ggtatttttt tttaatcg    2698
```

<210> SEQ ID NO 7
<211> LENGTH: 1676
<212> TYPE: DNA
<213> ORGANISM: Artificial sequence
<220> FEATURE:
<223> OTHER INFORMATION: RNAi cassette

<400> SEQUENCE: 7

-continued

```
cccggggtgt tagtcacatc tcccgcagtg ggcaagtttc agaggagcag aactgtaaaa      60
ggaaagaaac aatctcctag ctgcaaagag ggtgatgcaa taaaggaagg ccaagttatt     120
ggatacttac atcagttggg aacagaactt ccagtgacgt cagatgtagc tggagaagtc     180
cttaagcttc tttcagatga cggagactcc gtaggttatg gagatcctct ggttgcagtc     240
ttgccatctt ccacgacat caacatcgag ctccactgaa ttgaattgtt taaggtttgg      300
tgagcctaaa agaatttgaa ctggttttca ataaatgaa ttaagatgtt aattaggaga      360
attgaagttt attacaattt ggattgggga ttagaatttg aagctacatt taaaattcga     420
aaaaaaaaga cagtgaaact taaaacgttc ataaaaagga ccaaaagttt ttaaaaaaat     480
tgtcgctaaa actcaaacat atatattaca atgccatatg tgcttataag gacttaagga     540
gcagtttctt gggtggctag gggatatgac atttttttac tgcacaataa atatcctggc     600
cgttgcaccc ggagatgcac agagctttga gcagatcaga tgaatgatta aattgttttg     660
aagagaatct attccttcac actgaattct tgcacaaaac cttgacactg aatttaattg     720
tgccaaatca acaattcttt tagcccagga aatataatcc atttttttaat tttctgctac     780
ttattttcat cttcttaata caaagatata caagtatttt gcatattcag attttttttt     840
gccaaaacaa taaatctagc tatatacatt ttcctttgac caactcggct actaaaattg     900
gttggattct gattttacta tttgtgaatt tcaatcttag ctttgaccta tacccaaaat     960
aaaccctcct gatctgtttc tccagtggcg agagacatga tttaacgaga gttgaacaca    1020
agatctagac tctagaataa aaaaagacac gaatattaga aaatgatcta atataaaata    1080
attataagga gtgagacttc aaatctaggt cagctagccc accatcttgt ggagctagtt    1140
ggaaaacccc tgggtgtgtt tctctagact ctagaataac attgatcagc ctaaccaaac    1200
ataacgaacg aagatttaat atcaggacat atatatggat cttggcaagt caattaatta    1260
attaattaat ttccagccca acaccttaca gaaattagca tgtatgagac tacttgtaag    1320
gaaaaacgag caatgaaaga tgcatgtgat cgatctgaat aagaggggaa acaaagaatt    1380
ataaacatat atgtataccct tcctaggat gttgatgtcg tggaaagatg caagactgc     1440
aaccagagga tctccataac ctacggagtc tccgtcatct gaaagaagct taaggacttc    1500
tccagctaca tctgacgtca ctggaagttc tgttcccaac tgatgtaagt atccaataac    1560
ttggcctctcc tttattgcat cccctctctt gcagctagga gattgtttct ttccttttac    1620
agttctgctc ctctgaaact tgcccactgc gggagatgtg actaacacgg cgcgcc        1676
```

<210> SEQ ID NO 8
<211> LENGTH: 234
<212> TYPE: PRT
<213> ORGANISM: Arabidopsis thaliana

<400> SEQUENCE: 8

Met Lys Tyr Leu Ser Leu Arg Thr Thr Leu Arg Ser Val Lys Ala Ile
1               5                   10                  15

Gln Leu Ser Thr Val Pro Pro Ala Glu Thr Glu Ala Ile Ala Asp Val
            20                  25                  30

Lys Asp Ser Asp Glu Thr Lys Ser Thr Val Val Asn Thr His Leu Met
        35                  40                  45

Pro Lys Ser Ser Glu Val Glu Ala Leu Ile Ser Glu Ile Thr Asp Ser
    50                  55                  60

Ser Ser Ile Ala Glu Phe Glu Leu Lys Leu Gly Gly Phe Arg Leu Tyr
65                  70                  75                  80

```
Val Ala Arg Lys Leu Thr Asp Glu Ser Ser Pro Pro Gln Gln Ile
            85                  90                  95

Gln Pro Val Val Ala Ala Ser Ala Thr Pro Glu Gly Val His Thr Asn
            100                 105                 110

Gly Ser Ala Thr Ser Ser Ser Leu Ala Ile Thr Lys Thr Ser Ser Ser
            115                 120                 125

Ser Ala Asp Arg Pro Gln Thr Leu Ala Asn Lys Ala Ala Asp Gln Gly
    130                 135                 140

Leu Val Ile Leu Gln Ser Pro Thr Val Gly Tyr Phe Arg Arg Ser Lys
145                 150                 155                 160

Thr Ile Lys Gly Lys Arg Thr Pro Thr Ile Cys Lys Glu Lys Asp Ile
                165                 170                 175

Val Lys Glu Gly Gln Val Leu Cys Tyr Ile Glu Gln Leu Gly Gly Gln
            180                 185                 190

Ile Pro Val Glu Ser Asp Val Ser Gly Glu Ile Val Lys Ile Leu Arg
            195                 200                 205

Glu Asp Gly Glu Pro Val Gly Tyr Asn Asp Ala Leu Ile Thr Val Leu
    210                 215                 220

Pro Ser Phe Pro Gly Ile Lys Lys Leu Gln
225                 230

<210> SEQ ID NO 9
<211> LENGTH: 275
<212> TYPE: PRT
<213> ORGANISM: Arabidopsis thaliana

<400> SEQUENCE: 9

Met Ala Ser Cys Ser Leu Gly Val Pro Lys Ile Lys Ile Ser Ala Val
1               5                   10                  15

Asp Leu Ser Arg Val Arg Ser Gly Ser Leu Leu Ile Pro Tyr Asn Gln
            20                  25                  30

Arg Ser Leu Leu Arg Gln Arg Pro Val Lys Tyr Leu Ser Leu Lys Thr
            35                  40                  45

Thr Phe Gly Ser Val Lys Ala Val Gln Val Ser Thr Val Pro Thr Ala
    50                  55                  60

Glu Thr Ser Ala Thr Ile Glu Val Lys Asp Ser Lys Glu Ile Lys Ser
65                  70                  75                  80

Ser Arg Leu Asn Ala Gln Leu Val Pro Lys Pro Ser Glu Val Glu Ala
            85                  90                  95

Leu Val Thr Glu Ile Cys Asp Ser Ser Ser Ile Ala Glu Phe Glu Leu
            100                 105                 110

Lys Leu Gly Gly Phe Arg Leu Tyr Val Ala Arg Asn Ile Ala Asp Asn
            115                 120                 125

Ser Ser Leu Gln Pro Pro Thr Pro Ala Val Thr Ala Ser Asn Ala
    130                 135                 140

Thr Thr Glu Ser Pro Glu Ser Asn Gly Ser Ala Ser Ser Thr Ser Leu
145                 150                 155                 160

Ala Ile Ser Lys Pro Ala Ser Ser Ala Ala Asp Gln Gly Leu Met Ile
                165                 170                 175

Leu Gln Ser Pro Lys Val Gly Phe Phe Arg Arg Ser Lys Thr Ile Lys
            180                 185                 190

Gly Lys Arg Leu Pro Ser Ser Cys Lys Glu Lys Asp Gln Val Lys Glu
            195                 200                 205

Gly Gln Ile Leu Cys Tyr Ile Glu Gln Leu Gly Gly Gln Phe Pro Ile
```

```
            210                 215                 220
Glu Ser Asp Val Thr Gly Glu Val Val Lys Ile Leu Arg Glu Asp Gly
225                 230                 235                 240

Gly Lys Ser Leu Val Phe Phe Asn Leu Ser Ser Phe Leu Lys Pro
                245                 250                 255

Arg Cys Asn Asp Phe Ser Tyr Arg Phe Leu Ile Arg Asn Arg Ala Cys
                260                 265                 270

Arg Ile Gln
        275

<210> SEQ ID NO 10
<211> LENGTH: 263
<212> TYPE: PRT
<213> ORGANISM: Arabidopsis thaliana

<400> SEQUENCE: 10

Met Ala Ser Cys Ser Leu Gly Val Pro Lys Ile Lys Ile Ser Ala Val
1               5                   10                  15

Asp Leu Ser Arg Val Arg Ser Gly Ser Leu Leu Ile Pro Tyr Asn Gln
                20                  25                  30

Arg Ser Leu Leu Arg Gln Arg Pro Val Lys Tyr Leu Ser Leu Lys Thr
            35                  40                  45

Thr Phe Gly Ser Val Lys Ala Val Gln Val Ser Thr Val Pro Thr Ala
    50                  55                  60

Glu Thr Ser Ala Thr Ile Glu Val Lys Asp Ser Lys Glu Ile Lys Ser
65                  70                  75                  80

Ser Arg Leu Asn Ala Gln Leu Val Pro Lys Pro Ser Glu Val Glu Ala
                85                  90                  95

Leu Val Thr Glu Ile Cys Asp Ser Ser Ser Ile Ala Glu Phe Glu Leu
                100                 105                 110

Lys Leu Gly Gly Phe Arg Leu Tyr Val Ala Arg Asn Ile Ala Asp Asn
            115                 120                 125

Ser Ser Leu Gln Pro Pro Thr Pro Ala Val Thr Ala Ser Asn Ala
130                 135                 140

Thr Thr Glu Ser Pro Glu Ser Asn Gly Ser Ala Ser Ser Thr Ser Leu
145                 150                 155                 160

Ala Ile Ser Lys Pro Ala Ser Ser Ala Ala Asp Gln Gly Leu Met Ile
                165                 170                 175

Leu Gln Ser Pro Lys Val Gly Phe Phe Arg Arg Ser Lys Thr Ile Lys
            180                 185                 190

Gly Lys Arg Leu Pro Ser Ser Cys Lys Glu Lys Asp Gln Val Lys Glu
        195                 200                 205

Gly Gln Ile Leu Cys Tyr Ile Glu Gln Leu Gly Gly Gln Phe Pro Ile
    210                 215                 220

Glu Ser Asp Val Thr Gly Glu Val Val Lys Ile Leu Arg Glu Asp Gly
225                 230                 235                 240

Glu Pro Val Gly Tyr Asn Asp Ala Leu Ile Ser Ile Leu Pro Ser Phe
                245                 250                 255

Pro Gly Ile Lys Lys Leu Gln
                260

<210> SEQ ID NO 11
<211> LENGTH: 274
<212> TYPE: PRT
<213> ORGANISM: Arabidopsis thaliana
```

<400> SEQUENCE: 11

Met Asn Ser Cys Ser Leu Gly Ala Pro Lys Val Arg Ile Phe Ala Thr
1               5                   10                  15

Asn Phe Ser Arg Leu Arg Cys Gly Asn Leu Leu Ile Pro Asn Asn Gln
                20                  25                  30

Arg Leu Phe Val Asp Gln Ser Pro Met Lys Tyr Leu Ser Leu Arg Thr
            35                  40                  45

Thr Leu Arg Ser Val Lys Ala Ile Gln Leu Ser Thr Val Pro Pro Ala
    50                  55                  60

Glu Thr Glu Ala Ile Ala Asp Val Lys Asp Ser Asp Glu Thr Lys Ser
65                  70                  75                  80

Thr Val Val Asn Thr His Leu Met Pro Lys Ser Ser Glu Val Glu Ala
                85                  90                  95

Leu Ile Ser Glu Ile Thr Asp Ser Ser Ser Ile Ala Glu Phe Glu Leu
            100                 105                 110

Lys Leu Gly Gly Phe Arg Leu Tyr Val Ala Arg Lys Leu Thr Asp Glu
        115                 120                 125

Ser Ser Pro Pro Gln Gln Ile Gln Pro Val Val Ala Ala Ser Ala
130                 135                 140

Thr Pro Glu Gly Val His Thr Asn Gly Ser Ala Thr Ser Ser Ser Leu
145                 150                 155                 160

Ala Ile Thr Lys Thr Ser Ser Ser Ala Asp Arg Pro Gln Thr Leu
                165                 170                 175

Ala Asn Lys Ala Ala Asp Gln Gly Leu Val Ile Leu Gln Ser Pro Thr
            180                 185                 190

Val Gly Tyr Phe Arg Arg Ser Lys Thr Ile Lys Gly Lys Arg Thr Pro
        195                 200                 205

Thr Ile Cys Lys Glu Lys Asp Ile Val Lys Glu Gly Val Leu Cys
    210                 215                 220

Tyr Ile Glu Gln Leu Gly Gly Gln Ile Pro Val Glu Ser Asp Val Ser
225                 230                 235                 240

Gly Glu Ile Val Lys Ile Leu Arg Glu Asp Gly Glu Pro Val Gly Tyr
                245                 250                 255

Asn Asp Ala Leu Ile Thr Val Leu Pro Ser Phe Pro Gly Ile Lys Lys
            260                 265                 270

Leu Gln

<210> SEQ ID NO 12
<211> LENGTH: 281
<212> TYPE: PRT
<213> ORGANISM: Arabidopsis thaliana

<400> SEQUENCE: 12

Met Ala Ser Ser Ala Ala Leu Gly Ser Leu His Gln Thr Leu Gly Ser
1               5                   10                  15

Ala Ile Asn Ser Gln Ser Glu Val His Ser Leu Ser Gly Asn Trp Ser
                20                  25                  30

Ala Ser Gly Asn Ser Cys Val Pro Arg Trp Arg Leu Ser Asn Arg Asn
            35                  40                  45

Ser Asn Tyr Arg Leu Val Leu Arg Ala Lys Ala Lys Ser Ser Thr
    50                  55                  60

Thr Thr Ile Ser Asp Gly Ser Ser Asp Ala Ser Val Ser Asp Gly Lys
65                  70                  75                  80

Lys Thr Val Arg Arg Ile Thr Phe Pro Lys Glu Val Glu Ala Leu Val

```
                85                  90                  95
His Glu Met Cys Asp Glu Thr Glu Val Ala Val Leu Gln Leu Lys Val
            100                 105                 110
Gly Asp Phe Glu Met Asn Leu Lys Arg Lys Ile Gly Ala Ala Thr Asn
        115                 120                 125
Pro Ile Pro Val Ala Asp Ile Ser Pro Thr Val Ala Pro Pro Ile Pro
    130                 135                 140
Ser Glu Pro Met Asn Lys Ser Ala Ser Ala Pro Ser Pro Ser Gln
145                 150                 155                 160
Ala Lys Pro Ser Ser Glu Lys Val Ser Pro Phe Lys Asn Thr Ser Tyr
                165                 170                 175
Gly Lys Pro Ala Lys Leu Ala Ala Leu Glu Ala Ser Gly Ser Thr Asn
            180                 185                 190
Tyr Val Leu Val Thr Ser Pro Ala Val Gly Lys Phe Gln Arg Ser Arg
        195                 200                 205
Thr Val Lys Gly Lys Lys Gln Ser Pro Ser Cys Lys Glu Gly Asp Ala
    210                 215                 220
Ile Lys Glu Gly Gln Val Ile Gly Tyr Leu His Gln Leu Gly Thr Glu
225                 230                 235                 240
Leu Pro Val Thr Ser Asp Val Ala Gly Glu Val Leu Lys Leu Leu Ser
                245                 250                 255
Asp Asp Gly Asp Ser Val Gly Tyr Gly Asp Pro Leu Val Ala Val Leu
            260                 265                 270
Pro Ser Phe His Asp Ile Asn Ile Gln
        275                 280

<210> SEQ ID NO 13
<211> LENGTH: 80
<212> TYPE: PRT
<213> ORGANISM: Polytomella parva

<400> SEQUENCE: 13

Gly Lys Arg Val Gly Lys Asn Asn Cys Val Asn Lys Gly Asp Arg Leu
1               5                   10                  15
Lys Lys Gly Gln Thr Leu Gly Phe Ile Glu Gln Leu Gly Thr His Val
            20                  25                  30
Pro Val Glu Cys Pro Val Ala Gly Glu Leu Ile Lys Phe Asn Val Glu
        35                  40                  45
Asp Gly Lys Pro Val Glu Tyr Ser Gln Ala Ile Cys Glu Ile Thr Pro
    50                  55                  60
Phe Phe Gly Gly Tyr Thr Gly Ser Asp Arg Ala Thr Lys Val Val Ala
65                  70                  75                  80

<210> SEQ ID NO 14
<211> LENGTH: 299
<212> TYPE: PRT
<213> ORGANISM: Picea sitchensis

<400> SEQUENCE: 14

Met Ala Ala Ser Cys Pro Tyr Ser Pro Phe His Cys Ser Leu Gly Thr
1               5                   10                  15
Ser Thr Gln Ala Gln Gly Leu Leu Glu Lys Gly Val Val Arg Asn Leu
            20                  25                  30
His Tyr Gly Phe Ser Tyr Arg Ser Leu Pro Arg Met Asp Ser Gly Asp
        35                  40                  45
Ser Phe Arg Asn Lys Arg Gly Thr Leu Ser Asn Ala Gly Arg Ser Lys
```

Val Trp Leu Ser Ser Asn Val Lys Ala Ser His Ala Thr Phe Ala Met
65                  70                  75                  80

Ala Ser Asp Lys Asp Ala Leu Glu Ser Gly Ser Leu Gly Glu Leu Glu
                85                  90                  95

Lys Gly Asn Gln Asn Gly Ala Leu Phe Pro Asp Gly Ile Glu Ser Phe
            100                 105                 110

Ile Thr Glu Val Cys Asp Glu Thr Asp Ile Ala Glu Ile Lys Leu Lys
        115                 120                 125

Ala Gly Ser Phe Ala Met His Ile Arg Arg Asn Ile Glu Lys Ser Lys
    130                 135                 140

Arg Pro Ser Ser Val Ala Ser Pro Leu Thr Ala Pro Pro Val Pro Ser
145                 150                 155                 160

Glu Pro Met Val Asp Phe Asp His Thr Val Thr Pro Pro Ser Ser
                165                 170                 175

Pro Ala Pro Lys Ala Pro Pro Thr Arg Ser Phe Asn Pro Phe Thr Thr
            180                 185                 190

Lys Leu Ser Leu Ser Lys Thr Ser Lys Phe Gly Leu Leu Glu Ala Ala
        195                 200                 205

Gly Asp Glu Gly Leu Cys Phe Val Thr Ala Pro Lys Val Gly Leu Phe
    210                 215                 220

Lys Arg Ser Arg Val Val Lys Gly Arg Asn Gly Arg Pro Leu Cys Glu
225                 230                 235                 240

Glu Gly Gln Ser Ile Lys Glu Gly Gln Val Val Cys Phe Leu Asp Gln
                245                 250                 255

Leu Gly Gly Gln Thr Pro Val Thr Ser Glu Val Ser Gly Glu Ile Val
            260                 265                 270

Lys Ile Leu Trp Ser Asp Gly Glu Pro Val Gly Tyr Gly Asp Pro Leu
        275                 280                 285

Ile Ala Val Leu Pro Ser Phe Arg Gly Ile Lys
    290                 295

<210> SEQ ID NO 15
<211> LENGTH: 282
<212> TYPE: PRT
<213> ORGANISM: Medicago truncatula

<400> SEQUENCE: 15

Met Val Ile Trp Val Ile Lys His Ile Thr Gly Ser Leu Gly Thr Gln
1               5                   10                  15

Asn Val Lys Val Leu Asn Leu His Phe Gly Gln Glu Arg Ala Glu Phe
                20                  25                  30

Ser Gln His Phe Gly Thr Arg Ser Trp Ile Ser Arg Lys Ser Leu Gln
            35                  40                  45

Tyr Ala Arg Leu Val Ala Ser Lys Gln Thr Val Arg Ser Leu Thr Pro
        50                  55                  60

Ser Asn Asp Gln Ser Ala Glu Ile Gln Ser Val Ser Arg Ser Glu Asp
65                  70                  75                  80

Gly Ser Glu Glu Ser Lys Ser Ser Gly Leu Thr Asn Gln Leu Phe Pro
                85                  90                  95

Asn Phe Asn Asp Val Glu Phe Leu Leu Thr Asn Leu Cys Asp Thr Ala
            100                 105                 110

Ser Ile Gly Glu Leu Glu Leu Lys Leu Asp Gly Phe His Leu Arg Val
        115                 120                 125

```
Val Arg Asp Leu Thr Glu Lys Ser Lys Thr Leu Pro Pro Ser Ile Pro
    130                 135                 140

Ala Pro Val Ser Ile Asn Thr Pro Ala Glu Ala Pro Lys Pro Asn Gly
145                 150                 155                 160

Ser Val Ser Thr Leu Thr Thr Leu Ala Ile Ser Lys Pro Ala Pro Ser
                165                 170                 175

Ser Leu Ser Ile Glu Gly Phe Leu Glu Lys Ala Ala Asp Glu Gly Leu
                180                 185                 190

Val Ile Ile His Ser Pro Thr Val Gly Ile Phe Arg Ser Arg Thr
                195                 200                 205

Ile Lys Gly Lys Arg Ala Pro Pro Ser Cys Gln Glu Met Gln Asn Val
210                 215                 220

Glu Glu Gly Lys Val Ile Cys Tyr Ile Glu Gln Leu Gly Gly Gln Leu
225                 230                 235                 240

Pro Val Glu Ser Asp Val Ser Gly Glu Val Ile Lys Ile Leu Arg Glu
                245                 250                 255

Asp Gly Asp Pro Val Gly Tyr Gly Asp Thr Leu Ile Ala Ile Leu Pro
                260                 265                 270

Ser Phe Pro Gly Ile Lys Lys Leu Gln Tyr
                275                 280

<210> SEQ ID NO 16
<211> LENGTH: 252
<212> TYPE: PRT
<213> ORGANISM: Vitis vinifera

<400> SEQUENCE: 16

Met Ala Asn Asn Lys Asp His Lys Leu Pro Ala Thr Pro Ala Met Gly
1               5                   10                  15

Lys Asn Met Val Ile Pro Phe Leu Leu Trp Phe Ala Lys Thr Met Ala
                20                  25                  30

Ile Asn Lys Arg Ser Val Pro Thr Pro Glu Leu Val Gly Ser Ala Val
                35                  40                  45

Asn Leu Glu Asp Gly Ser Glu Glu Thr Lys Ser Ser Gly Leu Thr Ser
50                  55                  60

Gln Leu Thr Pro Asn Ala Tyr Glu Val Glu Ser Leu Leu Ser Glu Ile
65                  70                  75                  80

Cys Asp Thr Thr Ser Ile Ala Glu Phe Glu Leu Lys Leu Gly Gly Phe
                85                  90                  95

Arg Leu Tyr Met Met Arg Asp Leu Ala Gly Lys Ile Glu Pro Thr Pro
                100                 105                 110

Pro Pro Ser Ser Thr Pro Val Thr Val Ser Leu Asn Asp Glu Ala Pro
                115                 120                 125

Lys Leu Asn Gly Ser Ala Ser Met Ser Ser Leu Pro Ile Ser Lys Ser
130                 135                 140

Ala Leu Leu Leu Gly Gln Ser Gln Thr Leu Leu Asp Arg Ala Ala Asp
145                 150                 155                 160

Glu Gly Leu Met Ile Leu Gln Ser Pro Lys Val Gly Phe Phe Arg Arg
                165                 170                 175

Ser Arg Thr Ile Lys Gly Lys Arg Ala Pro Pro Ser Cys Lys Glu Lys
                180                 185                 190

Gln Ile Val Lys Glu Gly Gln Val Leu Cys Tyr Ile Glu Gln Leu Gly
                195                 200                 205

Gly Glu Ile Pro Ile Glu Ser Asp Val Ser Gly Glu Val Ile Lys Ile
210                 215                 220
```

```
Leu Arg Glu Asp Gly Glu Pro Val Gly Tyr Gly Asp Ala Leu Ile Ala
225                 230                 235                 240

Ile Leu Pro Ser Phe Pro Gly Ile Lys Lys Leu Gln
            245                 250
```

<210> SEQ ID NO 17
<211> LENGTH: 209
<212> TYPE: PRT
<213> ORGANISM: Elaeis guineensis
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (135)..(135)
<223> OTHER INFORMATION: Xaa can be any naturally occurring amino acid

<400> SEQUENCE: 17

```
Met Gly Thr Cys Ser Leu Gly Ser Thr Ser Lys Ile Lys Leu Leu Ser
1               5                   10                  15

Phe His Pro Glu Phe Lys Lys Leu Arg Cys Thr Ala Arg Leu Thr His
                20                  25                  30

His Asn Leu Lys Cys Gly Arg Leu Glu Thr Pro Asn Gly Ser Xaa Gly
            35                  40                  45

Thr Gln Ile Trp Lys Glu Leu Val Arg Ala Ala Gly Phe Asp Lys Gln
        50                  55                  60

Ala Arg Arg Phe Ser Asn Ser Leu Gly Ala Arg Cys Ser Ile Ser Ser
65                  70                  75                  80

Gly Thr Glu Asn Asn Ser Asn Ile Leu Glu Leu Glu Asn Arg Ser
                85                  90                  95

Asn Gly Asn Gln Ile Ile Pro Ile Ser Leu Glu Val Glu Pro Leu Leu
            100                 105                 110

Thr Ala Val Cys Asp Ala Thr Ser Val Ala Glu Phe Lys Leu Asp Val
        115                 120                 125

Gly Phe Phe Arg Arg Ser Xaa Thr Ile Lys Gly Lys Gln Ala Pro Arg
    130                 135                 140

Ser Cys Lys Val Gly Gln Asp Gly Lys Lys Gly Gln Val Leu Cys Tyr
145                 150                 155                 160

Ile Glu Gln Ile Gly Gly Glu Ile Pro Val Glu Ser Asp Val Ser Gly
                165                 170                 175

Glu Val Ile Lys Ile Leu Arg Glu Glu Gly Glu Ala Val Gly Tyr Gly
            180                 185                 190

Asp Ala Leu Ile Ala Ile Leu Pro Ser Phe Pro Gly Ile Lys Lys Leu
        195                 200                 205

Gln
```

<210> SEQ ID NO 18
<211> LENGTH: 232
<212> TYPE: PRT
<213> ORGANISM: Chlamydomonas reinhardtii

<400> SEQUENCE: 18

```
Met Leu Cys Arg Thr Val Ala Pro Thr Arg Pro Ala Gly Val Ala Arg
1               5                   10                  15

Ser Val Arg Ser Val Arg Pro Ser Pro Ile Ala Arg Val Pro Pro Met
                20                  25                  30

Lys Ala Thr Ala Ser Thr Ala Glu Lys Lys Ala Glu Ala Ala Glu Val
```

```
                35                  40                  45
Glu Glu Glu Phe Asp Gly Pro Glu Val Asn Pro Ser Thr Gln Glu Val
 50                  55                  60
Ala Ala Phe Ile Asn Thr Leu Cys Asn Asp Thr Glu Ile Ala Glu Met
 65                  70                  75                  80
His Leu Lys Met Gly Ser Phe Glu Leu Lys Val Lys Arg Ser Val Ser
                 85                  90                  95
Gly Gly Ala Pro Val Tyr Ala His Ala Pro Val Ala Pro Ala Ala
                100                 105                 110
Pro Ala Pro Ala Ala Thr Val Ser Val Asp Val Pro Ala Pro Thr Val
                115                 120                 125
Glu Asp Thr Val Asp Glu Ser Leu Val Tyr Val Asn Ala Pro Lys Val
                130                 135                 140
Gly Val Phe Arg Arg Gly Lys Tyr Ala Gly Lys Arg Val Gly Lys
145                 150                 155                 160
Gly Asn Leu Ile Glu Val Gly Ala Gln Val Lys Lys Gly Gln Cys Ile
                165                 170                 175
Gly Tyr Val Glu Gln Leu Gly Thr Phe Val Glu Val Lys Cys Pro Ile
                180                 185                 190
Ala Gly Glu Leu Val Lys Val His Val Glu Asp Gly Lys Pro Val Glu
                195                 200                 205
Tyr Gln Gln Leu Val Ala Glu Val Ala Pro Phe Phe Gly Gly His Ile
                210                 215                 220
Ile Gly Asp Ser Lys Tyr Ala Phe
225                 230

<210> SEQ ID NO 19
<211> LENGTH: 294
<212> TYPE: PRT
<213> ORGANISM: Physcomitrella patens

<400> SEQUENCE: 19

Met Ala Leu Ala Ala Val Gly Arg Phe Ala Val Thr Gly Ser Ser Leu
 1                   5                  10                  15
Gln Ser Val Ile Gly Ser Glu Lys Gln Cys Val Ala Ala Pro Ala
                 20                  25                  30
Glu Arg Ile Ser Ile Ser Ser Arg Arg Ser Ser Ile Ala Ala Pro Leu
                 35                  40                  45
Arg Glu Cys Ile Ile Thr Gly Leu Ala Pro Val Thr Arg Thr Phe Gln
 50                  55                  60
Pro Arg Ala Val Thr Ala Asp Tyr Leu Gly Glu Ser Glu Val Leu
 65                  70                  75                  80
Asp Ala Glu Asn Glu Val Glu Glu Ala Asp Asn Pro Leu Val Pro
                 85                  90                  95
Ser Ala Phe Glu Val Gln Asn Leu Leu Met Gln Val Cys Asp Glu Thr
                100                 105                 110
Ser Asn Ile Ala Glu Val Gln Leu Lys Val Gly Ser Phe Ser Leu Arg
                115                 120                 125
Val Lys Arg Lys Ile Gly Lys Ala Ala Pro Ala Pro Lys Pro Val Ala
                130                 135                 140
Ala Gly Pro Pro Val Leu Gly Lys Pro Met Val Glu Ser Ile Pro Ala
145                 150                 155                 160
Asp Ser Val Pro Thr Ala Pro Ala Pro Lys Ser Thr Lys Leu Thr Lys
                165                 170                 175
```

-continued

Asn Thr Ala Leu Ser Ala Ala Ser Leu Lys Pro Val Ser Asn Phe Gly
            180                 185                 190

Leu Met Glu Ala Ala Ala Asp Ala Gly Ile Val Phe Thr Ser Pro
        195                 200                 205

Lys Val Gly Leu Phe Arg Lys Gly Arg Thr Val Lys Gly Arg Ser Gly
        210                 215                 220

Pro Pro Leu Cys Glu Glu Gly Gln Val Ile Lys Lys Gly Gln Val Val
225                 230                 235                 240

Cys Tyr Leu Glu Gln Leu Gly Thr Gln Gln Pro Val Glu Ala Glu Val
                245                 250                 255

Thr Gly Glu Val Glu Lys Val Leu Trp Glu Asp Gly Ala Pro Val Gly
            260                 265                 270

Tyr Gly Asp Pro Leu Ile Ala Ile Arg Pro Ser Phe Pro Gly Ile Lys
            275                 280                 285

Val Lys Gly Gln Ile Gln
            290

<210> SEQ ID NO 20
<211> LENGTH: 260
<212> TYPE: PRT
<213> ORGANISM: Populus trichocarpa

<400> SEQUENCE: 20

Met Glu Ser Ser Val Leu Leu Arg Ser Phe Gln Cys Asn Leu Leu Ala
1               5                   10                  15

Gln Gly Gln Gly Leu Thr Val Gly Arg Lys Leu Ile Ser Tyr Pro Ser
            20                  25                  30

Lys Arg Asn Leu Arg Leu Val Ser Cys Val Lys Thr Ser Glu Ala Pro
        35                  40                  45

Ala Ile Ala Lys Ser Asp Asp Gly Asn Lys Gln Gly Ser Leu Glu Lys
    50                  55                  60

Asn Ser Leu Arg Asn Ala Thr Phe Pro Asn Gly Phe Glu Ala Leu Val
65                  70                  75                  80

Leu Glu Val Cys Asp Glu Thr Glu Ile Ala Glu Leu Lys Leu Lys Val
                85                  90                  95

Gly Asp Phe Glu Met His Leu Lys Arg Asn Val Gly Ala Ala Lys Ala
            100                 105                 110

Pro Leu Ile Ser Ser Thr Pro Leu Pro Ile Pro Thr Pro Pro Met
        115                 120                 125

Glu Val Ser Ala Ala Val Ser Pro Ser Pro Ser Pro Ser Lys Ser Ser
    130                 135                 140

Val Glu Lys Thr Thr Pro Phe Thr Asn Val Ser Phe Gly Lys Ser Ser
145                 150                 155                 160

Lys Leu Ala Ala Leu Glu Ala Ser Gly Ala Ser Gly Tyr Val Leu Val
                165                 170                 175

Ala Ser Pro Thr Val Gly Ser Phe Arg Arg Asn Arg Thr Val Lys Gly
            180                 185                 190

Lys Lys Gln Pro Pro Ile Cys Lys Glu Gly Asp Val Ile Lys Glu Gly
        195                 200                 205

Gln Val Ile Gly Tyr Leu Asp Gln Phe Gly Thr Glu Leu Pro Val Lys
    210                 215                 220

Ser Asp Val Ala Gly Glu Val Leu Lys Leu Phe Asn Asp Gly Asp
225                 230                 235                 240

Ala Val Gly Tyr Gly Asp Pro Leu Ile Ala Val Leu Pro Ser Phe His
                245                 250                 255

Gly Ile Asn Thr
            260

<210> SEQ ID NO 21
<211> LENGTH: 274
<212> TYPE: PRT
<213> ORGANISM: Vitis vinifera

<400> SEQUENCE: 21

Met Ala Ser Cys Gly Leu Gly Ala Pro Ser Ile Lys Ile Ser Asn Leu
1               5                   10                  15

Asp Leu Val Arg Thr Arg Leu Gly Val Leu Gln Ser Arg Phe Ser Ile
            20                  25                  30

Arg Thr Ser Thr Ala Trp Thr Pro Leu Asn Asn Ser Gly Leu Val Ile
        35                  40                  45

Ser Gln Arg Ser Gln Lys Ala Ile Ile Leu Cys Arg Gly Ser Ser Ser
    50                  55                  60

Glu Ala Glu Ser Ala Val Asn Leu Glu Asp Gly Ser Glu Glu Thr Lys
65                  70                  75                  80

Ser Ser Gly Leu Thr Ser Gln Leu Thr Pro Asn Ala Tyr Glu Val Glu
                85                  90                  95

Ser Leu Leu Ser Glu Ile Cys Asp Thr Thr Ser Ile Ala Glu Phe Glu
            100                 105                 110

Leu Lys Leu Gly Gly Phe Arg Leu Tyr Met Met Arg Asp Leu Ala Gly
        115                 120                 125

Lys Ile Glu Pro Thr Pro Pro Ser Ser Thr Pro Val Thr Val Ser
    130                 135                 140

Leu Asn Asp Glu Ala Pro Lys Leu Asn Gly Ser Ala Ser Met Ser Ser
145                 150                 155                 160

Leu Pro Ile Ser Lys Ser Ala Leu Leu Leu Gly Gln Ser Gln Thr Leu
                165                 170                 175

Leu Asp Arg Ala Ala Asp Glu Gly Leu Met Ile Leu Gln Ser Pro Lys
            180                 185                 190

Val Gly Phe Phe Arg Arg Ser Arg Thr Ile Lys Gly Lys Arg Ala Pro
        195                 200                 205

Pro Ser Cys Lys Glu Lys Gln Ile Val Lys Glu Gly Gln Val Leu Cys
    210                 215                 220

Tyr Ile Glu Gln Leu Gly Gly Glu Ile Pro Ile Glu Ser Asp Val Ser
225                 230                 235                 240

Gly Glu Val Ile Lys Ile Leu Arg Glu Asp Gly Glu Pro Val Gly Tyr
                245                 250                 255

Gly Asp Ala Leu Ile Ala Ile Leu Pro Ser Phe Pro Gly Ile Lys Lys
            260                 265                 270

Leu Gln

<210> SEQ ID NO 22
<211> LENGTH: 225
<212> TYPE: PRT
<213> ORGANISM: Ricinus communis
<220> FEATURE:
<221> NAME/KEY: misc_feature
<222> LOCATION: (29)..(30)
<223> OTHER INFORMATION: Xaa can be any naturally occurring amino acid

<400> SEQUENCE: 22

Met Asp Glu Lys Glu Thr Lys Ser Ser Gly Leu Thr Ser Gln Leu Leu
1               5                   10                  15

-continued

```
Pro Asn Ser Ala Glu Met Ser Val Trp Cys Ile Met Xaa Xaa Glu Ser
            20                  25                  30

Leu Ile Thr Glu Ile Cys Asn Ser Thr Ser Ile Ala Glu Phe Glu Leu
        35                  40                  45

Lys Leu Asp Gly Phe Arg Leu Tyr Val Thr Arg Asp Leu Thr Glu Lys
    50                  55                  60

Ser Lys Leu Gln Pro Leu Ser Ala Ser Ala Ser Ala Pro Ala Leu Ser
65                  70                  75                  80

Pro Pro Pro Ala Pro Ala Ala Ala Leu Ala Ser Val Ser Thr Asp Thr
                85                  90                  95

Thr Thr Ala Ala Pro Asp Leu Asn Gly Ser Val Ser Ser Thr Ser Arg
            100                 105                 110

Ala Ile Ser Lys Ser Gly Ser Phe Ser Gly Gly Val Gln Ser Ile Leu
        115                 120                 125

Asp Arg Ala Ala Asp Glu Gly Leu Met Ile Leu Gln Ser Pro Arg Val
    130                 135                 140

Gly Phe Phe Arg Arg Ser Arg Thr Ile Lys Gly Lys Arg Ala Pro Pro
145                 150                 155                 160

Ser Cys Lys Glu Lys Gln Ile Val Lys Glu Gly Gln Val Leu Cys Tyr
                165                 170                 175

Ile Glu Gln Leu Gly Gly Glu Leu Pro Ile Glu Ser Asp Val Ser Gly
            180                 185                 190

Glu Val Ile Lys Ile Leu Arg Glu Asp Gly Glu Pro Val Gly Tyr Gly
        195                 200                 205

Asp Ala Leu Ile Ala Ile Leu Pro Ser Phe Pro Gly Ile Lys Lys Leu
    210                 215                 220

Gln
225

<210> SEQ ID NO 23
<211> LENGTH: 258
<212> TYPE: PRT
<213> ORGANISM: Ricinus communis

<400> SEQUENCE: 23

Met Glu Ser Ser Ser Ile Ala Leu Gln Cys Lys Met Tyr Gly Gln Arg
1               5                   10                  15

Leu Thr Val Gly Arg Lys Leu Met Ser Ser Ser Tyr Pro Lys Met Arg
            20                  25                  30

Arg Asn Val Met Ser Val Ser Cys Val Lys Ala Pro Glu Val Gly Ala
        35                  40                  45

Thr Ala Lys Ser Asp Ala Ala Asp Gly Ala Val Glu Lys Thr Arg Pro
    50                  55                  60

Arg Thr Ala Thr Phe Pro Ser Gly Phe Glu Ala Leu Met Leu Glu Val
65                  70                  75                  80

Cys Asp Glu Thr Glu Val Ala Glu Leu Lys Leu Lys Val Gly Asp Phe
                85                  90                  95

Glu Met His Leu Arg Arg Asn Val Gly Ala Thr Lys Ala Pro Leu Ser
            100                 105                 110

His Ile Ser Pro Ile Glu Pro Pro Pro Ile Pro Thr Lys Pro Met Asp
        115                 120                 125

Val Pro Ala Thr Val Ala Ala Pro Ala Ser Pro Pro Lys Pro Ser Ser
    130                 135                 140

Glu Lys Ala Thr Pro Phe Thr Asn Val Ser Phe Gly Lys Ser Ala Lys
```

```
            145                 150                 155                 160
Leu Ala Ala Leu Glu Ala Ser Gly Ala Thr Gly Tyr Val Leu Val Ala
                165                 170                 175
Ser Pro Thr Val Gly Ser Phe Arg Arg Asn Arg Ser Val Lys Gly Lys
                180                 185                 190
Arg Gln Pro Pro Ile Phe Lys Glu Gly Asp Leu Ile Lys Glu Gly Gln
                195                 200                 205
Val Ile Gly Tyr Leu Asp Gln Phe Gly Thr Glu Leu Pro Val Lys Ser
            210                 215                 220
Asp Val Ala Gly Glu Val Leu Lys Leu Leu Phe Asp Asp Gly Asp Ala
225                 230                 235                 240
Val Gly Tyr Gly Asp Pro Leu Val Ala Val Leu Pro Ser Phe His Gly
                245                 250                 255
Ile Gln

<210> SEQ ID NO 24
<211> LENGTH: 291
<212> TYPE: PRT
<213> ORGANISM: Glycine max

<400> SEQUENCE: 24

Met Glu Ser Ser Ala Ala Ile Arg Ser Phe His Tyr Pro Ile Gly Thr
1               5                   10                  15
Met Ser His Val Arg Ala Ser Leu Glu Lys Gln Ala Val Val Pro Ile
                20                  25                  30
His Asn Ala Gly Trp Asn Ser Lys Ser Arg Leu Phe Ile Gln His Leu
            35                  40                  45
Ala Tyr Gly Gln Lys His Ile Asn Ser His Thr Lys Gly Lys Asn Thr
        50                  55                  60
Leu Ile Ser Cys Gly Lys Thr Ala Glu Ala Ile Asn Ala Ser Lys Ser
65                  70                  75                  80
Asp Ala Ser Ser Asp Asn Thr Pro Gln Gly Ser Leu Glu Lys Lys Pro
                85                  90                  95
Leu Gln Thr Ala Thr Phe Pro Asn Gly Phe Glu Ala Leu Val Leu Glu
                100                 105                 110
Val Cys Asp Glu Thr Glu Ile Ala Glu Leu Lys Val Lys Val Gly Asp
            115                 120                 125
Phe Glu Met His Ile Lys Arg Asn Ile Gly Ala Thr Lys Val Pro Leu
        130                 135                 140
Ser Asn Ile Ser Pro Thr Thr Pro Pro Ile Pro Ser Lys Pro Met
145                 150                 155                 160
Asp Glu Ser Ala Pro Gly Ser Leu Pro Pro Ser Pro Lys Ser Ser
                165                 170                 175
Pro Glu Lys Asn Asn Pro Phe Ala Asn Val Ser Lys Glu Lys Ser Pro
                180                 185                 190
Arg Leu Ala Ala Leu Glu Ala Ser Gly Thr Asn Thr Tyr Val Leu Val
            195                 200                 205
Ser Ser Pro Thr Val Gly Leu Phe Arg Arg Gly Arg Thr Val Lys Gly
        210                 215                 220
Lys Lys Gln Pro Pro Ile Cys Lys Glu Gly Asp Val Ile Lys Glu Gly
225                 230                 235                 240
Gln Val Ile Gly Tyr Leu Asp Gln Phe Gly Thr Gly Leu Pro Ile Lys
                245                 250                 255
Ser Asp Val Ala Gly Glu Val Leu Lys Leu Leu Val Glu Asp Gly Glu
```

```
                    260                 265                 270
Pro Val Gly Tyr Gly Asp Pro Leu Ile Ala Val Leu Ser Ser Phe His
                275                 280                 285
Asp Ile Lys
        290

<210> SEQ ID NO 25
<211> LENGTH: 281
<212> TYPE: PRT
<213> ORGANISM: Arabidopsis lyrata subsp. lyrata

<400> SEQUENCE: 25

Met Ala Ser Ser Ala Ala Leu Gly Ser Leu His Gln Thr Leu Val Cys
1               5                   10                  15

Ala Ile Asn Ser Gln Ser Glu Val His Ser Leu Ser Gly Asn Trp Ser
            20                  25                  30

Ala Ser Gly Asn Ser Cys Val Pro Arg Trp Arg Leu Ser Asn Arg Asn
        35                  40                  45

Ser Lys Tyr Thr Leu Val Leu Arg Ala Lys Ala Ala Lys Ser Ser Thr
    50                  55                  60

Ala Thr Lys Ser Asp Asp Ser Ser Glu Ala Ser Val Ser Asn Gly Lys
65                  70                  75                  80

Lys Thr Val Arg Arg Ile Thr Phe Pro Lys Glu Val Glu Ala Leu Val
                85                  90                  95

His Glu Met Cys Asp Glu Thr Glu Val Ala Val Leu Gln Leu Lys Val
            100                 105                 110

Gly Asp Phe Glu Met Asn Leu Lys Arg Lys Ile Gly Ala Ala Thr Asn
        115                 120                 125

Pro Ile Pro Met Val Asp Ile Ser Pro Thr Ile Ala Pro Pro Ile Pro
    130                 135                 140

Ser Glu Pro Met Asn Lys Ser Val Ser Ser Ala Pro Ser Pro Ser Lys
145                 150                 155                 160

Ala Lys Pro Ser Ser Glu Lys Val Ser Pro Phe Lys Asn Thr Ser Tyr
                165                 170                 175

Gly Lys Pro Ala Lys Leu Ala Ala Leu Glu Ala Ser Gly Ser Asn Asn
            180                 185                 190

Tyr Val Leu Val Thr Ser Pro Ala Val Gly Lys Phe Gln Arg Ser Arg
        195                 200                 205

Thr Val Lys Gly Lys Lys Gln Ser Pro Ser Cys Lys Glu Gly Asp Ala
    210                 215                 220

Ile Lys Glu Gly Gln Val Ile Gly Tyr Leu His Gln Leu Gly Thr Glu
225                 230                 235                 240

Leu Pro Val Thr Ser Asp Val Ala Gly Glu Val Leu Lys Leu Leu Ser
                245                 250                 255

Asp Asp Gly Asp Ser Val Gly Tyr Gly Asp Pro Leu Val Ala Ile Leu
            260                 265                 270

Pro Ser Phe His Asp Ile Asn Ile Gln
        275                 280

<210> SEQ ID NO 26
<211> LENGTH: 263
<212> TYPE: PRT
<213> ORGANISM: Arabidopsis lyrata subsp. lyrata

<400> SEQUENCE: 26

Met Ala Ser Cys Ser Leu Gly Val Pro Lys Ile Lys Ile Ser Ala Val
```

```
            1               5                  10                 15
        Asp Leu Ser Arg Val Arg Ser Ala Ser Phe Leu Ile Pro Tyr Asn Gln
                        20                 25                 30

Lys Ser Leu Leu Gly Gln Arg Pro Val Lys Tyr Leu Ser Leu Arg Thr
                        35                 40                 45

Thr Phe Gly Ser Val Lys Ala Val Gln Leu Ser Thr Val Pro Ala Ala
                    50                 55                 60

Glu Thr Ser Ala Thr Ile Glu Val Lys Asp Ser Glu Glu Thr Lys Ser
        65                  70                 75                 80

Ser Arg Leu Asn Ala Gln Leu Val Pro Lys Pro Ser Glu Val Glu Ala
                        85                 90                 95

Leu Val Thr Glu Ile Cys Asp Ser Ser Ile Ala Glu Phe Glu Leu
                        100                105                110

Lys Leu Gly Gly Phe Arg Leu Tyr Val Ala Arg Asn Ile Ala Asp Asn
                        115                120                125

Ser Ser Pro Gln Pro Pro Thr Pro Ala Val Ala Ala Ser Asn Ala
                    130                135                140

Thr Thr Glu Ser Pro Asp Leu Asn Gly Ser Ala Ser Thr Ser Leu
        145                 150                155                160

Ala Ile Ser Lys Pro Ala Ser Ser Ala Ala Asp Gln Gly Leu Met Ile
                        165                170                175

Leu Gln Ser Pro Lys Val Gly Phe Phe Arg Arg Ser Lys Thr Ile Lys
                        180                185                190

Gly Lys Arg Leu Pro Ser Ser Cys Lys Glu Lys Asp Leu Val Lys Glu
                        195                200                205

Gly Gln Ile Leu Cys Tyr Ile Glu Gln Leu Gly Gly Gln Phe Pro Ile
                        210                215                220

Glu Ala Asp Val Thr Gly Glu Val Val Lys Ile Leu Arg Glu Asp Gly
        225                 230                235                240

Glu Pro Val Gly Tyr Asn Asp Ala Leu Ile Ser Ile Leu Pro Ser Phe
                        245                250                255

Pro Gly Ile Lys Lys Leu Gln
                        260

<210> SEQ ID NO 27
<211> LENGTH: 275
<212> TYPE: PRT
<213> ORGANISM: Arabidopsis lyrata subsp. lyrata

<400> SEQUENCE: 27

Met Asn Ser Cys Ser Leu Gly Ala Pro Arg Val Arg Ile Ser Ala Thr
        1               5                  10                 15

Ser Phe Ser Arg Leu Arg Cys Gly Asn Phe Leu Ile Pro Asn Asn Gln
                        20                 25                 30

Thr Leu Phe Ile Asp Gln Ser Pro Ile Lys Asn Leu Ser Gln Arg Thr
                        35                 40                 45

Thr Thr Leu Arg Ser Val Lys Ala Ile Gln Leu Ser Thr Val Pro Pro
                    50                 55                 60

Ala Glu Thr Gln Ala Ile Ala Asp Val Glu Asp Ser Glu Glu Thr Lys
        65                  70                 75                 80

Ser Thr Val Val Asn Ser Gln Leu Ile Pro Asn Ser Ser Glu Val Glu
                        85                 90                 95

Ala Leu Ile Ser Glu Ile Thr Asp Ser Thr Ser Ile Ala Glu Phe Glu
                        100                105                110
```

```
Leu Lys Leu Gly Gly Phe Arg Leu Tyr Val Ala Arg Lys Leu Ala Asp
            115                 120                 125

Gln Ser Ser Pro Leu Pro Gln Gln Ile Pro Pro Val Val Ala Ala Ser
        130                 135                 140

Ala Thr Pro Glu Gly Val His Thr Asn Gly Ser Ala Thr Ser Ser Ser
145                 150                 155                 160

Leu Ala Ile Thr Lys Thr Ser Thr Ser Ser Ala Asp Arg Pro Gln Thr
                165                 170                 175

Leu Ala Asn Lys Ala Ala Asp Gln Gly Leu Val Ile Leu Gln Ser Pro
            180                 185                 190

Thr Val Gly Tyr Phe Arg Arg Ser Lys Thr Ile Lys Gly Lys Arg Thr
        195                 200                 205

Pro Thr Ile Cys Lys Glu Lys Asp Ile Val Lys Glu Gly Gln Val Leu
210                 215                 220

Cys Tyr Ile Glu Gln Leu Gly Gly Gln Ile Pro Val Glu Ser Asp Val
225                 230                 235                 240

Ser Gly Glu Ile Val Lys Ile Leu Arg Glu Asp Gly Pro Val Gly
                245                 250                 255

Tyr Asn Asp Ala Leu Ile Thr Val Leu Pro Ser Phe Pro Gly Ile Lys
            260                 265                 270

Lys Leu Gln
        275

<210> SEQ ID NO 28
<211> LENGTH: 245
<212> TYPE: PRT
<213> ORGANISM: Selaginella moellendorffii

<400> SEQUENCE: 28

Met Ala Ala Ser Ser Leu Leu Gln Ala Gln Phe Ser Pro Ala Ser Ser
1               5                   10                  15

Ser Leu Asp Ala Cys His Val Ser Tyr Gly Ser Ser Ala Ile Ile Ser
            20                  25                  30

Val Ser Arg Val Ser Val Arg Gln Cys Trp Ala Arg Arg Ser Gln Arg
        35                  40                  45

Val Phe Cys Val Ala Thr Lys Ile Glu Glu Leu Glu Pro Val Ile Pro
50                  55                  60

Thr Ser Ala Glu Ile His Thr Leu Leu Arg Glu Val Cys Asp Glu Thr
65                  70                  75                  80

Lys Ile Ala Glu Leu Asn Val Lys Val Gly Ala Phe Asn Leu His Met
                85                  90                  95

Arg Arg Ser Val Pro Ala Pro Lys Pro Pro Ala Ala Ser Val Ala
            100                 105                 110

Ala Pro Pro Val Ala Ala Pro Ala Ala Pro Val Ser Ser Lys Pro
        115                 120                 125

Ala Ala Pro Ser Lys Pro Ala Ala Lys Thr Ser Lys Val Ser Pro Met
            130                 135                 140

Met Ser Lys Ala Val Ala Tyr Asp Glu Leu Gln Lys Ala Ala Ala Glu
145                 150                 155                 160

Thr Gly Val Val Phe Val Asn Ala Pro Lys Val Gly Leu Phe Arg Arg
                165                 170                 175

Ser Arg Leu Val Lys Gly Lys Phe Gly Ala Pro Leu Cys Gln Glu Gly
            180                 185                 190

Gln Thr Val Lys Glu Gly Gln Val Val Cys Tyr Leu Gly Gln Phe Gly
        195                 200                 205
```

Thr Gln Thr Ala Val Glu Ser Glu Thr Ser Gly Asp Val Ile Lys Val
    210                 215                 220

Leu Trp Glu Asp Gly Val Pro Val Gly Tyr Gly Asp Pro Leu Ile Ala
225                 230                 235                 240

Leu Lys Pro Lys Lys
            245

<210> SEQ ID NO 29
<211> LENGTH: 239
<212> TYPE: PRT
<213> ORGANISM: Volvox carteri f. nagariensis

<400> SEQUENCE: 29

Met Leu Thr Arg Ser Ser Ala Pro Gln Arg Pro Ala Gly Val Ala Ala
1               5                   10                  15

Ser Arg Ser Val Arg Ala Val Arg Thr Thr Ile Thr Thr Arg Leu Pro
            20                  25                  30

Ile Leu Lys Ala Ala Ala Thr Glu Ala Lys Lys Glu Val Asp Val Ser
        35                  40                  45

Val Glu Asp Glu Tyr Asn Gly Pro Asp Ile Ala Pro Ser Thr Gln Gln
50                  55                  60

Val Ala Ser Phe Leu Asn Thr Leu Cys Asn Glu Thr Glu Ile Ala Glu
65                  70                  75                  80

Met His Leu Lys Met Gly Asn Phe Glu Leu Lys Val Lys Arg Ser Val
                85                  90                  95

Ala Gly Ser Ala Ala Ala Pro Leu Tyr Ala Ser Thr Val Ala Pro
            100                 105                 110

Ala Thr Pro Ala Glu Pro Val Val Ala Ser Ser Pro Leu Gln Ser Val
        115                 120                 125

Glu Ala Pro Pro Ala Ser Val Glu Asp Thr Val Asp Glu Ser Leu
130                 135                 140

Val Tyr Val Thr Ser Pro Lys Val Gly Thr Phe Arg Arg Gly Lys Tyr
145                 150                 155                 160

Ala Gly Gly Lys Arg Val Gly Lys Gly Asn Cys Ala Asp Val Asn Ala
                165                 170                 175

Pro Val Lys Lys Gly Gln Thr Leu Gly Tyr Val Glu Gln Leu Gly Thr
            180                 185                 190

Phe Val Glu Val Lys Ala Pro Ile Ala Gly Glu Leu Val Lys Val His
        195                 200                 205

Leu Glu Asp Gly Ala Pro Val Glu Tyr Gln Gln Leu Ile Phe Glu Val
    210                 215                 220

Ala Pro Phe Phe Gly Gly His Ile Ile Gly Asp Ser Lys Tyr Ala
225                 230                 235

<210> SEQ ID NO 30
<211> LENGTH: 298
<212> TYPE: PRT
<213> ORGANISM: Glycine max

<400> SEQUENCE: 30

Met Leu Phe Thr Phe Phe Thr Ser Leu Pro Thr Leu Leu Cys Asp
1               5                   10                  15

Thr His Ser Phe Cys Phe Thr Phe Ser Met Ala Ser Cys Ser Ile Gly
            20                  25                  30

Thr Pro Asn Ile Lys Val Leu Asn Leu His Phe Gly Gly Lys Lys Val
        35                  40                  45

```
Gly Leu Ser Arg Gln Phe Gly Thr Arg Ser Trp Ile Ser Arg Leu Gln
         50                  55                  60

Tyr Thr Ser Leu Val Met Ser Arg Gln Thr Val Arg Phe Leu Ala Ser
 65                  70                  75                  80

Ser Asn Gly Pro Ser Thr Glu Ile Gln Phe Ala Ala Arg Ser Glu Gly
                 85                  90                  95

Ser Glu Glu Ile Arg Ser Ser Gly Leu Thr Ser Glu Leu Ile Pro Asn
            100                 105                 110

Ile Asn Glu Val Glu Phe Leu Leu Thr Lys Leu Cys Asp Thr Ser Ser
            115                 120                 125

Ile Gly Glu Leu Asp Leu Lys Leu Ala Gly Phe His Leu His Val Val
        130                 135                 140

Arg Asp Leu Thr Glu Lys Thr Lys Thr Leu Pro Pro Leu Ile Pro Ala
145                 150                 155                 160

Ser Val Ser Ile Ile Asn Val Thr Glu Thr Pro Lys Thr Asn Gly Ser
                165                 170                 175

Val Pro Thr Thr Ser Leu Ala Val Ser Lys Pro Val Asp Pro Val Pro
            180                 185                 190

Ser Ser Gly Ser Ile Gln Arg Phe Leu Asp Lys Ala Ala Asp Glu Gly
        195                 200                 205

Leu Val Ile Ile Gln Ser Pro Lys Val Gly Phe Phe Arg Arg Ser Arg
210                 215                 220

Thr Ile Lys Gly Lys Arg Ala Pro Pro Ser Cys Lys Glu Lys Gln Asn
225                 230                 235                 240

Val Glu Glu Gly Gln Val Ile Cys Tyr Ile Glu Gln Leu Gly Gly Glu
                245                 250                 255

Leu Pro Ile Glu Ser Asp Val Ser Gly Glu Val Ile Lys Ile Leu Arg
            260                 265                 270

Gln Asp Gly Asp Pro Val Gly Tyr Gly Asp Ala Leu Val Ala Ile Leu
        275                 280                 285

Pro Ser Phe Pro Gly Ile Lys Lys Leu Gln
        290                 295

<210> SEQ ID NO 31
<211> LENGTH: 269
<212> TYPE: PRT
<213> ORGANISM: Glycine max

<400> SEQUENCE: 31

Met Ala Ser Cys Ser Ile Gly Thr Pro Asn Ile Lys Ala Leu Asn Leu
 1               5                  10                  15

His Phe Gly Gly Lys Lys Val Gly Leu Ser Gln Gln Phe Gly Thr Arg
             20                  25                  30

Ser Trp Ile Ser Lys Gln Ser Leu Gln Tyr Thr Ser Leu Val Met Ser
         35                  40                  45

Arg Gln Lys Val Arg Phe Ser Pro Thr Glu Ile Gln Phe Val Thr Arg
 50                  55                  60

Ser Glu Gly Ser Glu Glu Val Lys Ser Ser Gly Leu Thr Ser Glu Leu
 65                  70                  75                  80

Ile Pro Asn Leu Ile Glu Val Glu Phe Leu Leu Thr Lys Leu Cys Asp
                 85                  90                  95

Thr Ser Ser Ile Gly Glu Leu Asp Leu Lys Leu Ala Gly Phe His Leu
            100                 105                 110

His Val Val Arg Asp Leu Thr Glu Lys Thr Lys Thr Leu Pro Pro Pro
```

```
                115                 120                 125
Ile Pro Ala Ser Glu Ser Ile Ile Asn Val Thr Glu Thr Pro Lys Thr
130                 135                 140

Asn Gly Ser Val Ser Thr Thr Ser Leu Ala Val Ser Lys Pro Val Asp
145                 150                 155                 160

Pro Ile Pro Ser Ser Gly Ser Ile Gln Arg Phe Leu Asn Lys Ala Ala
                165                 170                 175

Asp Glu Gly Leu Val Ile Ile Gln Ser Pro Lys Val Gly Phe Phe Arg
                180                 185                 190

Arg Ser Arg Thr Ile Lys Gly Arg Arg Ala Pro Pro Ser Cys Lys Glu
                195                 200                 205

Lys Gln Asn Val Glu Glu Gly Gln Val Ile Cys Tyr Ile Glu Gln Leu
                210                 215                 220

Gly Gly Glu Leu Pro Ile Glu Ser Asp Val Ser Gly Glu Val Ile Lys
225                 230                 235                 240

Ile Leu Gln Lys Asp Gly Asp Pro Val Gly Tyr Gly Asp Ala Leu Val
                245                 250                 255

Ala Ile Leu Pro Ser Phe Pro Gly Ile Lys Lys Leu Gln
                260                 265

<210> SEQ ID NO 32
<211> LENGTH: 278
<212> TYPE: PRT
<213> ORGANISM: Glycine max

<400> SEQUENCE: 32

Met Gly Thr Met Ser His Val Arg Ala Cys Leu Glu Lys Gln Ala Val
1               5                   10                  15

Leu Pro Ile His Asn Ala Arg Trp Asn Ser Lys Arg Arg Leu Phe Ile
                20                  25                  30

Gln His Leu Ala Tyr Gly Gln Lys His Ile Asn Ser His Met Lys Gly
                35                  40                  45

Lys Ser Thr Leu Val Ser Ser Ala Lys Thr Ala Glu Ala Ile Asn Thr
            50                  55                  60

Ser Asn Ser Asp Ala Ser Ser Asp Asn Thr Pro Gln Gly Ser Leu Glu
65                  70                  75                  80

Lys Lys Pro Leu Gln Thr Ala Thr Phe Pro Asn Gly Phe Glu Ala Leu
                85                  90                  95

Val Leu Glu Val Cys Asp Glu Thr Glu Ile Ala Glu Leu Lys Val Lys
                100                 105                 110

Val Gly Asp Phe Glu Met His Ile Lys Arg Asn Ile Gly Ala Thr Lys
                115                 120                 125

Val Pro Leu Ser Asn Ile Ser Pro Thr Thr Pro Pro Ile Pro Ser
130                 135                 140

Lys Pro Met Asp Glu Ser Ala Pro Asn Ser Leu Pro Pro Ser Pro Pro
145                 150                 155                 160

Lys Ser Ser Pro Glu Lys Asn Asn Pro Phe Ala Asn Val Ser Lys Glu
                165                 170                 175

Lys Ser Pro Lys Leu Ala Ala Leu Glu Ala Ser Gly Thr Asn Thr Tyr
                180                 185                 190

Val Leu Val Thr Ser Pro Thr Val Gly Leu Phe Arg Arg Gly Arg Thr
                195                 200                 205

Val Lys Gly Lys Lys Gln Pro Pro Ile Cys Lys Glu Gly Asp Val Ile
210                 215                 220
```

```
Lys Glu Gly Gln Val Ile Gly Tyr Leu Asp Gln Phe Gly Thr Gly Leu
225                 230                 235                 240

Pro Ile Arg Ser Asp Val Ala Gly Glu Val Leu Lys Leu Leu Val Glu
            245                 250                 255

Asp Gly Glu Pro Val Gly Tyr Gly Asp Arg Leu Ile Ala Val Leu Pro
        260                 265                 270

Ser Phe His Asp Ile Lys
            275

<210> SEQ ID NO 33
<211> LENGTH: 284
<212> TYPE: PRT
<213> ORGANISM: Medicago truncatula

<400> SEQUENCE: 33

Met Val Ile Trp Val Ile Lys His Ile Thr Gly Ser Leu Gly Thr Gln
1               5                   10                  15

Asn Val Lys Val Leu Asn Leu His Phe Gly Gln Glu Arg Ala Glu Phe
            20                  25                  30

Ser Gln His Phe Gly Thr Arg Ser Trp Ile Ser Arg Lys Ser Leu Gln
        35                  40                  45

Tyr Ala Arg Leu Val Ala Ser Lys Gln Thr Val Arg Ser Leu Thr Pro
    50                  55                  60

Ser Asn Asp Gln Ser Ala Glu Ile Gln Ser Val Ser Arg Ser Glu Asp
65                  70                  75                  80

Gly Ser Glu Glu Ser Lys Ser Ser Gly Leu Thr Asn Gln Leu Phe Pro
                85                  90                  95

Asn Phe Asn Asp Val Ser Val Glu Phe Leu Leu Thr Asn Leu Cys Asp
            100                 105                 110

Thr Ala Ser Ile Gly Glu Leu Glu Leu Lys Leu Asp Gly Phe His Leu
        115                 120                 125

Arg Val Val Arg Asp Leu Thr Glu Lys Ser Lys Thr Leu Pro Pro Ser
    130                 135                 140

Ile Pro Ala Pro Val Ser Ile Asn Thr Pro Ala Glu Ala Pro Lys Pro
145                 150                 155                 160

Asn Gly Ser Val Ser Thr Leu Thr Thr Leu Ala Ile Ser Lys Pro Ala
                165                 170                 175

Pro Ser Ser Leu Ser Ile Glu Gly Phe Leu Glu Lys Ala Ala Asp Glu
            180                 185                 190

Gly Leu Val Ile Ile His Ser Pro Thr Val Gly Ile Phe Arg Arg Ser
        195                 200                 205

Arg Thr Ile Lys Gly Lys Arg Ala Pro Pro Ser Cys Gln Glu Met Gln
    210                 215                 220

Asn Val Glu Glu Gly Lys Val Ile Cys Tyr Ile Glu Gln Leu Gly Gly
225                 230                 235                 240

Gln Leu Pro Val Glu Ser Asp Val Ser Gly Glu Val Ile Lys Ile Leu
                245                 250                 255

Arg Glu Asp Gly Asp Pro Val Gly Tyr Gly Asp Thr Leu Ile Ala Ile
            260                 265                 270

Leu Pro Ser Phe Pro Gly Ile Lys Lys Leu Gln Tyr
        275                 280

<210> SEQ ID NO 34
<211> LENGTH: 274
<212> TYPE: PRT
<213> ORGANISM: Medicago truncatula
```

<400> SEQUENCE: 34

Met Asp Ser Ser Ala Ala Ile Arg Ser Phe His Tyr Pro Ile Gly Thr
1               5                   10                  15

Ile Ser His Val Arg Ser Ile Glu Arg Ala Ala Val Val Pro Cys
            20                  25                  30

His Lys Ile Arg Trp Asn Ser Asn Arg Gly Lys Lys Ala Leu Val Ser
        35                  40                  45

Cys Ala Lys Ala Val Glu Ala Ile Asn Thr Thr Lys Ser Asp Ala Ser
    50                  55                  60

Leu Asp Ser Thr Gln Gln Asp Lys Leu Glu Lys Lys Pro Leu Gln Thr
65                  70                  75                  80

Ala Thr Phe Pro Asp Gly Phe Glu Ala Leu Ile Leu Asp Val Cys Asp
                85                  90                  95

Glu Thr Glu Ile Ala Glu Leu Lys Leu Lys Val Gly Glu Phe Glu Met
                100                 105                 110

His Leu Lys Arg Asn Ile Gly Ala Thr Lys Ala Pro Leu Ser Asn Ile
            115                 120                 125

Ser Pro Thr Thr Pro Pro Ile Pro Ser Lys Pro Met Asp Glu Ser
130                 135                 140

Ala Pro Thr Thr Ala Gln Pro Leu Pro Pro Thr Ser Ser Ser Glu Lys
145                 150                 155                 160

Thr Asn Pro Phe Ala Asn Val Ser Ser Gln Lys Ser Ser Lys Leu Ile
                165                 170                 175

Ala Leu Glu Ala Ser Gly Thr Ser Thr Tyr Ala Leu Val Ser Ser Pro
            180                 185                 190

Thr Val Gly Ser Phe Arg Arg Gly Arg Thr Val Lys Gly Gln Lys His
            195                 200                 205

Pro Pro Ile Cys Lys Glu Gly Asp Val Ile Arg Glu Gly Gln Val Ile
210                 215                 220

Gly Tyr Leu Asp Gln Phe Gly Val Gly Ala Gly Ile Pro Ile Lys Ser
225                 230                 235                 240

Asp Val Ala Gly Glu Val Leu Lys Leu Leu Glu Glu Gly Asp Pro
            245                 250                 255

Val Gly Phe Gly Asp Pro Ile Leu Ala Val Leu Pro Ser Phe His Asp
                260                 265                 270

Ile Lys

<210> SEQ ID NO 35
<211> LENGTH: 288
<212> TYPE: PRT
<213> ORGANISM: Vitis vinifera

<400> SEQUENCE: 35

Met Glu Ser Val Ala Val Leu Arg Ser Val His Tyr Ser Val Gly Ala
1               5                   10                  15

Ile Ser Asn Val Arg Ser Phe Ile Glu Arg Pro Thr Met Val Pro Met
            20                  25                  30

Tyr Asn Ala Thr Trp Pro Thr Ser Asn Thr Leu His Val Gln Gly Leu
        35                  40                  45

Thr Val Gly Gly Lys Leu Ile Ser Ser Pro Ile Lys Gln Lys Gly Thr
    50                  55                  60

Leu Ile Ser Cys Val Lys Thr Pro Glu Thr Ala Gly Thr Ala Lys Cys
65                  70                  75                  80

-continued

Asp Asp Gly Asn Pro Gln Gly Leu Leu Gln Lys Asp Thr Leu Pro Ser
            85                  90                  95

Ala Thr Phe Pro Asn Gly Phe Glu Ala Leu Ile Leu Glu Val Cys Asp
            100                 105                 110

Glu Thr Asp Val Ala Glu Leu Lys Leu Lys Val Gly Asp Phe Glu Met
            115                 120                 125

His Leu Arg Arg Asn Val Gly Val Thr Asn Pro Pro Met Pro Val Ile
            130                 135                 140

Ala Pro Thr Ala Pro Pro Thr Val Ser Ala Lys Pro Pro Val Glu Ser
145                 150                 155                 160

Ala Pro Ala Ala Pro Pro Ser Leu Pro Pro Lys Pro Ser Gln Glu Lys
            165                 170                 175

Ile Ser Pro Phe Thr Lys Ser Leu Leu Glu Lys Pro Ser Lys Leu Arg
            180                 185                 190

Ala Leu Glu Ala Ser Gly Ala Asn Ala Tyr Val Leu Val Ser Ser Pro
            195                 200                 205

Thr Val Gly Ser Phe Arg Thr Gly Arg Thr Leu Lys Gly Lys Arg Gln
            210                 215                 220

Pro Pro Val Cys Lys Glu Gly Asp Val Ile Lys Glu Gly Gln Val Ile
225                 230                 235                 240

Gly Tyr Leu Asp Gln Phe Gly Ser Glu Leu Pro Val Lys Ser Asp Thr
            245                 250                 255

Ala Gly Glu Val Leu Lys Val Ile Phe Asn Asp Gly Glu Ala Val Gly
            260                 265                 270

Tyr Gly Asp Pro Leu Val Ala Val Leu Pro Ser Phe His Gly Ile Glu
            275                 280                 285

<210> SEQ ID NO 36
<211> LENGTH: 291
<212> TYPE: PRT
<213> ORGANISM: Glycine max

<400> SEQUENCE: 36

Met Glu Ser Ser Pro Ala Ile Arg Ser Phe His Tyr Pro Met Gly Thr
1               5                   10                  15

Met Ser His Val Arg Ala Cys Leu Glu Lys Gln Ala Val Leu Pro Ile
            20                  25                  30

His Asn Ala Arg Trp Asn Ser Lys Arg Arg Leu Phe Ile Gln His Leu
            35                  40                  45

Ala Tyr Gly Gln Lys His Ile Asn Ser His Met Lys Gly Lys Ser Thr
        50                  55                  60

Leu Val Ser Ser Ala Lys Thr Ala Glu Ala Ile Asn Thr Ser Asn Ser
65              70                  75                  80

Asp Ala Ser Ser Asp Asn Thr Pro Gln Gly Ser Leu Glu Lys Lys Pro
            85                  90                  95

Leu Gln Thr Ala Thr Phe Pro Asn Gly Phe Glu Ala Leu Val Leu Glu
            100                 105                 110

Val Cys Asp Glu Thr Glu Ile Ala Glu Leu Lys Val Lys Val Gly Asp
            115                 120                 125

Phe Glu Met His Ile Lys Arg Asn Ile Gly Ala Thr Lys Val Pro Leu
            130                 135                 140

Ser Asn Ile Ser Pro Thr Thr Pro Pro Ile Pro Ser Lys Pro Met
145                 150                 155                 160

Asp Glu Ser Ala Pro Asn Ser Leu Pro Pro Ser Pro Lys Ser Ser
            165                 170                 175

```
Pro Glu Lys Asn Asn Pro Phe Ala Asn Val Ser Lys Glu Lys Ser Pro
            180                 185                 190

Lys Leu Ala Ala Leu Glu Ala Ser Gly Thr Asn Thr Tyr Val Leu Val
        195                 200                 205

Thr Ser Pro Thr Val Gly Leu Phe Arg Arg Gly Arg Thr Val Lys Gly
    210                 215                 220

Lys Lys Gln Pro Pro Ile Cys Lys Glu Gly Asp Val Ile Lys Glu Gly
225                 230                 235                 240

Gln Val Ile Gly Tyr Leu Asp Gln Phe Gly Thr Gly Leu Pro Ile Arg
                245                 250                 255

Ser Asp Val Ala Gly Glu Val Leu Lys Leu Leu Val Glu Asp Gly Glu
                260                 265                 270

Pro Val Gly Tyr Gly Asp Arg Leu Ile Ala Val Leu Pro Ser Phe His
            275                 280                 285

Asp Ile Lys
        290

<210> SEQ ID NO 37
<211> LENGTH: 279
<212> TYPE: PRT
<213> ORGANISM: Medicago truncatula

<400> SEQUENCE: 37

Met Asp Ser Ser Ala Ala Ile Arg Ser Arg Ser His Cys Phe Met His
1               5                   10                  15

Met Gln Ser Ser Leu Gln Lys Pro Gly Leu Ile His Val Gln Asn Val
            20                  25                  30

Gly Cys Asn Phe Gln Ser Arg Ser Phe Val Gln Asn Leu Ala Ile Ser
        35                  40                  45

Asp Lys His Ile Val Ser His Asn Lys Trp Asn Arg Val Leu Val Ser
    50                  55                  60

Cys Thr Lys Thr Ala Lys Glu Ile Asp Ala Ala Lys Ser Glu Thr Ser
65                  70                  75                  80

Leu Glu Ser Ile Ala Lys Glu Ser Leu Val Lys Lys Pro Leu Gln Thr
                85                  90                  95

Phe Pro Asn Gly Phe Glu Ala Leu Ile Ser Glu Val Cys Asp Glu Thr
            100                 105                 110

Glu Ile Ala Glu Leu Lys Leu Lys Val Gly Glu Phe Glu Met His Met
        115                 120                 125

Lys Arg Asn Ile Gly Leu Ser Ala Ala Pro Val Ser Asn Ile Ser Pro
    130                 135                 140

Thr Lys Pro Met Val Asp Ser Ala Ser Ser Thr Pro Thr Pro Ser Pro
145                 150                 155                 160

Ser Lys Ser Ser Pro Ala Lys Thr Asn Pro Phe Val Asn Asp Ser Asn
                165                 170                 175

Asp Lys Ser Pro Lys Leu Ala Ala Leu Glu Ala Ser Gly Asn Lys Asn
            180                 185                 190

Tyr Val Leu Val Ala Ser Thr Thr Val Gly Ser Phe Gln Arg Gly Arg
        195                 200                 205

Thr Val Lys Gly Asn Lys Leu Pro Pro Val Cys Lys Glu Gly Asp Met
    210                 215                 220

Ile Lys Asp Gly Gln Val Ile Gly Tyr Val Asp Asn Phe Gly Thr Ser
225                 230                 235                 240

Leu Pro Val Lys Ser Asp Val Asp Gly Glu Val Leu Lys Leu Leu Phe
```

```
                        245                 250                 255
Gln Asp Gly Glu Ala Val Gly Tyr Gly Asp Ala Leu Ile Ala Val Leu
            260                 265                 270

Pro Ser Phe His Asp Ile Lys
        275
```

<210> SEQ ID NO 38
<211> LENGTH: 288
<212> TYPE: PRT
<213> ORGANISM: Lotus japonicus

<400> SEQUENCE: 38

```
Met Glu Ser Ser Ala Ala Ile Arg Ser Phe His Cys Thr Val Pro His
1               5                   10                  15

Val Arg Ser Ser Phe Glu Lys Val Ala Val Pro Cys His Asn Ala
            20                  25                  30

Arg Trp Asn Ser Lys Ser Gly Leu Phe Ile Gln Arg Leu Ala Asn Asp
            35                  40                  45

Arg Met Leu Ile Asn Ser Gln Ala Lys Gly Arg Lys Thr Leu Val Ser
        50                  55                  60

Cys Ala Lys Ala Val Glu Ala Ile Asn Thr Ala Lys Ser Asp Ala Ser
65                  70                  75                  80

Leu Asp Ser Thr Ser Gln Asp Ser Val Glu Lys Lys Ala Leu Gln Ser
                85                  90                  95

Ala Thr Phe Pro Asn Gly Leu Glu Ala Leu Val Leu Glu Val Cys Asp
            100                 105                 110

Glu Thr Glu Ile Ala Glu Leu Lys Val Lys Val Gly Glu Phe Glu Met
        115                 120                 125

His Leu Lys Arg Asn Ile Gly Ala Thr Lys Ala Pro Leu Ser Asn Ile
130                 135                 140

Ser Pro Thr Thr Pro Pro Ile Pro Ser Lys Pro Met Asp Glu Ser
145                 150                 155                 160

Ala Pro Ser Thr Pro Gln Ser Leu Pro Pro Lys Ser Ser Pro Glu Lys
                165                 170                 175

Thr Asn Pro Phe Val Asn Ala Ser Val Gln Lys Ser Ser Lys Leu Ala
            180                 185                 190

Gln Leu Glu Ala Ser Gly Thr Asn Asn Tyr Val Ile Ile Ser Ser Pro
        195                 200                 205

Thr Val Gly Leu Phe Arg Arg Gly Arg Thr Val Lys Gly Lys Arg Gln
210                 215                 220

Pro Pro Thr Tyr Lys Glu Gly Asp Leu Ile Lys Glu Gly Gln Val Ile
225                 230                 235                 240

Gly Tyr Leu Asp Gln Phe Gly Thr Gly Leu Pro Val Lys Ser Asp Val
                245                 250                 255

Ala Gly Glu Val Leu Lys Leu Val Glu Asp Gly Glu Pro Val Gly
            260                 265                 270

Tyr Gly Asp Asn Leu Ile Ala Val Leu Pro Ser Phe His Asp Ile Lys
        275                 280                 285
```

<210> SEQ ID NO 39
<211> LENGTH: 267
<212> TYPE: PRT
<213> ORGANISM: Lotus japonicus

<400> SEQUENCE: 39

Met Ala Ser Cys Asn Val Lys Ala Leu Asn Leu Cys Phe Gly Gly Lys

```
            1               5                  10                 15
        Arg Val Ser Leu Ser Gln Gln Phe Gly Thr Arg Asn Trp Ile Ile Arg
                        20                 25                 30

Lys Ser Val Gln Tyr Thr Ser Leu Asp Met Ser Gln His Arg Val Gly
                        35                 40                 45

Phe Leu Lys Ser Ser Asn Gly Pro Leu Ser Gln Ile Gln Pro Val Thr
                        50                 55                 60

Ser Ser Glu Asn Gly Ser Lys Glu Ile Glu Ser Ser Gly Leu Thr Ser
        65                  70                 75                  80

Thr Leu Ile Pro Lys Leu Asn Glu Val Glu Phe Leu Leu Thr Lys Leu
                        85                 90                 95

Cys Glu Thr Ser Ile Gly Glu Leu Glu Leu Lys Leu Ala Gly Phe His
                        100                105                110

Leu His Val Leu Arg Asp Ser Thr Glu Lys Val Lys Thr Leu Pro Arg
                        115                120                125

Gln Thr Pro Ala Ser Val Asn Ile Asn Val Val Pro Glu Ala Pro Lys
                        130                135                140

Ser Asn Gly Pro Val Ala Ser Ser Leu Ala Ile Leu Lys Pro Glu
        145                 150                155                160

Pro Ser Ser Gly Ser Val Gln Arg Phe Leu Asp Lys Ala Ala Asp Glu
                        165                170                175

Gly Phe Val Ile Ile Tyr Ser Pro Lys Val Gly Phe Phe Arg Arg Ser
                        180                185                190

Arg Thr Ile Lys Gly Lys Arg Ala Pro Pro Ser Cys Lys Glu Thr Gln
                        195                200                205

Lys Val Gln Glu Gly Gln Val Ile Cys Tyr Ile Glu Gln Leu Gly Gly
                        210                215                220

Gln Leu Pro Ile Glu Ser Asp Val Ser Gly Glu Val Ile Arg Ile Leu
        225                 230                235                240

Arg Glu Asp Gly Asp Pro Val Gly Tyr Gly Asp Ala Leu Ile Ala Ile
                        245                250                255

Leu Pro Ser Phe Pro Gly Ile Lys Lys Leu Gln
                        260                265

<210> SEQ ID NO 40
<211> LENGTH: 277
<212> TYPE: PRT
<213> ORGANISM: Medicago truncatula

<400> SEQUENCE: 40

Met Ala Ser Ser His Cys Ser Leu Gly Thr Gln Asn Val Lys Val Leu
        1                   5                  10                 15

Asn Leu His Phe Gly Gln Glu Arg Ala Glu Phe Ser Gln His Phe Gly
                        20                 25                 30

Thr Arg Ser Trp Ile Ser Arg Lys Ser Leu Gln Tyr Ala Arg Leu Val
                        35                 40                 45

Ala Ser Lys Gln Thr Val Arg Ser Leu Thr Pro Ser Asn Asp Gln Ser
                        50                 55                 60

Ala Glu Ile Gln Ser Val Ser Arg Ser Glu Asp Gly Ser Glu Glu Ser
        65                  70                 75                  80

Lys Ser Ser Gly Leu Thr Asn Gln Leu Phe Pro Asn Phe Asn Asp Val
                        85                 90                 95

Glu Phe Leu Leu Thr Asn Leu Cys Asp Thr Ala Ser Ile Gly Glu Leu
                        100                105                110
```

Glu Leu Lys Leu Asp Gly Phe His Leu Arg Val Val Arg Asp Leu Thr
            115                 120                 125

Glu Lys Ser Lys Thr Leu Pro Pro Ser Ile Ser Ala Pro Val Ser Ile
130                 135                 140

Asn Thr Pro Ala Glu Ala Pro Lys Pro Asn Gly Ser Val Ser Thr Leu
145                 150                 155                 160

Thr Thr Leu Ala Ile Ser Lys Pro Ala Pro Ser Ser Leu Ser Phe Glu
                165                 170                 175

Gly Phe Leu Glu Lys Ala Ala Asp Glu Gly Leu Val Ile Ile His Ser
            180                 185                 190

Pro Thr Val Gly Ile Phe Arg Arg Ser Arg Thr Ile Lys Gly Lys Arg
            195                 200                 205

Ala Pro Pro Ser Cys Gln Glu Met Gln Asn Val Glu Glu Gly Lys Val
210                 215                 220

Ile Cys Tyr Ile Glu Gln Leu Gly Gly Gln Leu Pro Val Glu Ser Asp
225                 230                 235                 240

Val Ser Gly Glu Val Ile Lys Ile Leu Arg Glu Asp Gly Asp Pro Val
                245                 250                 255

Gly Tyr Gly Asp Thr Leu Ile Ala Ile Leu Pro Ser Phe Pro Gly Ile
            260                 265                 270

Lys Lys Leu Gln Tyr
        275

<210> SEQ ID NO 41
<211> LENGTH: 277
<212> TYPE: PRT
<213> ORGANISM: Cucumis sativus

<400> SEQUENCE: 41

Met Ala Phe Cys Ser Leu Arg Ala Ala Asp Ile Lys Phe Ser Lys Leu
1               5                   10                  15

Asp Ile Arg Arg Gly Arg Val Ser Thr Leu Gln Pro Cys Ser Leu Arg
            20                  25                  30

Asn Trp Ile Gly Arg Thr Pro His Gln Tyr Ser Ser Leu Val Ile Ser
        35                  40                  45

His Ser Ser Gln Lys Ala Leu His Ala Cys Ser Gly Ala Ser Pro Lys
    50                  55                  60

Ala Gln Thr Val Ile Lys Ser Glu Thr Gly Ser Glu Glu Ile Lys Pro
65                  70                  75                  80

Ser Ser Leu Gly Ser Gln Leu Ile Pro Asn Phe His Glu Val Glu Thr
                85                  90                  95

Leu Leu Thr Asn Val Cys Asp Thr Ser Ser Ile Ala Glu Phe Glu Leu
            100                 105                 110

Lys Leu Ser Gly Phe Asn Leu Arg Met Val Arg Ser Leu Lys Ser Lys
            115                 120                 125

Asn Leu Pro Leu Pro Pro Val Pro Ala Pro Ala Pro Asp Ile Gln Asn
        130                 135                 140

Thr Ser Ser Ile Pro Ser Asp Ser Asn Gly Leu Val Lys Thr Thr Ser
145                 150                 155                 160

Leu Ala Leu Val Lys Pro Glu Pro Val Ser Ser Pro Arg Gly Ile
                165                 170                 175

Ser Arg Tyr Val Glu Lys Ala Arg Asp Gly Val Thr Ile Leu Ser
            180                 185                 190

Ser Pro Asn Val Gly Val Phe Arg Arg Ser Arg Thr Ile Lys Gly Lys
        195                 200                 205

```
Arg Ala Pro Pro Ser Cys Ala Glu Asp Gln Val Val Arg Glu Gly Gln
            210                 215                 220

Val Leu Cys Tyr Ile Glu Gln Leu Gly Gly Gln Ile Pro Val Lys Ser
225                 230                 235                 240

Asp Thr Pro Gly Glu Ile Leu Lys Ile Leu Arg Lys Asp Gly Glu Pro
                245                 250                 255

Val Gly Tyr Gly Asp Ala Leu Ile Ala Val Leu Pro Ser Phe Pro Gly
            260                 265                 270

Ile Lys Lys Leu Arg
            275

<210> SEQ ID NO 42
<211> LENGTH: 271
<212> TYPE: PRT
<213> ORGANISM: Cucumis sativus

<400> SEQUENCE: 42

Met Glu Ser Ser Ala Ser Leu Arg Ser Phe His Tyr Phe Ala Gly Gly
1               5                   10                  15

Ser Arg Leu Gln Leu Ile Glu Lys Pro Ser Arg Ile Tyr Val Ser Ser
            20                  25                  30

Thr Asn Lys Thr Ser Ile Gln Arg Leu Ser Ile Phe Gly Lys Pro Ile
        35                  40                  45

His Asn Pro Thr Ser Gln Lys Lys Ile Ala Val Ser Cys Thr Lys Thr
    50                  55                  60

Pro Glu Val Thr Glu Thr Gly Lys Asp Ser Ala Lys Gly Ser Leu Gln
65                  70                  75                  80

Lys Lys Pro Ala Ser Asn Val Thr Phe Pro Asn Gly Phe Glu Glu Leu
                85                  90                  95

Leu Leu Glu Val Cys Asp Asp Thr Glu Ile Ala Glu Leu Lys Leu Lys
            100                 105                 110

Val Gly Glu Phe Glu Met His Val Lys Arg Asn Ile Gly Val Val Ser
        115                 120                 125

Ala Pro Leu Ser Ala Ile Ser Pro Thr Val Pro Pro Ile Pro Ser
    130                 135                 140

Lys Pro Met Val Glu Ser Ala Leu Ala Ala Pro Ala Pro Ile Pro
145                 150                 155                 160

Ser Pro Glu Lys Ala Asn Ala Phe Thr Asp Val Pro Phe Lys Lys Ser
                165                 170                 175

Ser Lys Leu Ala Ala Leu Glu Ala Ser Gly Ala Lys Gly Tyr Val Leu
            180                 185                 190

Val Gly Ser Phe Arg Ser Gly Arg Thr Val Lys Gly Arg Arg Met Pro
        195                 200                 205

Pro Ile Cys Lys Glu Asn Asp Leu Ile Arg Glu Gly Gln Val Val Ala
    210                 215                 220

Tyr Val Asp Gln Phe Gly Ser Gln Leu Pro Val Lys Ser Asp Val Ala
225                 230                 235                 240

Gly Glu Val Leu Arg Ile Leu Phe Lys Glu Asp Glu Pro Val Gly Phe
                245                 250                 255

Gly Asp Pro Leu Ile Ala Val Leu Pro Ile Phe His Gly Ile Arg
            260                 265                 270

<210> SEQ ID NO 43
<211> LENGTH: 276
<212> TYPE: PRT
```

<213> ORGANISM: Cucumis sativus

<400> SEQUENCE: 43

Met Glu Ser Ser Ala Ser Leu Arg Ser Phe His Tyr Phe Ala Gly Gly
1               5                   10                  15

Ser Arg Leu Gln Leu Asn Glu Lys Pro Ser Arg Ile Tyr Val Ser Ser
            20                  25                  30

Thr Asn Lys Thr Ser Ile Gln Arg Leu Ser Ile Phe Gly Lys Pro Ile
        35                  40                  45

His Asn Pro Thr Ser Gln Lys Lys Ile Val Val Ser Cys Thr Lys Thr
    50                  55                  60

Pro Glu Val Thr Glu Thr Ala Lys Asp Ser Ala Lys Gly Ser Leu Gln
65                  70                  75                  80

Lys Lys Pro Ala Ser Asn Val Thr Phe Pro Asn Gly Phe Glu Glu Leu
                85                  90                  95

Leu Leu Glu Val Cys Asp Asp Thr Glu Ile Ala Glu Leu Lys Leu Lys
            100                 105                 110

Val Gly Glu Phe Glu Met His Val Lys Arg Asn Ile Gly Val Val Ser
        115                 120                 125

Ala Pro Leu Ser Ala Ile Ser Pro Thr Val Pro Pro Ile Pro Ser
    130                 135                 140

Lys Pro Met Val Glu Ser Ala Leu Ala Ala Pro Ala Pro Ile Pro
145                 150                 155                 160

Ser Pro Glu Lys Ala Asn Ala Phe Thr Asp Val Pro Phe Lys Lys Ser
                165                 170                 175

Ser Lys Leu Ala Ala Leu Glu Ala Ser Gly Ala Lys Gly Tyr Val Leu
            180                 185                 190

Val Thr Ser Pro Thr Val Gly Ser Phe Arg Ser Gly Arg Thr Val Lys
        195                 200                 205

Gly Arg Arg Met Pro Pro Ile Cys Lys Glu Asn Asp Leu Ile Arg Glu
    210                 215                 220

Gly Gln Val Val Ala Tyr Val Asp Gln Phe Gly Ser Gln Leu Pro Val
225                 230                 235                 240

Lys Ser Asp Val Ala Gly Glu Val Leu Arg Ile Leu Phe Lys Glu Asp
                245                 250                 255

Glu Pro Val Gly Phe Gly Asp Pro Leu Ile Ala Val Leu Pro Ile Phe
            260                 265                 270

His Gly Ile Arg
        275

<210> SEQ ID NO 44
<211> LENGTH: 290
<212> TYPE: PRT
<213> ORGANISM: Solanum lycopersicum

<400> SEQUENCE: 44

Met Glu Ser Ala Ala Val Leu Arg Ser Phe His His Ser Val Gly Thr
1               5                   10                  15

Thr Ser His Val Arg Ser Val Ile Glu Met Pro Gly Val Ile Pro Thr
            20                  25                  30

Asn Asn Ile Ala Phe Ser Lys Pro Thr Lys Phe Ser Leu Lys Gly Ser
        35                  40                  45

Ser Asn Gly Ala Arg Arg Ile Ser Ser Pro Asn Lys His Gly Arg Leu
    50                  55                  60

Ile Leu Ser Cys Ala Lys Thr Ser Glu Thr Thr Val Thr Ala Lys Ser

```
                65                  70                  75                  80
Gly Asp Gly Asn His Lys Val Pro Thr Glu Ser Ser Pro Leu Pro Thr
                    85                  90                  95

Ala Thr Phe Pro Lys Gly Phe Glu Ala Leu Ile Thr Glu Val Cys Asp
                100                 105                 110

Asp Thr Glu Val Ala Glu Leu Lys Leu Lys Val Gly Asp Phe Glu Leu
            115                 120                 125

His Leu Lys Arg Asn Ile Glu Ala Pro Val Val Pro Ala Pro Val Val
        130                 135                 140

Ser Ala Pro Pro Pro Pro Pro Pro Ser Ala Ser Lys Pro Ser
145                 150                 155                 160

Ile Ser Ser Thr Ala Ala Pro Ala Ala Ser Pro Gly Lys Ser Thr Ser
                165                 170                 175

Gly Lys Ile Ser Pro Phe Thr Asn Val Ala Ala Glu Lys Ser Ala Lys
            180                 185                 190

Leu Ala Ala Leu Glu Ser Thr Gly Ala Ser Gly Tyr Val Leu Val Ser
        195                 200                 205

Cys Pro Thr Val Gly Ser Phe Arg Arg Ala Arg Thr Leu Lys Gly Lys
210                 215                 220

Lys Gln Pro Pro Ala Cys Lys Glu Gly Asp Ile Ile Lys Glu Gly Gln
225                 230                 235                 240

Ile Ile Gly Phe Leu Asp Gln Phe Gly Thr Glu Leu Pro Val Arg Ser
                245                 250                 255

Asp Ala Ala Gly Glu Val Leu Lys Ile Leu Phe Asn Asp Gly Glu Ala
            260                 265                 270

Val Gly Tyr Gly Asp Pro Leu Ile Ala Val Leu Pro Ser Phe His Gly
        275                 280                 285

Ile Asn
    290

<210> SEQ ID NO 45
<211> LENGTH: 288
<212> TYPE: PRT
<213> ORGANISM: Solanum lycopersicum

<400> SEQUENCE: 45

Met Glu Ser Ala Ala Val Leu Arg Ser Phe His His Ser Val Gly Thr
1               5                   10                  15

Thr Ser His Val Arg Ser Val Ile Glu Met Pro Gly Val Ile Pro Thr
                20                  25                  30

Asn Asn Ile Ala Phe Ser Lys Pro Thr Lys Phe Ser Leu Lys Gly Ser
            35                  40                  45

Ser Asn Gly Ala Arg Arg Ile Ser Ser Pro Asn Lys His Gly Arg Leu
        50                  55                  60

Ile Leu Ser Cys Ala Lys Thr Ser Glu Thr Thr Val Thr Ala Lys Ser
65                  70                  75                  80

Gly Asp Gly Asn His Lys Val Pro Thr Glu Ser Ser Pro Leu Pro Thr
                85                  90                  95

Ala Thr Phe Pro Lys Gly Phe Glu Ala Leu Ile Thr Glu Val Cys Asp
                100                 105                 110

Asp Thr Glu Val Ala Glu Leu Lys Leu Lys Val Gly Asp Phe Glu Leu
            115                 120                 125

His Leu Lys Arg Asn Ile Glu Ala Pro Val Val Pro Ala Pro Val Val
        130                 135                 140
```

Ser Ala Pro Pro Pro Pro Pro Pro Ser Ala Ser Lys Pro Ser
145                 150                 155                 160

Ile Ser Ser Thr Ala Ala Pro Ala Ala Ser Pro Gly Lys Ser Thr Ser
            165                 170                 175

Gly Lys Ile Ser Pro Phe Thr Asn Val Ala Ala Glu Lys Ser Ala Lys
            180                 185                 190

Leu Ala Ala Leu Glu Ser Thr Gly Ala Ser Gly Tyr Val Leu Val Ser
            195                 200                 205

Cys Pro Thr Val Gly Ser Phe Arg Arg Ala Arg Thr Leu Lys Gly Lys
            210                 215                 220

Lys Gln Pro Pro Ala Cys Lys Glu Gly Asp Ile Ile Lys Glu Gly Gln
225                 230                 235                 240

Ile Ile Gly Phe Leu Asp Gln Phe Gly Thr Glu Leu Pro Val Arg Ser
            245                 250                 255

Asp Ala Ala Gly Glu Val Leu Lys Ile Leu Phe Asn Asp Gly Glu Ala
            260                 265                 270

Val Gly Tyr Gly Asp Pro Leu Ile Ala Val Leu Pro Ser Phe His Gly
            275                 280                 285

<210> SEQ ID NO 46
<211> LENGTH: 274
<212> TYPE: PRT
<213> ORGANISM: Solanum lycopersicum

<400> SEQUENCE: 46

Met Ala Ala Cys Gly Phe Gly Ala Ser Gly Leu Lys Leu Thr Ser Leu
1               5                   10                  15

Asn Leu Gly Ser Thr Lys Pro Lys Leu Ser Val Val His Asn Leu Arg
                20                  25                  30

Thr Lys Lys Phe Val Gln Ser Asp Gly Leu Leu Leu Thr Thr Lys Ser
            35                  40                  45

Arg Lys Thr Phe Asp Cys Arg Cys Ser Thr Val Glu Ala Glu Ser Val
        50                  55                  60

Ala Ala Thr Ala Ile Pro Asn Ser Asp Asp Ser Ser Ser Lys Ile Val
65                  70                  75                  80

Ser Ser Glu Thr Ala Ser Pro Leu Thr Pro Asn Ser Tyr Glu Val Glu
                85                  90                  95

Ser Leu Leu Thr Glu Ile Cys Asp Thr Thr Ser Ile Ala Glu Val Asp
            100                 105                 110

Leu Lys Leu Gly Gly Phe Arg Leu Tyr Val Lys Arg Asp Leu Thr Gly
            115                 120                 125

Gln Ser Thr Thr Ser Leu Pro Pro Ile Ser Ser Pro Val Ser Val Ser
        130                 135                 140

Ser Ser Val Glu Val Ala Asp Ser Asn Gly Ser Ala Ser Ser Thr Ser
145                 150                 155                 160

Leu Ala Ile Thr Lys Ser Ser Pro Pro Ser Asp Gly Ile Gln Thr Met
                165                 170                 175

Ile Glu Lys Ala Ala Asp Glu Gly Leu Val Ile Ile Gln Ser Pro Arg
            180                 185                 190

Val Gly Phe Phe Arg Arg Ser Arg Thr Ile Lys Gly Lys Arg Ala Pro
        195                 200                 205

Pro Ala Cys Lys Glu Lys Gln Gln Val Lys Glu Gly Gln Val Val Phe
    210                 215                 220

Tyr Ile Glu Gln Leu Gly Gly Glu Leu Pro Val Glu Ser Asp Val Ser
225                 230                 235                 240

```
Gly Glu Val Ile Arg Ile Leu Arg Lys Asp Gly Asp Pro Val Gly Tyr
                245                 250                 255

Gly Asp Pro Leu Ile Ser Ile Leu Pro Ser Phe Pro Gly Ile Lys Lys
            260                 265                 270

Leu Gln

<210> SEQ ID NO 47
<211> LENGTH: 272
<212> TYPE: PRT
<213> ORGANISM: Fragaria vesca subsp. vesca

<400> SEQUENCE: 47

Met Ala Ser Cys Ser Leu Gly Thr Ser Tyr Pro Lys Ile Thr Asn Leu
1               5                   10                  15

Asn Leu Gly Arg Thr Arg Val Gly Ile Ser Gln Ser Tyr Gly Val Arg
            20                  25                  30

Thr Trp Thr Leu Gln Arg Pro Gln Leu Tyr Ser Gly Leu Ser Ile Ser
        35                  40                  45

Arg Arg Ser Glu Lys Val Ser His Val His Ser Ala Pro Ser Leu Glu
    50                  55                  60

Ile Ile Ser Ala Thr Ser Ser Asp Asp Gly Ser Lys Glu Ser Asp Ser
65                  70                  75                  80

Gly Ser Ala Ser Pro Arg Ile Pro Asn Phe Asp Glu Ile Gln Ser Leu
                85                  90                  95

Leu Thr Thr Ile Cys Asp Thr Thr Ser Val Ala Glu Val Gln Leu Lys
            100                 105                 110

Leu Gly Gly Phe Arg Leu His Val Val Arg Glu Leu Thr Glu Asn Val
        115                 120                 125

Ser Thr Pro Pro Pro Ser Ile Pro Ala Pro Val Ser Val Ser Thr Pro
    130                 135                 140

Ala Glu Val Pro Glu Ser Asn Gly Ser Val Pro Thr Gln Ser Leu Ala
145                 150                 155                 160

Ile Thr Arg Ala Glu Ser Ser Arg Asp Ile Gln Thr Leu Leu Asp
                165                 170                 175

Lys Ala Ala Asp Glu Gly Leu Val Leu Ile Gln Ser Pro Arg Val Gly
            180                 185                 190

Ser Phe Arg Arg Ser Arg Thr Ile Lys Gly Lys Arg Ala Pro Pro Ser
        195                 200                 205

Cys Lys Glu Lys Gln Ile Val Lys Glu Gly Gln Val Ile Cys Tyr Ile
    210                 215                 220

Glu Gln Leu Gly Gly Glu Leu Pro Ile Glu Ser Asp Val Ala Gly Glu
225                 230                 235                 240

Val Ile Lys Ile Leu Arg Glu Asp Gly Glu Pro Val Gly Tyr Gly Asp
                245                 250                 255

Ala Leu Val Ala Val Leu Pro Ser Phe Pro Gly Ile Lys Lys Leu Gln
            260                 265                 270

<210> SEQ ID NO 48
<211> LENGTH: 291
<212> TYPE: PRT
<213> ORGANISM: Fragaria vesca subsp. vesca

<400> SEQUENCE: 48

Met Glu Ser Ser Ala Val Leu Arg Ser Leu Asn Cys Ser Val Gly Thr
1               5                   10                  15
```

```
Val Ser Gln Ile Arg Ser Phe Ile Asp Lys Pro Gly Val Leu Pro Val
            20                  25                  30

Tyr Asn Ala Arg Arg Pro Thr Tyr Ser Arg Ser Tyr Phe Gln Gly Met
        35                  40                  45

Met Val Ser Glu Lys Phe Ile Tyr Ser Pro Gln Lys Arg Lys Gly Val
 50                  55                  60

Leu Ile Ser Cys Val Lys Thr Thr Glu Ala Ala Lys Thr Glu Asn Ser
 65                  70                  75                  80

Ser Val Leu Leu Asp Thr Lys Ser Glu Ser Thr Ser Glu Gly Ser Pro
                85                  90                  95

Gln Ser Thr Val Phe Pro Ser Gly Tyr Glu Ala Leu Met Leu Glu Val
            100                 105                 110

Cys Asp Glu Thr Glu Ile Ala Glu Leu Lys Leu Lys Ile Gly Asp Phe
        115                 120                 125

Gln Met His Ile Lys Arg Asn Ile Gly Ala Thr Ser Ala Pro Val Ser
130                 135                 140

Asn Ile Ser Pro Thr Val Ala Pro Pro Ile Pro Ser Pro Pro Met Ala
145                 150                 155                 160

Ala Ser Ala Pro Ala Pro Pro Ala Ala Pro Lys Ser Ser Pro Ala
                165                 170                 175

Lys Ala Thr Pro Phe Asn Asn Gly Ser Val Ala Lys Ser Ser Lys Leu
            180                 185                 190

Ala Ala Leu Glu Ala Ser Gly Ser Asn Gly Tyr Val Leu Val Thr Ser
        195                 200                 205

Pro Thr Val Gly Ser Phe Arg Arg Gly Arg Thr Val Lys Gly Lys Lys
210                 215                 220

Gln Pro Pro Ile Phe Asn Glu Gly Asp Leu Ile Lys Glu Gly Gln Val
225                 230                 235                 240

Ile Gly Tyr Val Asp Gln Phe Gly Thr Glu Leu Pro Val Lys Thr Asp
                245                 250                 255

Val Gly Gly Glu Val Leu Lys Leu Leu Phe Asn Asp Gly Asp Ala Val
            260                 265                 270

Gly Tyr Gly Asp Ala Leu Ile Ala Val Leu Pro Ser Phe Arg Gly Ile
        275                 280                 285

Gly Val Leu
    290

<210> SEQ ID NO 49
<211> LENGTH: 276
<212> TYPE: PRT
<213> ORGANISM: Cicer arietinum

<400> SEQUENCE: 49

Met Ala Ser Ser Ser Cys Asn Leu Gly Thr Gln Asn Val Glu Val Leu
1               5                   10                  15

Asn Leu His Phe Gly Gln Lys Arg Ile Gly Leu Ser Gln Gln Phe Gly
            20                  25                  30

Thr Lys Asn Trp Ile Ser Arg Lys Ser Leu Gln Tyr Thr Ser Leu Val
        35                  40                  45

Thr Ser Gln Gln Arg Val Arg Ser Leu Thr Ser Thr Asn Gly Gln Leu
 50                  55                  60

Ala Glu Ile Gln Ser Val Ser Ser Glu Glu Asp Ser Glu Glu Ile
 65                  70                  75                  80

Lys Ser Ser Gly Leu Ala Ser Glu Leu Ile Pro Asn Phe Asn Glu Val
            85                  90                  95
```

```
Glu Phe Leu Leu Thr Asn Leu Cys Asp Thr Thr Ser Ile Ala Glu Leu
                100                 105                 110

Glu Leu Lys Leu Asp Gly Phe His Leu His Val Val Arg Asp Leu Thr
            115                 120                 125

Glu Lys Thr Thr Thr Leu Pro Pro Pro Ile Pro Thr Pro Ala Ser Thr
        130                 135                 140

Ser Ile Ala Ala Glu Ala Pro Lys Pro Asn Gly Leu Val Ser Thr Leu
145                 150                 155                 160

Ser Ser Leu Ala Ile Ser Lys Ser Gly Pro Ser Ser Val Ser Met Gln
                165                 170                 175

Gly Phe Leu Asp Lys Ala Ala Asp Glu Gly Leu Val Ile Ile Gln Ser
            180                 185                 190

Pro Lys Val Gly Phe Phe Arg Arg Ser Arg Thr Ile Lys Gly Lys Arg
        195                 200                 205

Ala Arg Pro Ser Cys Lys Glu Met Gln Lys Val Glu Glu Gly Gln Val
    210                 215                 220

Ile Cys Tyr Ile Glu Gln Leu Gly Gly Glu Leu Pro Ile Glu Cys Asp
225                 230                 235                 240

Val Ser Gly Glu Val Ile Lys Ile Leu Arg Lys Asp Gly Asp Pro Val
                245                 250                 255

Gly Tyr Gly Asp Ala Leu Val Ala Val Leu Pro Ser Phe Pro Gly Ile
            260                 265                 270

Lys Lys Leu Gln
        275

<210> SEQ ID NO 50
<211> LENGTH: 292
<212> TYPE: PRT
<213> ORGANISM: Cicer arietinum

<400> SEQUENCE: 50

Met Asp Ser Ser Leu Ala Ile Arg Ser Phe Gln Tyr Pro Ile Gly Thr
1               5                   10                  15

Met Pro Gln Val Arg Ser Pro Ile Glu Arg Ala Thr Val Ile Pro Cys
            20                  25                  30

His Lys Val Arg Trp Asn Ser Asn Ser Gly Ile Phe Gln His Leu Thr
        35                  40                  45

His Ser Glu Asn His Ile Tyr Phe His Thr Arg Gly Lys Lys Thr Leu
    50                  55                  60

Val Ser Cys Ala Lys Thr Val Glu Ala Ile Asn Thr Thr Lys Ser Asp
65                  70                  75                  80

Ala Ser Ser Asp Ser Thr Leu Gln Asn Ser Leu Glu Lys Glu Gln Leu
                85                  90                  95

Gln Ile Ala Ala Phe Pro Asn Gly Phe Glu Ala Leu Val Leu Glu Val
            100                 105                 110

Cys Asp Glu Thr Glu Ile Ala Glu Leu Lys Leu Lys Val Gly Glu Phe
        115                 120                 125

Glu Met His Leu Lys Arg Asn Ile Gly Ala Thr Lys Ala Pro Leu Ser
    130                 135                 140

Asn Ile Ser Pro Thr Ile Pro Pro Ile Pro Ser Lys Pro Met Asp
145                 150                 155                 160

Glu Ser Ala Pro Ala Thr Pro Gln Pro Leu Leu Pro Lys Ser Ser Ser
                165                 170                 175

Glu Lys Thr Asn Pro Phe Ala Asn Val Ser Ser Gln Lys Ser Ser Lys
```

```
              180                 185                 190
Leu Thr Ala Leu Glu Ala Ser Gly Ser Asn Thr Tyr Val Leu Val Ser
            195                 200                 205

Ser Pro Thr Val Gly Leu Phe Arg Arg Gly Arg Thr Val Lys Gly Lys
        210                 215                 220

Lys His Pro Pro Leu Cys Lys Glu Gly Asp Val Ile Lys Glu Gly Gln
225                 230                 235                 240

Val Ile Gly Tyr Leu Asp Gln Phe Ser Thr Ser Leu Pro Val Lys Ser
                245                 250                 255

Asp Val Ala Gly Glu Val Leu Lys Leu Leu Glu Asp Gly Glu Pro
            260                 265                 270

Val Gly Tyr Gly Asp Pro Leu Leu Ala Val Leu Pro Ser Phe His Asp
        275                 280                 285

Ile Asn Ile Met
        290

<210> SEQ ID NO 51
<211> LENGTH: 252
<212> TYPE: PRT
<213> ORGANISM: Genlisea aurea

<400> SEQUENCE: 51

Leu Glu Met Ala Ala Cys Gly Phe Gly Ala Ser Gly Leu Lys His Val
1               5                   10                  15

His Leu Asn Ser Ser Ile Ile Gly Pro Lys Leu Ser Ile Leu Ala Pro
            20                  25                  30

Phe His Gly Leu Lys Thr Pro Lys Thr Ile Arg Phe Gly Gly Met Val
        35                  40                  45

Leu Leu Arg Arg Glu Asn Asn Gly Thr Thr Asn Cys Arg Ser Leu Lys
    50                  55                  60

Ser Glu Asn Asp Ser Ser Ala Gln Leu Glu Asp Asp Ser Lys Gly Thr
65                  70                  75                  80

Val Ser Ser Asp Ala Val Arg Thr Leu Leu Pro Asn Ser Leu Glu Val
                85                  90                  95

Glu Ser Leu Leu Lys Thr Val Cys Asp Thr Thr Ser Ile Ala Glu Leu
            100                 105                 110

Glu Leu Lys Leu Gly Gly Phe Arg Leu His Val Arg Arg Ser Leu Thr
        115                 120                 125

Glu Gln Gly Leu Pro Leu Gln Leu Pro Ser Pro Ala Pro Val Val Ala
    130                 135                 140

His Ser Val Val Ala Ala Thr Pro Ala Asn Gly Ser Ala Ser Ser Thr
145                 150                 155                 160

Ser Leu Ala Ile Ala Asn Ala Gly Pro Ser Ser Asp Gly Ala Arg Ser
                165                 170                 175

Phe Leu Asp Lys Ala Ser Asp Glu Gly Leu Thr Ile Leu Gln Ser Pro
            180                 185                 190

Arg Val Gly Phe Phe Arg Arg Ser Arg Thr Ile Lys Gly Lys Arg Ala
        195                 200                 205

Pro Pro Ser Cys Lys Glu Lys Asp Thr Val Lys Glu Gly Gln Val Leu
    210                 215                 220

Cys Phe Ile Glu Gln Leu Gly Gly Glu Ile Pro Val Glu Ser Asp Thr
225                 230                 235                 240

Ser Gly Glu Val Val Lys Ile Leu Lys Asp Glu Gly
                245                 250
```

<210> SEQ ID NO 52
<211> LENGTH: 283
<212> TYPE: PRT
<213> ORGANISM: Coccomyxa subellipsoidea

<400> SEQUENCE: 52

Met Ala Ser Gln Cys Leu Thr Met Gln Ser Asn Ile Val Arg Pro Gln
1               5                   10                  15

Lys Leu Asn Ser Cys Gln Lys Arg Thr Gln Phe Ala Arg Ala Asn Val
            20                  25                  30

Ser Gln Val Phe Arg Ile Lys Gly Gly Ser Phe Gly Arg Arg Ala Gly
        35                  40                  45

Arg Cys Leu Gly Thr Thr Lys Thr Arg Ala Val Asn Phe Lys Glu Glu
    50                  55                  60

Thr Ala Val Gly Thr Ser Asp Glu Val Trp Val Asp Glu Glu Glu
65                  70                  75                  80

Glu Phe Asp Asp Gly Pro Asp Gly Gln Gly Leu Ser Thr Gln Gln
                85                  90                  95

Val Gln Ser Leu Leu His Val Leu Cys Asp Glu Thr Glu Val Ala Glu
            100                 105                 110

Leu Glu Leu Lys Met Gly Ser Phe Glu Leu Leu Val Arg Arg Ser Thr
        115                 120                 125

Lys Gly Asp Ile Ser Ser Ser Leu Asn Gly Ala Ala Ser Asn Gly
130                 135                 140

Ala Met Val Ala Pro Pro Ala Ser Ala Phe Ala Ser Thr Gln Ser
145                 150                 155                 160

Met Asp Ile Pro Ala Gly Asp Phe Pro Ala Ala Gln Ser Val Ser Val
                165                 170                 175

Ser Ser Ile Asp Glu Asp Ile Asp Asp Glu Ser Thr Ile Phe Leu Thr
            180                 185                 190

Ala Pro Lys Val Gly Ile Ile Arg Leu Gly Arg Tyr Val Lys Gly Lys
        195                 200                 205

Lys Val Gly Lys Gly Asn Ile Ile Asn Val Gly Asp Glu Val Lys Lys
    210                 215                 220

Gly Gln Thr Leu Gly Phe Ile Glu Gln Leu Gly Thr Tyr Val Pro Met
225                 230                 235                 240

Glu Ala Pro Gln Ala Gly Glu Ile Val Asp Phe Leu Val Asp Glu Gly
                245                 250                 255

Thr Ala Val Glu Tyr Asn Gln Pro Val Val Glu Leu Met Pro Phe Phe
            260                 265                 270

Gly Gly His Ile Ile Gly Asp Arg Lys His Ala
        275                 280

<210> SEQ ID NO 53
<211> LENGTH: 275
<212> TYPE: PRT
<213> ORGANISM: Chlorella variabilis

<400> SEQUENCE: 53

Met Ala Ala Ala Gln Leu Ser Ala Ala Arg Cys Ser Arg Val Ile Gly
1               5                   10                  15

Ser Arg Gln Val Thr Ala Pro Arg Arg Leu Pro Ala Ala Ser Asn Val
            20                  25                  30

Arg Lys Leu Val Leu Ser Arg Val Ala Gln Val Glu Ala Asn Ser Ser
        35                  40                  45

Val Lys His Thr Glu Lys Ala Glu Lys Lys His Lys Glu Glu Glu
        50                  55                  60
Glu Glu Glu Leu Glu Gly Ser Glu Asp Gly Leu Asn Pro Gln Gln
65                  70                  75                  80
Ala Arg Pro Gln Ser Pro Ala Pro Val Pro Leu Arg Arg Val Val Pro
                85                  90                  95
Trp Ala Thr Val Glu Ser Phe Leu Ser Val Leu Cys Glu Glu Thr Asp
                100                 105                 110
Ile Ala Glu Val Glu Leu Lys Met Gly Ser Phe Lys Met Arg Val Arg
                115                 120                 125
Arg Ser Leu Asn Gly Ala Ala Ala Pro Ala Ala Ala Ala Pro
130                 135                 140
Ala Ala Ala Ala Pro Ala Pro Ala Ala Ala Pro Pro Ala Tyr Val Pro
145                 150                 155                 160
Glu Ala Pro Ala Ala Arg Pro Ala Ala Ala Val Glu Thr Val Asp Glu
                165                 170                 175
Asp Glu Ser Leu Leu Asp Val Thr Ala Asn Lys Val Gly Ile Leu Arg
                180                 185                 190
Arg Gly Arg Tyr Met Lys Gly Lys Gln Val Gly Lys Gly Thr Met Val
                195                 200                 205
Gln Pro Gly Asp Gln Val Lys Lys Gly Gln Thr Leu Ala Phe Ile Glu
                210                 215                 220
Gln Leu Gly Thr His Trp Pro Leu Glu Ala Pro Gln Ala Gly Glu Val
225                 230                 235                 240
Val Glu Phe Leu Val Asp Glu Gly Ser Pro Val Glu Tyr Lys Gln Pro
                245                 250                 255
Val Leu Val Ile Ala Pro Phe Phe Gly Gly His Ile Ile Gly Asp Arg
                260                 265                 270
Lys His Ala
        275

<210> SEQ ID NO 54
<211> LENGTH: 289
<212> TYPE: PRT
<213> ORGANISM: Solanum tuberosum

<400> SEQUENCE: 54

Met Glu Ser Ala Ala Val Leu Arg Ser Phe His His Ser Val Gly Thr
1               5                   10                  15
Thr Ser His Val Arg Ser Val Ile Glu Met Pro Gly Val Ile Pro Thr
                20                  25                  30
Asn Ser Ile Ala Phe Ser Lys Pro Thr Lys Leu Ser Leu Lys Gly Ser
                35                  40                  45
Ser Asn Gly Ala Arg Leu Met Ser Ser Pro Asn Lys His Gly Arg Leu
        50                  55                  60
Thr Leu Ser Cys Ala Lys Thr Ser Glu Thr Thr Val Thr Ala Lys Ser
65                  70                  75                  80
Gly Asp Ser Asn Gln Lys Val Pro Thr Glu Ser Ser Pro Leu Pro Thr
                85                  90                  95
Ala Thr Phe Pro Lys Gly Phe Glu Ala Leu Ile Ile Glu Val Cys Asp
                100                 105                 110
Asp Thr Glu Val Ala Glu Leu Lys Leu Lys Val Gly Asp Phe Glu Leu
                115                 120                 125
His Leu Lys Arg Asn Ile Glu Ala Pro Val Val Pro Ala Pro Val Val
                130                 135                 140

```
Ser Ala Pro Pro Pro Pro Pro Ser Ala Ser Lys Thr Ser Ile Ser
145                 150                 155                 160

Ser Thr Ala Ala Ala Pro Ala Ala Ser Pro Gly Lys Ser Ser Gly
            165                 170                 175

Lys Ile Ser Pro Phe Thr Asn Val Ala Ala Glu Lys Ser Ala Lys Leu
        180                 185                 190

Ala Ala Leu Glu Ser Thr Gly Ala Ser Gly Tyr Val Leu Val Ser Cys
        195                 200                 205

Pro Thr Val Gly Ser Phe Arg Arg Ala Arg Thr Leu Lys Gly Lys Lys
210                 215                 220

Gln Pro Pro Ala Cys Lys Glu Gly Asp Ile Ile Lys Glu Gly Gln Ile
225                 230                 235                 240

Ile Gly Phe Leu Asp Gln Phe Gly Thr Glu Leu Pro Val Arg Ser Asp
            245                 250                 255

Ala Ala Gly Glu Val Leu Lys Ile Leu Phe Asn Asp Gly Glu Ala Val
            260                 265                 270

Gly Tyr Gly Asp Pro Leu Ile Ala Val Leu Pro Ser Phe Arg Gly Ile
            275                 280                 285

Asn

<210> SEQ ID NO 55
<211> LENGTH: 274
<212> TYPE: PRT
<213> ORGANISM: Solanum tuberosum

<400> SEQUENCE: 55

Met Ala Ala Cys Gly Phe Gly Ala Ser Gly Leu Lys Leu Thr Ser Leu
1               5                   10                  15

Asn Leu Gly Ser Thr Lys Pro Lys Leu Ser Val Val His Asn Leu Arg
            20                  25                  30

Thr Lys Lys Phe Val Gln Asn Asp Gly Leu Leu Leu Thr Thr Lys Ser
        35                  40                  45

Arg Lys Thr Phe Asp Cys Arg Cys Ser Thr Val Glu Ala Lys Pro Ala
50                  55                  60

Ala Ala Thr Ala Ile Pro Lys Ser Asp Asp Ser Ser Ser Lys Ile Val
65                  70                  75                  80

Ser Ser Glu Thr Ala Ser Pro Leu Ile Pro Asn Ser Tyr Glu Val Glu
            85                  90                  95

Ser Leu Leu Ala Glu Ile Cys Asp Thr Thr Ser Ile Ala Glu Val Asp
            100                 105                 110

Leu Lys Leu Gly Gly Phe Arg Leu Tyr Val Lys Arg Asp Leu Thr Gly
        115                 120                 125

Gln Ser Thr Thr Ser Leu Pro Pro Ile Thr Ser Pro Val Ser Ile Pro
130                 135                 140

Ser Ser Val Glu Val Ala Asp Ser Asn Gly Ser Ala Ser Ser Thr Ser
145                 150                 155                 160

Leu Ala Ile Thr Lys Ser Ser Pro Ser Asp Gly Ile Gln Thr Met
        165                 170                 175

Ile Glu Lys Ala Ala Asp Glu Gly Leu Val Ile Ile Gln Ser Pro Arg
        180                 185                 190

Val Gly Phe Phe Arg Arg Ser Arg Thr Ile Lys Gly Lys Arg Ala Pro
        195                 200                 205

Pro Ala Cys Lys Glu Lys Gln Gln Val Lys Glu Gly Gln Val Val Phe
210                 215                 220
```

```
Tyr Ile Glu Gln Leu Gly Gly Glu Leu Pro Val Ser Asp Val Ser
225                 230                 235                 240

Gly Glu Val Ile Lys Ile Leu Arg Lys Asp Gly Asp Pro Val Gly Tyr
                245                 250                 255

Gly Asp Pro Leu Ile Ser Ile Leu Pro Ser Phe Pro Gly Ile Lys Lys
            260                 265                 270

Leu Gln

<210> SEQ ID NO 56
<211> LENGTH: 323
<212> TYPE: PRT
<213> ORGANISM: Capsella rubella

<400> SEQUENCE: 56

Ser Glu Pro Asn Gln Gln Arg Ala Leu Thr Ser Ile Phe Cys Phe Leu
1               5                   10                  15

Phe Tyr Phe Asp Leu Ile Ile Ser Thr Leu Val Lys Ser Cys Val Leu
                20                  25                  30

Val Gly Ile Val Ile Val Ser Ala His Thr Ile Ser Phe Leu Phe Leu
            35                  40                  45

Ser Phe Phe Cys Phe Ser Asn Pro Leu Ser Pro Ser Met Ala Ser Cys
    50                  55                  60

Ser Leu Gly Val Pro Lys Ile Lys Ile Ser Ala Val Asp Leu Ser Arg
65                  70                  75                  80

Val Arg Ser Gly Ser Leu Leu Ile Pro Phe Asn Gln Arg Ser Leu Leu
                85                  90                  95

Gly Gln Lys Pro Val Lys Tyr Leu Ser Leu Arg Thr Thr Phe Gly Thr
            100                 105                 110

Val Lys Ala Val Gln Val Ser Thr Val Pro Ala Pro Glu Thr Ser Ala
        115                 120                 125

Thr Ile Glu Val Glu Asp Ser Asp Thr Lys Ser Ser Lys Leu Asn
130                 135                 140

Ala Gln Leu Val Pro Lys Pro Ser Glu Val Glu Ala Leu Val Thr Glu
145                 150                 155                 160

Ile Cys Asp Thr Ser Ser Ile Ala Glu Phe Glu Leu Lys Leu Gly Gly
                165                 170                 175

Phe Arg Leu Tyr Val Ala Arg Asp Leu Ala Asp Lys Ser Ser Pro Gln
            180                 185                 190

Pro His Ala Thr Pro Ala Val Ala Ala Thr Ser Glu Thr Thr Asn Ser
        195                 200                 205

Thr Asp Ser Asn Gly Ser Ala Pro Ser Thr Ser Leu Ala Ile Thr Arg
    210                 215                 220

Pro Ala Ser Ser Ala Ala Asp Lys Gly Leu Met Ile Leu Gln Ser Pro
225                 230                 235                 240

Lys Val Gly Phe Phe Arg Arg Ser Lys Thr Ile Lys Gly Lys Arg Met
                245                 250                 255

Pro Ser Ser Cys Lys Glu Lys Asp Gln Val Lys Glu Gly Gln Ile Leu
            260                 265                 270

Cys Tyr Ile Glu Gln Leu Gly Gly Gln Phe Pro Ile Glu Ser Asp Val
        275                 280                 285

Thr Gly Glu Val Val Lys Ile Leu Arg Glu Asp Gly Glu Pro Val Gly
    290                 295                 300

Tyr Asn Asp Ala Leu Ile Ser Ile Leu Pro Ser Phe Pro Gly Ile Lys
305                 310                 315                 320
```

Lys Leu Gln

<210> SEQ ID NO 57
<211> LENGTH: 272
<212> TYPE: PRT
<213> ORGANISM: Capsella rubella

<400> SEQUENCE: 57

```
Met Asn Ser Cys Ser Leu Gly Ala Pro Lys Leu Arg Ile Ser Leu Ala
1               5                   10                  15

Asn Phe Ser Arg Leu Arg Cys Gly Asn Leu Leu Ile Pro Asn Asn Gln
            20                  25                  30

Arg Leu Phe Ile Asp Gln Gly Gln Ser Pro Ile Lys Phe Pro Ser Leu
        35                  40                  45

Arg Thr Thr Leu Arg Ala Val Lys Ala Val Gln Leu Ser Thr Val Pro
    50                  55                  60

Pro Ala Glu Thr Ser Asp Val Glu Asp Ser Glu Glu Thr Glu Pro Thr
65                  70                  75                  80

Ile Val Asn Thr Gln Leu Ile Pro Asn Ser Ser Glu Val Glu Ala Leu
                85                  90                  95

Ile Ser Glu Ile Thr Asp Ser Ser Ser Ile Ala Glu Phe Glu Leu Lys
            100                 105                 110

Leu Gly Gly Phe Arg Leu Tyr Val Ala Arg Lys Leu Ala Asp Gln Ser
        115                 120                 125

Ser Pro Pro Gln Gln Ile Pro Asn Val Val Ala Ala Ser Ala Ala
    130                 135                 140

Pro Glu Gly Val His Thr Asn Gly Ser Ala Thr Ser Ser Ser Leu Ala
145                 150                 155                 160

Ile Thr Lys Ser Ser Ser Ser Asp Arg Pro Gln Thr Leu Ser Asn
                165                 170                 175

Lys Ala Ala Asp Gln Gly Leu Val Ile Leu Gln Ser Pro Thr Val Gly
            180                 185                 190

Tyr Phe Arg Arg Ser Lys Thr Ile Lys Gly Lys Arg Thr Pro Thr Ile
        195                 200                 205

Cys Lys Glu Lys Asp Ile Val Lys Glu Gly Gln Val Leu Cys Tyr Ile
    210                 215                 220

Glu Gln Leu Gly Gly Gln Ile Pro Val Glu Ser Asp Val Ser Gly Glu
225                 230                 235                 240

Ile Val Lys Ile Leu Arg Glu Asp Gly Glu Pro Val Gly Tyr Asn Asp
                245                 250                 255

Ala Leu Ile Thr Val Leu Pro Ser Phe Pro Gly Ile Lys Lys Leu Gln
            260                 265                 270
```

<210> SEQ ID NO 58
<211> LENGTH: 271
<212> TYPE: PRT
<213> ORGANISM: Populus trichocarpa

<400> SEQUENCE: 58

```
Met Ala Ser Cys Ser Leu Gly Ala Ser Asn Met Lys Leu Ser Lys Leu
1               5                   10                  15

Asp Phe Gly Arg Ala Thr Val Val Asn Leu Gln Lys Gln Ser Gly Leu
            20                  25                  30

Ile Ala Trp Arg Gly Arg Gly Arg Leu Gln His Ala Gly Val Ala Ile
        35                  40                  45
```

```
Ser His Lys Ser Arg Glu Ala Phe Arg Cys Arg Gly Ser Ala Ser Glu
 50                  55                  60
Thr Glu Leu Thr Thr Lys Glu Thr Lys Ser Ser Gly Leu Thr Ser Gln
 65                  70                  75                  80
Leu Ile Pro Asn Ser Ser Glu Ile Glu Ser Leu Val Thr Glu Ile Cys
                 85                  90                  95
Asn Thr Thr Ser Val Ala Glu Leu Glu Leu Lys Leu Gly Gly Phe Arg
                100                 105                 110
Leu Tyr Val Arg Arg Asp Leu Thr Glu Lys Asn Lys Asp Thr His Gln
                115                 120                 125
Pro Leu Pro Ala Pro Pro Ala Ser Leu Ala Val Thr Val Lys Thr Thr
130                 135                 140
Thr Asp Ala Ser Asp Leu Asn Gly Ser Val Ser Thr Ser Leu Ala Ile
145                 150                 155                 160
Ser Lys Gln Glu Pro Ser Gly Gly Ile Ile Ser Phe Leu Asp Arg
                165                 170                 175
Ala Ala Asp Glu Gly Leu Met Ile Leu Gln Ser Pro Arg Val Gly Phe
                180                 185                 190
Phe Arg Arg Ser Arg Thr Ile Lys Gly Lys Arg Ala Pro Pro Ser Cys
                195                 200                 205
Lys Glu Lys Gln Ile Val Lys Glu Gly Gln Val Leu Cys Phe Ile Glu
210                 215                 220
Gln Leu Gly Gly Glu Leu Pro Ile Glu Thr Asp Ile Ser Gly Glu Val
225                 230                 235                 240
Ile Arg Ile Leu Arg Glu Asp Gly Glu Pro Val Gly Tyr Gly Asp Ala
                245                 250                 255
Leu Ile Ala Ile Leu Pro Ser Phe Pro Gly Ile Lys Lys Leu Gln
                260                 265                 270

<210> SEQ ID NO 59
<211> LENGTH: 210
<212> TYPE: PRT
<213> ORGANISM: Populus trichocarpa

<400> SEQUENCE: 59

Met Pro Ser Cys Gln Thr Thr Arg Met Asp Ser Leu Gly Ala Leu Asn
 1                5                  10                  15
Val Lys Leu Ser Lys Leu Asp Phe Gly Gly Lys Phe Gly Asn Leu
                 20                  25                  30
Gln Gln Arg Ser Gly Val Arg Val Trp Met Gly Arg Val Gln Leu Gln
                 35                  40                  45
Tyr Ala Gly Thr Thr Lys Glu Thr Thr Ser Leu Gly Leu Thr Ser Gln
 50                  55                  60
Leu Ile Pro Asn Ser Ser Glu Ile Glu Ser Leu Val Thr Glu Ile Cys
 65                  70                  75                  80
Asn Thr Thr Ser Ile Ala Glu Phe Glu Leu Lys Leu Ala Ser Thr Ser
                 85                  90                  95
Leu Ala Ile Ser Lys Gln Glu Pro Ser Phe Gly Gly Ile Lys Ser Phe
                100                 105                 110
Leu Asp Arg Thr Ala Asp Glu Gly Leu Met Ile Leu Pro Ser Pro Arg
                115                 120                 125
Val Gly Phe Phe Arg Arg Ser Arg Thr Ile Lys Gly Lys Arg Ala Pro
                130                 135                 140
Pro Ser Cys Lys Glu Lys Gln Ile Ile Lys Glu Gly Gln Val Leu Cys
145                 150                 155                 160
```

Tyr Ile Glu Gln Leu Gly Gly Glu Leu Pro Ile Ser Asp Ile Ser
            165                 170                 175

Gly Glu Val Ile Lys Ile Leu Arg Glu Asp Gly Glu Pro Val Gly Tyr
        180                 185                 190

Gly Asp Ala Leu Ile Ala Ile Leu Pro Ser Phe Pro Gly Ile Lys Lys
            195                 200                 205

Leu Gln
    210

<210> SEQ ID NO 60
<211> LENGTH: 270
<212> TYPE: PRT
<213> ORGANISM: Eutrema salsugineum

<400> SEQUENCE: 60

Met Ser Ser Cys Ser Leu Gly Ala Pro Lys Ile Lys Ile Tyr Ala Ser
1               5                   10                  15

Asn Leu Ile Arg Cys Asp Lys Phe Leu Leu Ile Pro Asn Asn Gln Arg
            20                  25                  30

Leu Cys Ile Gly Gln Ile Pro Met Lys Tyr Pro Ser Leu Arg Thr Thr
        35                  40                  45

Leu Gln Ser Val Lys Ala Ser Gln Leu Ser Val Val Pro Thr Ala Glu
50                  55                  60

Thr Ala Asp Val Glu Asp Ser Glu Glu Thr Lys Ser Ser Val Val Asn
65                  70                  75                  80

Ala Gln Leu Ile Pro Lys Ser Ser Glu Val Glu Ala Leu Ile Ser Glu
                85                  90                  95

Ile Ala Glu Ser Pro Ser Ile Ala Glu Phe Glu Leu Lys Leu Gly Gly
            100                 105                 110

Phe Arg Leu Tyr Val Ala Lys Lys Leu Ala Asp Gln Ser Ser Pro Pro
        115                 120                 125

Pro His Gln Thr Pro His Val Val Ala Ala Ser Val Thr Pro Glu Gly
    130                 135                 140

Ile Asn Thr Asn Gly Ser Ala Thr Ser Ser Ser Leu Ser Ile Thr Lys
145                 150                 155                 160

Thr Ser Ser Ser Ser Gly Asp Arg Pro Gln Thr Leu Ala Asn Lys Ala
                165                 170                 175

Ala Asn Asn Glu Gly Leu Val Ile Leu Gln Ser Pro Thr Val Gly Tyr
            180                 185                 190

Phe Arg Arg Ser Lys Thr Val Lys Gly Lys Arg Leu Pro Thr Ile Cys
        195                 200                 205

Lys Glu Lys Asp Ile Val Lys Glu Gly Gln Val Leu Cys Tyr Ile Glu
    210                 215                 220

Gln Leu Gly Gly Gln Ile Pro Val Glu Ser Asp Val Ser Gly Glu Ile
225                 230                 235                 240

Val Lys Ile Leu Arg Glu Asp Gly Glu Pro Val Gly Tyr Asp Asp Ala
                245                 250                 255

Leu Ile Thr Val Leu Pro Ser Phe Pro Gly Ile Lys Lys Leu
            260                 265                 270

<210> SEQ ID NO 61
<211> LENGTH: 281
<212> TYPE: PRT
<213> ORGANISM: Eutrema salsugineum

<400> SEQUENCE: 61

Met Glu Ser Ser Ala Ala Leu Gly Ser Leu His Gln Thr Leu Gly Ser
1               5                   10                  15

Ala Ile Lys Ser Glu Ser Lys Val His Ser Leu Ser Gly Asn Trp Ser
            20                  25                  30

Ser Ser Gly Asn Ser Cys Val Pro Arg Trp Arg Leu Phe Asn Arg Asn
        35                  40                  45

Ser Asn Phe Thr Leu Val Leu Arg Ala Glu Ala Ser Lys Ser Ser Thr
    50                  55                  60

Thr Thr Lys Ser Asp Asp Ser Ser Asp Ala Cys Val Ser Asn Gly Lys
65                  70                  75                  80

Asn Thr Val Arg Arg Thr Thr Phe Pro Lys Glu Val Glu Ala Leu Val
                85                  90                  95

His Glu Met Cys Asp Glu Thr Glu Val Ala Val Leu Lys Leu Lys Val
            100                 105                 110

Gly Asp Phe Glu Met Asn Leu Lys Arg Lys Ile Gly Glu Thr Ala Asn
        115                 120                 125

Pro Ile Pro Val Ala Asp Ile Ser Pro Thr Ile Ala Pro Pro Ile Pro
    130                 135                 140

Ser Glu Pro Met Asn Lys Ser Val Ser Ala Ala Pro Ser Pro Ser Lys
145                 150                 155                 160

Ala Lys Pro Ala Ser Glu Lys Val Ser Pro Phe Met Asn Val Ser Tyr
                165                 170                 175

Arg Lys Ser Ser Lys Leu Ser Ala Leu Glu Ala Ser Gly Thr Asn Asn
            180                 185                 190

Tyr Val Leu Val Thr Ser Pro Ser Val Gly Lys Phe Gln Arg Ser Arg
        195                 200                 205

Thr Val Lys Gly Lys Lys Gln Pro Pro Ser Cys Lys Glu Gly Asp Ala
    210                 215                 220

Ile Lys Glu Gly Gln Val Ile Gly Tyr Leu His Gln Leu Gly Thr Glu
225                 230                 235                 240

Leu Pro Val Lys Ser Asp Val Ala Gly Glu Val Leu Lys Leu Leu Ser
                245                 250                 255

Asp Asp Gly Asp Thr Val Gly Tyr Gly Glu Pro Leu Val Ala Val Leu
            260                 265                 270

Pro Ser Phe His Asp Ile Asn Ile His
        275                 280

<210> SEQ ID NO 62
<211> LENGTH: 261
<212> TYPE: PRT
<213> ORGANISM: Eutrema salsugineum

<400> SEQUENCE: 62

Met Ala Ser Cys Ser Leu Gly Val Pro Lys Ile Lys Ile Ser Ala Val
1               5                   10                  15

Glu Leu Ser Arg Val Arg Ser Gly Ser Leu Gln Ile Val Pro Cys Asn
            20                  25                  30

Gln Arg Ser Leu Ile Cys Gln Arg Pro Val Lys Tyr Leu Ser Leu Arg
        35                  40                  45

Ala Thr Leu Gly Ser Val Lys Ala Val Gln Ala Ser Thr Val Thr Ala
    50                  55                  60

Ala Glu Thr Ala Glu Val Glu Asp Ser Glu Glu Thr Lys Ser Tyr Pro
65                  70                  75                  80

Leu Asn Ala Gln Leu Ile Pro Lys Pro Ser Glu Val Glu Ala Leu Val

```
            85                  90                  95
Thr Glu Ile Cys Asp Ser Ser Ile Ala Glu Phe Glu Leu Lys Leu
            100                 105                 110

Gly Gly Phe Arg Leu Tyr Val Ala Arg Asn Leu Ala Glu Lys Ser Ser
            115                 120                 125

Pro Gln Pro Gln Pro Ile Pro Ala Val Val Ala Ala Asn Ala Thr Thr
130                 135                 140

Glu Asn Leu Asp Ser Asn Gly Ser Ala Ser Ser Thr Ser Leu Ala Ile
145                 150                 155                 160

Thr Lys Pro Ala Ser Ser Ala Ala Asp Gln Gly Leu Val Ile Leu Gln
                165                 170                 175

Ser Pro Lys Val Gly Phe Phe Arg Arg Ser Lys Thr Ile Lys Gly Lys
                180                 185                 190

Arg Thr Pro Ser Ser Cys Lys Glu Lys Asp Gln Val Lys Glu Gly Gln
                195                 200                 205

Val Leu Cys Tyr Ile Glu Gln Leu Gly Gly Gln Phe Pro Ile Glu Ser
                210                 215                 220

Asp Val Thr Gly Glu Val Val Lys Ile Leu Arg Glu Asp Gly Glu Pro
225                 230                 235                 240

Val Gly Tyr Asn Asp Ala Leu Ile Ser Ile Leu Pro Ser Phe Pro Gly
                245                 250                 255

Ile Lys Lys Leu Gln
                260

<210> SEQ ID NO 63
<211> LENGTH: 270
<212> TYPE: PRT
<213> ORGANISM: Citrus clementina

<400> SEQUENCE: 63

Met Ala Ser Tyr Ser Leu Gly Ala Ser Asn Ile Lys Ile Pro Lys Gly
1               5                   10                  15

Asn Leu Gly Arg Ala Arg Val Gly Asp Leu Gln Pro Arg Ser Asp Val
                20                  25                  30

Arg Lys Trp Met Gly Arg Lys Pro Phe Gln Tyr Ala Gly Leu Ala Met
            35                  40                  45

Ser Gln Pro Leu Glu Lys Ala Phe Thr Val Phe Cys Gly Gln Ser Ser
        50                  55                  60

Glu Ala Glu Ser Thr Arg Asn Ala Arg Asp Gly His Glu Asp Met Lys
65                  70                  75                  80

Ser Thr Gln Leu Ile Pro Asp Ser Ser Glu Val Glu Ser Leu Val Thr
                85                  90                  95

Asp Ile Cys Asn Thr Thr Ser Val Ala Glu Phe Glu Leu Lys Leu Asp
            100                 105                 110

Gly Phe Arg Leu Tyr Val Thr Arg Asp Ile Ala Gly Ala Ser Ser Pro
        115                 120                 125

Leu Leu Pro Ser Ser Pro Ala Pro Val Thr Val Asn Lys Pro Ala Asp
    130                 135                 140

Arg Pro Asp Ser Asn Gly Ser Val Pro Thr Pro Ser Leu Ala Ile Thr
145                 150                 155                 160

Lys Pro Val Ser Ser Ser Gly Gly Ile Gln Thr Leu Leu Asp Lys Ala
                165                 170                 175

Ala Asp Glu Gly Leu Val Ile Leu Glu Ser Pro Lys Val Gly Tyr Phe
                180                 185                 190
```

```
Arg Arg Ser Arg Thr Ile Lys Gly Lys Arg Ala Pro Pro Ser Cys Lys
            195                 200                 205

Glu Lys Gln Thr Val Arg Glu Gly Gln Val Leu Cys Tyr Ile Glu Gln
210                 215                 220

Leu Gly Gly Glu Ile Pro Ile Glu Ser Asp Ile Ala Gly Glu Val Ile
225                 230                 235                 240

Lys Ile Leu Arg Lys Asp Gly Asp Pro Ile Gly Tyr Gly Asp Pro Leu
                245                 250                 255

Ile Val Ile Leu Pro Ser Phe Pro Gly Ile Lys Leu Leu Gln
            260                 265                 270

<210> SEQ ID NO 64
<211> LENGTH: 287
<212> TYPE: PRT
<213> ORGANISM: Citrus clementina

<400> SEQUENCE: 64

Met Ala Ser Ser Ala Ala Leu Arg Ser Phe His Tyr Ser Val Gly Ala
1               5                   10                  15

Val Ala Lys Ser Gly Ser Ser Phe Glu Arg Pro Gly Ile Val Leu Pro
            20                  25                  30

Val Arg Asn Ser Ser Trp Pro Ser Ala Ala Ser Lys Ser Phe Asn Leu
        35                  40                  45

Val Thr Pro Pro Val Trp Arg Gly Val Thr Val Val Ser Ser Ala
50                  55                  60

Lys Thr Ser Glu Asn Thr Ser Thr Ala Lys Thr Asp Glu Ser Thr Glu
65                  70                  75                  80

Glu Ser Ser Ser Glu Lys Ser Thr Leu Arg Ser Pro Ile Phe Pro Ser
                85                  90                  95

Gly Phe Glu Ala Leu Met Leu Glu Val Cys Asp Glu Thr Glu Ile Ala
            100                 105                 110

Glu Leu Lys Leu Lys Val Gly Asp Phe Glu Met His Leu Lys Arg Asn
        115                 120                 125

Val Gly Ala Pro Lys Ala Pro Ala Pro Leu Ser Asn Ile Ser Pro Thr
130                 135                 140

Thr Pro Pro Pro Ile Pro Thr Glu Pro Met Glu Val Ser Asp Pro Val
145                 150                 155                 160

Ser Pro Pro Pro Pro Ser Pro Pro Lys Pro Tyr Ser Glu Lys Ala
                165                 170                 175

Ala Pro Phe Ile Asn His Ser Phe Gly Lys Ser Ser Lys Leu Ala Ala
            180                 185                 190

Leu Glu Ala Ser Gly Ser Asn Gly Tyr Val Leu Val Phe Ser Pro Thr
        195                 200                 205

Val Gly Ser Phe Arg Arg Asn Arg Thr Val Lys Gly Lys Lys Gln Ser
210                 215                 220

Pro Ile Cys Lys Glu Gly Asp Val Ile Lys Glu Gly Gln Ile Ile Gly
225                 230                 235                 240

Tyr Leu Asp Gln Phe Gly Thr Glu Leu Pro Val Lys Ser Asp Val Ala
                245                 250                 255

Gly Glu Val Leu Lys Leu Leu Phe Asp Asp Gly Asp Ala Val Gly Phe
            260                 265                 270

Gly Asp Pro Leu Ile Ala Val Leu Pro Ser Phe His Asp Ile Lys
        275                 280                 285

<210> SEQ ID NO 65
```

```
<211> LENGTH: 271
<212> TYPE: PRT
<213> ORGANISM: Citrus sinensis

<400> SEQUENCE: 65
```

| | | | | | | | | | | | | | | |
|---|---|---|---|---|---|---|---|---|---|---|---|---|---|---|
| Met | Ala | Ser | Tyr | Ser | Leu | Gly | Ala | Ser | Asn | Ile | Lys | Ile | Pro | Lys | Gly |
| 1 | | | | 5 | | | | | 10 | | | | | 15 | |

| Asn | Leu | Gly | Arg | Ala | Arg | Val | Gly | Asp | Leu | Gln | Pro | Arg | Ser | Asp | Val |
|---|---|---|---|---|---|---|---|---|---|---|---|---|---|---|---|
| | | | 20 | | | | | 25 | | | | | 30 | | |

| Arg | Lys | Trp | Met | Gly | Arg | Lys | Pro | Phe | Gln | Tyr | Ala | Gly | Leu | Ala | Met |
|---|---|---|---|---|---|---|---|---|---|---|---|---|---|---|---|
| | | | 35 | | | | | 40 | | | | | 45 | | |

| Ser | Gln | Pro | Leu | Glu | Lys | Ala | Phe | Thr | Val | Phe | Cys | Gly | Gln | Ser | Ser |
|---|---|---|---|---|---|---|---|---|---|---|---|---|---|---|---|
| | 50 | | | | | 55 | | | | | 60 | | | | |

| Glu | Ala | Glu | Ser | Thr | Arg | Asn | Ala | Arg | Asp | Gly | His | Glu | Asp | Met | Lys |
|---|---|---|---|---|---|---|---|---|---|---|---|---|---|---|---|
| 65 | | | | | 70 | | | | | 75 | | | | | 80 |

| Ser | Pro | Gln | Leu | Ile | Pro | Asp | Ser | Ser | Glu | Val | Ser | Leu | Val | Thr | |
|---|---|---|---|---|---|---|---|---|---|---|---|---|---|---|---|
| | | | | 85 | | | | | 90 | | | | | 95 | |

| Asp | Ile | Cys | Asn | Thr | Thr | Ser | Val | Ala | Glu | Phe | Glu | Leu | Lys | Leu | Asp |
|---|---|---|---|---|---|---|---|---|---|---|---|---|---|---|---|
| | | | | 100 | | | | | 105 | | | | | 110 | |

| Gly | Phe | Arg | Leu | Tyr | Val | Thr | Arg | Asp | Ile | Ala | Gly | Asp | Ser | Ile | Pro |
|---|---|---|---|---|---|---|---|---|---|---|---|---|---|---|---|
| | | | 115 | | | | | 120 | | | | | 125 | | |

| Pro | Leu | Pro | Pro | Ser | Ser | Pro | Ala | Pro | Val | Thr | Val | Asn | Lys | Pro | Ala |
|---|---|---|---|---|---|---|---|---|---|---|---|---|---|---|---|
| | 130 | | | | | 135 | | | | | 140 | | | | |

| Asp | Arg | Pro | Asp | Ser | Asn | Gly | Ser | Val | Pro | Thr | Ser | Ser | Leu | Ala | Ile |
|---|---|---|---|---|---|---|---|---|---|---|---|---|---|---|---|
| 145 | | | | | 150 | | | | | 155 | | | | | 160 |

| Thr | Lys | Pro | Val | Ser | Ser | Gly | Gly | Ile | Gln | Thr | Leu | Leu | Asp | Lys | |
|---|---|---|---|---|---|---|---|---|---|---|---|---|---|---|---|
| | | | | 165 | | | | | 170 | | | | | 175 | |

| Ala | Ala | Asp | Glu | Gly | Leu | Val | Ile | Leu | Glu | Ser | Pro | Lys | Val | Gly | Tyr |
|---|---|---|---|---|---|---|---|---|---|---|---|---|---|---|---|
| | | | 180 | | | | | 185 | | | | | 190 | | |

| Phe | Arg | Arg | Ser | Arg | Thr | Ile | Lys | Gly | Lys | Arg | Ala | Pro | Pro | Ser | Cys |
|---|---|---|---|---|---|---|---|---|---|---|---|---|---|---|---|
| | | 195 | | | | | 200 | | | | | 205 | | | |

| Lys | Glu | Lys | Gln | Thr | Val | Arg | Glu | Gly | Gln | Val | Leu | Cys | Tyr | Ile | Glu |
|---|---|---|---|---|---|---|---|---|---|---|---|---|---|---|---|
| | 210 | | | | | 215 | | | | | 220 | | | | |

| Gln | Leu | Gly | Gly | Glu | Ile | Pro | Ile | Glu | Ser | Asp | Ile | Ala | Gly | Glu | Val |
|---|---|---|---|---|---|---|---|---|---|---|---|---|---|---|---|
| 225 | | | | | 230 | | | | | 235 | | | | | 240 |

| Ile | Lys | Ile | Leu | Arg | Lys | Asp | Gly | Asp | Pro | Ile | Gly | Tyr | Gly | Asp | Pro |
|---|---|---|---|---|---|---|---|---|---|---|---|---|---|---|---|
| | | | | 245 | | | | | 250 | | | | | 255 | |

| Leu | Ile | Val | Ile | Leu | Pro | Ser | Phe | Pro | Gly | Ile | Lys | Leu | Leu | Gln | |
|---|---|---|---|---|---|---|---|---|---|---|---|---|---|---|---|
| | | | 260 | | | | | 265 | | | | | 270 | | |

```
<210> SEQ ID NO 66
<211> LENGTH: 297
<212> TYPE: PRT
<213> ORGANISM: Glycine max

<400> SEQUENCE: 66
```

| Met | Phe | Leu | Gln | Ile | Tyr | Asn | Gln | Arg | Met | Leu | Cys | Asn | His | Pro | Arg |
|---|---|---|---|---|---|---|---|---|---|---|---|---|---|---|---|
| 1 | | | | 5 | | | | | 10 | | | | | 15 | |

| Ala | Tyr | Pro | Ile | Gly | Thr | Met | Ser | His | Val | Arg | Ala | Ser | Leu | Glu | Lys |
|---|---|---|---|---|---|---|---|---|---|---|---|---|---|---|---|
| | | | 20 | | | | | 25 | | | | | 30 | | |

| Gln | Ala | Val | Val | Pro | Ile | His | Asn | Ala | Gly | Trp | Asn | Ser | Lys | Ser | Arg |
|---|---|---|---|---|---|---|---|---|---|---|---|---|---|---|---|
| | | | 35 | | | | | 40 | | | | | 45 | | |

| Leu | Phe | Ile | Gln | His | Leu | Ala | Tyr | Gly | Gln | Lys | His | Ile | Asn | Ser | His |
|---|---|---|---|---|---|---|---|---|---|---|---|---|---|---|---|
| | 50 | | | | | 55 | | | | | 60 | | | | |

| Thr | Lys | Gly | Lys | Asn | Thr | Leu | Ile | Ser | Cys | Gly | Lys | Thr | Ala | Glu | Ala |
|---|---|---|---|---|---|---|---|---|---|---|---|---|---|---|---|
| 65 | | | | | 70 | | | | | 75 | | | | | 80 |

```
Ile Asn Ala Ser Lys Ser Asp Ala Ser Ser Asp Asn Thr Pro Gln Gly
                85                  90                  95

Ser Leu Glu Lys Lys Pro Leu Gln Thr Ala Thr Phe Pro Asn Gly Phe
               100                 105                 110

Glu Ala Leu Val Leu Glu Val Cys Asp Glu Thr Glu Ile Ala Glu Leu
           115                 120                 125

Lys Val Lys Val Gly Asp Phe Glu Met His Ile Lys Arg Asn Ile Gly
       130                 135                 140

Ala Thr Lys Val Pro Leu Ser Asn Ile Ser Pro Thr Thr Pro Pro Pro
145                 150                 155                 160

Ile Pro Ser Lys Pro Met Asp Glu Ser Ala Pro Gly Ser Leu Pro Pro
               165                 170                 175

Ser Pro Pro Lys Ser Ser Pro Glu Lys Asn Asn Pro Phe Ala Asn Val
           180                 185                 190

Ser Lys Glu Lys Ser Pro Arg Leu Ala Ala Leu Glu Ala Ser Gly Thr
       195                 200                 205

Asn Thr Tyr Val Leu Val Ser Ser Pro Thr Val Gly Leu Phe Arg Arg
210                 215                 220

Gly Arg Thr Val Lys Gly Lys Gln Pro Pro Ile Cys Lys Glu Gly
225                 230                 235                 240

Asp Val Ile Lys Glu Gly Gln Val Ile Gly Tyr Leu Asp Gln Phe Gly
               245                 250                 255

Thr Gly Leu Pro Ile Lys Ser Asp Val Ala Gly Glu Val Leu Lys Leu
           260                 265                 270

Leu Val Glu Asp Gly Glu Pro Val Gly Tyr Gly Asp Pro Leu Ile Ala
       275                 280                 285

Val Leu Pro Ser Phe His Asp Ile Lys
290                 295

<210> SEQ ID NO 67
<211> LENGTH: 234
<212> TYPE: PRT
<213> ORGANISM: Amborella trichopoda

<400> SEQUENCE: 67

Met Thr His Gln Ser Asn Gly Lys Glu Val Ser Leu Ile Phe Ala Asp
1               5                   10                  15

Glu Asp Pro Thr Arg Gly Ala Val Thr Ser Glu Ser Ser Ser Asp Gly
               20                  25                  30

Lys Leu Glu Lys Lys Ser Leu His Lys Thr Thr Phe Pro Asp Gly Phe
           35                  40                  45

Glu Ala Trp Val Ser Asp Ile Cys Asp Glu Thr Glu Val Ala Glu Leu
       50                  55                  60

Lys Leu Lys Val Gly Asp Phe Glu Met His Leu Arg Arg Asn Ile Gly
65                  70                  75                  80

Asn Thr Lys Ala Pro Ala Pro Ser Pro Ile Val Ser Pro Ser Thr Pro
               85                  90                  95

Pro Pro Val Pro Thr Lys Pro Met Val Glu Ser Ala Pro Ala Thr Ala
               100                 105                 110

Pro Ser Val Thr Gln Lys Ala Pro Pro Val Ala Ser Ser Pro Phe Ser
           115                 120                 125

Asn Val Ser Ala Lys Ala Ser Lys Leu Ala Ser Leu Asp Ser Asp Gly
       130                 135                 140

Ala Asn Ala Tyr Val Ile Val Ala Ser Pro Thr Val Gly Lys Phe Arg
```

```
                145                 150                 155                 160
            Thr Gly Arg Thr Val Lys Gly Lys Arg Gln Pro Val Ala Lys Glu
                            165                 170                 175

Gly Asp Val Ile Lys Glu Asp Gln Ile Ile Gly Tyr Leu Asp Gln Phe
                            180                 185                 190

Gly Ser Glu Leu Pro Val Lys Ser Asp Val Ala Gly Glu Val Leu Lys
                            195                 200                 205

Ile Leu Phe Arg Asp Gly Glu Ala Val Gly Tyr Gly Asp Pro Leu Ile
            210                 215                 220

Ala Val Leu Pro Ser Phe His Gly Ile Lys
            225                 230

<210> SEQ ID NO 68
<211> LENGTH: 297
<212> TYPE: PRT
<213> ORGANISM: Amborella trichopoda

<400> SEQUENCE: 68

Met Ile Arg Ser Tyr Leu Lys Ile Pro Phe Val Thr Glu Pro Ile Pro
1               5                   10                  15

Glu Ile Ala Arg Leu Ser Cys Ser Phe Gly Pro Leu Ala Lys Val Glu
            20                  25                  30

Leu Ser Thr Leu Asn Leu Pro Asn His Ser Thr Cys Lys Tyr Ile Gly
        35                  40                  45

Pro Pro Asp Leu Arg Met Met Arg Arg Cys Thr Gly Pro Gln Ser
    50                  55                  60

Leu His Tyr Glu Gly Phe Arg Met Gln Ser Arg Asn Leu Val Lys Pro
65                  70                  75                  80

Val Ser Leu Leu Ser Gly Pro Ser Ala Glu Ala Met Ser Thr Ser Asp
                85                  90                  95

Asp Gly Ser Lys Glu Asp Pro Lys Gly Lys Ser Ser Pro Ile Val Pro
            100                 105                 110

Asn Ser Leu Glu Val Gln Ser Leu Val Lys Glu Ile Cys Glu Thr Thr
        115                 120                 125

Ser Ile Ala Glu Phe Glu Leu Lys Leu Asp Gly Phe Arg Leu Tyr Val
    130                 135                 140

Ala Arg Asp Ile Asn Gly Lys Asp Met Pro Pro Thr Ser Pro Ser
145                 150                 155                 160

Ser Pro Ile His Thr Thr Asn Val Ala Glu Thr Leu Asp Ser
                165                 170                 175

Asn Gly Ser Ala Ser Pro Pro Thr Ile Ser Lys Pro Glu Pro Pro
            180                 185                 190

Leu Thr Arg Ile Gln Arg Leu Leu Glu Ala Ala Asp Glu Gly Leu
        195                 200                 205

Val Ile Ile Asn Ser Pro Lys Val Gly Tyr Phe Arg Arg Ala Arg Thr
    210                 215                 220

Val Lys Gly Lys Arg Gly Pro Ala Ala Cys Lys Glu Lys Gln Ile Val
225                 230                 235                 240

Lys Glu Gly Gln Val Ile Cys Tyr Val Glu Gln Leu Gly Gly Glu Val
                245                 250                 255

Pro Val Glu Ser Asp Val Ala Gly Glu Val Ile Lys Ile Leu Arg Glu
            260                 265                 270

Asp Gly Glu Pro Val Gly Tyr Gly Asp Pro Leu Ile Ala Ile Leu Pro
        275                 280                 285
```

```
Ser Phe Pro Gly Ile Lys Lys Leu Gln
    290                 295

<210> SEQ ID NO 69
<211> LENGTH: 290
<212> TYPE: PRT
<213> ORGANISM: Theobroma cacao

<400> SEQUENCE: 69

Met Glu Ser Ser Ala Ala Leu Arg Ser Phe His Tyr Ser Val Gly Ala
1               5                   10                  15

Val Ser Gln Ala His Cys Ser Leu Glu Arg Pro Ser Thr Val His Met
            20                  25                  30

Tyr Ser Cys Gly Leu Ala Thr Ser Arg Lys Ser Cys Val Pro Gly Leu
        35                  40                  45

Met Phe Gly Gly Lys Asn Asn Ser Ala Thr Lys Arg Asn Val Thr Leu
    50                  55                  60

Ile Ser Cys Met Lys Thr Pro Glu Ala Ser Val Thr Ala Lys Ser Asn
65                  70                  75                  80

Val Pro Leu Asp Ser Thr Ala Gln Gly Ser Met Glu Lys Lys Thr Ser
                85                  90                  95

Arg Asn Ala Thr Phe Pro Asn Gly Phe Glu Ala Leu Val Leu Glu Val
            100                 105                 110

Cys Asp Glu Thr Glu Val Ala Glu Leu Lys Met Lys Ile Gly Asp Phe
        115                 120                 125

Glu Met His Leu Lys Arg Asn Val Gly Ala Thr Lys Ala Pro Leu Ser
    130                 135                 140

Asn Ile Ser Pro Thr Thr Ala Pro Pro Ile Pro Thr Lys Pro Met Asn
145                 150                 155                 160

Glu Ser Ala Ala Val Ala Pro Pro Ser Pro Lys Pro Ser Pro
                165                 170                 175

Glu Lys Pro Thr Pro Phe Lys Asn Ala Ala Phe Gly Lys Ser Ser Lys
            180                 185                 190

Leu Ala Ala Leu Glu Ala Ser Gly Ser Ser Asn Tyr Val Leu Val Pro
        195                 200                 205

Ser Pro Ile Val Gly Thr Phe Arg Arg Gly Arg Thr Val Lys Gly Lys
    210                 215                 220

Lys Gln Pro Pro Ile Cys Lys Glu Gly Asp Leu Ile Lys Glu Gly Gln
225                 230                 235                 240

Val Ile Gly Phe Leu Asp Gln Phe Gly Thr Glu Leu Pro Val Lys Ser
                245                 250                 255

Asp Val Ala Gly Glu Val Leu Lys Leu Leu Phe Asp Asp Gly Asp Ala
            260                 265                 270

Val Gly Tyr Gly Asp Pro Leu Ile Ala Val Leu Pro Ser Phe His Gly
        275                 280                 285

Ile Glu
    290

<210> SEQ ID NO 70
<211> LENGTH: 274
<212> TYPE: PRT
<213> ORGANISM: Theobroma cacao

<400> SEQUENCE: 70

Met Ala Ser Cys Gly Ile Gly Ala Pro Asn Ile Lys Val Pro Lys Leu
1               5                   10                  15
```

```
Ser Phe Gly Lys Ala Arg Val Asp Lys Leu Lys Leu Asn Asn Val Arg
            20                  25                  30

Ile Trp Thr Arg Gln Arg Thr Met Gln Tyr Ala Gly Leu Val Arg His
        35                  40                  45

Ser Glu Lys Thr Phe Asn Ile Gly Cys Gly Pro Thr Leu Gln Thr Leu
 50                  55                  60

Ala Thr Thr Asn Leu Ala Asp Asp Phe Glu Glu Thr Lys Met Ser Gly
 65                  70                  75                  80

Leu Thr Ser Gln Leu Ile Pro Asn Ser Ser Gly Val Glu Ser Leu Val
                85                  90                  95

Arg Asp Ile Cys Asp Thr Thr Ser Val Ala Glu Phe Glu Leu Lys Leu
            100                 105                 110

Gly Gly Phe Arg Leu Tyr Ile Met Arg Asp Leu Ala Gly Lys Ser Glu
        115                 120                 125

Pro Pro Pro Ala Ile Pro Ser Pro Pro Val Ser Val Ser Thr Ser
130                 135                 140

Lys Thr Val Glu Ala Pro Asp Ser Asn Gly Ser Val Ser Thr Pro Thr
145                 150                 155                 160

Leu Ala Ile Thr Lys Pro Leu Ser Ser Ser Gly Arg Ile Gln Leu Leu
                165                 170                 175

Leu Asp Lys Ala Ala Asp Glu Gly Leu Val Ile Leu Gln Ser Pro Lys
            180                 185                 190

Val Gly Phe Phe Arg Arg Ser Arg Thr Ile Lys Gly Lys Arg Ala Pro
        195                 200                 205

Pro Ser Cys Lys Glu Lys Gln Thr Val Lys Glu Gly Gln Val Leu Cys
210                 215                 220

Tyr Ile Glu Gln Leu Gly Gly Glu Ile Pro Ile Glu Ser Asp Val Ser
225                 230                 235                 240

Gly Glu Val Ile Lys Ile Leu Arg Asp Asp Gly Asp Pro Val Gly Tyr
                245                 250                 255

Gly Asp Ala Leu Ile Ala Leu Leu Pro Ser Phe Pro Gly Ile Lys Lys
            260                 265                 270

Leu Gln

<210> SEQ ID NO 71
<211> LENGTH: 277
<212> TYPE: PRT
<213> ORGANISM: Phaseolus vulgaris

<400> SEQUENCE: 71

Met Ala Ser Cys Cys Leu Gly Thr Pro Lys Ile Lys Val Leu Asn Leu
1               5                   10                  15

Arg Phe Ser Gly Lys Asn Val Gly Leu Ser Gln Gln Val Gly Thr Arg
            20                  25                  30

Ser Trp Arg Arg Gln Ser Leu Gln Tyr Thr Ser Leu Val Met Ser Arg
        35                  40                  45

Gln Thr Asp Arg Phe Leu Ala Ser Ala Asn Ala Pro Ser Ser Glu Thr
 50                  55                  60

Gln Ile Ile Thr Arg Ser Glu Glu Gly Ser Glu Gly Thr Lys Ser Ser
65                  70                  75                  80

Val Leu Thr Ser Gln Leu Ile Pro Asn Phe Asn Glu Val Glu Phe Leu
                85                  90                  95

Val Thr Lys Leu Cys Asp Ser Ser Ile Gly Glu Ile Asp Leu Lys
            100                 105                 110
```

```
Leu Ala Gly Phe His Leu His Ile Val Arg Asp Leu Thr Glu Gln Asn
            115                 120                 125

Glu Thr Leu Pro Pro Pro Thr Pro Ile Pro Ala Ser Val Ser Val Asn
        130                 135                 140

Asp Val Glu Thr Pro Lys Thr Asn Gly Ser Val Ser Thr Thr Ser
145                 150                 155                 160

Leu Ala Ile Ser Asn Pro Leu Gly Gln Val Tyr Phe Pro Gly Ser Ile
                165                 170                 175

Gln Arg Phe Leu Asp Lys Ala Lys Asp Glu Gly Leu Val Ile Ile Pro
            180                 185                 190

Cys Pro Lys Val Gly Tyr Phe Arg Arg Ser Arg Thr Ile Lys Gly Lys
            195                 200                 205

Arg Ala Pro Pro Ser Cys Lys Glu Lys Gln Ile Val Glu Glu Gly Gln
210                 215                 220

Val Ile Cys Tyr Ile Glu Met Leu Gly Val Glu Val Ala Ile Glu Ala
225                 230                 235                 240

Asp Val Ser Gly Glu Ile Ile Lys Ile Leu Arg Lys Asp Gly Glu Pro
                245                 250                 255

Val Ala Tyr Gly Asp Ala Leu Ile Ala Ile Leu Pro Ser Phe Pro Gly
            260                 265                 270

Ile Lys Lys Leu Gln
            275

<210> SEQ ID NO 72
<211> LENGTH: 289
<212> TYPE: PRT
<213> ORGANISM: Phaseolus vulgaris

<400> SEQUENCE: 72

Met Glu Ser Ser Ala Ala Ile Arg Ser Phe His Tyr Pro Met Gly Thr
1               5                   10                  15

Met Ser His Met Arg Pro Ser Tyr Asp Lys Gln Val Val Val Pro Ile
            20                  25                  30

His Asn Val Arg Trp Asn Ser Lys Ser Arg Leu Phe Ile Gln His Leu
        35                  40                  45

Ala Tyr Asp Arg Lys His Ile Asn Ser His Met Lys Gly Ser Thr Thr
    50                  55                  60

Leu Val Ser Cys Ala Lys Thr Ala Glu Pro Ile Asn Thr Ser Asn Ser
65                  70                  75                  80

Asp Asp Ala Ser Pro Gly Ser Thr Pro Gln Gly Ser Leu Glu Lys Lys
                85                  90                  95

Pro Leu Gln Ala Ala Thr Phe Pro Asn Gly Phe Glu Asp Leu Val Leu
            100                 105                 110

Glu Val Cys Asp Glu Thr Glu Ile Ala Glu Leu Lys Val Lys Val Gly
            115                 120                 125

Asp Phe Glu Met His Ile Lys Arg Asn Ile Gly Ala Thr Thr Val Pro
        130                 135                 140

Leu Ser Asn Ile Ser Pro Thr Thr Pro Pro Ile Pro Ser Lys Pro
145                 150                 155                 160

Met Asp Ser Ala Pro Gly Thr Leu Pro Pro Ser Pro Lys Ser Ser
                165                 170                 175

Pro Glu Lys Lys Asn Pro Ile Ile Asp Ala Ser Arg Lys Lys Ser Pro
            180                 185                 190

Ile Leu Thr Ala Leu Glu Ala Ser Glu Ser Gly Thr Tyr Val Leu Ile
            195                 200                 205
```

```
Pro Ser Pro Thr Val Gly Phe Phe Arg Arg Gly Arg Thr Val Lys Gly
    210                 215                 220

Lys Arg Gln Pro Pro Ile Cys Lys Glu Gly Asp Phe Val Gln Glu Gly
225                 230                 235                 240

Gln Val Ile Gly Tyr Leu Asp Gln Leu Gly Ser Gly Asn Pro Val Lys
                245                 250                 255

Thr Asp Val Thr Gly Gln Val Leu Lys Leu Leu Val Glu Asp Gly Glu
                260                 265                 270

Pro Val Gly Tyr Gly Asp Pro Leu Ile Ala Val Phe Pro Leu Asp Leu
                275                 280                 285

Lys

<210> SEQ ID NO 73
<211> LENGTH: 275
<212> TYPE: PRT
<213> ORGANISM: Prunus persica

<400> SEQUENCE: 73

Met Ile Trp Val Ala Gly Ser Leu Gly Thr Leu Asn Ala Lys Ile Thr
1               5                   10                  15

Asn Leu Asn Phe Gly Arg Thr Arg Val Gly Ile Leu Gln Ser Ser Gly
                20                  25                  30

Leu Lys Pro Trp Thr Gly Gln Lys Pro Gln Leu Tyr Ser Cys Leu Ser
            35                  40                  45

Ile Ser Arg Arg Pro Asp Asn Val Leu Arg Ala His Ser Gly Pro Ser
        50                  55                  60

Leu Glu Thr Leu Pro Thr Thr Ser Leu Glu Asp Gly Pro Ala Glu Ser
65                  70                  75                  80

Arg Asp Ser Gly Ser Thr Asn Gln Leu Ile Pro Asn Phe Asp Glu Val
                85                  90                  95

Glu Ser Leu Val Thr Thr Ile Cys Asp Thr Thr Ser Val Ala Glu Phe
            100                 105                 110

Glu Leu Lys Ile Gly Gly Phe Arg Leu His Val Leu Arg Glu Leu Thr
        115                 120                 125

Glu Lys Ile Ser Thr Leu Pro Pro Ser Pro Ala Pro Val Ser Val
    130                 135                 140

Asn Ala Thr Ser Glu Ala Pro Ala Ser Asn Gly Ser Val Pro Thr Gln
145                 150                 155                 160

Ser Leu Ala Val Ile Arg Gln Glu His Ser Ser Arg Asn Ile Gln Thr
                165                 170                 175

Leu Leu Asp Arg Ala Ala Asp Asp Gly Leu Val Leu Ile His Ser Pro
            180                 185                 190

Arg Val Gly Leu Phe Arg Arg Ser Arg Thr Ile Lys Gly Lys Arg Ala
        195                 200                 205

Pro Pro Ser Cys Lys Glu Lys Gln Ile Val Lys Glu Gly Gln Val Ile
    210                 215                 220

Cys Tyr Ile Glu Gln Leu Gly Gly Glu Leu Pro Ile Glu Ser Asp Val
225                 230                 235                 240

Ser Gly Glu Val Ile Lys Ile Leu Arg Glu Asp Gly Asp Pro Val Gly
                245                 250                 255

Tyr Gly Asp Ala Leu Ile Ala Val Leu Pro Ser Phe Pro Gly Ile Lys
            260                 265                 270

Lys Leu Gln
    275
```

<210> SEQ ID NO 74
<211> LENGTH: 291
<212> TYPE: PRT
<213> ORGANISM: Prunus persica

<400> SEQUENCE: 74

Met Glu Ser Ser Ala Val Phe Arg Ser Phe Asn Cys Ser Val Gly Thr
1               5                   10                  15

Val Ser His Val Arg Ser Ser Leu Asp Lys Pro Gly Met Leu Pro Ala
            20                  25                  30

Tyr Asn Thr Ala Arg Pro Thr Val Ser Arg Ser Tyr Phe Gln Gly Leu
        35                  40                  45

Met Val Ser Glu Lys Phe Ile Tyr Ser Pro Gln Lys Arg Arg Gly Val
    50                  55                  60

Gln Val Ser Cys Val Lys Thr Ser Glu Ala Ala Lys Ser Glu Lys Ser
65                  70                  75                  80

Ser Asp Ser Lys Pro Gln Val Ser Glu Arg Thr Thr Gln Pro Ala
                85                  90                  95

Thr Phe Pro Asn Gly Phe Glu Ala Leu Met Leu Glu Val Cys Asp Glu
            100                 105                 110

Thr Glu Val Ala Glu Leu Lys Leu Lys Val Gly Asp Phe Glu Met His
        115                 120                 125

Leu Lys Arg Asn Ile Gly Ala Thr Ser Ala Pro Val Ser Ser Ile Ser
    130                 135                 140

Pro Ala Ala Ala Pro Pro Ile Pro Ser Lys Pro Met Val Glu Ser Ala
145                 150                 155                 160

Pro Ala Pro Pro Ala Pro Ala Pro Ala Pro Lys Ser Ser Ser Glu
                165                 170                 175

Lys Ala Thr Pro Phe Thr Asn Thr Ser Val Asp Lys Ser Ser Arg Leu
            180                 185                 190

Ala Ala Leu Glu Ala Ser Gly Ala Asn Gly Tyr Val Leu Val Ser Ser
        195                 200                 205

Pro Thr Val Gly Ser Phe Arg Arg Gly Arg Thr Val Lys Gly Lys Lys
    210                 215                 220

Gln Pro Pro Ile Cys Lys Glu Gly Asp Leu Ile Lys Gly Gln Val
225                 230                 235                 240

Ile Gly Tyr Val Asp Gln Phe Gly Thr Glu Leu Pro Val Lys Ser Asp
                245                 250                 255

Val Gly Gly Glu Val Leu Lys Leu Leu Phe Asn Asp Gly Glu Ala Val
            260                 265                 270

Gly Tyr Gly Asp Pro Leu Ile Ala Val Leu Pro Ser Phe His Gly Ile
        275                 280                 285

Asn Ile Asn
    290

<210> SEQ ID NO 75
<211> LENGTH: 292
<212> TYPE: PRT
<213> ORGANISM: Erythranthe guttata

<400> SEQUENCE: 75

Met Glu Ser Ala Ala Val Leu Arg Ser Phe Gln Tyr Ala Val Gly Ser
1               5                   10                  15

Ser Ser His Leu Lys Ser Gly Val Glu Arg Pro Ala Met Ile Thr Met
            20                  25                  30

```
Asn Asn Ala Ala Phe Tyr Asn Leu Ser Arg Leu Pro Val Phe Gly Gly
            35                  40                  45

Asn Thr Val Ser Ser Thr Asn Arg His Gly Ala Leu Leu Val Ser Cys
        50                  55                  60

Val Lys Thr Ser Glu Ala Thr Val Thr Ala Lys Ser Lys Gly Asp Pro
 65                  70                  75                  80

Asn Gly Ala Val Leu Ala Asp Ser Pro Gln Asn Gly Ser Pro Glu Lys
                85                  90                  95

Lys Ser Pro Ile Asn Ala Thr Phe Pro Asn Gly Phe Glu Asn Leu Leu
            100                 105                 110

Ser Glu Val Cys Asp Glu Thr Lys Ile Ala Glu Leu Lys Val Lys Ile
        115                 120                 125

Gly Gly Phe Glu Leu His Met Lys Arg Asn Ile Asp Gly Pro Ala Ile
    130                 135                 140

Ser Ala Pro Val Val Ser Gln Thr Thr Val Pro Ser Leu Pro Ser Lys
145                 150                 155                 160

Pro Ala Asn Glu Leu Ser Pro Ser Ala Pro Pro Pro Ser Lys Ser
                165                 170                 175

Ser Ala Glu Lys Val Asn Pro Phe Ala Asn Val Ser Val Glu Lys Ala
            180                 185                 190

Ala Lys Leu Ala Ala Leu Asp Ala Ser Gly Ser Ser Gly Tyr Val Ile
        195                 200                 205

Val Ser Ser Pro Thr Val Gly Ser Phe Arg Arg Ala Arg Thr Leu Lys
    210                 215                 220

Gly Lys Lys Gln Pro Ala Cys Lys Glu Gly Asp Leu Ile Lys Glu
225                 230                 235                 240

Gly Gln Val Ile Gly Tyr Leu Asp Gln Phe Gly Thr Glu Leu Pro Val
                245                 250                 255

Asn Ser Asp Val Ala Gly Glu Val Leu Lys Leu Leu Tyr Asn Asp Gly
            260                 265                 270

Glu Ala Val Gly Tyr Gly Asp Pro Leu Ile Ala Val Leu Pro Ser Phe
        275                 280                 285

His Gly Ile Arg
    290

<210> SEQ ID NO 76
<211> LENGTH: 273
<212> TYPE: PRT
<213> ORGANISM: Erythranthe guttata

<400> SEQUENCE: 76

Met Ala Ala Cys Gly Phe Gly Ala Ser Gly Ile Lys Ile Lys Ser Leu
1               5                   10                  15

Asp Phe Gly Ser Val Arg Pro Lys Leu Arg Thr Leu Gln Pro Leu His
            20                  25                  30

Gly Leu Lys Thr Pro Ser Ile Val Arg Phe Asp Gly Leu Val Leu Ser
        35                  40                  45

Asn Arg Ser Lys Lys Met Leu Ile Gly Cys Arg Ser Ser Ser Leu Glu
    50                  55                  60

Ser Asp Ser Asn Ala Ser Ile Glu Asp Ile Ser Lys Glu Thr Glu Ser
65                  70                  75                  80

Pro Glu Ala Val Ser Thr Leu Ile Pro Asn Ala Phe Glu Val Glu Ser
                85                  90                  95

Leu Leu Thr Val Leu Cys Asp Thr Thr Ser Ile Ala Glu Ile Glu Leu
```

```
            100                 105                 110
Lys Leu Gly Gly Phe Arg Leu Tyr Val Ser Arg Asp Leu Ala Glu Gln
        115                 120                 125

Asn Ala Pro Pro Gln Pro Ala Pro Ala His Val Ile Ala His Ser
    130                 135                 140

Val Val Glu Thr Pro Ser Ser Asn Gly Ser Ala Ser Ser Pro Ser Leu
145                 150                 155                 160

Ala Leu Ser Lys Pro Thr Ser Ser Ala Gly Ile Gln Thr Met Leu
                165                 170                 175

Asp Lys Ala Ala Asp Glu Gly Leu Val Ile Leu Gln Ser Pro Arg Val
                180                 185                 190

Gly Tyr Phe Lys Arg Cys Arg Thr Ile Lys Gly Lys Lys Ala Pro Pro
            195                 200                 205

Ser Cys Lys Glu Lys Asp Thr Val Lys Glu Gly Gln Val Leu Cys Phe
210                 215                 220

Ile Glu Gln Leu Gly Gly Glu Ile Pro Ile Glu Ser Asp Ile Ser Gly
225                 230                 235                 240

Glu Val Val Lys Ile Leu Arg Glu Asp Gly Ala Pro Val Gly Tyr Gly
                245                 250                 255

Asp Ala Leu Ile Ala Ile Leu Pro Ser Phe Pro Gly Ile Lys Lys Leu
                260                 265                 270

Gln
```

<210> SEQ ID NO 77
<211> LENGTH: 287
<212> TYPE: PRT
<213> ORGANISM: Eucalyptus grandis

<400> SEQUENCE: 77

```
Met Glu Ser Ser Val Ser Ala Leu Arg Ser Ser Leu His Ser Asn Ile
1               5                   10                  15

Ala Gly Ala Leu Pro Arg Val Glu Pro Leu Pro His Lys Pro Gly Val
                20                  25                  30

Val Pro Val Gln Ser Tyr Ser Pro Pro Ser Lys Lys Leu Tyr Val His
            35                  40                  45

Gly Phe Ala Ala Arg Gly Ile Ala Pro Ser Arg Thr Arg Asn Ala Ala
        50                  55                  60

Val Val Ser Cys Leu Lys Thr Ser Glu Ala Thr Gly Val Ala Lys Ser
65                  70                  75                  80

Ser Gly Asn Thr Arg Asp Ser Lys Asp Lys Thr Thr Leu Pro Arg Ala
                85                  90                  95

Thr Phe Pro Ser Ala Phe Glu Glu Leu Leu Leu Glu Val Cys Asp Glu
                100                 105                 110

Thr Gln Ile Ala Glu Leu Lys Leu Lys Ile Gly Asp Ile Glu Met Gln
            115                 120                 125

Val Lys Arg Asn Leu Gly Ala Thr Lys Glu Ala Phe Ala Ser Ile Pro
        130                 135                 140

Ser Pro Thr Thr Pro Pro Ile Pro Thr Glu Pro Met Glu Asn Ser
145                 150                 155                 160

Gly Ala Val Val Pro Pro Lys Pro Ser Pro Glu Lys Thr Ser Pro
                165                 170                 175

Phe Thr Asn Phe Ser Phe Gly Lys Ser Ser Lys Leu Ala Ala Leu Glu
                180                 185                 190

Ala Pro Gly Ser Ser Gly Tyr Val Leu Val Ser Ser Pro Thr Val Gly
```

```
                195                 200                 205
Ser Phe Arg Arg Gly Arg Thr Leu Lys Gly Lys Lys Gln Pro Pro Ser
210                 215                 220

Cys Lys Glu Gly Asp Val Ile Lys Glu Gly Gln Val Ile Gly Trp Leu
225                 230                 235                 240

Asp Gln Phe Gly Thr Glu Leu Pro Val Lys Ser Asp Val Ser Gly Glu
                245                 250                 255

Val Leu Lys Leu Leu Val Asn Asp Gly Glu Pro Val Gly Tyr Gly Asp
            260                 265                 270

Pro Leu Ile Ala Val Leu Pro Ala Phe His Ser Ile Asn Ile Met
            275                 280                 285

<210> SEQ ID NO 78
<211> LENGTH: 142
<212> TYPE: PRT
<213> ORGANISM: Eucalyptus grandis

<400> SEQUENCE: 78

Met Cys Ser Tyr Phe Ala Lys Pro Val Asn Lys Ser Ser Gly Val
1               5                   10                  15

Ser Pro Pro Ser Ala Leu Lys Pro Ser Ser Glu Lys Ala Ala Pro Phe
            20                  25                  30

Met Asn Val Thr Phe Gly Lys Ser Ala Lys Val Lys Ala Leu Glu Ala
            35                  40                  45

Ser Gly Ser Ser Gly Tyr Ala Leu Val Ser Ser Pro Thr Val Gly Ser
        50                  55                  60

Phe Gln Lys Gly Arg Thr Val Lys Gly Lys Gln Gly Pro Ser Cys
65                  70                  75                  80

Lys Glu Gly Asp Leu Ile Lys Glu Gly Gln Val Ile Gly Trp Leu Asp
                85                  90                  95

Gln Phe Gly Thr Glu Leu Pro Val Lys Ser Asp Val Ser Gly Glu Val
            100                 105                 110

Leu Lys Leu Leu Ile Asp Asp Gly Glu Ala Val Gly Tyr Gly Asp Pro
        115                 120                 125

Leu Leu Ala Val Leu Pro Ser Phe Pro Gly Val Gly Val Gln
    130                 135                 140

<210> SEQ ID NO 79
<211> LENGTH: 304
<212> TYPE: PRT
<213> ORGANISM: Helicosporidium sp.

<400> SEQUENCE: 79

Met Ser Ala Leu Ser Ser Ala Ala Leu Pro Ser Ile Gly Pro Cys Ile
1               5                   10                  15

Gly Gln Ala Leu Ser Ala Arg Asn Ala Val Val Ser Arg Val Val Ala
            20                  25                  30

Lys Arg Arg Glu Pro Ile Arg Ser Arg Glu His Leu Ser Lys Arg Ala
        35                  40                  45

Gly Ala Asn Cys Ala Ala Leu Ala Val Thr Glu Glu Glu Glu Glu Glu
    50                  55                  60

Ser Asp Asn Asn Trp Ser Met Pro Thr Pro Glu Asp Asp Pro Ala
65                  70                  75                  80

Glu Leu Ser Pro Lys Gln Val Glu Ala Leu Leu Ser Thr Leu Cys Asn
                85                  90                  95

Glu Thr Glu Ile Ala Glu Leu Lys Leu Asp Leu Gly Ser Asn Phe His
```

```
            100                 105                 110
Leu Lys Val Thr Arg Ala Phe Gln Asn Thr Thr Ala Val Ala Pro Pro
            115                 120                 125

Thr Thr Pro Ala Pro Ala Leu Pro Ser Ala Gln Ser Val Pro Phe Ala
            130                 135                 140

Asn Ser Gly Ala Ile Ser Ser Asp Asp Glu Ala Glu Glu Val Arg Leu
145                 150                 155                 160

Val Val Arg Ala Ser Lys Val Gly Lys Ile Arg Tyr Gly Lys Phe Val
                165                 170                 175

Lys Gly Lys Arg Val Ser Pro Glu Pro Thr Val Lys Val Gly Asp Gln
            180                 185                 190

Val Lys Lys Gly Gln Val Ile Cys Tyr Thr Glu Gln Leu Gly Thr Val
            195                 200                 205

Trp Pro Leu Glu Ala Pro Gln Ala Gly Glu Leu Arg Glu Phe Leu Val
            210                 215                 220

Lys Glu Gly Glu Ala Leu Glu Arg Ser Arg Ala Gln Leu Asn Ala Leu
225                 230                 235                 240

Lys Leu Lys Asp Gly Arg Ser Met Ser Ala Thr Glu Ile Arg Lys Ala
                245                 250                 255

Phe Ala Lys Arg Glu Thr Ser Ile Ala Gln Asn Leu Glu Ser Met Thr
                260                 265                 270

Leu Lys Ser Val Arg Gln Gln Leu Ala Asp Asp Met Gly Val Asp Pro
            275                 280                 285

Asp Ser Leu Lys Ala His Lys Asp Leu Ile Ala Ser Leu Val Asp Lys
            290                 295                 300

<210> SEQ ID NO 80
<211> LENGTH: 170
<212> TYPE: PRT
<213> ORGANISM: Citrus sinensis

<400> SEQUENCE: 80

Val Gly Asp Phe Glu Met His Leu Lys Arg Asn Val Gly Ala Pro Lys
1               5                   10                  15

Ala Pro Ala Pro Leu Ser Asn Ile Ser Pro Thr Thr Pro Pro Pro Ile
                20                  25                  30

Pro Thr Glu Pro Met Glu Val Ser Asp Pro Val Ser Pro Pro Pro
            35                  40                  45

Pro Ser Pro Pro Lys Pro Tyr Ser Glu Lys Ala Ala Pro Phe Ile Asn
50                  55                  60

His Ser Phe Gly Lys Ser Ser Lys Leu Ala Ala Leu Glu Ala Ser Gly
65                  70                  75                  80

Ser Asn Gly Tyr Val Leu Val Phe Ser Pro Thr Val Gly Ser Phe Arg
                85                  90                  95

Arg Asn Arg Thr Val Lys Gly Lys Lys Gln Ser Pro Ile Cys Lys Glu
            100                 105                 110

Gly Asp Val Ile Lys Glu Gly Gln Thr Ile Gly Tyr Leu Asp Gln Phe
            115                 120                 125

Gly Thr Glu Leu Pro Val Lys Ser Asp Val Ala Gly Glu Val Leu Lys
            130                 135                 140

Leu Leu Phe Asp Asp Gly Asp Ala Val Gly Phe Gly Asp Pro Leu Ile
145                 150                 155                 160

Ala Val Leu Pro Ser Phe His Asp Ile Lys
                165                 170
```

<210> SEQ ID NO 81
<211> LENGTH: 271
<212> TYPE: PRT
<213> ORGANISM: Citrus sinensis

<400> SEQUENCE: 81

Met Ala Ser Tyr Ser Leu Gly Ala Ser Asn Ile Lys Ile Pro Lys Gly
1               5                   10                  15

Asn Leu Gly Arg Ala Arg Val Gly Asp Leu Gln Pro Arg Ser Asp Val
            20                  25                  30

Arg Lys Trp Met Gly Arg Lys Pro Phe Gln Tyr Ala Gly Leu Ala Met
        35                  40                  45

Ser Gln Pro Leu Glu Lys Ala Phe Thr Val Phe Cys Gly Gln Ser Ser
    50                  55                  60

Glu Ala Glu Ser Thr Arg Asn Ala Arg Asp Gly His Glu Asp Met Lys
65                  70                  75                  80

Ser Thr Gln Leu Ile Pro Asp Ser Ser Glu Val Glu Ser Leu Val Thr
                85                  90                  95

Asp Ile Cys Asn Thr Thr Ser Val Ala Glu Phe Glu Leu Lys Leu Asp
            100                 105                 110

Gly Phe Arg Leu Tyr Val Thr Arg Asp Ile Ala Gly Asp Ser Ile Pro
        115                 120                 125

Pro Leu Pro Pro Ser Ser Pro Ala Pro Val Thr Val Asn Lys Pro Ala
    130                 135                 140

Asp Arg Pro Asp Ser Asn Gly Ser Val Pro Thr Ser Ser Leu Ala Ile
145                 150                 155                 160

Thr Lys Pro Val Ser Ser Ser Gly Gly Ile Gln Thr Leu Leu Asp Lys
                165                 170                 175

Ala Ala Asp Glu Gly Leu Val Ile Leu Glu Ser Pro Lys Val Gly Tyr
            180                 185                 190

Phe Arg Arg Ser Arg Thr Ile Lys Gly Lys Arg Ala Pro Pro Ser Cys
        195                 200                 205

Lys Glu Lys Gln Thr Val Arg Glu Gly Gln Val Leu Cys Tyr Ile Glu
    210                 215                 220

Gln Leu Gly Gly Glu Ile Pro Ile Glu Ser Asp Ile Ala Gly Glu Val
225                 230                 235                 240

Ile Lys Ile Leu Arg Lys Asp Gly Asp Pro Ile Gly Tyr Gly Asp Pro
                245                 250                 255

Leu Ile Val Ile Leu Pro Ser Phe Pro Gly Ile Lys Leu Leu Gln
            260                 265                 270

<210> SEQ ID NO 82
<211> LENGTH: 285
<212> TYPE: PRT
<213> ORGANISM: Jatropha curcas

<400> SEQUENCE: 82

Met Ala Ser Cys Ser Leu Gly Ala Ser Asn Ile Lys Leu Ser Lys Leu
1               5                   10                  15

Asn Phe Gly Arg Glu Arg Ala Gly Asn Ile Gln Gln Trp Ser Gly Met
            20                  25                  30

Arg Thr Ser Ile Gly Trp Arg Gln Leu Gln Tyr Thr Gly Leu Thr Val
        35                  40                  45

Ile Tyr Lys Pro Lys Glu Thr Phe Ser Val Arg Cys Cys Pro Thr Leu
    50                  55                  60

```
Glu Lys Glu Thr Ser Thr Asn Arg Val Asp Ser Ile Lys Gln Thr Lys
 65                  70                  75                  80

Ser Ser Gly Leu Thr Ser Gln Leu Ile Pro Asn Ser Ser Glu Ile Glu
                 85                  90                  95

Phe Leu Val Thr Glu Val Cys Asn Ala Thr Ser Ile Ala Glu Phe Glu
                100                 105                 110

Leu Lys Val Gly Gly Phe Trp Leu Tyr Leu Thr Arg Asn Leu Thr Gln
            115                 120                 125

Lys Ser Lys Pro Ser Pro Val Pro Thr Leu Ala Pro Leu Pro Pro Asp
        130                 135                 140

Pro Ala Pro Ala Pro Asp Pro Leu Thr Ala Asp Lys Thr Ile Lys Ala
145                 150                 155                 160

Pro Glu Leu Asn Gly Ser Val Ser Ser Thr Ser Phe Ala Ile Ser Lys
                165                 170                 175

Pro Ala Pro Phe Ser Gly Gly Ile Gln Ser Phe Leu Asp Lys Ala Val
                180                 185                 190

Asp Glu Gly Leu Met Ile Leu Gln Ser Pro Arg Val Gly Phe Phe Arg
            195                 200                 205

Arg Ser Arg Thr Ile Lys Gly Lys Arg Ala Pro Pro Ser Cys Lys Glu
        210                 215                 220

Lys Gln Ile Val Lys Glu Gly Gln Val Leu Cys Tyr Ile Glu Gln Leu
225                 230                 235                 240

Gly Gly Glu Leu Pro Ile Glu Ser Asp Val Ser Gly Glu Val Ile Lys
                245                 250                 255

Ile Leu Arg Glu Asp Gly Asp Pro Val Gly Tyr Gly Asp Ala Leu Ile
                260                 265                 270

Ala Ile Leu Pro Ser Phe Pro Gly Ile Lys Lys Leu Gln
            275                 280                 285

<210> SEQ ID NO 83
<211> LENGTH: 236
<212> TYPE: PRT
<213> ORGANISM: Jatropha curcas

<400> SEQUENCE: 83

Met Val Ser Ser Pro Val Lys Arg Asn Val Ala Leu Val Ser Cys Val
 1               5                  10                  15

Lys Ala Pro Glu Ala Ala Glu Thr Val Lys Ser Asp Ala Gly Gly Ala
                 20                  25                  30

Lys Gly Ser Leu Glu Asn Ser Asn Leu Arg Ser Ala Thr Phe Pro Asn
             35                  40                  45

Gly Phe Glu Ala Leu Val Leu Glu Val Cys Asp Glu Thr Glu Ile Ala
 50                  55                  60

Glu Leu Lys Leu Lys Val Gly Asp Phe Glu Met His Leu Arg Arg Asn
 65                  70                  75                  80

Val Gly Ala Ile Thr Ala Pro Leu Ser His Ile Ser Pro Thr Glu Pro
                 85                  90                  95

Pro Pro Ile Pro Thr Glu Pro Met Asn Val Ser Ala Pro Val Thr Pro
                100                 105                 110

Pro Pro Ala Pro Pro Lys Pro Ser Thr Glu Lys Ser Thr Pro Phe Lys
            115                 120                 125

Asn Val Ser Phe Gly Lys Ser Ser Lys Leu Ala Ala Leu Glu Ala Ser
        130                 135                 140

Gly Ala Thr Gly Tyr Val Leu Val Thr Ser Pro Thr Val Gly Ser Phe
145                 150                 155                 160
```

```
Arg Arg Asn Arg Thr Val Lys Gly Lys Arg Gln Pro Pro Ile Phe Lys
                165                 170                 175

Glu Gly Asp Leu Ile Lys Glu Gly Gln Val Ile Gly Tyr Leu Asp Gln
            180                 185                 190

Phe Gly Thr Glu Leu Pro Val Lys Ser Asp Val Ala Gly Glu Val Leu
        195                 200                 205

Lys Leu Leu Phe Asp Asp Gly Asp Ala Val Gly Tyr Gly Asp Pro Leu
    210                 215                 220

Ile Ala Val Leu Pro Ser Phe His Asp Ile Asn Lys
225                 230                 235
```

<210> SEQ ID NO 84
<211> LENGTH: 273
<212> TYPE: PRT
<213> ORGANISM: Prunus mume

<400> SEQUENCE: 84

```
Met Ala Ser Cys Ser Leu Gly Thr Leu Asn Ala Lys Ile Thr Asn Leu
1               5                   10                  15

Asn Phe Gly Arg Thr Arg Val Gly Ile Leu Gln Ser Ser Gly Leu Lys
            20                  25                  30

Thr Trp Thr Gly Gln Lys Pro Gln Leu Tyr Ser Cys Leu Ser Met Ser
        35                  40                  45

Arg Arg Pro Asp Lys Val Leu Arg Ala His Ser Gly Pro Ser Leu Glu
    50                  55                  60

Thr Leu Pro Thr Thr Ser Leu Glu Asp Gly Pro Ala Glu Ser Arg Asp
65                  70                  75                  80

Ser Gly Ser Thr Asn Gln Leu Ile Pro Asn Phe Asp Glu Val Glu Ser
                85                  90                  95

Leu Val Thr Thr Ile Cys Asp Thr Thr Ser Val Ala Glu Phe Glu Leu
            100                 105                 110

Lys Ile Gly Gly Phe Arg Leu His Val Leu Arg Glu Leu Thr Glu Lys
        115                 120                 125

Ile Ser Thr Leu Pro Pro Ser Pro Ala Pro Val Ser Val Asn Ala
130                 135                 140

Thr Ala Glu Ala Pro Ala Ser Asn Gly Thr Val Pro Thr Gln Ser Leu
145                 150                 155                 160

Ala Ile Ile Arg Gln Glu His Ser Ser Arg Asn Ile Gln Thr Leu Leu
                165                 170                 175

Asp Arg Ala Ala Asp Asp Gly Leu Val Leu Ile His Ser Pro Arg Val
            180                 185                 190

Gly Leu Phe Arg Arg Ser Arg Thr Ile Lys Gly Lys Arg Ala Pro Pro
        195                 200                 205

Ser Cys Lys Glu Lys Gln Ile Val Lys Glu Gly Gln Val Ile Cys Tyr
    210                 215                 220

Ile Glu Gln Leu Gly Gly Glu Leu Pro Ile Glu Ser Asp Val Ser Gly
225                 230                 235                 240

Glu Val Ile Lys Ile Leu Arg Glu Asp Gly Asp Pro Val Gly Tyr Gly
                245                 250                 255

Asp Ala Leu Ile Ala Val Leu Pro Ser Phe Pro Gly Ile Lys Lys Leu
            260                 265                 270

Gln
```

<210> SEQ ID NO 85

```
<211> LENGTH: 289
<212> TYPE: PRT
<213> ORGANISM: Prunus mume

<400> SEQUENCE: 85
```

Met Glu Ser Ser Ala Val Phe Arg Ser Phe Asn Cys Ser Val Gly Thr
1               5                   10                  15

Val Ser His Val Arg Ser Ser Leu Asp Lys Pro Gly Met Leu Ala Ala
            20                  25                  30

Tyr Asn Thr Ala Arg Pro Thr Val Ser Arg Ser Tyr Phe Gln Gly Leu
        35                  40                  45

Met Val Ser Glu Lys Phe Ile Tyr Ser Pro Gln Lys Arg Arg Gly Val
    50                  55                  60

Pro Val Ser Cys Val Lys Thr Ser Glu Ala Ala Lys Ser Glu Lys Ser
65                  70                  75                  80

Ser Asp Ser Lys Pro Gln Val Ser Ser Glu Arg Thr Thr Gln Pro Ala
                85                  90                  95

Thr Phe Pro Ser Gly Phe Glu Ala Leu Met Leu Glu Val Cys Asp Glu
            100                 105                 110

Thr Glu Val Ala Glu Leu Lys Leu Lys Val Gly Asp Phe Glu Met His
        115                 120                 125

Leu Lys Arg Asn Ile Gly Ala Thr Ser Ala Pro Val Ser Ser Ile Ser
130                 135                 140

Pro Ala Val Ala Pro Pro Ile Pro Ser Lys Pro Met Val Glu Ser Ala
145                 150                 155                 160

Ser Ala Pro Pro Pro Ala Pro Ala Pro Lys Ser Ser Ser Glu Lys Ala
                165                 170                 175

Thr Pro Phe Thr Asn Thr Ser Val Asp Lys Ser Ser Arg Leu Ala Ala
            180                 185                 190

Leu Glu Ala Ser Gly Ala Asn Gly Tyr Val Leu Val Ser Ser Pro Thr
        195                 200                 205

Val Gly Ser Phe Arg Arg Gly Arg Thr Val Lys Gly Lys Lys Gln Pro
    210                 215                 220

Pro Ile Cys Lys Glu Gly Asp Leu Ile Lys Gly Gly Gln Val Val Gly
225                 230                 235                 240

Tyr Val Asp Gln Phe Gly Thr Glu Leu Pro Val Lys Ser Asp Val Gly
                245                 250                 255

Gly Glu Val Leu Lys Leu Leu Phe Asn Asp Gly Glu Ala Val Gly Tyr
            260                 265                 270

Gly Asp Pro Leu Ile Ala Val Leu Pro Ser Phe His Gly Ile Asn Ile
        275                 280                 285

Lys

```
<210> SEQ ID NO 86
<211> LENGTH: 277
<212> TYPE: PRT
<213> ORGANISM: Medicago truncatula

<400> SEQUENCE: 86
```

Met Ala Ser Ser His Cys Ser Leu Gly Thr Gln Asn Val Lys Val Leu
1               5                   10                  15

Asn Leu His Phe Gly Gln Glu Arg Ala Glu Phe Ser Gln His Phe Gly
            20                  25                  30

Thr Arg Ser Trp Ile Ser Arg Lys Ser Leu Gln Tyr Ala Arg Leu Val
        35                  40                  45

Ala Ser Lys Gln Thr Val Arg Ser Leu Thr Pro Ser Asn Asp Gln Ser
    50                  55                  60

Ala Glu Ile Gln Ser Val Ser Arg Ser Glu Asp Gly Ser Glu Glu Ser
65                  70                  75                  80

Lys Ser Ser Gly Leu Thr Asn Gln Leu Phe Pro Asn Phe Asn Asp Val
                85                  90                  95

Glu Phe Leu Leu Thr Asn Leu Cys Asp Thr Ala Ser Ile Gly Glu Leu
            100                 105                 110

Glu Leu Lys Leu Asp Gly Phe His Leu Arg Val Val Arg Asp Leu Thr
        115                 120                 125

Glu Lys Ser Lys Thr Leu Pro Pro Ser Ile Pro Ala Pro Val Ser Ile
    130                 135                 140

Asn Thr Pro Ala Glu Ala Pro Lys Pro Asn Gly Ser Val Ser Thr Leu
145                 150                 155                 160

Thr Thr Leu Ala Ile Ser Lys Pro Ala Pro Ser Ser Leu Ser Ile Glu
                165                 170                 175

Gly Phe Leu Glu Lys Ala Ala Asp Glu Gly Leu Val Ile Ile His Ser
            180                 185                 190

Pro Thr Val Gly Ile Phe Arg Arg Ser Arg Thr Ile Lys Gly Lys Arg
        195                 200                 205

Ala Pro Pro Ser Cys Gln Glu Met Gln Asn Val Glu Glu Gly Lys Val
    210                 215                 220

Ile Cys Tyr Ile Glu Gln Leu Gly Gly Gln Leu Pro Val Glu Ser Asp
225                 230                 235                 240

Val Ser Gly Glu Val Ile Lys Ile Leu Arg Glu Asp Gly Asp Pro Val
                245                 250                 255

Gly Tyr Gly Asp Thr Leu Ile Ala Ile Leu Pro Ser Phe Pro Gly Ile
            260                 265                 270

Lys Lys Leu Gln Tyr
        275

<210> SEQ ID NO 87
<211> LENGTH: 278
<212> TYPE: PRT
<213> ORGANISM: Cucumis melo

<400> SEQUENCE: 87

Met Glu Ser Ser Ala Ser Leu Arg Ser Phe His Tyr Phe Ala Gly Gly
1               5                   10                  15

Ser Arg Leu Gln Leu Val Asp Lys Pro Ser Lys Ile Tyr Val Ala Ser
                20                  25                  30

Thr Asn Lys Ser Ser Ile Gln Arg Leu Ser Ile Phe Gly Lys Pro Ile
            35                  40                  45

His Ser Pro Thr Ser Gln Lys Lys Ile Val Val Ser Cys Ile Lys Thr
        50                  55                  60

Pro Glu Val Ser Glu Ala Ala Lys Pro Lys Asp Ser Ala Gln Gly Ser
65                  70                  75                  80

Leu Gln Lys Lys Pro Ala Ser Asn Ala Thr Phe Pro Asn Gly Phe Glu
                85                  90                  95

Ala Leu Val Leu Glu Val Cys Asp Glu Thr Glu Ile Ala Glu Leu Lys
            100                 105                 110

Leu Lys Val Gly Glu Phe Glu Met His Leu Lys Arg Asn Ile Gly Val
        115                 120                 125

Val Arg Ala Pro Leu Ser Ser Ile Ser Pro Thr Val Pro Pro Pro Ile
    130                 135                 140

```
Pro Ser Lys Pro Met Val Glu Ser Ala Pro Thr Ala Pro Ala Pro Pro
145                 150                 155                 160

Lys Pro Ser Pro Glu Lys Ala Ala Ala Phe Thr Asn Ile Pro Leu Gln
            165                 170                 175

Lys Ser Ser Lys Leu Ala Ala Leu Glu Ser Ser Gly Ala Lys Gly Tyr
        180                 185                 190

Val Leu Val Pro Ser Pro Thr Val Gly Ser Phe Arg Ser Gly Arg Thr
            195                 200                 205

Ile Lys Gly Lys Lys Gln Pro Pro Ile Cys Lys Glu Asn Asp Leu Ile
        210                 215                 220

Lys Glu Gly Gln Val Ile Gly Tyr Val Asp Gln Phe Gly Thr Glu Leu
225                 230                 235                 240

Pro Val Lys Ser Asp Val Ala Gly Glu Val Leu Arg Val Leu Phe Lys
            245                 250                 255

Asp Gly Glu Ala Val Gly Tyr Gly Asp Pro Leu Ile Ala Val Leu Pro
            260                 265                 270

Glu Phe His Gly Ile Arg
        275

<210> SEQ ID NO 88
<211> LENGTH: 403
<212> TYPE: PRT
<213> ORGANISM: Cucumis melo

<400> SEQUENCE: 88

Met Ile Phe Phe Gln Asn Ser Phe Gly Lys Lys Leu Val Lys Leu Glu
1               5                   10                  15

Arg Asn Lys Ser Leu Thr Arg Leu Leu Gly Pro Thr Val His Leu Asn
            20                  25                  30

Gln Lys Arg Phe Glu Phe Leu Trp Gly Phe Ile Phe Phe Pro Val Phe
        35                  40                  45

Val Asn Glu Leu Lys Arg Val Ser Val Arg Leu Phe Gln Ser Pro
    50                  55                  60

Phe Cys Leu Gln Asn Leu Leu Phe Leu Ser Trp Asn Phe Ala His His
65                  70                  75                  80

Gln Asn Ser Ser Pro Phe Ser Ser Cys Leu Arg Arg Asn Gln Arg Gly
            85                  90                  95

Phe Leu Phe Leu Ile Leu Tyr Phe Cys Ser Val Gly Pro Tyr Ser Glu
        100                 105                 110

Leu Leu Cys Pro Ser His Ser Ala Arg Ser Phe Phe Phe Ser Thr Met
    115                 120                 125

Ala Ser Cys Ser Leu Arg Ala Val Asp Ile Lys Val Ser Lys Leu Asp
130                 135                 140

Ile Arg Arg Gly Arg Val Ser Thr Leu Gln Pro Cys Ser Leu Arg Asn
145                 150                 155                 160

Trp Ile Gly Arg Thr Pro His Gln Tyr Ser Thr Leu Val Ile Ser His
            165                 170                 175

Ser Ser Gln Lys Ala Leu His Ala Cys Ser Ser Ala Ser Pro Glu Thr
        180                 185                 190

Gln Thr Val Ile Lys Ser Glu Thr Gly Ser Glu Ile Lys Pro Ser
    195                 200                 205

Asn Leu Val Ser Gln Leu Ile Pro Asn Leu His Glu Val Glu Thr Leu
210                 215                 220

Leu Thr Asn Ile Cys Asp Thr Ser Ser Ile Ala Glu Phe Glu Leu Lys
```

-continued

```
            225                 230                 235                 240
        Leu Ser Gly Phe Asn Leu Arg Met Val Arg Ser Leu Lys Ser Glu Asn
                            245                 250                 255
        Leu Pro Leu Pro Pro Ala Pro Ala Pro Ala Pro Asp Ile Gln Asn Thr
                        260                 265                 270
        Ser Ser Ile Pro Ser Asp Ser Asn Gly Leu Val Lys Thr Ser Leu Ala
                    275                 280                 285
        Leu Val Lys Pro Glu Pro Val Ser Ser Pro Glu Gly Ile Ser Arg
                290                 295                 300
        Tyr Val Glu Lys Ala Thr Asp Gly Gly Leu Ser Ile Leu Val Ser Pro
        305                 310                 315                 320
        Lys Val Gly Val Phe Arg Arg Ser Arg Thr Ile Lys Gly Lys Arg Ala
                        325                 330                 335
        Pro Pro Ser Cys Glu Glu Asn Gln Val Val Lys Glu Gly Lys Val Leu
                    340                 345                 350
        Cys Tyr Ile Asp Gln Leu Gly Ala Glu Ile Pro Ile Glu Ser Asp Ile
                355                 360                 365
        Ser Gly Glu Ile Val Lys Ile Leu Arg Lys Asp Gly Glu Pro Val Gly
            370                 375                 380
        Tyr Gly Asp Pro Leu Ile Ala Val Leu Pro Ser Phe Pro Gly Ile Lys
        385                 390                 395                 400
        Lys Leu Leu

<210> SEQ ID NO 89
<211> LENGTH: 282
<212> TYPE: PRT
<213> ORGANISM: Coffea canephora

<400> SEQUENCE: 89

Met Glu Ser Ala Ala Val Leu Arg Ser Phe His Cys Ile Thr Ser Pro
1               5                   10                  15
Leu Lys Ser Ile Ile Asp Lys Pro Gly Ala Val Pro Met Thr Thr Val
                20                  25                  30
Gly Phe Ser Gly Leu Ala Lys Cys His Ile Gln Gly Leu Ala Tyr Asn
            35                  40                  45
Gly Lys Leu Ile Ser Ser Thr Ser Lys Met Gly Gly Val Ile Val Ser
        50                  55                  60
Cys Val Lys Thr Ser Glu Val Pro Val Thr Ala Lys Ser Asp Asp Ser
65                  70                  75                  80
Ser Gln Lys Glu Ser Gly Pro Lys Asn Ser Ile Arg Arg Ala Thr Phe
                85                  90                  95
Pro Asn Gly Phe Lys Ala Leu Leu Thr Glu Val Cys Asp Asp Thr Glu
            100                 105                 110
Ile Ala Glu Leu Arg Val Lys Val Gly Asp Phe Glu Met His Leu Lys
        115                 120                 125
Arg Asn Ile Gln Pro Pro Ile Ala Pro Ala Pro Val Glu Ser Pro Thr
    130                 135                 140
Val Ala Pro Pro Ile Pro Ser Glu Pro Met Asn Gln Ser Val Pro Pro
145                 150                 155                 160
Pro Ala Pro Pro Lys Pro Ala Thr Glu Lys Met Ser Pro Phe Thr Asn
                165                 170                 175
Val Pro Ala Glu Lys Ser Ala Lys Leu Ala Ala Leu Glu Ala Ser Gly
            180                 185                 190
Ala Ser Gly Tyr Val Leu Ala Ala Ser Pro Thr Val Gly Ser Phe Arg
```

```
                195                 200                 205
Arg Gly Arg Thr Leu Lys Gly Lys Arg Gln Pro Pro Ile Leu Lys Glu
            210                 215                 220
Gly Asp Leu Ile Lys Glu Gly Gln Thr Ile Gly Tyr Leu Asp Gln Phe
225                 230                 235                 240
Gly Thr Glu Leu Pro Val Lys Ser Asp Val Ala Gly Glu Val Leu Lys
                245                 250                 255
Ile Leu Tyr Asn Asp Gly Glu Ala Val Gly Tyr Gly Asp Pro Leu Ile
            260                 265                 270
Ala Val Leu Pro Ser Phe His Gly Ile Lys
            275                 280

<210> SEQ ID NO 90
<211> LENGTH: 272
<212> TYPE: PRT
<213> ORGANISM: Coffea canephora

<400> SEQUENCE: 90

Met Ala Ala Cys Gly Phe Gly Ala Ser Gly Leu Glu Ile Ser Ser Leu
1               5                   10                  15
Asn Leu Gly Ser Ala Arg Pro Lys Phe Ser Ala Leu Gln Pro Leu Asn
            20                  25                  30
Gly Phe Pro Val Gly Ile Leu Lys Phe Asn Gln Phe Asp Gly Leu Glu
        35                  40                  45
Ile Val Ser Ala Arg Ser Arg Arg Ala Val Ala Gly Cys Lys Phe Ser
    50                  55                  60
Ala Ser Glu Ala Ile Leu Thr Ile Thr Ala Lys Thr Asp Asp Ser Pro
65                  70                  75                  80
Glu Gly Ile Arg Ser Ser Asn Gly Ala Ser Lys Leu Ile Leu Asn Ser
                85                  90                  95
Phe Glu Val Glu Ser Leu Ile Lys Glu Val Cys Asp Thr Thr Ser Ile
            100                 105                 110
Ala Glu Leu Glu Leu Lys Leu Gly Gly Phe Arg Leu Tyr Val Met Arg
        115                 120                 125
Asn Leu Ala Val Pro Thr Pro Ala Ser Ala Pro Ile Ser Val Asn Thr
    130                 135                 140
Ala Ile Asp Val Pro Asn Glu Asn Gly Ser Ser Ser Thr Ser Leu
145                 150                 155                 160
Ala Ile Ser Lys Ser Glu Pro Ser Pro Ser Asp Ile Gln Thr Ser Leu
                165                 170                 175
Val Lys Ala Ala Asp Glu Gly Leu Val Met Leu Gln Ser Pro Arg Val
            180                 185                 190
Gly Phe Phe Arg Arg Ser Arg Thr Ile Lys Gly Lys Arg Ala Pro Pro
        195                 200                 205
Ser Cys Lys Lys Lys Gln Gln Val Lys Glu Gly Gln Val Leu Cys Phe
    210                 215                 220
Ile Glu Gln Leu Gly Gly Glu Ile Pro Ile Glu Ser Asp Val Ser Gly
225                 230                 235                 240
Glu Val Val Lys Ile Leu Arg Glu Asp Gly Glu Pro Val Gly Tyr Gly
                245                 250                 255
Asp Ala Leu Ile Ala Ile Leu Pro Ser Phe Pro Gly Ile Lys Asn Leu
            260                 265                 270

<210> SEQ ID NO 91
<211> LENGTH: 290
```

<212> TYPE: PRT
<213> ORGANISM: Phoenix dactylifera

<400> SEQUENCE: 91

```
Met Ala Thr Cys Gly Leu Gly Ser Thr Ser Asn Val Lys Leu Leu Ser
1               5                   10                  15

Phe Tyr Pro Asp Phe Lys Lys Leu Arg Ser Thr Ala Leu Leu Thr Pro
            20                  25                  30

His Asn Leu Lys Cys Gly Gly Leu Glu Thr Leu Asn Gly Ser Lys Gly
        35                  40                  45

Thr Gln Ile Trp Lys Glu Pro Val His Ala Ala Gly Phe Asp Lys Gln
    50                  55                  60

Ala Gln Arg Phe Ser Asn Ser Leu Val Ala Arg Cys Cys Ile Ser Pro
65                  70                  75                  80

Gly Thr Glu Asn Asp Ser Lys Val Ile Glu Leu Glu Asn Lys Ser
                85                  90                  95

Asn Gly Asp Gln Ile Ile Pro Val Ser Leu Glu Val Glu Pro Leu Leu
                100                 105                 110

Thr Ala Val Cys Asp Thr Thr Ser Ile Ala Glu Phe Lys Leu Asp Phe
            115                 120                 125

Ala Gly Phe Arg Leu Tyr Val Lys Arg Asp Leu Val Glu Lys Asn Val
        130                 135                 140

Pro Pro Pro Ile Pro Thr Leu Pro Pro Thr Gln Thr Asn Thr Thr Asn
145                 150                 155                 160

Gln Thr Thr Asp Ser Asn Gly Ser Ala Ala Thr Ala Ser Leu Ala Ile
                165                 170                 175

Ser Lys Pro Lys Pro Ser Thr Gly Gly Ile Gln Arg Thr Ala Ser Asp
            180                 185                 190

Glu Gly Leu Met Met Leu Pro Ser Pro Lys Val Gly Phe Phe Arg Arg
        195                 200                 205

Ser Arg Thr Ile Lys Gly Lys Gln Ala Pro Pro Ser Cys Lys Glu Gly
    210                 215                 220

Gln Asp Val Arg Glu Asp Gln Val Leu Cys Tyr Ile Glu Gln Leu Gly
225                 230                 235                 240

Gly Glu Val Pro Val Glu Ser Asp Val Ser Gly Glu Val Ile Lys Ile
                245                 250                 255

Leu Arg Glu Asp Gly Pro Val Gly Tyr Gly Asp Ala Ile Ile Ala
                260                 265                 270

Ile Leu Pro Ser Phe Pro Gly Ile Lys Lys Leu Gln Gln Ala Gly Ser
            275                 280                 285

Phe Pro
290
```

<210> SEQ ID NO 92
<211> LENGTH: 268
<212> TYPE: PRT
<213> ORGANISM: Phoenix dactylifera

<400> SEQUENCE: 92

```
Met Ala Thr Cys Gly Leu Gly Ser Thr Ser Asn Val Lys Leu Leu Ser
1               5                   10                  15

Phe Tyr Pro Asp Phe Lys Lys Leu Arg Ser Thr Ala Leu Leu Thr Pro
            20                  25                  30

His Asn Leu Lys Cys Gly Gly Leu Glu Thr Leu Asn Gly Ser Lys Gly
        35                  40                  45
```

```
Thr Gln Ile Trp Lys Glu Pro Val His Ala Ala Gly Phe Asp Lys Gln
    50                  55                  60

Ala Gln Arg Phe Ser Asn Ser Leu Val Ala Arg Cys Cys Ile Ser Pro
 65                 70                  75                  80

Gly Thr Glu Asn Asp Ser Lys Val Ile Glu Leu Glu Glu Asn Lys Ser
                85                  90                  95

Asn Gly Asp Gln Ile Ile Pro Val Ser Leu Glu Val Glu Pro Leu Leu
            100                 105                 110

Thr Ala Val Cys Asp Thr Thr Ser Ile Ala Glu Phe Lys Leu Asp Phe
            115                 120                 125

Ala Gly Phe Arg Leu Tyr Val Lys Arg Asp Leu Val Glu Lys Asn Val
        130                 135                 140

Pro Pro Pro Ile Pro Thr Leu Pro Pro Thr Gln Thr Asn Thr Thr Asn
145                 150                 155                 160

Gln Thr Thr Asp Ser Asn Gly Ser Ala Ala Thr Ala Ser Leu Ala Ile
                165                 170                 175

Ser Lys Pro Lys Pro Ser Thr Gly Gly Ile Gln Arg Thr Ala Ser Asp
            180                 185                 190

Glu Gly Leu Met Met Leu Pro Ser Pro Lys Val Gly Phe Phe Arg Arg
        195                 200                 205

Ser Arg Thr Ile Lys Gly Lys Gln Ala Pro Pro Ser Cys Lys Glu Gly
    210                 215                 220

Gln Asp Val Arg Glu Asp Gln Val Leu Cys Tyr Ile Glu Gln Leu Gly
225                 230                 235                 240

Gly Glu Val Pro Val Glu Ser Asp Val Ser Gly Glu Val Ile Lys Ile
                245                 250                 255

Leu Arg Glu Asp Gly Gly Lys Asp Ala Arg Asn Gln
            260                 265

<210> SEQ ID NO 93
<211> LENGTH: 284
<212> TYPE: PRT
<213> ORGANISM: Phoenix dactylifera

<400> SEQUENCE: 93

Met Glu Ala Ala Ala Val Leu Arg Ser Phe Arg Gly Gly Val Arg Thr
 1               5                  10                  15

Lys Gln Pro Ser Glu Ser Phe Leu Glu Lys Pro Ala Val Ala His Val
                20                  25                  30

Ser Asn Val Ser Asn Val Ala Leu Lys Thr Pro Phe Ser Gly Gly Phe
            35                  40                  45

Met Val Ala Gln Gly Trp Asn Arg Thr Phe Leu Pro Tyr Leu Lys Ala
 50                  55                  60

Ser Lys Thr Asn Ser Val Leu Thr Ser Glu Asp Arg Ser Ser Gln Glu
 65                  70                  75                  80

Pro Leu Glu Lys Ile Ser Val Gln Asn Ser Thr Phe Pro Ile Gly Phe
                85                  90                  95

Glu Ala Leu Ile Leu Glu Val Cys Asp Glu Thr Asn Ile Ala Glu Phe
            100                 105                 110

Lys Ile Lys Ile Gly Asp Phe Glu Met His Leu Lys Arg Asp Ile Glu
        115                 120                 125

Ser Pro Arg Ala Pro Ser Pro Gly Thr His Ile Val Ser Pro Thr Thr
    130                 135                 140

Ala Pro Pro Ile Pro Ser Gln Pro Met Asn Glu Ser Gly Ala Ala Ala
145                 150                 155                 160
```

```
Gln Pro Val Val Ser Gln Lys Ser Pro Thr Ala Ala Thr Ser Pro Phe
                165                 170                 175

Ala Asn Ile Ser Ser Ala Lys Ala Ser Lys Leu Val Ala Leu Glu Ala
            180                 185                 190

Ser Ala Ser Asn Ala Tyr Val Leu Val Ser Ser Pro Thr Val Gly Thr
        195                 200                 205

Phe Gln Arg Gly Arg Thr Leu Lys Gly Lys Lys Gln Pro Pro Ser Cys
    210                 215                 220

Lys Glu Gly Asp Val Ile Lys Glu Gly Gln Ile Ile Gly Phe Leu Asp
225                 230                 235                 240

Gln Phe Gly Asn Glu Leu Pro Val Lys Ser Asp Val Ala Gly Glu Val
                245                 250                 255

Val Lys Val Leu Cys Gln Asp Gly Glu Ala Val Gly Tyr Gly Asp Pro
            260                 265                 270

Leu Val Ala Val Leu Pro Ser Phe His Gly Ile Glu
        275                 280

<210> SEQ ID NO 94
<211> LENGTH: 296
<212> TYPE: PRT
<213> ORGANISM: Phoenix dactylifera

<400> SEQUENCE: 94

Met Glu Ser Ala Val Val Leu Arg Ser Phe Gln Gly Ser Leu Gln Pro
1               5                   10                  15

Thr Pro Tyr Ala His Ser Phe Leu Arg Lys Pro Ala Ala Val His Ile
            20                  25                  30

Cys Arg Ala Ala Ser Lys Lys Ser Ser Phe Trp Arg Leu His Val Glu
        35                  40                  45

Gly Trp Arg Asn Phe Ser Thr Met Ala Lys Lys Arg Pro Ser Leu Leu
    50                  55                  60

Ser Val Lys Ala Ser Glu Thr Thr Ser Ala Met Thr Ala Asp Ala Met
65                  70                  75                  80

Ser Leu Asp Ala Ala Asp Glu Ser Leu Gln Gly Ala Ile Gln Lys Ile
                85                  90                  95

Asn Ala Gln Asn Ser Thr Phe Pro Asn Gly Phe Glu Thr Phe Val Leu
            100                 105                 110

Glu Val Cys Asp Glu Thr Asn Val Ala Glu Leu Lys Leu Lys Val Gly
        115                 120                 125

Asp Phe Glu Met His Leu Lys Arg Gly Ile Glu Thr Pro Lys Val Pro
    130                 135                 140

Thr Ser Ile Ala Pro Pro Ile Glu Ser Pro Thr Thr Ala Pro Pro Ile
145                 150                 155                 160

Pro Ser Lys Pro Met Val Glu Ser Ala Pro Ala Pro Pro Ala Val
                165                 170                 175

Ser Gln Lys Ser Asp Pro Thr Ala Ile Ser Pro Phe Thr Asn Val Ser
            180                 185                 190

Thr Ala Ala Lys Ser Lys Leu Ala Ala Leu Glu Ala Ser Gly Ser Asn
        195                 200                 205

Ala Tyr Val Leu Val Ser Ser Pro Thr Val Gly Ser Phe Arg Ser Gly
    210                 215                 220

Arg Thr Leu Lys Gly Lys Lys Gln Pro Pro Ser Cys Lys Glu Gly Asp
225                 230                 235                 240

Ile Ile Lys Asp Gly Gln Ile Ile Gly Phe Leu Asp Gln Phe Gly Asn
```

```
                245                 250                 255
Glu Leu Pro Val Arg Ser Asp Val Glu Gly Glu Val Leu Lys Val Leu
            260                 265                 270

Leu Lys Asp Gly Glu Val Val Gly Tyr Gly Asp Pro Leu Val Ala Val
            275                 280                 285

Leu Pro Ser Phe His Gly Ile Lys
290                 295

<210> SEQ ID NO 95
<211> LENGTH: 285
<212> TYPE: PRT
<213> ORGANISM: Phoenix dactylifera

<400> SEQUENCE: 95

Met Ala Thr Cys Ser Gln Gly Ser Thr Ser Asn Ile Thr Leu Phe Asn
1               5                   10                  15

Phe His Pro Glu Phe Gln Lys Leu Arg Cys Thr Ala Leu Phe Thr Pro
            20                  25                  30

Arg Arg Thr Lys Ser Gly Arg Leu Glu Ala Leu Asn Gly Ser Lys Gly
        35                  40                  45

Thr Gln Ile Trp Gln Glu Pro Val His Ala Ala Gly Phe Asp Lys Gln
    50                  55                  60

Ala Gln Arg Leu Thr Asn Ser Leu Ala Ala Arg Cys Cys Leu Ser Ser
65                  70                  75                  80

Gly Ile Ala Glu Asn Asp Ser Asp Ala Ile Met Leu Glu Glu Asn Lys
                85                  90                  95

Ser Lys Val Asp Gln Ile Ile Pro Val Ser Leu Glu Val Glu Pro Leu
            100                 105                 110

Leu Thr Ala Ile Cys Asp Thr Ser Ser Ile Ser Glu Phe Lys Leu Asp
        115                 120                 125

Leu Ala Gly Phe His Leu Tyr Val Lys Arg Asp Leu Val Glu Glu Asn
    130                 135                 140

Val Pro Pro Val Pro Ile Leu Pro Pro Ala Gln Thr Asn Thr Thr
145                 150                 155                 160

Asn Gln Thr Ala Asp Ser Asn Gly Ser Ala Ala Thr Ala Ser Leu Ala
                165                 170                 175

Ile Ser Lys Pro Lys Pro Ser Ala Gly Gly Ile Gln Arg Thr Ala Ser
            180                 185                 190

Asp Glu Gly Leu Val Met Leu Pro Ser Pro Asn Val Gly Phe Phe Arg
        195                 200                 205

Thr Ser Arg Thr Ile Lys Gly Lys Arg Ala Pro Pro Leu Cys Lys Glu
    210                 215                 220

Lys Gln Glu Val Lys Glu Gly Gln Ile Leu Cys Cys Ile Glu Gln Leu
225                 230                 235                 240

Gly Gly Glu Ile Pro Val Glu Ser Asp Val Ser Gly Glu Ile Val Lys
                245                 250                 255

Ile Leu Arg Lys Asp Gly Glu Pro Val Gly Tyr Gly Asp Ala Leu Ile
            260                 265                 270

Ala Ile Leu Pro Ser Phe Pro Gly Ile Lys Lys Leu Gln
        275                 280                 285

<210> SEQ ID NO 96
<211> LENGTH: 277
<212> TYPE: PRT
<213> ORGANISM: Arabis alpina
```

<400> SEQUENCE: 96

Met Ala Ser Ser Ala Thr Leu Gly Ser Leu His Gln Thr Leu Gly Ser
1               5                   10                  15

Val Ser Lys Val His Ser Ile Ser Gly Asn Trp Ser Ala Ser Gly Asn
            20                  25                  30

Ser Cys Leu Pro Arg Trp Arg Leu Cys Asn Lys Asn Arg Asn Ser Met
        35                  40                  45

Phe Val Leu Ser Thr Lys Ala Ser Lys Ser Ser Thr Thr Thr Lys Ser
    50                  55                  60

Asp Asp Ser Ser Asp Thr Ser Val Ser Asn Gly Lys Asn Ala Val Arg
65                  70                  75                  80

Arg Ile Thr Phe Pro Lys Glu Val Glu Ala Leu Val His Glu Met Cys
                85                  90                  95

Asp Glu Thr Glu Val Ala Val Leu Gln Leu Lys Val Gly Asp Phe Glu
            100                 105                 110

Met Asn Leu Lys Arg Lys Ile Gly Gln Ala Ala Asn His Ile Pro Val
        115                 120                 125

Asp Asp Ile Ser Pro Thr Ile Ala Pro Pro Ile Pro Ser Glu Pro Met
    130                 135                 140

Asn Lys Ser Val Ser Ala Ala Pro Thr Pro Ser Gln Thr Lys Ala Ser
145                 150                 155                 160

Ser Glu Arg Val Ser Pro Phe Ile Asn Thr Ser Tyr Arg Lys Ser Ser
                165                 170                 175

Thr Leu Ala Ala Leu Glu Ala Ser Gly Ile Asn Asn Tyr Val Leu Val
            180                 185                 190

Thr Ser Pro Ser Val Gly Lys Phe Glu Arg Ser Arg Thr Val Lys Gly
        195                 200                 205

Lys Lys Gln Pro Pro Ser Cys Lys Glu Gly Asp Ala Ile Lys Glu Gly
    210                 215                 220

Gln Val Ile Gly Tyr Leu His Gln Leu Gly Thr Glu Leu Pro Val Thr
225                 230                 235                 240

Ser Asp Val Ala Gly Glu Val Leu Lys Leu Leu Ser Asn Asp Gly Asp
                245                 250                 255

Ser Val Gly Tyr Gly Glu Pro Leu Val Ala Val Leu Pro Ser Phe His
            260                 265                 270

Asp Ile Asn Ile Gln
        275

<210> SEQ ID NO 97
<211> LENGTH: 263
<212> TYPE: PRT
<213> ORGANISM: Arabis alpina

<400> SEQUENCE: 97

Met Ala Ser Cys Ser Leu Gly Val Pro Lys Ile Lys Ile Ser Ala Val
1               5                   10                  15

Asp Leu Ser Ile Val Arg Ser Val Ser Leu Gln Ile Pro Cys Ser Gln
            20                  25                  30

Arg Ser Leu Val Lys Gln Arg Pro Val Lys Tyr Leu Ser Leu Arg Thr
        35                  40                  45

Ser Leu Gly Ser Val Arg Ala Val Gln Val Ser Thr Val Pro Ala Ala
    50                  55                  60

Glu Ala Ser Ala Thr Val Glu Ile Glu Asp Ser Glu Glu Thr Lys Ser
65                  70                  75                  80

```
Tyr Pro Leu Asn Ala Gln Leu Val Pro Lys Pro Ser Glu Val Glu Ala
            85                  90                  95

Leu Val Thr Glu Ile Cys Asp Ser Ser Ile Ala Glu Phe Glu Leu
            100                 105                 110

Lys Leu Gly Gly Phe Arg Leu Tyr Val Ala Arg Asp Leu Ala Asp Lys
            115                 120                 125

Ser Ser Pro Gln Pro Gln Pro Ile Ser Ala Ala Val Thr Val Asn Ala
130                 135                 140

Thr Thr Glu Ser Ser Asp Ser Asn Gly Ser Ala Ser Ser Thr Ser Leu
145                 150                 155                 160

Ala Ile Ile Lys Pro Ala Ser Ser Ala Ala Asp Gln Gly Leu Met Ile
            165                 170                 175

Leu Gln Ser Pro Lys Val Gly Phe Phe Arg Arg Ser Lys Thr Ile Lys
            180                 185                 190

Gly Lys Arg Thr Pro Ser Ser Cys Lys Glu Lys Asp Gln Val Lys Glu
            195                 200                 205

Gly Gln Val Leu Cys Tyr Ile Glu Gln Leu Gly Gly Gln Phe Pro Ile
            210                 215                 220

Glu Ser Asp Val Thr Gly Glu Val Val Lys Ile Leu Arg Glu Asp Gly
225                 230                 235                 240

Glu Pro Val Gly Tyr Asn Asp Ala Leu Ile Ser Ile Leu Pro Ser Phe
            245                 250                 255

Pro Gly Ile Lys Lys Leu Gln
            260

<210> SEQ ID NO 98
<211> LENGTH: 254
<212> TYPE: PRT
<213> ORGANISM: Brassica napus

<400> SEQUENCE: 98

Met Ala Ser Cys Ser Leu Gly Val Pro Lys Ile Lys Ile Ser Ala Val
1               5                   10                  15

Asp Leu Ser Arg Val Arg Ser Gly Ser Leu Gln Ile Pro Cys Asn Gln
            20                  25                  30

Arg Val Leu Ile Gly Gln Arg Pro Val Lys Tyr Leu Ser Leu Arg Ala
            35                  40                  45

Thr Leu Gly Ser Val Lys Ala Pro Gln Ala Ser Thr Val Thr Ala Ala
            50                  55                  60

Glu Ser Ala Ala Thr Val Glu Val Glu Asp Ala Glu Met Thr Lys Pro
65                  70                  75                  80

Ser Pro Leu Asn Ala Gln Leu Val Pro Lys Pro Ser Glu Val Glu Ala
            85                  90                  95

Leu Val Thr Glu Ile Cys Asp Ser Ser Ile Ala Glu Phe Glu Leu
            100                 105                 110

Lys Leu Gly Gly Phe Arg Leu Tyr Val Ala Thr Asn Leu Ala Asp Asn
            115                 120                 125

Asn Ser Ser Pro Pro Gln Pro Gln Pro Ile Pro Ala Ala Val Ala Ala
130                 135                 140

Ser Ala Thr Thr Glu Gly Val Asp Ser Asn Gly Ser Ala Ser Ser Thr
145                 150                 155                 160

Ser Leu Ala Ile Thr Lys Pro Thr Ser Ala Ala Asp Gln Gly Leu
            165                 170                 175

Val Ile Leu Gln Ser Pro Lys Val Gly Phe Phe Arg Arg Ser Lys Thr
            180                 185                 190
```

```
Ile Lys Gly Lys Arg Thr Pro Ser Ser Cys Lys Glu Lys Asp Gln Val
    195                 200                 205

Lys Glu Gly Gln Val Leu Cys Tyr Ile Glu Gln Leu Gly Gly Gln Phe
210                 215                 220

Pro Ile Glu Ser Asp Val Thr Gly Glu Val Lys Ile Leu Arg Glu
225                 230                 235                 240

Asp Gly Gly Lys Ser Phe Phe Leu Leu Phe Phe Asn Leu Ser
                245                 250
```

<210> SEQ ID NO 99
<211> LENGTH: 270
<212> TYPE: PRT
<213> ORGANISM: Brassica napus

<400> SEQUENCE: 99

```
Met Glu Ser Ser Ala Ala Leu Gly Ser Leu Arg Gln Ser Leu Gly Ser
1               5                   10                  15

Ala Val Asn Val His Ser Leu Ser Gly Asn Trp Ser Pro Ser Gly Asn
                20                  25                  30

Ser Cys Ala Pro Arg Trp Ser Leu Phe Asn Arg Asn Met Leu Val Leu
            35                  40                  45

Arg Ala Asp Ser Ser Lys Ser Ser Thr Thr Thr Lys Thr Asp Glu
50                  55                  60

Ser Ser Asp Ala Ser Asn Gly Thr Lys Thr Lys Thr Val Arg Arg Thr
65                  70                  75                  80

Thr Phe Pro Lys Glu Val Glu Ala Leu Val His Glu Met Cys Asp Glu
                85                  90                  95

Thr Glu Val Gly Asp Phe Glu Met Asn Leu Lys Arg Lys Ile Gly Leu
                100                 105                 110

Ala Glu Thr Pro Ile Pro Val Pro Asp Ile Ser Pro Ser Val Ala Pro
            115                 120                 125

Pro Ile Pro Ser Glu Pro Met Asn Lys Ser Val Ser Ala Ser Ala Asp
    130                 135                 140

Ala Ser Pro Ser Lys Ala Lys Pro Ala Ser Glu Lys Val Ser Pro Phe
145                 150                 155                 160

Ile Asn Ala Ala Tyr Arg Lys Ser Ser Lys Leu Ala Ala Leu Glu Ala
                165                 170                 175

Ala Gly Ser Asn Asn Tyr Val Leu Val Thr Ser Pro Ser Val Gly Lys
                180                 185                 190

Phe Gln Arg Ser Arg Thr Val Lys Gly Lys Lys Gln Gly Pro Thr Cys
            195                 200                 205

Lys Glu Gly Asp Ala Ile Lys Glu Gly Gln Val Ile Gly Tyr Leu His
    210                 215                 220

Gln Leu Gly Lys Glu Leu Pro Val Thr Ser Asp Val Ala Gly Glu Val
225                 230                 235                 240

Leu Lys Leu Leu Ser Asp Asp Gly Asp Ser Val Gly Tyr Gly Glu Pro
                245                 250                 255

Leu Val Ala Val Leu Pro Ser Phe His Asp Ile Asn Ile Gln
                260                 265                 270
```

<210> SEQ ID NO 100
<211> LENGTH: 254
<212> TYPE: PRT
<213> ORGANISM: Brassica napus

<400> SEQUENCE: 100

```
Met Ala Ser Cys Ser Leu Gly Val Pro Lys Ile Lys Ile Ser Ala Val
1               5                   10                  15

Asp Val Ser Arg Val Arg Ser Gly Gly Leu Gln Ile Pro Tyr Ser Gln
            20                  25                  30

Arg Ser Leu Phe Val Gln Arg Gln Val Lys Tyr Leu Ser Leu Arg Thr
        35                  40                  45

Ser Val Gly Ser Leu Lys Ala Leu Gln Val Ser Thr Val Thr Ala Ala
    50                  55                  60

Glu Thr Ala Ala Ser Ala Glu Val Glu Asp Ala Glu Thr Lys Ser
65                  70                  75                  80

Ser Pro Leu Asn Ala Gln Leu Val Pro Lys Pro Ser Glu Val Glu Ala
                85                  90                  95

Leu Val Thr Glu Ile Cys Asp Ser Ser Ser Ile Ala Glu Phe Glu Leu
            100                 105                 110

Lys Leu Gly Gly Phe Arg Leu Tyr Val Ala Arg Asn Leu Ala Asp Asn
        115                 120                 125

Asn Ile Ser Pro Pro Gln Pro Gln Pro Ile Pro Ala Ala Phe Ser Ala
130                 135                 140

Ala Asn Glu Ser Ala Gly Ser Asn Gly Ser Ala Ser Ser Thr Ser Leu
145                 150                 155                 160

Ala Ile Thr Lys Pro Ala Ser Ser Ala Ala Asp Gln Gly Leu Ile Ile
                165                 170                 175

Leu Gln Ser Pro Lys Val Gly Phe Phe Arg Arg Ser Lys Thr Ile Lys
            180                 185                 190

Gly Lys Arg Thr Pro Ser Ser Cys Lys Glu Lys Asp Gln Val Lys Glu
        195                 200                 205

Gly Gln Val Leu Cys Tyr Ile Glu Gln Leu Gly Gly Gln Phe Pro Ile
210                 215                 220

Glu Ser Asp Val Thr Gly Glu Val Val Lys Ile Leu Arg Glu Asp Gly
225                 230                 235                 240

Gly Lys Ser Phe Phe Phe Asn Leu Phe Met Phe Phe Ser
            245                 250

<210> SEQ ID NO 101
<211> LENGTH: 249
<212> TYPE: PRT
<213> ORGANISM: Brassica napus

<400> SEQUENCE: 101

Met Ala Ser Cys Ser Leu Gly Val Pro Lys Ile Lys Ile Ser Ala Val
1               5                   10                  15

Asp Val Ser Arg Val Arg Ser Gly Arg Leu Gln Ile Pro Tyr Ser Gln
            20                  25                  30

Arg Ser Leu Phe Ala Gln Arg Gln Val Lys Tyr Leu Ser Leu Arg Thr
        35                  40                  45

Ser Val Gly Ser Leu Lys Ala Leu Gln Val Ser Thr Val Thr Ala Val
    50                  55                  60

Glu Thr Ser Ala Thr Val Glu Val Glu Asp Ala Glu Lys Thr Lys Ser
65                  70                  75                  80

Ser Pro Leu Asn Ala Gln Leu Val Pro Lys Pro Ser Glu Val Glu Ala
                85                  90                  95

Leu Val Thr Glu Ile Cys Asp Ser Ser Ser Ile Ala Glu Phe Glu Leu
            100                 105                 110

Lys Leu Gly Gly Phe Arg Leu Tyr Val Ala Arg Asn Leu Ala Asp Asn
```

```
            115                 120                 125
Asn Ile Ser Pro Pro Gln Pro Gln Pro Thr Pro Ala Ala Leu Ser Ala
        130                 135                 140
Asn Ala Val Thr Glu Ser Ala Asp Ser Asn Gly Ser Ala Ser Ser Thr
145                 150                 155                 160
Ser Leu Ala Ile Thr Lys Pro Ala Ser Ser Ala Ala Asp Gln Gly Leu
                165                 170                 175
Ile Ile Leu Gln Ser Pro Lys Val Gly Phe Phe Arg Arg Ser Lys Thr
            180                 185                 190
Ile Lys Gly Lys Arg Thr Pro Ser Ser Cys Lys Glu Lys Asp Gln Val
        195                 200                 205
Lys Glu Gly Gln Val Leu Cys Tyr Ile Glu Gln Leu Gly Gly Gln Phe
    210                 215                 220
Pro Ile Glu Ser Asp Val Thr Gly Glu Val Val Lys Ile Leu Arg Glu
225                 230                 235                 240
Asp Gly Gly Lys Ser Tyr Leu Leu Leu
                245

<210> SEQ ID NO 102
<211> LENGTH: 253
<212> TYPE: PRT
<213> ORGANISM: Brassica napus

<400> SEQUENCE: 102

Met Ala Ser Cys Ser Leu Ala Val Pro Lys Ile Lys Ile Ser Ala Ala
1               5                   10                  15
Val Asp Leu Ser Leu Val Arg Ser Gly Arg Phe Gln Ile Pro Cys Asn
            20                  25                  30
Gln Arg Val Leu Leu Ile Gly Gln Arg Pro Val Lys Tyr Leu Ser Leu
        35                  40                  45
Arg Ala Thr Leu Gly Ser Val Gln Ala Ser Thr Val Thr Ala Ala Glu
    50                  55                  60
Ser Ala Ala Thr Val Glu Val Glu Asp Thr Glu Thr Thr Lys Pro Ser
65                  70                  75                  80
Pro Leu Asn Ala Gln Leu Val Pro Lys Pro Ser Glu Val Glu Ala Leu
                85                  90                  95
Val Thr Glu Ile Cys Asp Ser Ser Ile Ala Glu Phe Glu Leu Lys
            100                 105                 110
Leu Gly Gly Phe Arg Leu Tyr Val Ala Arg Asn Leu Ala Asp Asn Asn
        115                 120                 125
Ser Ser Pro Pro Gln Pro Gln Pro Ile Pro Ala Ala Val Ala Ala Ser
    130                 135                 140
Ala Thr Thr Glu Ser Val Asp Ser Asn Gly Ser Ala Ser Ser Thr Ser
145                 150                 155                 160
Leu Ala Ile Thr Lys Pro Thr Ser Ser Ala Ala Asp Gln Gly Leu Val
                165                 170                 175
Ile Leu Gln Ser Pro Lys Val Gly Phe Phe Arg Arg Ser Lys Thr Ile
            180                 185                 190
Lys Gly Lys Arg Thr Pro Ser Ser Cys Lys Glu Lys Asp Gln Val Lys
        195                 200                 205
Glu Gly Gln Val Leu Cys Tyr Ile Glu Gln Leu Gly Gly Gln Phe Pro
    210                 215                 220
Ile Glu Ser Asp Val Thr Gly Glu Val Val Lys Ile Leu Arg Glu Asp
225                 230                 235                 240
```

```
Gly Gly Lys Ser Phe Phe Leu Leu Phe Phe Asn Leu Ser
                245                 250

<210> SEQ ID NO 103
<211> LENGTH: 258
<212> TYPE: PRT
<213> ORGANISM: Brassica napus

<400> SEQUENCE: 103

Met Glu Ser Leu Gly Ser Leu His Gln Ser Leu Gly Ser Ala Val Asn
1               5                   10                  15

Val His Ser Leu Ser Gly Lys Ser Cys Ala Pro Pro Arg Trp Ser Leu
            20                  25                  30

Phe Asn Arg Asn Thr Leu Val Leu Arg Ala Glu Ser Ser Lys Ser Ser
        35                  40                  45

Thr Thr Thr Lys Thr Asp Glu Ser Ser Asp Ala Ser Asn Gly Thr Lys
    50                  55                  60

Thr Val Arg Arg Thr Thr Phe Pro Lys Glu Val Glu Ala Leu Val His
65                  70                  75                  80

Glu Met Cys Asp Glu Thr Val Gly Asp Phe Glu Met Asn Leu Lys
                85                  90                  95

Arg Lys Ile Gly Leu Ala Glu Thr Pro Ile Pro Val Pro Asp Ile Ser
                100                 105                 110

Pro Ser Val Ala Pro Ile Pro Ser Glu Pro Met Asn Lys Ser Val
            115                 120                 125

Ser Ser Ser Ala Ala Ala Thr Ser Pro Ser Lys Ala Lys Pro Ala
        130                 135                 140

Val Ser Pro Phe Ile Asn Ala Ala Tyr Arg Lys Ser Ser Lys Leu Ala
145                 150                 155                 160

Ala Leu Asp Ala Ser Gly Ser Asn Asn Tyr Val Leu Val Thr Ser Pro
                165                 170                 175

Ser Val Gly Lys Phe Gln Arg Ser Arg Thr Val Lys Gly Lys Lys Gln
            180                 185                 190

Gly Pro Thr Cys Lys Glu Gly Asp Ala Ile Lys Glu Gly Gln Val Ile
        195                 200                 205

Gly Tyr Leu His Gln Leu Gly Lys Glu Leu Pro Val Thr Ser Asp Val
    210                 215                 220

Ala Gly Glu Val Leu Lys Leu Leu Ser Asp Asp Gly Asp Ser Val Gly
225                 230                 235                 240

Tyr Gly Glu Pro Leu Val Ala Val Leu Pro Ser Phe His Asp Ile Asn
                245                 250                 255

Ile Gln

<210> SEQ ID NO 104
<211> LENGTH: 237
<212> TYPE: PRT
<213> ORGANISM: Auxenochlorella prototheocoides

<400> SEQUENCE: 104

Met Ala Phe Arg Ala Ser Ala Met Arg Ala Ala Arg Pro Gln Gly Leu
1               5                   10                  15

Arg Leu His Ala Thr Arg Met Ala Glu Ile Ser Pro Ser Ser Ser
            20                  25                  30

Gly Lys Gly Gly Ala Lys Pro Lys Ser Lys Lys Glu Glu Glu Ser Asp
        35                  40                  45

Ser Glu Ser Glu Asp Glu Phe Phe Asp Glu Asp Gly Glu Gly Leu Asp
```

```
            50                  55                  60
Pro Gln Gln Val Glu Ser Leu Leu Ala Thr Leu Cys Glu Gly Thr Asp
 65                  70                  75                  80

Leu Ala His Leu Glu Leu Lys Leu Pro Gly Phe Gln Leu Arg Val Arg
                 85                  90                  95

Arg Ser Leu Ser Lys Ala Ala Ser Pro Ala Ala Ala Ala Ala Ala Pro
            100                 105                 110

Val Ala Ala Pro Ala Pro Val Pro Ala Pro Ala Pro Ala Pro Ala Thr
            115                 120                 125

Pro Pro Pro Val Ala Ser Ala Asp Glu Ala Asp Glu Ser Arg Leu Ala
130                 135                 140

Val Val Ala Thr Lys Val Gly Val Phe Arg Arg Gly Arg Tyr Val Lys
145                 150                 155                 160

Gly Lys Arg Val Gly Lys Gly Pro Leu Ala Ala Ala Gly Asp Ser Val
                165                 170                 175

Lys Lys Gly Gln Val Leu Ala Phe Val Glu Gln Leu Gly Thr His Trp
            180                 185                 190

Pro Val Glu Ala Pro Gln Ser Gly Glu Leu Glu Gly Phe Leu Leu Glu
            195                 200                 205

Asp Gly Asp Pro Val Glu Tyr Asn Gln Thr Val Leu Glu Leu Thr Pro
210                 215                 220

Phe Phe Gly Gly His Ile Ile Gly Asp Lys Lys Tyr Arg
225                 230                 235

<210> SEQ ID NO 105
<211> LENGTH: 265
<212> TYPE: PRT
<213> ORGANISM: Brassica rapa

<400> SEQUENCE: 105

Met Ala Ser Cys Ser Leu Gly Val Pro Lys Ile Lys Ile Ser Ala Val
  1               5                  10                  15

Asp Val Ser Arg Val Arg Ser Gly Arg Leu Gln Ile Pro Tyr Ser Gln
                 20                  25                  30

Arg Ser Leu Phe Ala Gln Arg Gln Val Lys Tyr Leu Ser Leu Arg Thr
             35                  40                  45

Ser Val Gly Ser Leu Lys Ala Leu Gln Val Ser Thr Val Thr Ala Val
 50                  55                  60

Glu Thr Ser Ala Thr Val Glu Val Glu Asp Ala Glu Lys Thr Lys Ser
 65                  70                  75                  80

Ser Pro Leu Asn Ala Gln Leu Val Pro Lys Pro Ser Glu Val Glu Ala
                 85                  90                  95

Leu Val Thr Glu Ile Cys Asp Ser Ser Ser Ile Ala Glu Phe Glu Leu
            100                 105                 110

Lys Leu Gly Gly Phe Arg Leu Tyr Val Ala Arg Asn Leu Ala Asp Asn
            115                 120                 125

Asn Ile Ser Pro Pro Gln Pro Gln Pro Thr Pro Ala Ala Leu Ser Ala
130                 135                 140

Asn Ala Val Thr Glu Ser Ala Asp Ser Asn Gly Ser Ala Ser Ser Thr
145                 150                 155                 160

Ser Leu Ala Ile Thr Lys Pro Ala Ser Ala Ala Asp Gln Gly Leu
                 165                 170                 175

Ile Ile Leu Gln Ser Pro Lys Val Gly Phe Phe Arg Arg Ser Lys Thr
            180                 185                 190
```

```
Ile Lys Gly Lys Arg Thr Pro Ser Ser Cys Lys Glu Lys Asp Gln Val
            195                 200                 205

Lys Glu Gly Gln Val Leu Cys Tyr Ile Glu Gln Leu Gly Gly Gln Phe
210                 215                 220

Pro Ile Glu Ser Asp Val Thr Gly Glu Val Val Lys Ile Leu Arg Glu
225                 230                 235                 240

Asp Gly Glu Pro Val Gly Tyr Asn Asp Ala Leu Ile Ser Ile Leu Pro
                245                 250                 255

Ser Phe Pro Gly Ile Lys Lys Leu Gln
            260                 265

<210> SEQ ID NO 106
<211> LENGTH: 264
<212> TYPE: PRT
<213> ORGANISM: Brassica rapa

<400> SEQUENCE: 106

Met Ala Ser Cys Ser Leu Gly Val Pro Lys Ile Lys Ile Ser Ala Ala
1               5                   10                  15

Val Asp Leu Ser Leu Val Arg Ser Gly Arg Phe Gln Ile Pro Cys Asn
            20                  25                  30

Gln Arg Val Leu Leu Ile Gly Gln Arg Pro Val Lys Tyr Leu Ser Leu
        35                  40                  45

Arg Ala Thr Leu Gly Ser Val Gln Ala Ser Thr Val Thr Ala Ala Glu
    50                  55                  60

Ser Ala Ala Thr Val Glu Val Glu Asp Thr Glu Thr Thr Lys Pro Ser
65                  70                  75                  80

Pro Leu Asn Ala Gln Leu Val Pro Lys Pro Ser Glu Val Glu Ala Leu
                85                  90                  95

Val Thr Glu Ile Cys Asp Ser Ser Ile Ala Glu Phe Glu Leu Lys
            100                 105                 110

Leu Gly Gly Phe Arg Leu Tyr Val Ala Arg Asn Leu Ala Asp Asn Asn
        115                 120                 125

Ser Ser Pro Pro Gln Pro Gln Pro Ile Pro Ala Ala Val Ala Ala Ser
    130                 135                 140

Ala Thr Thr Glu Ser Val Asp Ser Asn Gly Ser Ala Ser Ser Thr Ser
145                 150                 155                 160

Leu Ala Ile Thr Lys Pro Thr Ser Ala Ala Asp Gln Gly Leu Val
                165                 170                 175

Ile Leu Gln Ser Pro Lys Val Gly Phe Phe Arg Arg Ser Lys Thr Ile
        180                 185                 190

Lys Gly Lys Arg Thr Pro Ser Ser Cys Lys Glu Lys Asp Gln Val Lys
    195                 200                 205

Glu Gly Gln Val Leu Cys Tyr Ile Glu Gln Leu Gly Gly Gln Phe Pro
210                 215                 220

Ile Glu Ser Asp Val Thr Gly Glu Val Val Lys Ile Leu Arg Glu Asp
225                 230                 235                 240

Gly Glu Pro Val Gly Tyr Asn Asp Ala Leu Ile Ser Ile Leu Pro Ser
                245                 250                 255

Phe Pro Gly Ile Lys Lys Leu Gln
            260

<210> SEQ ID NO 107
<211> LENGTH: 277
<212> TYPE: PRT
<213> ORGANISM: Brassica rapa
```

<400> SEQUENCE: 107

Met Glu Ser Ser Ala Ala Leu Gly Ser Leu Arg Gln Ser Leu Gly Ser
1               5                   10                  15

Ala Val Asn Val His Ser Leu Ser Gly Asn Trp Ser Pro Ser Gly Asn
            20                  25                  30

Ser Cys Val Pro Arg Trp Ser Leu Phe Asn Arg Asn Met Leu Val Leu
        35                  40                  45

Arg Ala Asp Ser Ser Lys Ser Ser Thr Thr Thr Lys Thr Asp Glu
    50                  55                  60

Ser Ser Asp Ala Ser Asn Gly Thr Lys Thr Lys Thr Val Arg Arg Thr
65                  70                  75                  80

Thr Phe Pro Lys Glu Val Glu Ala Leu Val His Glu Met Cys Asp Glu
                85                  90                  95

Thr Glu Val Ala Val Leu Lys Leu Lys Val Gly Asp Phe Glu Met Asn
            100                 105                 110

Leu Lys Arg Lys Ile Gly Leu Ala Glu Thr Pro Ile Pro Val Pro Asp
        115                 120                 125

Ile Ser Pro Ser Val Ala Pro Pro Ile Pro Ser Glu Pro Met Asn Lys
130                 135                 140

Ser Val Ser Ala Ser Ala Asp Ala Ser Pro Ser Lys Ala Lys Pro Ala
145                 150                 155                 160

Ser Glu Lys Val Ser Pro Phe Ile Asn Ala Ala Tyr Arg Lys Ser Ser
                165                 170                 175

Lys Leu Ala Ala Leu Glu Ala Ala Gly Ser Asn Asn Tyr Val Leu Val
            180                 185                 190

Thr Ser Pro Ser Val Gly Lys Phe Gln Arg Ser Arg Thr Val Lys Gly
        195                 200                 205

Lys Lys Gln Gly Pro Thr Cys Lys Glu Gly Asp Ala Ile Lys Glu Gly
210                 215                 220

Gln Val Ile Gly Tyr Leu His Gln Leu Gly Lys Glu Leu Pro Val Thr
225                 230                 235                 240

Ser Asp Val Ala Gly Glu Val Leu Lys Leu Leu Ser Asp Asp Gly Asp
                245                 250                 255

Ser Val Gly Tyr Gly Glu Pro Leu Val Ala Val Leu Pro Ser Phe His
            260                 265                 270

Asp Ile Asn Ile Gln
        275

<210> SEQ ID NO 108
<211> LENGTH: 288
<212> TYPE: PRT
<213> ORGANISM: Pyrus x bretschneideri

<400> SEQUENCE: 108

Met Glu Ser Ser Ala Ala Leu Arg Ser Phe Asn Cys Ser Val Gly Thr
1               5                   10                  15

Val Ser His Val Gly Ser Leu Leu Asp Lys Arg Gly Met Leu Pro Val
            20                  25                  30

Tyr Asn Thr Arg Arg Pro Thr Pro Ser Arg Ser Tyr Phe Gln Gly Leu
        35                  40                  45

Met Val Ser Glu Lys Phe Ile Tyr Ser Ser Gln Lys Arg Lys Gly Val
    50                  55                  60

Leu Val Ser Cys Val Asn Thr Ser Glu Ala Ala Lys Thr Glu Asn Ser
65                  70                  75                  80

```
Ser Val Ser Ala Asp Ser Lys Pro Gln Cys Ser Ser Glu Lys Ala Ala
            85                  90                  95

His Pro Thr Ile Phe Pro Ser Gly Phe Glu Ala Leu Met Leu Glu Val
                100                 105                 110

Cys Asp Glu Thr Glu Val Ala Glu Leu Lys Leu Lys Val Gly Asp Phe
            115                 120                 125

Glu Met Tyr Leu Lys Arg Asn Ile Ala Val Thr Ser Ala Pro Val Pro
130                 135                 140

Ser Ile Ser Pro Ala Thr Pro Pro Val Pro Ser Lys Pro Met Asp
145                 150                 155                 160

Ser Thr Pro Ala Pro Pro Ala Ser Pro Lys Thr Ser Glu Lys
                165                 170                 175

Thr Thr Pro Phe Thr Asn Val Ser Val Asp Lys Leu Ser Arg Leu Ala
                180                 185                 190

Ala Leu Glu Ala Ser Gly Ala Lys Gly Tyr Asp Leu Val Ser Ser Pro
            195                 200                 205

Thr Val Gly Ser Phe Arg Arg Gly Arg Thr Val Lys Gly Lys Lys Gln
            210                 215                 220

Pro Pro Ile Phe Lys Glu Gly Asp Leu Ile Lys Lys Gly Gln Val Ile
225                 230                 235                 240

Gly Tyr Val Asp Gln Phe Gly Thr Glu Leu Pro Val Lys Thr Asp Val
                245                 250                 255

Gly Gly Glu Val Leu Lys Leu Leu Phe Asn Asp Gly Glu Ala Val Gly
                260                 265                 270

Phe Gly Asp Pro Leu Ile Ala Val Leu Pro Ser Phe Ala Gly Ile Gln
                275                 280                 285

<210> SEQ ID NO 109
<211> LENGTH: 441
<212> TYPE: PRT
<213> ORGANISM: Pyrus x bretschneideri

<400> SEQUENCE: 109

Met Lys Val Leu Phe Gln Gln Pro Val Thr Phe Gly Ala Trp Asp Met
1               5                   10                  15

Gly Gly Ser Phe His Lys Arg Leu Glu Ser Phe Leu Ser Gln Glu Glu
                20                  25                  30

Ser His Trp Arg Gln His Ser Lys Leu Ser Trp Leu Arg Asp Gly Asp
            35                  40                  45

Lys Asn Thr Arg Tyr Phe His Glu Lys Ala Ser Asn His Gln Arg Lys
50                  55                  60

Asn Cys Ile Lys Val Ile Phe Asp Gly Asn Gly Ile Leu Lys Ser Asp
65                  70                  75                  80

Ala Glu Ser Leu Glu Lys Val Val Asn Asp Tyr Phe Thr Asp Met Phe
                85                  90                  95

Ala Thr Asn Gly Asn Val Ser Phe Ser Glu Val Leu Asp Cys Ala Pro
            100                 105                 110

Arg Gln Val Asn Phe Glu Met Asn Gln Ser Leu Val Ala Asn Tyr Ser
            115                 120                 125

Asn Lys Glu Ile Arg Glu Thr Leu Phe Gln Met Asp Pro His Thr Ala
130                 135                 140

Ser Gly Phe Met Asp Ser Ile Ile Ser Asp Gln Gln Gly Ala Ser Val
145                 150                 155                 160

Pro Gly His Leu Ile Ser Asp Asn Phe Ile Val Val Leu Lys Gly Tyr
```

```
                    165                 170                 175
Leu Glu Glu Leu Asn Ala Asp Ala Leu Glu Asn Val Ile Thr Arg Ser
                180                 185                 190

Met Glu Leu Lys Thr Lys Gly Gly Glu Leu Leu Leu Thr His Gly Thr
            195                 200                 205

His Ala Leu Ser Leu Ala Val Pro Pro Ser Glu Glu Phe Ile Glu Leu
        210                 215                 220

Val Ala Ala Leu Glu Ser Leu Pro Lys His Asp Gly Trp Phe Ser Ile
225                 230                 235                 240

Asp Leu Asp Gly Ile Val Lys Tyr Arg Asp Ile Phe Thr Lys Ser Val
                245                 250                 255

Tyr Phe Leu Phe Pro Val Gln Ser Leu Leu Thr Ala Ile Cys Asp Thr
                260                 265                 270

Pro Thr Val Ala Glu Val Lys Val Lys Ile Gly Gly Phe Arg Leu Asn
            275                 280                 285

Val Val Arg Gln Pro Thr Glu Lys Phe Ser Thr Pro Pro Pro Pro Ser
        290                 295                 300

Pro Thr Pro Val Ser Ala Ser Glu Asn Thr Lys Ala Leu Asp Ser Asn
305                 310                 315                 320

Gly Ala Val Pro Thr Gln Ser Val Ala Ile Thr Arg Gln Val Ser Ser
                325                 330                 335

Ser Arg Ser Ile Gln Thr Leu Val Asp Arg Ala Thr Asp Asp Gly Leu
                340                 345                 350

Val Leu Ile Arg Ser Pro Arg Val Gly Leu Phe Arg Arg Ser Arg Thr
            355                 360                 365

Ile Lys Gly Lys Arg Ala Pro Pro Ser Cys Lys Glu Lys Gln Thr Val
        370                 375                 380

Lys Glu Gly Gln Val Ile Cys Tyr Ile Glu Gln Leu Gly Gly Glu Leu
385                 390                 395                 400

Pro Ile Glu Ser Asp Val Ala Gly Glu Val Ser Arg Ile Leu Arg Glu
                405                 410                 415

Asp Gly Asp Pro Val Gly Tyr Gly Asp Ala Leu Val Ala Val Leu Pro
                420                 425                 430

Ser Phe Pro Gly Ile Met Lys Leu Gln
            435                 440

<210> SEQ ID NO 110
<211> LENGTH: 273
<212> TYPE: PRT
<213> ORGANISM: Pyrus x bretschneideri

<400> SEQUENCE: 110

Met Ala Ser Ser Ser Leu Gly Thr Leu Asn Ala Lys Ile Thr Asn Leu
1               5                   10                  15

Asn Phe Gly Lys Ala Arg Val Gly Val Leu Lys Ser Tyr Gly Val Arg
            20                  25                  30

Ser Trp Thr Gly Arg Lys Pro Gln Leu Tyr Ser Cys Leu Ser Ile Ser
        35                  40                  45

Arg Gln Pro Glu Lys Ala Leu His Val Arg Ser Ile Pro Ser Leu Glu
    50                  55                  60

Thr Leu Ser Ala Thr Ser Leu Glu Glu Val Pro Glu Glu Ser Gly Asp
65                  70                  75                  80

Ser Gly Pro Thr Asn Gln Leu Ile Gln Asn Phe Asp Glu Val Gln Ser
                85                  90                  95
```

```
Leu Leu Thr Ala Ile Cys Asp Thr Pro Thr Val Ala Glu Val Lys Val
            100                 105                 110

Lys Ile Gly Gly Phe Arg Leu Asn Val Val Arg Gln Pro Thr Glu Lys
        115                 120                 125

Phe Ser Thr Pro Pro Pro Ser Pro Thr Pro Val Ser Ala Ser Glu
    130                 135                 140

Asn Thr Lys Ala Leu Asp Ser Asn Gly Ala Val Pro Thr Gln Ser Val
145                 150                 155                 160

Ala Ile Thr Arg Gln Val Ser Ser Arg Ser Ile Gln Thr Leu Val
                165                 170                 175

Asp Arg Ala Thr Asp Asp Gly Leu Val Leu Ile Arg Ser Pro Arg Val
            180                 185                 190

Gly Leu Phe Arg Arg Ser Arg Thr Ile Lys Gly Lys Arg Ala Pro Pro
        195                 200                 205

Ser Cys Lys Glu Lys Gln Thr Val Lys Glu Gly Gln Val Ile Cys Tyr
210                 215                 220

Ile Glu Gln Leu Gly Gly Glu Leu Pro Ile Glu Ser Asp Val Ala Gly
225                 230                 235                 240

Glu Val Ser Arg Ile Leu Arg Glu Asp Gly Asp Pro Val Gly Tyr Gly
                245                 250                 255

Asp Ala Leu Val Ala Val Leu Pro Ser Phe Pro Gly Ile Met Lys Leu
            260                 265                 270

Gln

<210> SEQ ID NO 111
<211> LENGTH: 273
<212> TYPE: PRT
<213> ORGANISM: Pyrus x bretschneideri

<400> SEQUENCE: 111

Met Ala Ser Ser Leu Gly Thr Leu Asn Ala Lys Ile Thr Asn Leu
1               5                   10                  15

Asn Phe Ser Arg Ala Arg Val Gly Val Leu Arg Ser Tyr Gly Ile Ile
                20                  25                  30

Thr Trp Thr Gly Arg Lys Pro Gln Leu Tyr Ser Cys Leu Ser Ile Ser
            35                  40                  45

Arg Gln Ser Glu Lys Val Leu His Ala Arg Ser Val Pro Ser Leu Glu
    50                  55                  60

Ile Leu Ser Ala Lys Ser Leu Glu Glu Val Ser Glu Glu Ser Gly Asp
65                  70                  75                  80

Ser Gly Pro Thr Asn Gln Leu Ile Gln Asn Phe Asp Glu Val Gln Ser
                85                  90                  95

Leu Leu Thr Ala Ile Cys Asp Thr Thr Thr Val Ala Glu Val Lys Leu
            100                 105                 110

Lys Ile Gly Gly Phe Gln Leu Asn Val Val Arg Lys Leu Thr Glu Lys
        115                 120                 125

Ile Ser Thr Pro Pro Pro Ser Pro Ala Pro Val Ser Ala Ser Glu
    130                 135                 140

Asn Ala Lys Ala Leu Asp Leu Asn Gly Ala Val Pro Thr Gln Ser Val
145                 150                 155                 160

Ala Ile Thr Arg Gln Glu Ser Ser Arg Ser Ile Gln Thr Leu Leu
                165                 170                 175

Asp Arg Ala Ala Asp Asp Gly Leu Val Leu Ile His Ser Pro Arg Val
            180                 185                 190
```

```
Gly Leu Phe Arg Arg Ser Arg Thr Ile Lys Gly Lys Arg Ala Pro Pro
            195                 200                 205

Ser Cys Lys Glu Lys Gln Ile Val Lys Glu Gly Gln Val Ile Cys Tyr
210                 215                 220

Ile Glu Gln Leu Gly Gly Glu Leu Pro Ile Glu Ser Asp Val Ala Gly
225                 230                 235                 240

Glu Val Ile Arg Ile Leu Arg Glu Asp Gly Asp Pro Val Gly Tyr Gly
                245                 250                 255

Asp Ala Leu Val Ala Val Leu Pro Ser Phe Pro Gly Ile Glu Lys Leu
            260                 265                 270

Pro
```

<210> SEQ ID NO 112
<211> LENGTH: 276
<212> TYPE: PRT
<213> ORGANISM: Musa acuminata subsp. malaccensis

<400> SEQUENCE: 112

```
Met Ala Leu Arg Leu Phe Pro Gly Ala Ser Lys Thr Ile Leu Gln Val
1               5                   10                  15

Asp Ser Ser Leu Asn Ser Lys Ser Leu Leu Trp Arg Val Pro Glu Glu
            20                  25                  30

Pro Gln Arg Leu Ile Ser Ser Gly Ala Phe Gln Lys Gln Phe Leu His
        35                  40                  45

Val Lys Ala Ser Gln Asn Thr Ser Ser Leu Thr Thr Asn Ala Asp Ile
50                  55                  60

Asn Lys Lys Asn Ala Thr Ala Thr Leu Gln Lys Lys Asn Val Tyr Lys
65                  70                  75                  80

Ser Thr Phe Pro Ser Gly Phe Gln Thr Leu Val Glu Glu Val Cys Asp
                85                  90                  95

Gln Thr Asp Val Ala Glu Leu Lys Leu Lys Val Gly Asp Phe Glu Met
            100                 105                 110

Leu Leu Lys Arg Asp Thr Gly Asn Ser Lys Ala Pro Ile Ser Val Ser
        115                 120                 125

Ala Pro Ile Glu Ser Pro Thr Thr Ala Pro Pro Ile Pro Ser Lys Pro
130                 135                 140

Met Val Glu Thr Ile Ser Ser Pro Ser Pro Val Ala Glu Gln Glu Ser
145                 150                 155                 160

Ala Ala Ala Thr Phe Gly Ser Phe Thr Asn Thr Ser Ala Ala Lys Thr
                165                 170                 175

Ser Lys Leu Ala Ala Leu Asp Ala Ser Gly Gln Asn Ala Tyr Val Leu
            180                 185                 190

Val Ser Ser Thr Val Gly Leu Phe Gln Arg Gly Arg Thr Leu Lys
        195                 200                 205

Glu Lys Arg Gln Pro Pro Ser Cys Lys Glu Gly Asp Ile Ile Lys Glu
210                 215                 220

Gly Gln Ile Ile Gly Phe Leu Asp Gln Phe Gly Asn Glu Leu Pro Val
225                 230                 235                 240

Arg Ser Asp Val Ala Gly Glu Val Leu Lys Ile Ile Tyr Glu Asp Gly
                245                 250                 255

Glu Ala Val Gly Tyr Gly Asp Pro Leu Val Ala Val Leu Pro Ser Phe
            260                 265                 270

His Gly Ile Lys
        275
```

<210> SEQ ID NO 113
<211> LENGTH: 278
<212> TYPE: PRT
<213> ORGANISM: Musa acuminata subsp. malaccensis

<400> SEQUENCE: 113

Met Ala Leu Pro Ser Phe Leu Gly Ala Pro Arg Thr Ile Phe His Gly
1               5                   10                  15

His Ser Ser Val Glu Lys Pro Val Pro Ile Leu Val Ser Ser Thr Val
            20                  25                  30

Ser Lys Tyr Leu Leu Gln Arg Val Pro Glu Glu Cys Gln Arg Ser Ile
        35                  40                  45

Ser Ser Met Val Leu Pro Lys His Ser Leu His Val Lys Ala Ser Gln
    50                  55                  60

Asn Thr Ser Ala Leu Thr Thr Asn Ala Asp Thr Asp Gln Lys Asn Ser
65                  70                  75                  80

Ile Thr Ser Thr Phe Pro Asn Gly Cys Gln Thr Leu Ile Glu Glu Val
                85                  90                  95

Cys Asp Leu Thr Asp Ile Ala Glu Leu Lys Met Lys Val Gly Asp Phe
            100                 105                 110

Glu Met Phe Leu Lys Arg Asp Val Gly Ile Ser Asn Ala Pro Asn Ser
        115                 120                 125

Val Ser Ala Pro Ile Glu Ser Pro Ile Thr Ala Pro Pro Ile Pro Ser
    130                 135                 140

Lys Pro Met Val Glu Ala Val Pro Ser Ser Pro Val Leu Glu Gln
145                 150                 155                 160

Lys Ser Pro Ala Thr Ala Ser Ser Pro Phe Thr Tyr Val Ser Ala Ala
                165                 170                 175

Lys Thr Ser Lys Leu Ala Ala Leu Glu Ala Ser Gly Leu Asn Ala Tyr
            180                 185                 190

Ala Leu Val Ser Ser Ser Thr Val Gly Ser Phe Gln Ser Gly Arg Ser
        195                 200                 205

Leu Lys Gly Glu Arg Gln Pro Pro Ile Cys Lys Glu Gly Asp Ile Ile
    210                 215                 220

Lys Glu Gly Gln Ile Ile Gly Phe Leu Asp Gln Phe Gly Asn Glu Leu
225                 230                 235                 240

Pro Ile Arg Ser Asp Val Ala Gly Glu Val Lys Ile Leu Cys Glu
                245                 250                 255

Asn Gly Glu Ala Val Gly Tyr Gly Asp Pro Leu Val Ala Val Leu Pro
            260                 265                 270

Ser Phe His Gly Val Lys
        275

<210> SEQ ID NO 114
<211> LENGTH: 285
<212> TYPE: PRT
<213> ORGANISM: Musa acuminata subsp. malaccensis

<400> SEQUENCE: 114

Met Glu Ile Ala Ala Phe Gly Ser His Gly Ser Val Gln Ile Leu Trp
1               5                   10                  15

Asn Ser His Ser Ser Ile Asp Lys Pro Asn Trp Ile Arg His Ser Asn
            20                  25                  30

Ser Ala Trp Lys Arg Ile Ile Phe Pro Lys Ala Trp Val Ser Gln Ala
        35                  40                  45

```
Gln Lys Gly Ser Leu Leu Lys Arg Leu Lys Ala Ser Glu Arg Thr Ala
     50                  55                  60

Asp Leu Thr Ser Asn Val Ala Ala Ser Glu Asn Ser Ser Gln Gly Pro
 65                  70                  75                  80

Leu Glu Lys Lys Ala Val Trp Lys Ser Thr Phe Pro Asn Gly Phe Glu
                 85                  90                  95

Glu Leu Val Leu Thr Val Cys Asp Glu Thr Ser Ile Ala Glu Leu Ser
            100                 105                 110

Met Lys Val Gly Asn Phe Glu Met His Leu Lys Arg Asp Ile Gly Ile
        115                 120                 125

Ser Glu Ala Leu Thr Ser Thr Ile Ser Thr Ile Val Ser Pro Thr Thr
    130                 135                 140

Ala Pro Pro Ile Pro Ser Glu Pro Met Cys Val Ser Thr Ile Ala Pro
145                 150                 155                 160

Ala Gln Gln Asp Val Pro Lys Glu Pro Val Leu Pro Glu Thr Ser Pro
                165                 170                 175

Phe Ser Asp Ile Tyr Ser Ser Lys Ala Leu Lys Leu Ala Ala Leu Gly
            180                 185                 190

Ala Ser Ser Ser Asn Ala Tyr Val Leu Ile Ser Ser Pro Ser Val Gly
        195                 200                 205

Thr Phe Arg Ile Gly Thr Thr Leu Lys Gly Lys Lys Gln Pro Pro Cys
    210                 215                 220

Cys Glu Val Gly Asp Met Ile Lys Glu Gly Gln Ala Ile Gly Phe Leu
225                 230                 235                 240

Asp Gln Phe Gly Asn Glu Leu Pro Ile Arg Ser Asn Val Ala Gly Glu
                245                 250                 255

Val Leu Lys Ile Leu Cys Lys Asp Gly Glu Ala Val Gly Tyr Gly Asp
            260                 265                 270

Ala Leu Ile Ala Val Leu Pro Phe Phe Ala Gly Ile Glu
        275                 280                 285

<210> SEQ ID NO 115
<211> LENGTH: 295
<212> TYPE: PRT
<213> ORGANISM: Nicotiana tomentosiformis

<400> SEQUENCE: 115

Met Glu Ser Ala Ala Val Leu Arg Ser Phe His His Ser Val Gly Ala
 1               5                  10                  15

Thr Ser His Met Arg Ser Val Ile Glu Met Pro Gly Val Phe Pro Met
                 20                  25                  30

Asn Asn Val Ala Phe Ser Lys Pro Thr Lys Leu Pro Val Lys Gly Ser
             35                  40                  45

Ser Ser Gly Ala Lys Leu Val Ser Ser Thr Asn Lys His Asn Arg Leu
 50                  55                  60

Ile Leu Tyr Cys Ala Lys Thr Ser Glu Thr Thr Val Thr Ala Lys Ser
 65                  70                  75                  80

Asp Gly Ala Val Leu Thr Asp Ser His Gln Lys Val Pro Thr Glu Lys
                 85                  90                  95

Ser Pro Leu Pro Thr Ala Thr Phe Pro Lys Gly Phe Glu Ala Leu Ile
            100                 105                 110

Thr Glu Val Cys Asp Asp Thr Glu Val Ala Glu Leu Lys Leu Lys Ile
        115                 120                 125

Gly Asp Phe Glu Leu His Leu Lys Arg Asn Ile Glu Ala Pro Ile Val
    130                 135                 140
```

```
Pro Ala Pro Val Val Ser Thr Pro Pro Pro Pro Pro Pro Pro Ser
145                 150                 155                 160

Ala Ser Lys Pro Ser Asn Ala Ser Thr Ala Ala Pro Ala Thr Ser
            165                 170                 175

Pro Gly Lys Ser Ser Ser Glu Lys Ile Ser Pro Phe Thr Asn Val Ala
            180                 185                 190

Ala Glu Lys Ser Ala Lys Leu Ala Ala Leu Glu Thr Thr Gly Ala Ser
            195                 200                 205

Gly Tyr Val Leu Val Ser Cys Pro Thr Val Gly Ser Phe Arg Arg Ala
            210                 215                 220

Arg Thr Leu Lys Gly Lys Lys Gln Pro Pro Ala Cys Lys Glu Gly Asp
225                 230                 235                 240

Val Ile Lys Glu Gly Gln Ile Ile Gly Phe Leu Asp Gln Phe Gly Thr
                245                 250                 255

Glu Leu Pro Val Arg Ser Asp Ala Ala Gly Glu Val Leu Lys Ile Leu
            260                 265                 270

Phe Asn Asp Gly Glu Ala Val Gly Tyr Gly Asp Pro Leu Ile Ala Val
            275                 280                 285

Leu Pro Ser Phe Arg Gly Ile
            290                 295

<210> SEQ ID NO 116
<211> LENGTH: 274
<212> TYPE: PRT
<213> ORGANISM: Nicotiana tomentosiformis

<400> SEQUENCE: 116

Met Ala Ala Cys Ser Phe Gly Ala Ala Gly Phe Lys Leu Thr Asn Leu
1               5                   10                  15

Asn Leu Gly Ser Thr Lys Pro Lys Phe Leu Leu His Asn Leu Arg Thr
            20                  25                  30

Lys Lys Leu Ile Gln Asn Asp Gly Leu Leu Leu Thr Lys Lys Ser Arg
        35                  40                  45

Lys Thr Leu Phe Gly Cys Arg Cys Ser Thr Val Glu Ala Glu Ser Ala
50                  55                  60

Ala Ala Val Val Ser Asp Asn Ser Asp Asp Ser Leu Arg Lys Ile Ile
65                  70                  75                  80

Ser Ser Glu Ala Ala Ser Pro Leu Ile Pro Asn Ser Tyr Glu Val Glu
                85                  90                  95

Ser Leu Leu Thr Glu Ile Cys Asp Thr Thr Ser Ile Ala Glu Val Glu
            100                 105                 110

Leu Lys Leu Gly Gly Phe His Leu Tyr Val Lys Arg Asp Leu Thr Gly
            115                 120                 125

Pro Ser Thr Thr Ser Leu Pro Ala Ile Ser Asn Pro Val Asn Ile His
130                 135                 140

Ser Ser Val Glu Val Ala Asp Ser Asn Gly Ser Ala Ser Ser Ser Ser
145                 150                 155                 160

Leu Ala Ile Thr Lys Ser Ser Pro Ser Asp Gly Ile Gln Thr Met
            165                 170                 175

Ile Asp Lys Ala Ala Asp Glu Gly Leu Val Ile Ile Gln Ser Pro Arg
            180                 185                 190

Val Gly Tyr Phe Arg Arg Ser Arg Thr Ile Lys Gly Lys Arg Ala Pro
            195                 200                 205

Pro Ser Cys Lys Glu Lys Gln Gln Val Lys Glu Gly Gln Val Val Cys
```

Phe Ile Glu Gln Leu Gly Gly Glu Leu Pro Val Ser Asp Val Ser
225                 230                 235                 240

Gly Glu Val Ile Lys Ile Leu Gln Lys Asp Gly Glu Pro Val Gly Tyr
            245                 250                 255

Gly Asp Pro Leu Ile Ser Ile Leu Pro Ser Phe Pro Gly Ile Lys Lys
            260                 265                 270

Leu Gln

<210> SEQ ID NO 117
<211> LENGTH: 254
<212> TYPE: PRT
<213> ORGANISM: Nicotiana tomentosiformis

<400> SEQUENCE: 117

Met Ala Ala Cys Ser Phe Gly Ala Ala Gly Phe Lys Leu Thr Asn Leu
1               5                   10                  15

Asn Leu Gly Ser Thr Lys Pro Lys Phe Leu Leu His Asn Leu Arg Thr
            20                  25                  30

Lys Lys Leu Ile Gln Asn Asp Gly Leu Leu Leu Thr Lys Lys Ser Arg
        35                  40                  45

Lys Thr Leu Phe Gly Cys Arg Cys Ser Thr Val Glu Ala Glu Ser Ala
    50                  55                  60

Ala Ala Val Val Ser Asp Asn Ser Asp Asp Ser Leu Arg Lys Ile Ile
65                  70                  75                  80

Ser Ser Glu Ala Ala Ser Pro Leu Ile Pro Asn Ser Tyr Glu Leu Gly
                85                  90                  95

Gly Phe His Leu Tyr Val Lys Arg Asp Leu Thr Gly Pro Ser Thr Thr
            100                 105                 110

Ser Leu Pro Ala Ile Ser Asn Pro Val Asn Ile His Ser Ser Val Glu
        115                 120                 125

Val Ala Asp Ser Asn Gly Ser Ala Ser Ser Ser Leu Ala Ile Thr
    130                 135                 140

Lys Ser Ser Pro Pro Ser Asp Gly Ile Gln Thr Met Ile Asp Lys Ala
145                 150                 155                 160

Ala Asp Glu Gly Leu Val Ile Ile Gln Ser Pro Arg Val Gly Tyr Phe
                165                 170                 175

Arg Arg Ser Arg Thr Ile Lys Gly Lys Arg Ala Pro Pro Ser Cys Lys
            180                 185                 190

Glu Lys Gln Gln Val Lys Glu Gly Gln Val Val Cys Phe Ile Glu Gln
        195                 200                 205

Leu Gly Gly Glu Leu Pro Val Glu Ser Asp Val Ser Gly Glu Val Ile
    210                 215                 220

Lys Ile Leu Gln Lys Asp Gly Glu Pro Val Gly Tyr Gly Asp Pro Leu
225                 230                 235                 240

Ile Ser Ile Leu Pro Ser Phe Pro Gly Ile Lys Lys Leu Gln
                245                 250

<210> SEQ ID NO 118
<211> LENGTH: 290
<212> TYPE: PRT
<213> ORGANISM: Nicotiana sylvestris

<400> SEQUENCE: 118

Met Glu Ser Ala Ala Val Leu Arg Ser Phe His His Ser Val Gly Thr
1               5                   10                  15

Thr Ser His Met Arg Ser Val Ile Glu Met Pro Gly Val Ile Pro Met
              20                  25                  30

Asn Asn Val Ala Phe Ser Lys Pro Thr Lys Leu Pro Leu Lys Gly Ser
              35                  40                  45

Ser Asn Gly Ala Lys Leu Val Ser Ser Thr Asn Lys His Ser Arg Leu
 50                  55                  60

Ile Leu Ser Cys Ala Lys Thr Ser Glu Thr Thr Val Thr Thr Lys Ser
 65                  70                  75                  80

Gly Ala Val Leu Thr Asp Ser His Gln Lys Val Ser Thr Glu Lys Ser
                 85                  90                  95

Pro Leu Pro Thr Ala Thr Phe Pro Lys Gly Phe Glu Ala Leu Ile Thr
                100                 105                 110

Glu Val Cys Asp Asp Thr Glu Val Ala Glu Leu Lys Leu Lys Ile Gly
                115                 120                 125

Asp Phe Glu Leu His Leu Lys Arg Asn Ile Glu Ala Pro Ile Val Pro
                130                 135                 140

Ala Pro Val Val Ser Thr Pro Pro Pro Ser Ala Ser Lys Pro Ser
145                 150                 155                 160

Thr Ala Ser Thr Ala Ala Pro Ala Thr Ser Pro Gly Lys Ser Ser
                165                 170                 175

Ser Glu Lys Ile Ser Pro Phe Thr Asn Val Ala Ala Glu Lys Ser Met
                180                 185                 190

Lys Leu Ala Glu Leu Gln Thr Thr Gly Ala Ser Gly Tyr Val Leu Val
                195                 200                 205

Ser Cys Pro Thr Val Gly Ser Phe Arg Arg Ala Arg Thr Leu Lys Gly
                210                 215                 220

Lys Lys Gln Pro Pro Ala Cys Lys Glu Gly Asp Val Ile Lys Glu Gly
225                 230                 235                 240

Gln Ile Ile Gly Phe Leu Asp Gln Phe Gly Thr Glu Leu Pro Val Arg
                245                 250                 255

Ser Asp Ala Ala Gly Glu Val Leu Lys Ile Leu Phe Asn Asp Gly Glu
                260                 265                 270

Ala Val Gly Tyr Gly Asp Pro Leu Ile Ala Val Leu Pro Ser Phe Arg
                275                 280                 285

Gly Ile
    290

<210> SEQ ID NO 119
<211> LENGTH: 360
<212> TYPE: PRT
<213> ORGANISM: Nicotiana sylvestris

<400> SEQUENCE: 119

Met Ser Leu Phe Leu Arg Val Phe Ser Arg Thr Val Arg Ala Arg Leu
1               5                   10                  15

Cys Trp Glu His Gly Ser Gly Phe Ala Ala Arg Leu Leu Leu Pro Val
              20                  25                  30

Glu Leu Ala Thr Phe Gln Arg Leu Leu Ala Ile Ile Arg Glu Thr Phe
              35                  40                  45

Ser Phe Leu Leu Ser Asn Phe Val Cys Ile Asp Asn Glu Gln Ser
 50                  55                  60

Phe Lys Leu Tyr Gln Gln Leu Ser Ala Leu Leu Cys Ser Ser Arg Arg
 65                  70                  75                  80

Val Leu Pro Leu Leu Met Ala Ala Cys Gly Phe Gly Ala Ser Gly Phe

```
                    85                  90                  95
Lys Leu Thr Asn Leu Asn Leu Gly Ser Ser Lys Pro Lys Leu Thr Ala
                100                 105                 110
Leu His Asn Leu Arg Thr Lys Lys Leu Ser Gln Ser Asp Gly Leu Leu
            115                 120                 125
Leu Thr Thr Lys Ser Arg Lys Thr Leu Phe Gly Cys Trp Cys Ser Thr
        130                 135                 140
Ala Glu Val Glu Ser Ala Ala Ala Val Ser His Ser Ser Asp Asp
145                 150                 155                 160
Ser Ser Arg Lys Ile Ile Ser Ser Glu Thr Ala Ser Pro Leu Ile Pro
                165                 170                 175
Ser Ser Tyr Glu Val Glu Ser Leu Leu Thr Glu Ile Cys Asp Thr Thr
            180                 185                 190
Ser Ile Ala Glu Val Asp Leu Lys Leu Gly Gly Phe His Leu Tyr Val
        195                 200                 205
Lys Arg Asp Leu Thr Gly Pro Ser Thr Thr Ser Leu Pro Ala Ile Ser
210                 215                 220
Asn Pro Val Asn Ile His Ser Ser Val Glu Val Ala Asp Ser Asn Gly
225                 230                 235                 240
Ser Ala Ser Ser Pro Ser Leu Ala Ile Thr Lys Ser Ser Pro Pro Ser
                245                 250                 255
Asp Gly Ile Arg Thr Ile Ile Asp Lys Ala Ala Asp Glu Gly Leu Val
            260                 265                 270
Ile Ile Gln Ser Pro Arg Val Gly Tyr Phe Arg Arg Ser Arg Thr Ile
        275                 280                 285
Lys Gly Lys Arg Ala Pro Pro Ser Cys Lys Glu Lys Gln Gln Val Lys
    290                 295                 300
Glu Gly Gln Val Val Cys Phe Ile Glu Gln Leu Gly Gly Glu Leu Pro
305                 310                 315                 320
Val Glu Ser Asp Val Ser Gly Glu Val Ile Lys Ile Leu Gln Lys Asp
                325                 330                 335
Gly Asp Pro Val Gly Tyr Gly Asp Pro Leu Ile Ser Ile Leu Pro Ser
            340                 345                 350
Phe Pro Gly Ile Lys Lys Leu Gln
        355                 360

<210> SEQ ID NO 120
<211> LENGTH: 274
<212> TYPE: PRT
<213> ORGANISM: Cucumis sativus

<400> SEQUENCE: 120

Met Glu Ser Ser Ala Ser Leu Arg Ser Phe His Tyr Phe Ala Gly Gly
1               5                   10                  15
Ser Arg Leu Gln Leu Ile Glu Lys Pro Ser Arg Ile Tyr Val Ser Ser
            20                  25                  30
Thr Asn Lys Thr Ser Ile Gln Arg Leu Ser Ile Phe Gly Lys Pro Ile
        35                  40                  45
His Asn Pro Thr Ser Gln Lys Lys Ile Ala Val Ser Cys Thr Lys Thr
    50                  55                  60
Pro Glu Val Thr Glu Thr Asp Ser Ala Lys Gly Ser Leu Gln Lys Lys
65                  70                  75                  80
Pro Ala Ser Asn Val Thr Phe Pro Asn Gly Phe Glu Glu Leu Leu Leu
                85                  90                  95
```

```
Glu Val Cys Asp Asp Thr Glu Ile Ala Glu Leu Lys Leu Lys Val Gly
                100                 105                 110

Glu Phe Glu Met His Val Lys Arg Asn Ile Gly Val Val Ser Ala Pro
        115                 120                 125

Leu Ser Ala Ile Ser Pro Thr Val Pro Pro Ile Pro Ser Lys Pro
    130                 135                 140

Met Val Glu Ser Ala Leu Ala Ala Pro Ala Pro Pro Ile Pro Ser Pro
145                 150                 155                 160

Glu Lys Ala Asn Ala Phe Thr Asp Val Pro Phe Lys Lys Ser Ser Lys
                165                 170                 175

Leu Ala Ala Leu Glu Ala Ser Gly Ala Lys Gly Tyr Val Leu Val Thr
            180                 185                 190

Ser Pro Thr Val Gly Ser Phe Arg Ser Gly Arg Thr Val Lys Gly Arg
        195                 200                 205

Arg Met Pro Pro Ile Cys Lys Glu Asn Asp Leu Ile Arg Glu Gly Gln
    210                 215                 220

Val Val Ala Tyr Val Asp Gln Phe Gly Ser Gln Leu Pro Val Lys Ser
225                 230                 235                 240

Asp Val Ala Gly Glu Val Leu Arg Ile Leu Phe Lys Glu Asp Glu Pro
                245                 250                 255

Val Gly Phe Gly Asp Pro Leu Ile Ala Val Leu Pro Ile Phe His Gly
            260                 265                 270

Ile Arg

<210> SEQ ID NO 121
<211> LENGTH: 280
<212> TYPE: PRT
<213> ORGANISM: Eucalyptus grandis

<400> SEQUENCE: 121

Met Ala Ser Gly Asp Val Ser Val Ser Leu Ser Tyr Phe Phe Leu Ser
1               5                   10                  15

Gly Thr Leu Gly Thr Ser Arg Val Asn Ile Ser Asn Leu Asn Phe Asn
            20                  25                  30

Ile Ala Arg Val Gly Glu Ala His Gln Ser Asn Leu Arg Ile Thr Trp
        35                  40                  45

Ile Val His Asn Leu Gln Asn His Ala Gly Leu Arg Ile Ser Ser Thr
    50                  55                  60

Thr Asp Asp Gln Trp Arg Ile Tyr Cys Thr Ser Ser Gly Ser Gln
65                  70                  75              80

His Gly Ser Asn Thr Ser Gly Phe Thr Arg Arg His Thr Pro Asp Leu
                85                  90                  95

Ser Glu Val Gly Ser Leu Ile Thr Gly Ile Cys Lys Ala Ser Ser Val
            100                 105                 110

Glu Glu Ile Glu Ile Lys Leu Ser Gly Phe Gln Leu Tyr Leu Ala Arg
        115                 120                 125

Asn Pro Thr Arg Lys Thr Thr Thr Leu Pro Pro Ser Pro Gln Leu His
    130                 135                 140

Ala Pro Pro Lys Ala Asp Ala Thr Pro Glu Glu Gln Val Ala Ser Ala
145                 150                 155                 160

Ser Leu Pro Lys Thr Ser Leu Ala Ile Thr Lys Ser Ile Phe Ser Ile
                165                 170                 175

Ser Arg Trp Gln Ile Thr Leu Lys Lys Ala Val Asn Glu Gly Leu Phe
            180                 185                 190
```

```
Val Leu Arg Ser Pro Arg Val Gly Phe Phe Lys Arg Ser Arg Thr Ile
            195                 200                 205

Lys Gly Lys Cys Ala Pro Ala Cys Lys Glu Arg Gln Ile Val Lys
            210                 215                 220

Glu Gly Gln Val Val Cys Tyr Ile Asp Gln Leu Gly Gly Met Pro
225                 230                 235                 240

Ile Lys Ala Asp Val Ser Gly Glu Val Ile Lys Ile Leu Leu Glu Asp
            245                 250                 255

Gly Asp Pro Val Gly Tyr Glu Asp Ala Leu Ile Thr Ile Leu Pro Tyr
            260                 265                 270

Ser Pro Glu Ile Lys Met Leu Gln
            275                 280
```

<210> SEQ ID NO 122
<211> LENGTH: 221
<212> TYPE: PRT
<213> ORGANISM: Eucalyptus grandis

<400> SEQUENCE: 122

```
Met Arg Thr Ser Asp Ser Ala Ile Ser Thr Asp Thr Asn Glu Cys Ile
1               5                   10                  15

Gly Arg Ser Val Glu Lys Gly Pro Leu Glu Asp Ala Thr Phe Pro Ser
            20                  25                  30

Gly Phe Gln Thr Leu Leu Leu Glu Val Cys Asp Glu Thr Gln Ile Ala
        35                  40                  45

Glu Leu Lys Leu Lys Val Gly Asn Phe Glu Met His Val Lys Arg Asn
    50                  55                  60

Val Gly Ala Ala Glu Val Pro Thr Val Ile Ala Ser Pro Val Thr Pro
65                  70                  75                  80

Pro Pro Ile Pro Ala Glu Pro Val Asn Lys Ser Ser Ser Gly Val Ser
                85                  90                  95

Pro Pro Ser Ala Leu Lys Pro Ser Ser Glu Lys Ala Ala Pro Phe Met
            100                 105                 110

Asn Val Thr Phe Gly Lys Ser Ala Lys Val Lys Ala Leu Glu Ala Ser
        115                 120                 125

Gly Ser Ser Gly Tyr Ala Leu Val Ser Pro Thr Val Gly Ser Phe
    130                 135                 140

Gln Lys Gly Arg Thr Val Lys Gly Lys Gln Gly Pro Ser Cys Lys
145                 150                 155                 160

Glu Gly Asp Leu Ile Lys Glu Gly Gln Val Ile Gly Trp Leu Asp Gln
                165                 170                 175

Phe Gly Thr Glu Leu Pro Val Lys Ser Asp Val Ser Gly Glu Val Leu
            180                 185                 190

Lys Leu Leu Ile Asp Asp Gly Glu Ala Val Gly Tyr Gly Asp Pro Leu
        195                 200                 205

Leu Ala Val Leu Pro Ser Phe Pro Gly Val Gly Val Gln
    210                 215                 220
```

<210> SEQ ID NO 123
<211> LENGTH: 288
<212> TYPE: PRT
<213> ORGANISM: Eucalyptus grandis

<400> SEQUENCE: 123

```
Met Glu Ser Ser Val Ser Ala Leu Arg Ser Ser Leu His Ser Asn Ile
1               5                   10                  15
```

```
Ala Gly Ala Leu Pro Arg Val Glu Pro Leu Pro His Lys Pro Gly Val
            20                  25                  30

Val Pro Val Gln Ser Tyr Ser Pro Pro Ser Lys Lys Leu Tyr Val His
        35                  40                  45

Gly Phe Ala Ala Arg Gly Ile Ala Pro Ser Arg Thr Arg Asn Ala Ala
    50                  55                  60

Val Val Ser Cys Leu Lys Thr Ser Glu Ala Thr Gly Val Ala Lys Ser
65                  70                  75                  80

Ser Glu Gly Asn Thr Arg Asp Ser Lys Asp Lys Thr Thr Leu Pro Arg
                85                  90                  95

Ala Thr Phe Pro Ser Ala Phe Glu Glu Leu Leu Leu Glu Val Cys Asp
            100                 105                 110

Glu Thr Gln Ile Ala Glu Leu Lys Leu Lys Ile Gly Asp Ile Glu Met
        115                 120                 125

Gln Val Lys Arg Asn Leu Gly Ala Thr Lys Glu Ala Phe Ala Ser Ile
    130                 135                 140

Pro Ser Pro Thr Thr Pro Pro Ile Pro Thr Glu Pro Met Glu Asn
145                 150                 155                 160

Ser Gly Ala Val Val Pro Pro Lys Pro Ser Pro Glu Lys Thr Ser
                165                 170                 175

Pro Phe Thr Asn Phe Ser Phe Gly Lys Ser Ser Lys Leu Ala Ala Leu
            180                 185                 190

Glu Ala Pro Gly Ser Ser Gly Tyr Val Leu Val Ser Ser Pro Thr Val
        195                 200                 205

Gly Ser Phe Arg Arg Gly Arg Thr Leu Lys Gly Lys Lys Gln Pro Pro
    210                 215                 220

Ser Cys Lys Glu Gly Asp Val Ile Lys Glu Gly Gln Val Ile Gly Trp
225                 230                 235                 240

Leu Asp Gln Phe Gly Thr Glu Leu Pro Val Lys Ser Asp Val Ser Gly
                245                 250                 255

Glu Val Leu Lys Leu Leu Val Asn Asp Gly Pro Val Gly Tyr Gly
            260                 265                 270

Asp Pro Leu Ile Ala Val Leu Pro Ala Phe His Ser Ile Asn Ile Met
        275                 280                 285

<210> SEQ ID NO 124
<211> LENGTH: 276
<212> TYPE: PRT
<213> ORGANISM: Eucalyptus grandis

<400> SEQUENCE: 124

Met Leu Leu Ser Met Ala Ser Cys Ser Leu Gly Ala Ser Asn Val Lys
1               5                   10                  15

Ile Ala Asn Leu Asn Ser Gly Arg Pro Lys Ile Gly Glu Ser Arg Leu
            20                  25                  30

Ser Tyr Gly Arg Ser Trp Ile Val Leu Lys Thr Pro Lys Tyr Ala Gly
        35                  40                  45

Leu Thr Leu Phe Gln Gln Leu Asp Lys Ile Cys Pro Val Cys Cys His
    50                  55                  60

Pro Ser Ser Gly Ser Pro Ser Thr Ser Ser Leu Leu Asp Asp Ser Glu
65                  70                  75                  80

Asp Ser Glu Pro Ser Ser Leu Thr Ser Gln Leu Ile Pro Asn Ser Ser
                85                  90                  95

Glu Val Glu Ser Leu Leu Thr Asp Ile Cys Glu Thr Ser Ile Ala Glu
            100                 105                 110
```

```
Phe Glu Leu Lys Leu Asn Gly Phe Arg Leu Tyr Val Ala Arg Asp Val
            115                 120                 125

Ser Gly Gly His Lys Pro Leu Pro Pro Phe Ser Pro Ala Pro Thr Pro
    130                 135                 140

Val His Ser Asn Val Glu Ala Thr Asp Thr Asn Gly Ser Leu Ser Lys
145                 150                 155                 160

Pro Ser Leu Ala Ile Ser Lys Ala Leu Thr Ser Ser Asp Gly Gly Pro
                165                 170                 175

Thr Trp Leu Asp Lys Ala Ala Asp Ala Gly Leu Val Ile Leu Gln Ser
                180                 185                 190

Pro Arg Val Gly Phe Phe Arg Arg Ser Arg Thr Ile Lys Gly Lys Arg
            195                 200                 205

Ala Pro Pro Ala Cys Lys Glu Lys Gln Ile Val Lys Glu Gly Gln Val
    210                 215                 220

Val Cys Tyr Ile Glu Gln Leu Gly Gly Glu Leu Pro Ile Glu Ser Asp
225                 230                 235                 240

Val Ser Gly Glu Val Val Lys Ile Leu Arg Glu Asp Gly Asp Pro Val
                245                 250                 255

Gly Tyr Gly Asp Ala Leu Ile Ser Ile Leu Pro Ser Phe Pro Gly Ile
                260                 265                 270

Lys Lys Leu Gln
            275

<210> SEQ ID NO 125
<211> LENGTH: 285
<212> TYPE: PRT
<213> ORGANISM: Morus notabilis

<400> SEQUENCE: 125

Met Glu Ser Ser Ala Val Leu Arg Ser Phe Gln Leu Asp Thr Ile Ser
1               5                   10                  15

Arg Thr Lys Ser Phe Leu Glu Lys Pro Gly Met Val Pro Val Tyr Asn
            20                  25                  30

Ala Arg Gln Leu Asn Ala Asn Arg Ser Cys Ile Pro Ser Leu Thr Ala
        35                  40                  45

Ser Gly Arg Leu Ile Asn Ser Pro Arg Lys Gln Lys Gly Phe Arg Val
    50                  55                  60

Ser Cys Val Lys Thr Ser Glu Ala Lys Glu Thr Ala Lys Ser Asn Asp
65                  70                  75                  80

Cys Val Pro Gln Ser Ser Leu Glu Lys Thr Pro Arg Ser Ala Ile Phe
                85                  90                  95

Pro Asn Gly Phe Glu Ala Leu Met Leu Glu Val Cys Asp Glu Thr Glu
            100                 105                 110

Ile Ala Glu Leu Lys Leu Lys Val Gly Asp Phe Glu Met His Leu Lys
        115                 120                 125

Arg Asn Ile Gly Ala Thr Val Ala Pro Leu Ser His Ile Ser Pro Thr
    130                 135                 140

Ser Pro Pro Ile Pro Ser Lys Pro Met Val Glu Ser Ala Pro Ala
145                 150                 155                 160

Ala Pro Pro Ser Pro Pro Lys Thr Ser Gln Thr Thr Ser Pro
                165                 170                 175

Phe Thr Asn Val Ser Met Val Lys Thr Ser Lys Leu Ala Ala Leu Glu
            180                 185                 190

Ala Ser Gly Ser Asn Ala Tyr Val Leu Val Ser Ser Pro Thr Val Gly
```

```
            195                 200                 205
Ser Phe Arg Arg Gly Arg Thr Val Lys Gly Lys Lys Gln Pro Pro Ile
210                 215                 220

Cys Lys Glu Gly Asp Val Ile Lys Glu Gly Gln Val Ile Gly Tyr Val
225                 230                 235                 240

Asp Gln Phe Gly Thr Glu Leu Pro Val Lys Ser Asp Ile Gly Gly Glu
                245                 250                 255

Val Leu Lys Val Leu Phe Thr Glu Gly Glu Ala Val Gly Tyr Gly Asp
                260                 265                 270

Pro Leu Ile Ala Val Leu Pro Ser Phe His Gly Ile Lys
                275                 280                 285

<210> SEQ ID NO 126
<211> LENGTH: 439
<212> TYPE: PRT
<213> ORGANISM: Morus notabilis

<400> SEQUENCE: 126

Met Val His Glu Phe His Asp Ser Val Ile Gly Gly His Ser Gly Phe
1               5                   10                  15

Leu Arg Thr Tyr Lys Arg Leu Ser Ala Val Val Leu Trp Arg Gly Met
                20                  25                  30

Lys Arg Phe Ile Arg Asp Tyr Val Ala His Cys Glu Ile Cys Gln Gln
                35                  40                  45

Asn Glu Ser Glu Asp Leu Ser Pro Val Gly Leu Leu Gln Pro Leu Pro
            50                  55                  60

Ile Pro Asp Leu Val Trp Asp Asp Val Ser Met Asn Phe Val Gly Gly
65                  70                  75                  80

Leu Pro Lys Ser Gly Gly Phe Asp Thr Ile Leu Val Val Val Asp Arg
                85                  90                  95

Leu Ser Lys Tyr Ala His Phe Cys Pro Leu Ala His Pro Tyr Ala Ala
                100                 105                 110

Lys Gln Val Ala Ala Leu Phe Val Ser His Ile Val Lys Leu His Gly
                115                 120                 125

Val Pro Arg Ser Ile Val Ser Asp Arg Asp Ala Ile Phe Met Ser Gly
                130                 135                 140

Phe Trp Arg Glu Leu Phe Lys Leu Gln Gly Thr Lys Leu Tyr Thr Ser
145                 150                 155                 160

Ser Ala Tyr His Pro Glu Ser Asp Gly Gln Thr Glu Val Val Asn Cys
                165                 170                 175

Cys Leu Glu Ala Val Val Ser Ser Glu Asp Asp Gly Glu Gln Ser Lys
                180                 185                 190

Tyr Ser Gly Leu Thr Ser Gln Leu Val Pro Asn Phe Asp Glu Val Glu
                195                 200                 205

Ser Leu Leu Ser Thr Ile Cys Asp Thr Thr Ser Ile Ala Glu Phe Glu
210                 215                 220

Met Lys Leu Ser Gly Phe Arg Leu His Val Arg Arg Lys Leu Thr Glu
225                 230                 235                 240

Glu Val Asn Thr Ser Pro Pro Ser Ala Ala Pro Thr Ser Ala Tyr
                245                 250                 255

Asn Val Ile Ala Glu Ser Ser Asp Leu Asn Gly Phe Val Ser Thr Pro
                260                 265                 270

Ser Leu Ala Ile Thr Lys Ser Glu Thr Ser Ser Lys Asn Ile Gln Thr
                275                 280                 285
```

```
Leu Val Asp Arg Ala Ala Asp Ala Gly Leu Val Ile Ile Arg Ser Pro
290                 295                 300

Arg Val Gly Phe Phe Arg Arg Ser Arg Thr Ile Lys Gly Lys Arg Ala
305                 310                 315                 320

Pro Pro Pro Cys Lys Glu Lys Gln Glu Val Lys Glu Gly Gln Val Val
                325                 330                 335

Cys Tyr Ile Glu Gln Leu Gly Gly Glu Leu Pro Ile Glu Ser Asp Val
                340                 345                 350

Ser Gly Glu Val Ile Lys Ile Leu Arg Glu Asp Gly Asp Ser Ile Asn
            355                 360                 365

Tyr Arg Tyr Asn Glu Glu Ser Leu Phe Tyr Phe Ile Phe Ser Met Lys
370                 375                 380

Pro Asn Lys Ile Leu Ile Arg Glu Ala Ala Gly Pro Ser Lys Asn Thr
385                 390                 395                 400

Gln Arg Glu Gly Lys Lys Glu Gly Gly Ala Ile Met Val Arg Gly Ser
                405                 410                 415

Ala Gln Ala Arg His Arg Met Leu Ser Phe Gly Arg Gly Ser Cys His
                420                 425                 430

Leu Arg Arg Arg Asn Gly Cys
            435

<210> SEQ ID NO 127
<211> LENGTH: 289
<212> TYPE: PRT
<213> ORGANISM: Nelumbo nucifera

<400> SEQUENCE: 127

Met Val Ser Val Thr Val Phe Arg Ser Phe His Gly Ala Ile Asp Ser
1               5                   10                  15

Ile Thr His Leu Gln Ser Leu Ser Glu Arg Pro Gly Ala Val Pro Ile
            20                  25                  30

Tyr Asn Ala Asn Ala Lys Lys Leu Ser Phe Ala Gln Gly Leu Ala Leu
        35                  40                  45

Gly Ser Arg Ile Thr Ser Ala Asn Glu Lys Arg Ala Phe Val Pro Cys
    50                  55                  60

Leu Lys Ala Ser Glu Ser Thr Thr Glu Ile Thr Ser Val Val Tyr Leu
65                  70                  75                  80

Asp Gly Lys Ser Gln Glu Pro Leu Glu Lys Arg Ser Leu Gln Ser Thr
                85                  90                  95

Thr Phe Pro Asn Gly Phe Glu Ala Leu Val Leu Glu Val Cys Asp Glu
            100                 105                 110

Thr Asn Val Ala Glu Leu Lys Leu Lys Val Gly Asp Phe Glu Met His
        115                 120                 125

Leu Lys Arg Asn Ile Asp Thr Thr Lys His Thr Thr Pro Ile Ile Ser
    130                 135                 140

Pro Thr Pro Pro His Leu Ser Ser Glu Pro Met Val Lys Ala Thr Pro
145                 150                 155                 160

Val Ala Pro Pro Ser Ser Pro Lys Ser Ser Glu Thr Ala Ser
                165                 170                 175

Pro Phe Lys Asn Lys Ser Ser Thr Lys Ser Ser Lys Leu Ala Ala Leu
            180                 185                 190

Glu Ala Ser Gly Ala Asn Ser Tyr Val Leu Val Ser Ser Pro Lys Val
        195                 200                 205

Gly Ser Phe Arg Arg Gly Lys Thr Val Lys Gly Lys Lys Gln Pro Pro
    210                 215                 220
```

```
Ile Cys Lys Glu Gly Asp Val Ile Lys Glu Gly Gln Thr Ile Gly Tyr
225                 230                 235                 240

Leu Asn Gln Phe Gly Ser Glu Leu Pro Val Met Gln Ser Asp Val Ala
                245                 250                 255

Gly Glu Val Leu Lys Phe Leu Tyr Asn Asp Gly Asp Ala Val Gly Tyr
            260                 265                 270

Gly Asp Pro Leu Val Ala Ile Leu Pro Ser Phe His Asp Ile Asn Ile
        275                 280                 285

Asn
```

```
<210> SEQ ID NO 128
<211> LENGTH: 279
<212> TYPE: PRT
<213> ORGANISM: Nelumbo nucifera

<400> SEQUENCE: 128

Met Ala Ala Phe Leu Ile Ser Gly Asn Leu Gly Cys Val Ser Asn Ala
1               5                   10                  15

Arg Leu Ser Ser Phe Tyr Met Asp Phe Gly Arg Thr Arg Ser Ala Ser
            20                  25                  30

Met Gln Thr Ser Tyr Ala Ile Arg Ser Trp Gly Arg Gln Lys Gln Pro
        35                  40                  45

Gln Tyr Ala Gly Phe Ile Ser Thr Lys Gln Lys Pro Leu Ser Val
    50                  55                  60

Ser Cys Ser Ser Ser Glu Val Glu Thr Ala Ala Asp Leu Asp Ser
65                  70                  75                  80

Leu Gln Glu Lys Lys Ser Asn Gly Ile Thr Arg Gln Ile Ile Pro Asn
                85                  90                  95

Ser Thr Glu Val Gln Ala Leu Leu Thr Glu Ile Cys Asp Thr Thr Tyr
            100                 105                 110

Ile Ala Glu Phe Glu Leu Lys Leu Ala Gly Phe Arg Leu Tyr Val Thr
        115                 120                 125

Arg Asp Val Ala Gly Lys Ser Ala Pro Pro Pro Pro Ser Ser Leu
    130                 135                 140

Pro Ala Asn Val Ser Thr Thr Ser Asp Ala Pro Ala Leu Asn Gly Ser
145                 150                 155                 160

Val Ser Thr Pro Ser Leu Ala Ile Ala Lys Ala Val Pro Ser Ser Gly
                165                 170                 175

Glu Ile Gln Arg Met Leu Asn Lys Asp Thr Asp Glu Ser Leu Val Ile
            180                 185                 190

Leu Gln Ser Pro Lys Val Gly Tyr Phe Arg Arg Ser Arg Thr Ile Lys
        195                 200                 205

Gly Lys Arg Ala Pro Pro Ser Cys Gln Glu Lys Gln Val Val Lys Glu
    210                 215                 220

Gly Gln Val Leu Cys Phe Ile Glu Gln Leu Gly Gly Gln Ile Pro Ile
225                 230                 235                 240

Glu Ser Asp Val Ser Gly Glu Val Ile Lys Ile Leu Arg Asp Asp Gly
                245                 250                 255

Glu Pro Val Gly Tyr Gly Asp Ala Leu Ile Ala Ile Leu Pro Ser Phe
            260                 265                 270

Pro Gly Ile Lys Lys Leu Gln
        275
```

```
<210> SEQ ID NO 129
```

```
<211> LENGTH: 263
<212> TYPE: PRT
<213> ORGANISM: Camelina sativa

<400> SEQUENCE: 129

Met Ala Ser Cys Ser Leu Gly Val Pro Lys Ile Lys Ile Ser Ala Val
1               5                   10                  15

Asp Leu Ser Arg Val Ser Ser Gly Ser Leu Leu Ile Pro Phe Ser Gln
            20                  25                  30

Arg Ser Leu Leu Gly Gln Arg Pro Val Lys Tyr Leu Ser Leu Arg Thr
        35                  40                  45

Thr Phe Gly Ser Val Lys Ala Val Gln Val Ser Thr Val Pro Thr Ala
50                  55                  60

Glu Thr Ser Ala Thr Ile Glu Val Asp Ser Glu Thr Lys Ser
65                  70                  75                  80

Ser Pro Leu Asn Ala Gln Leu Val Pro Lys Pro Ser Glu Val Glu Ala
            85                  90                  95

Leu Val Thr Glu Ile Cys Asp Ser Ser Ile Ala Glu Phe Glu Leu
        100                 105                 110

Lys Leu Gly Gly Phe Arg Leu Tyr Val Ala Arg Asp Leu Thr Asp Lys
    115                 120                 125

Ser Ser Pro Gln Pro His Pro Val Pro Ala Val Ala Ala Ser Glu
130                 135                 140

Thr Thr Lys Ser Pro Asp Ser Asn Gly Ser Thr Pro Ser Thr Ser Leu
145                 150                 155                 160

Ala Ile Thr Arg Pro Ala Ser Ser Ala Ala Asp His Gly Leu Met Ile
                165                 170                 175

Leu Gln Ser Pro Lys Val Gly Phe Phe Arg Arg Ser Lys Thr Ile Lys
            180                 185                 190

Gly Lys Arg Met Pro Ser Ser Cys Lys Glu Lys Asp Gln Val Lys Glu
        195                 200                 205

Gly Gln Ile Leu Cys Tyr Ile Glu Gln Leu Gly Gly Gln Phe Pro Ile
    210                 215                 220

Glu Ser Asp Val Ser Gly Glu Val Val Lys Ile Leu Arg Glu Asp Gly
225                 230                 235                 240

Glu Pro Val Gly Tyr Asn Asp Ala Leu Ile Ser Ile Leu Pro Ser Phe
                245                 250                 255

Pro Gly Ile Lys Lys Leu Gln
            260

<210> SEQ ID NO 130
<211> LENGTH: 263
<212> TYPE: PRT
<213> ORGANISM: Camelina sativa

<400> SEQUENCE: 130

Met Ala Ser Cys Ser Leu Gly Val Pro Lys Ile Lys Ile Ser Ala Val
1               5                   10                  15

Asp Leu Ser Arg Val Ser Ser Gly Ser Leu Leu Ile Pro Phe Ser Gln
            20                  25                  30

Arg Ser Leu Leu Gly Gln Arg Pro Val Lys Tyr Leu Ser Leu Arg Thr
        35                  40                  45

Thr Phe Gly Ser Val Lys Ala Val Gln Val Ser Thr Val Pro Ala Ala
50                  55                  60

Glu Thr Ser Ala Thr Val Gly Val Glu Asp Ser Glu Glu Thr Lys Ser
65                  70                  75                  80
```

```
Ser Pro Leu Asn Ala Gln Leu Val Pro Lys Arg Ser Glu Val Glu Ala
                85                  90                  95

Leu Val Thr Glu Ile Cys Asp Ser Ser Ile Ala Glu Phe Glu Leu
            100                 105                 110

Lys Leu Gly Gly Phe Arg Leu Tyr Val Ala Arg Asp Leu Ala Asp Lys
        115                 120                 125

Ser Ser Pro Gln Pro His Pro Ile Pro Ala Val Ala Ala Ser Glu
130                 135                 140

Thr Thr Lys Ser Pro Asp Ser Asn Gly Ser Thr Pro Ser Thr Ser Leu
145                 150                 155                 160

Ala Ile Thr Arg Pro Ala Ser Ser Ala Ala Asp Gln Gly Leu Met Ile
                165                 170                 175

Leu Gln Ser Pro Lys Val Gly Phe Phe Arg Arg Ser Lys Thr Ile Lys
            180                 185                 190

Gly Lys Arg Met Pro Ser Ser Cys Lys Glu Lys Asp Gln Val Lys Glu
        195                 200                 205

Gly Gln Ile Leu Cys Tyr Ile Glu Gln Leu Gly Gly Gln Phe Pro Ile
210                 215                 220

Glu Ser Asp Val Ser Gly Glu Val Val Lys Ile Leu Arg Glu Asp Gly
225                 230                 235                 240

Glu Pro Val Gly Tyr Asn Asp Ala Leu Ile Ser Ile Leu Pro Ser Phe
                245                 250                 255

Pro Gly Ile Lys Lys Leu Gln
                260

<210> SEQ ID NO 131
<211> LENGTH: 231
<212> TYPE: PRT
<213> ORGANISM: Camelina sativa

<400> SEQUENCE: 131

Met Ala Ser Cys Ser Leu Gly Val Pro Lys Ile Lys Ile Ser Ala Val
1               5                   10                  15

Asp Leu Ser Arg Val Ser Ser Gly Ser Leu Leu Ile Pro Phe Ser Gln
            20                  25                  30

Arg Ser Leu Leu Gly Gln Arg Pro Val Lys Tyr Leu Ser Leu Arg Thr
        35                  40                  45

Thr Phe Gly Ser Val Lys Ala Val Gln Val Ser Thr Val Pro Thr Ala
    50                  55                  60

Glu Thr Ser Ala Thr Ile Glu Val Glu Asp Ser Glu Glu Thr Lys Ser
65                  70                  75                  80

Ser Pro Leu Asn Ala Gln Leu Val Pro Lys Pro Ser Glu Val Glu Ala
                85                  90                  95

Leu Val Thr Glu Ile Cys Asp Ser Ser Ile Ala Glu Phe Glu Leu
            100                 105                 110

Lys Leu Gly Gly Phe Arg Leu Tyr Val Ala Arg Asp Leu Thr Asp Lys
        115                 120                 125

Ser Ser Pro Gln Pro His Pro Val Pro Ala Val Ala Ala Ser Glu
130                 135                 140

Thr Thr Lys Ser Pro Asp Ser Asn Gly Ser Thr Pro Ser Thr Ser Leu
145                 150                 155                 160

Ala Ile Thr Arg Pro Ala Ser Ser Ala Ala Asp His Gly Leu Met Ile
                165                 170                 175

Leu Gln Ser Pro Lys Val Gly Phe Phe Arg Arg Ser Lys Thr Ile Lys
```

```
              180                 185                 190
Gly Lys Arg Met Pro Ser Ser Cys Lys Glu Lys Asp Gln Val Lys Glu
            195                 200                 205

Glu Pro Val Gly Tyr Asn Asp Ala Leu Ile Ser Ile Leu Pro Ser Phe
        210                 215                 220

Pro Gly Ile Lys Lys Leu Gln
225                 230

<210> SEQ ID NO 132
<211> LENGTH: 269
<212> TYPE: PRT
<213> ORGANISM: Camelina sativa

<400> SEQUENCE: 132

Met Asn Ser Cys Ser Leu Gly Ala Pro Lys Val Arg Ile Ser Ala Ala
1               5                   10                  15

Tyr Phe Ser Arg Leu Arg Cys Gly Asn Leu Leu Ile Pro Asn Asn Gln
            20                  25                  30

Arg Leu Leu Ile Gly Gln Ser Pro Ile Lys Tyr Gln Ser Leu Arg Thr
        35                  40                  45

Thr Leu Arg Ala Val Gln Leu Ser Thr Val Pro Pro Ala Glu Ile Ala
    50                  55                  60

Ala Val Ala Asp Val Glu Asp Ser Glu Glu Thr Glu Ser Thr Val Val
65                  70                  75                  80

Asn Thr Gln Leu Ile Pro Lys Ser Ser Glu Val Glu Ala Leu Ile Lys
                85                  90                  95

Glu Ile Thr Asp Ser Ser Ser Ile Ala Glu Phe Glu Leu Lys Leu Gly
            100                 105                 110

Gly Phe Arg Leu Tyr Val Ala Arg Lys Leu Ala Asp Gln Ser Ser Pro
        115                 120                 125

Pro Pro Gln Gln Ile Pro Pro Val Ala Ala Ser Ser Ala Pro Glu
    130                 135                 140

Gly Val His Thr Asn Gly Ser Ala Thr Ser Ser Leu Ala Ile Thr
145                 150                 155                 160

Lys Ser Ala Ser Pro Ser Asp Arg Pro Gln Thr Leu Ala Asn Lys Ala
                165                 170                 175

Ala Asp Gln Gly Leu Val Ile Leu Gln Ser Pro Thr Val Gly Tyr Phe
            180                 185                 190

Arg Arg Ser Lys Thr Ile Lys Gly Lys Arg Thr Pro Thr Ile Cys Lys
        195                 200                 205

Glu Lys Asp Thr Val Lys Glu Gly Gln Val Leu Cys Tyr Ile Glu Gln
    210                 215                 220

Leu Gly Gly Gln Ile Pro Val Glu Ser Asp Val Ser Gly Glu Ile Val
225                 230                 235                 240

Lys Ile Leu Arg Glu Asp Gly Glu Pro Val Gly Tyr Asn Asp Ala Leu
                245                 250                 255

Ile Thr Val Leu Pro Ser Phe Pro Gly Ile Lys Lys Leu
            260                 265

<210> SEQ ID NO 133
<211> LENGTH: 276
<212> TYPE: PRT
<213> ORGANISM: Camelina sativa

<400> SEQUENCE: 133

Met Asn Ser Cys Ser Leu Gly Ala Pro Lys Val Arg Ile Ala Ala Ala
```

```
              1               5                  10                 15
          Asn Phe Ser Arg Leu Arg Cys Gly Asn Leu Leu Ile Pro Asn Asn Gln
                          20                  25                  30
          Arg Leu Phe Ile Asp Gln Ser Gln Ser Gln Ser Pro Ile Lys Tyr Pro
                          35                  40                  45
          Ser Leu Arg Thr Thr Leu Arg Ala Val Lys Ala Val Gln Leu Ser Thr
                          50                  55                  60
          Val Pro Pro Ala Asp Ile Ala Val Ala Asp Val Glu Asp Ser Gln
          65                          70                  75              80
          Glu Thr Glu Ser Thr Val Val Asn Thr Gln Leu Ile Pro Lys Ser Ser
                                  85                  90                  95
          Glu Val Glu Ala Leu Ile Lys Glu Ile Thr Asp Ser Ser Ile Ala
                          100                 105                 110
          Glu Phe Glu Leu Lys Leu Gly Gly Phe Arg Leu Tyr Val Ala Arg Lys
                          115                 120                 125
          Leu Ala Asp Gln Ser Ser Pro Pro Gln Gln Ile Pro Pro Val Val
          130                         135                 140
          Ala Ala Ser Ser Ala Pro Glu Gly Val His Thr Asn Gly Ser Ala Thr
          145                         150                 155                 160
          Ser Ser Ser Leu Ala Ile Thr Lys Ser Ala Ser Pro Ser Asp Arg Pro
                          165                 170                 175
          Gln Thr Leu Ala Asn Lys Ala Ala Asp Gln Gly Leu Val Ile Leu Gln
                          180                 185                 190
          Ser Pro Thr Val Gly Tyr Phe Arg Arg Ser Lys Thr Ile Lys Gly Lys
                          195                 200                 205
          Arg Thr Pro Thr Ile Cys Lys Glu Lys Asp Ile Val Lys Glu Gly Gln
                          210                 215                 220
          Val Leu Cys Tyr Ile Glu Gln Leu Gly Gly Gln Ile Pro Val Glu Ser
          225                         230                 235                 240
          Asp Val Ser Gly Glu Ile Val Lys Ile Leu Arg Glu Asp Gly Glu Pro
                          245                 250                 255
          Val Gly Tyr Asn Asp Ala Leu Ile Thr Val Leu Pro Ser Phe Pro Gly
                          260                 265                 270
          Ile Lys Lys Leu
                          275

<210> SEQ ID NO 134
<211> LENGTH: 276
<212> TYPE: PRT
<213> ORGANISM: Camelina sativa

<400> SEQUENCE: 134

Met Ala Ser Ser Ala Ala Leu Gly Ser Leu His Gln Thr Leu Gly Ser
          1               5                  10                 15
          Gln Ser Glu Leu His Leu Leu Ser Gly Asn Trp Ser Ala Ser Gly Thr
                          20                  25                  30
          Ser Cys Val Pro Arg Trp Arg Leu Ser Asn Arg Ser Asn Tyr Thr
                          35                  40                  45
          Leu Val Leu Arg Ala Lys Ala Ser Lys Thr Ser Thr Thr Lys Ser
                          50                  55                  60
          Asp Asp Ser Ser Asp Ala Thr Val Ser Asn Gly Lys Lys Ser Val Arg
          65                          70                  75              80
          Arg Thr Thr Phe Pro Lys Glu Val Glu Ala Leu Val His Glu Met Cys
                                  85                  90                  95
```

-continued

```
Asp Glu Thr Glu Val Ala Val Leu Lys Leu Lys Val Gly Asp Phe Glu
            100                 105                 110

Met Asn Leu Lys Arg Lys Ile Gly Ala Ala Thr Asn Pro Ile Pro Val
        115                 120                 125

Glu Asp Ile Ser Pro Thr Val Ala Pro Pro Ile Pro Ser Glu Pro Met
    130                 135                 140

Asp Lys Ser Val Ser Ser Ala Pro Ser Pro Ser Lys Ala Lys Pro Ser
145                 150                 155                 160

Glu Lys Val Ser Pro Phe Met Asn Thr Ser Tyr Gly Lys Pro Ala Lys
                165                 170                 175

Leu Val Ala Leu Glu Ala Ser Gly Ser Asn Asn Tyr Val Leu Val Lys
            180                 185                 190

Ser Pro Ser Val Gly Glu Phe His Arg Ser Arg Thr Val Lys Gly Lys
        195                 200                 205

Lys Leu Ser Pro Ser Cys Lys Glu Gly Asp Glu Ile Lys Glu Gly Gln
    210                 215                 220

Val Ile Gly Tyr Leu His Gln Leu Gly Thr Glu Leu Pro Val Thr Ser
225                 230                 235                 240

Asp Val Ala Gly Glu Val Leu Lys Leu Leu Ser Asp Asp Gly Asp Ser
                245                 250                 255

Val Gly Tyr Gly Asp Pro Leu Val Ala Val Leu Pro Ser Phe His Asp
            260                 265                 270

Ile Asn Ile Gln
        275
```

<210> SEQ ID NO 135
<211> LENGTH: 44
<212> TYPE: PRT
<213> ORGANISM: Arabidopsis thaliana

<400> SEQUENCE: 135

```
Val Gly Lys Phe Gln Arg Ser Arg Thr Val Lys Gly Lys Lys Gln Ser
1               5                   10                  15

Pro Ser Cys Lys Glu Gly Asp Ala Ile Lys Glu Gly Gln Val Ile Gly
            20                  25                  30

Tyr Leu His Gln Leu Gly Thr Glu Leu Pro Val Thr
        35                  40
```

<210> SEQ ID NO 136
<211> LENGTH: 44
<212> TYPE: PRT
<213> ORGANISM: Artificial sequence
<220> FEATURE:
<223> OTHER INFORMATION: Polypeptide
<220> FEATURE:
<221> NAME/KEY: misc_feature
<222> LOCATION: (3)..(10)
<223> OTHER INFORMATION: Xaa can be any naturally occurring amino acid
<220> FEATURE:
<221> NAME/KEY: misc_feature
<222> LOCATION: (13)..(27)
<223> OTHER INFORMATION: Xaa can be any naturally occurring amino acid
<220> FEATURE:
<221> NAME/KEY: misc_feature
<222> LOCATION: (30)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(41)

```
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid

<400> SEQUENCE: 136

Val Gly Xaa Xaa Xaa Xaa Xaa Xaa Xaa Lys Gly Xaa Xaa Xaa Xaa
1               5                   10                  15

Xaa Xaa Xaa Xaa Xaa Xaa Xaa Xaa Xaa Xaa Gly Gln Xaa Xaa Xaa
            20                  25                  30

Xaa Xaa Xaa Gln Xaa Gly Xaa Xaa Xaa Pro Xaa Xaa
        35                  40

<210> SEQ ID NO 137
<211> LENGTH: 44
<212> TYPE: PRT
<213> ORGANISM: Artificial sequence
<220> FEATURE:
<223> OTHER INFORMATION: Polypeptide
<220> FEATURE:
<221> NAME/KEY: MISC_FEATURE
<222> LOCATION: (3)..(3)
<223> OTHER INFORMATION: X = S or T or L or F or K or Y or I or V or L
<220> FEATURE:
<221> NAME/KEY: MISC_FEATURE
<222> LOCATION: (4)..(4)
<223> OTHER INFORMATION: X = F or I or L
<220> FEATURE:
<221> NAME/KEY: MISC_FEATURE
<222> LOCATION: (5)..(5)
<223> OTHER INFORMATION: X = R or Q or K
<220> FEATURE:
<221> NAME/KEY: MISC_FEATURE
<222> LOCATION: (6)..(6)
<223> OTHER INFORMATION: X = R or S or K or T or I or L or Y
<220> FEATURE:
<221> NAME/KEY: MISC_FEATURE
<222> LOCATION: (7)..(7)
<223> OTHER INFORMATION: X = N or G or A or S or C
<220> FEATURE:
<221> NAME/KEY: MISC_FEATURE
<222> LOCATION: (8)..(8)
<223> OTHER INFORMATION: X = R or I or K or T
<220> FEATURE:
<221> NAME/KEY: MISC_FEATURE
<222> LOCATION: (9)..(9)
<223> OTHER INFORMATION: X = T or K or S or V or Y or L or F
<220> FEATURE:
<221> NAME/KEY: MISC_FEATURE
<222> LOCATION: (10)..(10)
<223> OTHER INFORMATION: X = V or L or I or A or M
<220> FEATURE:
<221> NAME/KEY: MISC_FEATURE
<222> LOCATION: (13)..(13)
<223> OTHER INFORMATION: X = K or R or N or E
<220> FEATURE:
<221> NAME/KEY: MISC_FEATURE
<222> LOCATION: (14)..(14)
<223> OTHER INFORMATION: X = K or R or N or Q or C or S or F
<220> FEATURE:
<221> NAME/KEY: MISC_FEATURE
<222> LOCATION: (15)..(15)
<223> OTHER INFORMATION: X = Q or M or L or G or A or T
<220> FEATURE:
<221> NAME/KEY: MISC_FEATURE
<222> LOCATION: (16)..(16)
<223> OTHER INFORMATION: X = P or R or E or A or G or N or S
<220> FEATURE:
<221> NAME/KEY: MISC_FEATURE
<222> LOCATION: (17)..(17)
<223> OTHER INFORMATION: X = P or L or R or A or N or T or S
<220> FEATURE:
<221> NAME/KEY: MISC_FEATURE
<222> LOCATION: (18)..(18)
```

```
<223> OTHER INFORMATION: X = I or S or T or L or V or C
<220> FEATURE:
<221> NAME/KEY: MISC_FEATURE
<222> LOCATION: (19)..(19)
<223> OTHER INFORMATION: X = C or F or A or V or I
<220> FEATURE:
<221> NAME/KEY: MISC_FEATURE
<222> LOCATION: (20)..(20)
<223> OTHER INFORMATION: X = K or N or E or A or D or Q
<220> FEATURE:
<221> NAME/KEY: MISC_FEATURE
<222> LOCATION: (21)..(21)
<223> OTHER INFORMATION: X = E or V or K or D
<220> FEATURE:
<221> NAME/KEY: MISC_FEATURE
<222> LOCATION: (22)..(22)
<223> OTHER INFORMATION: X = G or N or K or R or D or M or T
<220> FEATURE:
<221> NAME/KEY: MISC_FEATURE
<222> LOCATION: (23)..(23)
<223> OTHER INFORMATION: X = D or Q or A
<220> FEATURE:
<221> NAME/KEY: MISC_FEATURE
<222> LOCATION: (24)..(24)
<223> OTHER INFORMATION: X = V or L or F or A or I or M or S or T or E
      or D or R or P or Q or K or N
<220> FEATURE:
<221> NAME/KEY: MISC_FEATURE
<222> LOCATION: (25)..(25)
<223> OTHER INFORMATION: X = I or V or G or L
<220> FEATURE:
<221> NAME/KEY: MISC_FEATURE
<222> LOCATION: (26)..(26)
<223> OTHER INFORMATION: X = K or R or Q or E
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: MISC_FEATURE
<222> LOCATION: (30)..(30)
<223> OTHER INFORMATION: X = T or V or I
<220> FEATURE:
<221> NAME/KEY: MISC_FEATURE
<222> LOCATION: (31)..(31)
<223> OTHER INFORMATION: X = I or V or L
<220> FEATURE:
<221> NAME/KEY: MISC_FEATURE
<222> LOCATION: (32)..(32)
<223> OTHER INFORMATION: X = G or A or C or F
<220> FEATURE:
<221> NAME/KEY: MISC_FEATURE
<222> LOCATION: (33)..(33)
<223> OTHER INFORMATION: X = Y or F or W or C
<220> FEATURE:
<221> NAME/KEY: MISC_FEATURE
<222> LOCATION: (34)..(34)
<223> OTHER INFORMATION: X = L or V or I
<220> FEATURE:
<221> NAME/KEY: MISC_FEATURE
<222> LOCATION: (35)..(35)
<223> OTHER INFORMATION: X = D or N or H or E
<220> FEATURE:
<221> NAME/KEY: MISC_FEATURE
<222> LOCATION: (37)..(37)
<223> OTHER INFORMATION: X = F or L or I
<220> FEATURE:
<221> NAME/KEY: MISC_FEATURE
<222> LOCATION: (39)..(39)
<223> OTHER INFORMATION: X = G or T or S or K or N or A or V
<220> FEATURE:
<221> NAME/KEY: MISC_FEATURE
<222> LOCATION: (40)..(40)
<223> OTHER INFORMATION: X = E or Q or G or S or H or Y or F or V
<220> FEATURE:
<221> NAME/KEY: MISC_FEATURE
<222> LOCATION: (41)..(41)
<223> OTHER INFORMATION: X = L or N or T or V or I or M or W or Q or F
<220> FEATURE:
```

```
<221> NAME/KEY: MISC_FEATURE
<222> LOCATION: (43)..(43)
<223> OTHER INFORMATION: X = V or I or M or L
<220> FEATURE:
<221> NAME/KEY: MISC_FEATURE
<222> LOCATION: (44)..(44)
<223> OTHER INFORMATION: X = E or K or R or M or T or N

<400> SEQUENCE: 137
```

Val Gly Xaa Xaa Xaa Xaa Xaa Xaa Xaa Lys Gly Xaa Xaa Xaa Xaa
1               5                   10                  15

Xaa Xaa Xaa Xaa Xaa Xaa Xaa Xaa Xaa Gly Gln Xaa Xaa Xaa
            20                  25                  30

Xaa Xaa Xaa Gln Xaa Gly Xaa Xaa Xaa Pro Xaa Xaa
        35                  40

```
<210> SEQ ID NO 138
<211> LENGTH: 1650
<212> TYPE: DNA
<213> ORGANISM: Artificial sequence
<220> FEATURE:
<223> OTHER INFORMATION: RNAi cassette

<400> SEQUENCE: 138
gcggccgcca aggctcattg agaaaaagc  ctttgcaaac tgctactttt cctaatggat      60
ttgaggcttt ggtattagag gtctgtgatg agactgaaat tgctgaactg aaagtaaagg     120
ttggagattt tgaaatgcat attaagcgaa acattggagc aacaaaggtt cctttgtcta     180
acatttcacc tgaggtggag ttcctgctca caaaattatg cgacacaagt tcaattgggg     240
agttagattt aaaacttgct ggcactgaat tgaattgttt aaggtttggt gagcctaaaa     300
gaatttgaac tggttttcaa ataaatgaat taagatgtta attaggagaa ttgaagttta     360
ttacaatttg gattggggat tagaatttga agctacattt aaaattcgaa aaaaaaagac     420
agtgaaactt aaaacgttca taaaaggac caaaagttt taaaaaaatt gtcgctaaaa       480
ctcaaacata tatattacaa tgccatatgt gcttataagg acttaaggag cagtttcttg     540
ggtggctagg ggatatgaca tttttttact gcacaataaa tatcctggcc gttgcacccg     600
gagatgcaca gagctttgag cagatcagat gaatgattaa attgttttga agagaatcta     660
ttccttcaca ctgaattctt gcacaaaacc ttgacactga atttaattgt gccaaatcaa     720
caattctttt agcccaggaa atataatcca ttttttaatt ttctgctact tattttcatc    780
ttcttaatac aaagatatac aagtattttg catattcaga ttttttttg ccaaaacaat     840 aaatctagct atatacattt tcctttgacc aactcggcta ctaaaattgg ttggattctg    900
attttactat ttgtgaattt caatcttagc tttgacctat acccaaaata aaccctcctg    960
atctgtttct ccagtggcga gagacatgat ttaacgagag ttgaacacaa gatctagact   1020
ctagaataaa aaagacacg aatattagaa aatgatctaa tataaaataa ttataaggag   1080
tgagacttca atctaggtc agctagccca ccatcttgtg gagctagttg gaaaccccct    1140
gggtgtgttt ctctagactc tagaataaca ttgatcagcc taaccaaaca taacgaacga   1200
agatttaata tcaggacata tatatggatc ttggcaagtc aattaattaa ttaattaatt   1260
tccagcccaa caccttacag aaattagcat gtatgagact acttgtaagg aaaaacgagc   1320
aatgaaagat gcatgtgatc gatctgaata agaggggaaa caagaattaa taaacatata   1380
tgtatacctt ccagcaagtt ttaaatctaa ctccccaatt gaacttgtgt cgcataattt   1440
tgtgagcagg aactccacct caggtgaaat gttagacaaa ggaacctttg ttgctccaat   1500
```

```
gtttcgctta atatgcattt caaaatctcc aacctttact ttcagttcag caatttcagt    1560
ctcatcacag acctctaata ccaaagcctc aaatccatta ggaaaagtag cagtttgcaa    1620 aggcttttc tccaatgagc cttgccgcgg                                      1650
```

<210> SEQ ID NO 139
<211> LENGTH: 48
<212> TYPE: PRT
<213> ORGANISM: Arabidopsis thaliana

<400> SEQUENCE: 139

Gln Lys Gly Gln Val Leu Cys Ile Val Glu Ala Met Lys Leu Met Asn
1               5                   10                  15

Glu Ile Glu Ser Asp His Thr Gly Thr Val Val Asp Ile Val Ala Glu
            20                  25                  30

Asp Gly Lys Pro Val Ser Leu Asp Thr Pro Leu Phe Val Gln Pro
        35                  40                  45

<210> SEQ ID NO 140
<211> LENGTH: 48
<212> TYPE: PRT
<213> ORGANISM: Arabidopsis thaliana

<400> SEQUENCE: 140

Gln Lys Gly Gln Ile Val Cys Ile Ile Glu Ala Met Lys Leu Met Asn
1               5                   10                  15

Glu Ile Glu Ala Glu Lys Ser Gly Thr Ile Met Glu Leu Leu Ala Glu
            20                  25                  30

Asp Gly Lys Pro Val Ser Val Asp Thr Pro Leu Phe Val Ile Ala Pro
        35                  40                  45

<210> SEQ ID NO 141
<211> LENGTH: 56
<212> TYPE: PRT
<213> ORGANISM: Arabidopsis thaliana

<400> SEQUENCE: 141

Lys Glu Gly Gln Val Ile Gly Tyr Leu His Gln Leu Gly Thr Glu Leu
1               5                   10                  15

Pro Val Thr Ser Asp Val Ala Gly Glu Val Leu Lys Leu Leu Ser Asp
            20                  25                  30

Asp Gly Asp Ser Val Gly Tyr Gly Asp Pro Leu Val Ala Val Leu Pro
        35                  40                  45

Ser Phe His Asp Ile Asn Ile Gln
        50                  55

<210> SEQ ID NO 142
<211> LENGTH: 57
<212> TYPE: PRT
<213> ORGANISM: Arabidopsis thaliana

<400> SEQUENCE: 142

Lys Glu Gly Gln Val Leu Cys Tyr Ile Glu Gln Leu Gly Gly Gln Ile
1               5                   10                  15

Pro Val Glu Ser Asp Val Ser Gly Glu Ile Val Lys Ile Leu Arg Glu
            20                  25                  30

Asp Gly Glu Pro Val Gly Tyr Asn Asp Ala Leu Ile Thr Val Leu Pro
        35                  40                  45

Ser Phe Pro Gly Ile Lys Lys Leu Gln
        50                  55

<210> SEQ ID NO 143
<211> LENGTH: 57
<212> TYPE: PRT
<213> ORGANISM: Arabidopsis thaliana

<400> SEQUENCE: 143

Lys Glu Gly Gln Ile Leu Cys Tyr Ile Glu Gln Leu Gly Gly Gln Phe
1               5                   10                  15

Pro Ile Glu Ser Asp Val Thr Gly Glu Val Val Lys Ile Leu Arg Glu
            20                  25                  30

Asp Gly Glu Pro Val Gly Tyr Asn Asp Ala Leu Ile Ser Ile Leu Pro
        35                  40                  45

Ser Phe Pro Gly Ile Lys Lys Leu Gln
    50                  55

<210> SEQ ID NO 144
<211> LENGTH: 36
<212> TYPE: DNA
<213> ORGANISM: Artificial sequence
<220> FEATURE:
<223> OTHER INFORMATION: Primer

<400> SEQUENCE: 144
catatgtcag ctgaaggaaa ggagaaaaac tcattg                                 36

<210> SEQ ID NO 145
<211> LENGTH: 32
<212> TYPE: DNA
<213> ORGANISM: Artificial sequence
<220> FEATURE:
<223> OTHER INFORMATION: Primer

<400> SEQUENCE: 145
ggatccctac ggttgaacca caaacagagg ag                                     32

<210> SEQ ID NO 146
<211> LENGTH: 33
<212> TYPE: DNA
<213> ORGANISM: Artificial sequence
<220> FEATURE:
<223> OTHER INFORMATION: Primer

<400> SEQUENCE: 146
catatggaat ttatggctaa agtctctggt ctt                                    33

<210> SEQ ID NO 147
<211> LENGTH: 29
<212> TYPE: DNA
<213> ORGANISM: Artificial sequence
<220> FEATURE:
<223> OTHER INFORMATION: Primer

<400> SEQUENCE: 147
ggatcctcaa ggtgcgatga caaaaagag                                         29

<210> SEQ ID NO 148
<211> LENGTH: 29
<212> TYPE: DNA
<213> ORGANISM: Artificial sequence
<220> FEATURE:
<223> OTHER INFORMATION: Primer

<400> SEQUENCE: 148
gaattcgcta aggccgctaa atcttcgac                                    29

<210> SEQ ID NO 149
<211> LENGTH: 27
<212> TYPE: DNA
<213> ORGANISM: Artificial sequence
<220> FEATURE:
<223> OTHER INFORMATION: Primer

<400> SEQUENCE: 149
ctcgagtcac tggatgttga tgtcgtg                                      27

<210> SEQ ID NO 150
<211> LENGTH: 30
<212> TYPE: DNA
<213> ORGANISM: Artificial sequence
<220> FEATURE:
<223> OTHER INFORMATION: Primer

<400> SEQUENCE: 150
catatgacga ctctgcgatc tgtgaaagct                                   30

<210> SEQ ID NO 151
<211> LENGTH: 31
<212> TYPE: DNA
<213> ORGANISM: Artificial sequence
<220> FEATURE:
<223> OTHER INFORMATION: Primer

<400> SEQUENCE: 151
ggatccttac tgaagcttct tgatgccagg a                                 31

<210> SEQ ID NO 152
<211> LENGTH: 29
<212> TYPE: DNA
<213> ORGANISM: Artificial sequence
<220> FEATURE:
<223> OTHER INFORMATION: Primer

<400> SEQUENCE: 152
catatggctg tccaagtgtc tactgtccc                                    29

<210> SEQ ID NO 153
<211> LENGTH: 31
<212> TYPE: DNA
<213> ORGANISM: Artificial sequence
<220> FEATURE:
<223> OTHER INFORMATION: Primer

<400> SEQUENCE: 153
ggatccttac tgaagcttct tgatcccagg g                                 31

<210> SEQ ID NO 154
<211> LENGTH: 23
<212> TYPE: DNA
<213> ORGANISM: Artificial sequence
<220> FEATURE:
<223> OTHER INFORMATION: Primer

<400> SEQUENCE: 154
gtgttagtca catctcccgc agt                                          23

<210> SEQ ID NO 155
<211> LENGTH: 25
<212> TYPE: DNA
<213> ORGANISM: Artificial sequence
<220> FEATURE:
<223> OTHER INFORMATION: Primer

<400> SEQUENCE: 155
gatgttgatg tcgtggaaag atggc           25

<210> SEQ ID NO 156
<211> LENGTH: 20
<212> TYPE: DNA
<213> ORGANISM: Artificial sequence
<220> FEATURE:
<223> OTHER INFORMATION: Primer

<400> SEQUENCE: 156
gctcctagcc catctcaagc           20

<210> SEQ ID NO 157
<211> LENGTH: 20
<212> TYPE: DNA
<213> ORGANISM: Artificial sequence
<220> FEATURE:
<223> OTHER INFORMATION: Primer

<400> SEQUENCE: 157
tccagatgcc tccaaagcag           20

<210> SEQ ID NO 158
<211> LENGTH: 21
<212> TYPE: DNA
<213> ORGANISM: Artificial sequence
<220> FEATURE:
<223> OTHER INFORMATION: Primer

<400> SEQUENCE: 158
ccagatcttc atcgtcgtgg t           21

<210> SEQ ID NO 159
<211> LENGTH: 22
<212> TYPE: DNA
<213> ORGANISM: Artificial sequence
<220> FEATURE:
<223> OTHER INFORMATION: Primer

<400> SEQUENCE: 159
atccagcctt aaccattcca gt           22

<210> SEQ ID NO 160
<211> LENGTH: 35
<212> TYPE: DNA
<213> ORGANISM: Artificial sequence
<220> FEATURE:
<223> OTHER INFORMATION: Primer

<400> SEQUENCE: 160
gcattgttga agccatgagg ttaatgaatg aaata           35

<210> SEQ ID NO 161
<211> LENGTH: 35
<212> TYPE: DNA
<213> ORGANISM: Artificial sequence
<220> FEATURE:
<223> OTHER INFORMATION: Primer

<400> SEQUENCE: 161
tatttcattc attaacctca tggcttcaac aatgc           35

<210> SEQ ID NO 162
<211> LENGTH: 2625
<212> TYPE: DNA
<213> ORGANISM: Pisum sativum

<400> SEQUENCE: 162

| | | | | | |
|---|---|---|---|---|---|
| atggcttcct | cttctgcaac | tcttgttggt | tctactgctt | ctgatcttct | caggagttca | 60 |
| actactggtt | tcactggtgt | ccctttgaga | accttgggaa | gggcagggtt | ggtcttgaaa | 120 |
| agaagggatt | taactgttag | tgttactgct | aagttgagga | aggtgaagag | gcgtgaatat | 180 |
| ccatggtcaa | gtaaccctga | tcccaatatg | aaaggtgggc | ggttgcgtca | tctctcaacg | 240 |
| ttccagccac | tcaaacagcc | gccaaagcct | gttattttgg | agtttgaaaa | gcctcttatt | 300 |
| aatatggaaa | agaagattaa | tgattttcgg | aaggtggcag | aaaaaactgg | tgtggattta | 360 |
| agtgatcaga | ttctcgcatt | ggaggctaag | taccaaaagg | ctttggtgga | attgtataca | 420 |
| aatctaactc | ctatacagcg | ggtcaccgtt | gcacggcatc | ctaacaggcc | tactttcctg | 480 |
| gatcacatgt | ataacatgac | tgaaaagttt | gtggaactcc | atggtgatcg | tgaaggatac | 540 |
| gatgatcctg | ctattgccgc | tggtctaggg | agtatagatg | gtaaaaccta | catgttcatc | 600 |
| ggccaccaaa | agggtagaga | tactaaagaa | aatattaagc | gtaactttgc | gatgccaact | 660 |
| ccacacggtt | ataggaaagc | tctgcgcttg | atggaatatg | cagatcatca | cgggttcccg | 720 |
| atagttactt | tcattgacac | ccctggggca | tttgctgacc | tcaaatccga | gcaacttggt | 780 |
| caaggtgaag | caattgctca | taatttgaga | tccatgtttg | ctctgaaggt | gccagttatt | 840 |
| tctatagtta | ttggcgaagg | tggatctggc | ggtgcccttg | ccattggatg | tgctaataaa | 900 |
| ttactcatgc | ttgaaaattc | agtgttcttt | gttgccatgc | cagaggcatg | cggtgcaatc | 960 |
| ttgtggaaga | gtaataaagc | tgctccaaag | gctgctgagc | gactgaagat | tacagcatct | 1020 |
| gcattgttgg | atttggaaat | tgcagatggc | attataccgg | agccctggc | tggtgcacat | 1080 |
| actgatccaa | gttggatgtc | tcaacagatt | aaaattgcaa | tcaatgaagc | tatggatgaa | 1140 |
| ctcaccaagt | tgagcacaga | agacctaata | aaagatcgca | tgcataagtt | ccgaaaactc | 1200 |
| ggtgttgatg | ggatccagga | aggaattcct | ttagttccca | gtaagaaagt | caacacgaaa | 1260 |
| aagagggaaa | taggtgttcc | gccgaagagg | caggaggtac | ctattcctga | ttctcaaata | 1320 |
| gaggctgaaa | ttgagaaact | gaagaaagct | attttcgaag | gggaggactc | ttctgcggca | 1380 |
| aagaagaatc | ctggttctca | ataggggtct | gcaattgaca | aactgaaggg | tttattttg | 1440 |
| gaaggtaagg | actcttctgc | ggcaaagaag | actcctggtt | ctcaaatagt | ggctgaactt | 1500 |
| gacaaactga | agggtttata | tttggaagct | aaggactctt | ctgcggcaaa | ggttcctggt | 1560 |
| tctcaaatag | tggctgaaat | tgagaaactg | aagaatagta | ttttcgaaga | tgaggactcc | 1620 |
| tcttctgctg | tttctgccaga | aagattcct | ggttctgaaa | tagcggttga | aattgcgaaa | 1680 |
| ctgaagaaaa | atattttgga | aggtaaggac | tcctcttctg | agccttcaaa | actcgatctg | 1740 |
| gacaagacaa | tagagactct | gaaaagggag | gttaatcgaa | attctctga | ggccgttaaa | 1800 |
| gccgcgggct | taacaaaaac | attgacgaaa | ctacgggtg | aaatttcaaa | agcaaaggca | 1860 |
| ggtaaccaac | ctttgactcc | attgctgaag | gtggagataa | aagtttaa | ccaaaggtta | 1920 |
| tcagcggctc | ctaattccag | aaagctgctg | aagaagcgtg | gcttgttaag | agaagtgact | 1980 |
| aaagtcaagc | ttttgttgga | taaaaacaag | gctgcaacac | gtaagcaaga | gctaaagaaa | 2040 |
| aagtcggatg | aacacaagga | ggctgcaaga | cttgagcaag | aactaaagaa | aaagtttgat | 2100 |
| gaagtcatgg | atactcctag | aataaaggaa | aagtatgaag | cattacggtc | tgaagtccgg | 2160 |

```
cgcgttgacg catcctcagg aagtggcttg gacgatgaac tgaagaagaa aatcattgag    2220
ttcaataagg aggtagactt ggagctggct acagctgtga agtcggtagg gttagaggtt    2280
gagtctgtga aaccaggaca tggctggaac aagtcttcag tgccagagat agaagaacta    2340
aacaaagatg tacaaaagga aattgaaatt gtggcaaact cgtcaccgaa tgttaagaga    2400
ctgatagagc aattgaaact ggaggttgcc aagtctggag ggaaaccaga ttctgaatcg    2460
aagagtagaa ttgatgcttt gacgcaacag attaagaaga gccttgctga ggctgttgat    2520
tcgcctagcc tgaaagagaa gtatgaaaac ctcactcgac cagcaggaga cactctcacc    2580
gatgacaaat tgagagagaa agttggtgta aatcgcaact tctct                    2625
```

<210> SEQ ID NO 163
<211> LENGTH: 875
<212> TYPE: PRT
<213> ORGANISM: Pisum sativum

<400> SEQUENCE: 163

```
Met Ala Ser Ser Ala Thr Leu Val Gly Ser Thr Ala Ser Asp Leu
1               5                   10                  15

Leu Arg Ser Ser Thr Thr Gly Phe Thr Gly Val Pro Leu Arg Thr Leu
            20                  25                  30

Gly Arg Ala Gly Leu Val Leu Lys Arg Arg Asp Leu Thr Val Ser Val
        35                  40                  45

Thr Ala Lys Leu Arg Lys Val Lys Arg Arg Glu Tyr Pro Trp Ser Ser
    50                  55                  60

Asn Pro Asp Pro Asn Met Lys Gly Gly Arg Leu Arg His Leu Ser Thr
65                  70                  75                  80

Phe Gln Pro Leu Lys Gln Pro Lys Pro Val Ile Leu Glu Phe Glu
            85                  90                  95

Lys Pro Leu Ile Asn Met Glu Lys Lys Ile Asn Asp Phe Arg Lys Val
            100                 105                 110

Ala Glu Lys Thr Gly Val Asp Leu Ser Asp Gln Ile Leu Ala Leu Glu
        115                 120                 125

Ala Lys Tyr Gln Lys Ala Leu Val Glu Leu Tyr Thr Asn Leu Thr Pro
    130                 135                 140

Ile Gln Arg Val Thr Val Ala Arg His Pro Asn Arg Pro Thr Phe Leu
145                 150                 155                 160

Asp His Met Tyr Asn Met Thr Glu Lys Phe Val Glu Leu His Gly Asp
                165                 170                 175

Arg Glu Gly Tyr Asp Asp Pro Ala Ile Ala Ala Gly Leu Gly Ser Ile
            180                 185                 190

Asp Gly Lys Thr Tyr Met Phe Ile Gly His Gln Lys Gly Arg Asp Thr
        195                 200                 205

Lys Glu Asn Ile Lys Arg Asn Phe Ala Met Pro Thr Pro His Gly Tyr
    210                 215                 220

Arg Lys Ala Leu Arg Leu Met Glu Tyr Ala Asp His His Gly Phe Pro
225                 230                 235                 240

Ile Val Thr Phe Ile Asp Thr Pro Gly Ala Phe Ala Asp Leu Lys Ser
                245                 250                 255

Glu Gln Leu Gly Gln Gly Glu Ala Ile Ala His Asn Leu Arg Ser Met
            260                 265                 270

Phe Ala Leu Lys Val Pro Val Ile Ser Ile Val Ile Gly Glu Gly Gly
        275                 280                 285
```

-continued

```
Ser Gly Gly Ala Leu Ala Ile Gly Cys Ala Asn Lys Leu Leu Met Leu
    290                 295                 300

Glu Asn Ser Val Phe Phe Val Ala Met Pro Glu Ala Cys Gly Ala Ile
305                 310                 315                 320

Leu Trp Lys Ser Asn Lys Ala Ala Pro Lys Ala Ala Glu Arg Leu Lys
                325                 330                 335

Ile Thr Ala Ser Ala Leu Leu Asp Leu Glu Ile Ala Asp Gly Ile Ile
                340                 345                 350

Pro Glu Pro Leu Ala Gly Ala His Thr Asp Pro Ser Trp Met Ser Gln
            355                 360                 365

Gln Ile Lys Ile Ala Ile Asn Glu Ala Met Asp Glu Leu Thr Lys Leu
    370                 375                 380

Ser Thr Glu Asp Leu Ile Lys Asp Arg Met His Lys Phe Arg Lys Leu
385                 390                 395                 400

Gly Val Asp Gly Ile Gln Glu Gly Ile Pro Leu Val Pro Ser Lys Lys
                405                 410                 415

Val Asn Thr Lys Lys Arg Glu Ile Gly Val Pro Pro Lys Arg Gln Glu
                420                 425                 430

Val Pro Ile Pro Asp Ser Gln Ile Glu Ala Glu Ile Glu Lys Leu Lys
            435                 440                 445

Lys Ala Ile Phe Glu Gly Glu Asp Ser Ser Ala Ala Lys Lys Asn Pro
    450                 455                 460

Gly Ser Gln Ile Gly Ser Ala Ile Asp Lys Leu Lys Gly Leu Phe Leu
465                 470                 475                 480

Glu Gly Lys Asp Ser Ser Ala Ala Lys Lys Thr Pro Gly Ser Gln Ile
                485                 490                 495

Val Ala Glu Leu Asp Lys Leu Lys Gly Leu Tyr Leu Glu Ala Lys Asp
            500                 505                 510

Ser Ser Ala Ala Lys Val Pro Gly Ser Gln Ile Val Ala Glu Ile Glu
    515                 520                 525

Lys Leu Lys Asn Ser Ile Phe Glu Asp Glu Asp Ser Ser Ser Ala Val
    530                 535                 540

Leu Pro Glu Lys Ile Pro Gly Ser Glu Ile Ala Val Glu Ile Ala Lys
545                 550                 555                 560

Leu Lys Lys Asn Ile Leu Glu Gly Lys Asp Ser Ser Ser Glu Pro Ser
                565                 570                 575

Lys Leu Asp Leu Asp Lys Thr Ile Glu Thr Leu Lys Arg Glu Val Asn
            580                 585                 590

Arg Glu Phe Ser Glu Ala Val Lys Ala Ala Gly Leu Thr Lys Thr Leu
    595                 600                 605

Thr Lys Leu Arg Gly Glu Ile Ser Lys Ala Lys Ala Gly Asn Gln Pro
610                 615                 620

Leu Thr Pro Leu Leu Lys Val Glu Ile Lys Ser Phe Asn Gln Arg Leu
625                 630                 635                 640

Ser Ala Ala Pro Asn Ser Arg Lys Leu Leu Lys Arg Gly Leu Leu
                645                 650                 655

Arg Glu Val Thr Lys Val Lys Leu Leu Asp Lys Asn Lys Ala Ala
                660                 665                 670

Thr Arg Lys Gln Glu Leu Lys Lys Ser Asp Glu His Lys Glu Ala
            675                 680                 685

Ala Arg Leu Glu Gln Glu Leu Lys Lys Phe Asp Glu Val Met Asp
690                 695                 700

Thr Pro Arg Ile Lys Glu Lys Tyr Glu Ala Leu Arg Ser Glu Val Arg
```

```
                705                 710                 715                 720
Arg Val Asp Ala Ser Ser Gly Ser Gly Leu Asp Asp Glu Leu Lys Lys
                    725                 730                 735

Lys Ile Ile Glu Phe Asn Lys Glu Val Asp Leu Glu Leu Ala Thr Ala
                740                 745                 750

Val Lys Ser Val Gly Leu Glu Val Ser Val Lys Pro Gly His Gly
            755                 760                 765

Trp Asn Lys Ser Ser Val Pro Glu Ile Glu Leu Asn Lys Asp Val
        770                 775                 780

Gln Lys Glu Ile Glu Ile Val Ala Asn Ser Ser Pro Asn Val Lys Arg
785                 790                 795                 800

Leu Ile Glu Gln Leu Lys Leu Glu Val Ala Lys Ser Gly Gly Lys Pro
                805                 810                 815

Asp Ser Glu Ser Lys Ser Arg Ile Asp Ala Leu Thr Gln Gln Ile Lys
                820                 825                 830

Lys Ser Leu Ala Glu Ala Val Asp Ser Pro Ser Leu Lys Glu Lys Tyr
            835                 840                 845

Glu Asn Leu Thr Arg Pro Ala Gly Asp Thr Leu Thr Asp Asp Lys Leu
        850                 855                 860

Arg Glu Lys Val Gly Val Asn Arg Asn Phe Ser
865                 870                 875

<210> SEQ ID NO 164
<211> LENGTH: 1215
<212> TYPE: DNA
<213> ORGANISM: Pisum sativum

<400> SEQUENCE: 164
atggcttcct cttctgcaac tcttgttggt tctactgctt ctgatcttct caggagttca      60
actactggtt tcactggtgt cccctttgaga accttgggaa gggcagggtt ggtcttgaaa    120
agaagggatt taactgttag tgttactgct aagttgagga aggtgaagag gcgtgaatat    180
ccatggtcaa gtaaccctga tcccaatatg aaaggtgggc ggttgcgtca tctctcaacg    240
ttccagccac tcaaacagcc gccaaagcct gttattttgg agtttgaaaa gcctcttatt    300
aatatggaaa agaagattaa tgattttcgg aaggtggcag aaaaaactgg tgtggattta    360
agtgatcaga ttctcgcatt ggaggctaag taccaaaagg cttggtgga attgtataca    420 aatctaactc ctatacagcg ggtcaccgtt gcacggcatc taacaggcc tacttttcctg   480 gatcacatgt ataacatgac tgaaaagttt gtggaactcc atggtgatcg tgaaggatac    540
gatgatcctg ctattgccgc tggtctaggg agtatagatg gtaaaaccta catgttcatc    600
ggccaccaaa agggtagaga tactaaagaa aatattaagc gtaactttgc gatgccaact    660
ccacacggtt ataggaaagc tctgcgcttg atggaatatg cagatcatca cgggttcccg    720
atagttactt tcattgacac ccctggggca tttgctgacc tcaaatccga gcaacttggt    780
caaggtgaag caattgctca taatttgaga tccatgtttg ctctgaaggt gccagttatt    840
tctatagtta ttggcgaagg tggatctggc ggtgcccttg ccattggatg tgctaataaa    900
ttactcatgc ttgaaaattc agtgttcttt gttgccatgc cagaggcatg cggtgcaatc    960
ttgtggaaga gtaataaagc tgctccaaag gctgctgagc gactgaagat tacagcatct   1020
gcattgttgg atttggaaat tgcagatggc attataccgg agcccctggc tggtgcacat   1080
actgatccaa gttggatgtc tcaacagatt aaaattgcaa tcaatgaagc tatggatgaa   1140
ctcaccaagt tgagcacaga agacctaata aaagatcgca tgcataagtt ccgaaaactc   1200
```
ggtgttgatg ggatc                                                        1215

<210> SEQ ID NO 165
<211> LENGTH: 405
<212> TYPE: PRT
<213> ORGANISM: Pisum sativum

<400> SEQUENCE: 165

Met Ala Ser Ser Ala Thr Leu Val Gly Ser Thr Ala Ser Asp Leu
1               5                   10                  15

Leu Arg Ser Ser Thr Thr Gly Phe Thr Gly Val Pro Leu Arg Thr Leu
                20                  25                  30

Gly Arg Ala Gly Leu Val Leu Lys Arg Arg Asp Leu Thr Val Ser Val
                35                  40                  45

Thr Ala Lys Leu Arg Lys Val Lys Arg Glu Tyr Pro Trp Ser Ser
        50                  55                  60

Asn Pro Asp Pro Asn Met Lys Gly Gly Arg Leu Arg His Leu Ser Thr
65                  70                  75                  80

Phe Gln Pro Leu Lys Gln Pro Pro Lys Pro Val Ile Leu Glu Phe Glu
                85                  90                  95

Lys Pro Leu Ile Asn Met Glu Lys Lys Ile Asn Asp Phe Arg Lys Val
                100                 105                 110

Ala Glu Lys Thr Gly Val Asp Leu Ser Asp Gln Ile Leu Ala Leu Glu
                115                 120                 125

Ala Lys Tyr Gln Lys Ala Leu Val Glu Leu Tyr Thr Asn Leu Thr Pro
                130                 135                 140

Ile Gln Arg Val Thr Val Ala Arg His Pro Asn Arg Pro Thr Phe Leu
145                 150                 155                 160

Asp His Met Tyr Asn Met Thr Glu Lys Phe Val Glu Leu His Gly Asp
                165                 170                 175

Arg Glu Gly Tyr Asp Asp Pro Ala Ile Ala Ala Gly Leu Gly Ser Ile
                180                 185                 190

Asp Gly Lys Thr Tyr Met Phe Ile Gly His Gln Lys Gly Arg Asp Thr
                195                 200                 205

Lys Glu Asn Ile Lys Arg Asn Phe Ala Met Pro Thr Pro His Gly Tyr
210                 215                 220

Arg Lys Ala Leu Arg Leu Met Glu Tyr Ala Asp His His Gly Phe Pro
225                 230                 235                 240

Ile Val Thr Phe Ile Asp Thr Pro Gly Ala Phe Ala Asp Leu Lys Ser
                245                 250                 255

Glu Gln Leu Gly Gln Gly Glu Ala Ile Ala His Asn Leu Arg Ser Met
                260                 265                 270

Phe Ala Leu Lys Val Pro Val Ile Ser Ile Val Ile Gly Glu Gly Gly
                275                 280                 285

Ser Gly Gly Ala Leu Ala Ile Gly Cys Ala Asn Lys Leu Leu Met Leu
                290                 295                 300

Glu Asn Ser Val Phe Phe Val Ala Met Pro Glu Ala Cys Gly Ala Ile
305                 310                 315                 320

Leu Trp Lys Ser Asn Lys Ala Ala Pro Lys Ala Ala Glu Arg Leu Lys
                325                 330                 335

Ile Thr Ala Ser Ala Leu Leu Asp Leu Glu Ile Ala Asp Gly Ile Ile
                340                 345                 350

Pro Glu Pro Leu Ala Gly Ala His Thr Asp Pro Ser Trp Met Ser Gln
                355                 360                 365

```
Gln Ile Lys Ile Ala Ile Asn Glu Ala Met Asp Glu Leu Thr Lys Leu
        370                 375                 380

Ser Thr Glu Asp Leu Ile Lys Asp Arg Met His Lys Phe Arg Lys Leu
385                 390                 395                 400

Gly Val Asp Gly Ile
            405

<210> SEQ ID NO 166
<211> LENGTH: 2310
<212> TYPE: DNA
<213> ORGANISM: Arabidopsis thaliana

<400> SEQUENCE: 166
atggcttcaa tatcgcattc atcactagct ttaggaggag cttcttctgc ttctgcttca      60
gattacttgc gtagttcgag caatggtgtt aatggggtac cattgaaaac cttaggaaga     120
gcagtgttta ctaccatcag gaggaaggac ttggcggtga catctcggct caagaaaggg     180
aagaaatttg agcatccatg gcctgcaaat cctgacccga atgtgaaagg aggagtcttg     240
tcttacctgg ccgagttcaa accattgggg gatactcaaa agcctgtcac tttggatttc     300
gagaagccac tagtcgaatt ggagaagaag attgttgatg tgaggaagat ggcgaatgaa     360
acggggttgg atttcactga gcagattatc actttggaga caagtatag  acaggcactg     420 aaagatcttt acacgcatct tactccgata caacgtgtga acattgcgcg ccatcccaac     480
cgacctactt tccttgatca tatacataac ataactgaca gtttatggaa gcttcatgga     540
gaccgagcgg gtatgatgacc cctgcaatt gtgacggta ttggaaccat agatggaaaa     600
cgttacatgt tcataggtca ccagaaaggt agaaacacca agaaaatat aatgcggaac     660 tttggtatgc ctactcctca cggatatagg aaagcacttc ggatgatgta ttatgcagac     720
catcacggtt ttccaatcgt gacatttatc gacactcctg agcctatgc agatcttaaa      780 tccgaggaac ttggacaggg tgaagcgatt gccaacaatc tgaggacgat gttcggcctg     840
aaagtgccaa ttctttctat tgtcattggg aaggtggtt ctggtggtgc cctagccatt     900
ggctgtgcga taaaaatgct gatgctcgaa acgcagtttt ctatgttgc cagtccagag     960 gcatgtgcag cgatcttgtg aagacttct aaggctgctc ctgagctgc tgaaaagctt    1020 agaattacct ccaaggagct ggtcaagctt aatgtagctg atggaatcat tcctgaaccg    1080
cttggagggg cccatgccga tccttcatgg acgtcgcagc aaataaagat tgctatcaat    1140
gaaaacatga tgaattcgg aaaaatgagt ggggaggagc tcctgaaaca caggatggct    1200
aagtaccgaa agattggagt gttcatagag ggcgaaccaa tagagccaag taggaaaatc    1260
aacatgaaga aagggaagc cgtgttctca gatagccgga agctgcaggg tgaggttgac    1320
aagctgaagg agcagattct gaaagccaag gagacgtcta cggaagccga gccttcgagt    1380
gaagttctta tgagatgat tgagaaactc aaatccgaga tagatgacga gtacactgaa    1440
gctgcaatag cagtaggttt ggaggagaga ctaacggcaa tgcgcgaaga gttctcgaaa    1500
gcgagttcag aagagcacct tatgcacccg gttctgatcg agaaaattga agctcaag      1560 gaagaattca atacccgttt gactgacgca cctaactacg agagcctaaa atctaagctt    1620
aacatgctta gggactttc cagagccaaa gcagcatcag aagctacttc attgaaaaag    1680
gagatcaata gcggttcca ggaagctgta gaccgcccag aaattagaga aaaggtcgag    1740
gcaatcaaag ctgaggtcgc gagctcagga gcttcttctt ttgacgagtt acctgatgca    1800
ctgaaagaaa aagttctgaa gactaaaggg gaggtcgaag cagagatggc gggtgtgtta    1860
```

-continued

```
aagtcaatgg gtctggagct tgacgctgtt aaacagaatc agaaggatac ggctgagcag   1920
atctatgccg caaacgaaaa ccttcaagaa aaacttgaaa agctgaacca gaaaatcacc   1980
agcaagattg aggaggtggt gaggacacca gagatcaaga gcatggtgga gttgctgaaa   2040 gtggaaccg caaaggcgag caaaacgcct ggtgtcaccg aagcatatca gaaaatcgag   2100
gcacttgagc agcagatcaa gcagaagatt gcagaggctc tgaacacgtc cggactgcag   2160
gaaaagcaag acgagctcga aaggagctt gcagctgcac gtgaactagc tgcagaggaa   2220
tcagacggga gtgtgaagga agatgatgac gatgacgaag atagttcaga atccgggaaa   2280
tcggagatgg ttaaccccag cttcgcctga                                   2310
```

<210> SEQ ID NO 167
<211> LENGTH: 769
<212> TYPE: PRT
<213> ORGANISM: Arabidopsis thaliana

<400> SEQUENCE: 167

```
Met Ala Ser Ile Ser His Ser Ser Leu Ala Leu Gly Gly Ala Ser Ser
1               5                   10                  15

Ala Ser Ala Ser Asp Tyr Leu Arg Ser Ser Asn Gly Val Asn Gly
            20                  25                  30

Val Pro Leu Lys Thr Leu Gly Arg Ala Val Phe Thr Thr Ile Arg Arg
        35                  40                  45

Lys Asp Leu Ala Val Thr Ser Arg Leu Lys Lys Gly Lys Lys Phe Glu
    50                  55                  60

His Pro Trp Pro Ala Asn Pro Asp Pro Asn Val Lys Gly Gly Val Leu
65                  70                  75                  80

Ser Tyr Leu Ala Glu Phe Lys Pro Leu Gly Asp Thr Gln Lys Pro Val
                85                  90                  95

Thr Leu Asp Phe Glu Lys Pro Leu Val Glu Leu Glu Lys Lys Ile Val
            100                 105                 110

Asp Val Arg Lys Met Ala Asn Glu Thr Gly Leu Asp Phe Thr Glu Gln
        115                 120                 125

Ile Ile Thr Leu Glu Asn Lys Tyr Arg Gln Ala Leu Lys Asp Leu Tyr
    130                 135                 140

Thr His Leu Thr Pro Ile Gln Arg Val Asn Ile Ala Arg His Pro Asn
145                 150                 155                 160

Arg Pro Thr Phe Leu Asp His Ile His Asn Ile Thr Asp Lys Phe Met
                165                 170                 175

Glu Leu His Gly Asp Arg Ala Gly Tyr Asp Asp Pro Ala Ile Val Thr
            180                 185                 190

Gly Ile Gly Thr Ile Asp Gly Lys Arg Tyr Met Phe Ile Gly His Gln
        195                 200                 205

Lys Gly Arg Asn Thr Lys Glu Asn Ile Met Arg Asn Phe Gly Met Pro
    210                 215                 220

Thr Pro His Gly Tyr Arg Lys Ala Leu Arg Met Tyr Tyr Ala Asp
225                 230                 235                 240

His His Gly Phe Pro Ile Val Thr Phe Ile Asp Thr Pro Gly Ala Tyr
                245                 250                 255

Ala Asp Leu Lys Ser Glu Glu Leu Gly Gln Gly Glu Ala Ile Ala Asn
            260                 265                 270

Asn Leu Arg Thr Met Phe Gly Leu Lys Val Pro Ile Leu Ser Ile Val
        275                 280                 285
```

-continued

```
Ile Gly Glu Gly Gly Ser Gly Gly Ala Leu Ala Ile Gly Cys Ala Asn
    290                 295                 300
Lys Met Leu Met Leu Glu Asn Ala Val Phe Tyr Val Ala Ser Pro Glu
305                 310                 315                 320
Ala Cys Ala Ala Ile Leu Trp Lys Thr Ser Lys Ala Ala Pro Glu Ala
                325                 330                 335
Ala Glu Lys Leu Arg Ile Thr Ser Lys Glu Leu Val Lys Leu Asn Val
            340                 345                 350
Ala Asp Gly Ile Ile Pro Glu Pro Leu Gly Gly Ala His Ala Asp Pro
        355                 360                 365
Ser Trp Thr Ser Gln Gln Ile Lys Ile Ala Ile Asn Glu Asn Met Asn
    370                 375                 380
Glu Phe Gly Lys Met Ser Gly Glu Glu Leu Leu Lys His Arg Met Ala
385                 390                 395                 400
Lys Tyr Arg Lys Ile Gly Val Phe Ile Glu Gly Pro Ile Glu Pro
                405                 410                 415
Ser Arg Lys Ile Asn Met Lys Arg Glu Ala Val Phe Ser Asp Ser
            420                 425                 430
Arg Lys Leu Gln Gly Glu Val Asp Lys Leu Lys Glu Gln Ile Leu Lys
        435                 440                 445
Ala Lys Glu Thr Ser Thr Glu Ala Glu Pro Ser Ser Glu Val Leu Asn
    450                 455                 460
Glu Met Ile Glu Lys Leu Lys Ser Glu Ile Asp Asp Glu Tyr Thr Glu
465                 470                 475                 480
Ala Ala Ile Ala Val Gly Leu Glu Glu Arg Leu Thr Ala Met Arg Glu
                485                 490                 495
Glu Phe Ser Lys Ala Ser Ser Glu Glu His Leu Met His Pro Val Leu
            500                 505                 510
Ile Glu Lys Ile Glu Lys Leu Lys Glu Glu Phe Asn Thr Arg Leu Thr
        515                 520                 525
Asp Ala Pro Asn Tyr Glu Ser Leu Lys Ser Lys Leu Asn Met Leu Arg
    530                 535                 540
Asp Phe Ser Arg Ala Lys Ala Ala Ser Glu Ala Thr Ser Leu Lys Lys
545                 550                 555                 560
Glu Ile Asn Lys Arg Phe Gln Glu Ala Val Asp Arg Pro Glu Ile Arg
                565                 570                 575
Glu Lys Val Glu Ala Ile Lys Ala Glu Val Ala Ser Ser Gly Ala Ser
            580                 585                 590
Ser Phe Asp Glu Leu Pro Asp Ala Leu Lys Glu Lys Val Leu Lys Thr
        595                 600                 605
Lys Gly Glu Val Glu Ala Glu Met Ala Gly Val Leu Lys Ser Met Gly
    610                 615                 620
Leu Glu Leu Asp Ala Val Lys Gln Asn Gln Lys Asp Thr Ala Glu Gln
625                 630                 635                 640
Ile Tyr Ala Ala Asn Glu Asn Leu Gln Glu Lys Leu Glu Lys Leu Asn
                645                 650                 655
Gln Glu Ile Thr Ser Lys Ile Glu Glu Val Val Arg Thr Pro Glu Ile
            660                 665                 670
Lys Ser Met Val Glu Leu Leu Lys Val Glu Thr Ala Lys Ala Ser Lys
        675                 680                 685
Thr Pro Gly Val Thr Glu Ala Tyr Gln Lys Ile Glu Ala Leu Glu Gln
    690                 695                 700
Gln Ile Lys Gln Lys Ile Ala Glu Ala Leu Asn Thr Ser Gly Leu Gln
```

| | | 705 | | | 710 | | | 715 | | | 720 | |
|---|---|---|---|---|---|---|---|---|---|---|---|---|

Glu Lys Gln Asp Glu Leu Glu Lys Glu Leu Ala Ala Arg Glu Leu
               725                        730                       735

Ala Ala Glu Glu Ser Asp Gly Ser Val Lys Glu Asp Asp Asp Asp
           740                        745                        750

Glu Asp Ser Ser Glu Ser Gly Lys Ser Glu Met Val Asn Pro Ser Phe
       755                        760                        765

Ala

<210> SEQ ID NO 168
<211> LENGTH: 2130
<212> TYPE: DNA
<213> ORGANISM: Glycine max

<400> SEQUENCE: 168

```
atggctgctt cttctgcatc tctttctggt gcttctgctt cggatcttct gaggagttca      60
accagcggtt tcaatggtgt tcctttgaga accatgggga agggaaagtt ggttttgaag     120
aggagggact ttacagttgc tgccaggctg aggaaggtga agaagcatga atatccttgg     180
cctgctaacc ctgatcccaa tgtgaaaggt ggggtgctga gccacctttc cttgttcaag     240
ccactcaagg agaagccaaa gcctgtcact ttggattttg aaaggcctct tgttgatctg     300
caaaagaaga tcattgatgt acagaagatg gcgaacgaaa ctggactgga cttcagtgat     360
cagattctct cattggagac caagtaccac caggctttaa aggatctgta acgcatctg      420
actcctattc agcgggtcaa catcgctcgg caccctaaca ggccaacttt ccttgatcat     480
gtgtttaaca taactgagaa gtttgttgaa ctccatggtg atcgggcagg ttacgatgat     540
cctgctattg ttactggtct agggactata gatggtagaa gctacatgtt cattggtcac     600
caaaagggta gaaatactaa agaaaatatt cagcgtaact ttgggatgcc aactcctcat     660
ggttacagga aggcccttcg cttgatgaa tatgcagatc atcatgggtt ccccatagtt      720
actttcattg acacgcctgg ggcatatgct gaccttaaat cagaggaact aggacagggt     780
gaagcgattg ctcacaattt gagatccatg tttggtctga aggtgccagt tatatctata     840
gttattggag aaggtggttc aggtggcgcc ctagccattg atgtgctaa taaattactc      900
atgcttgaaa atgctgtttt ttatgttgcc agtccagagg catgtgcagc aatcttgtgg     960
aagacagcta aagcttctcc aaaggctgct gagaaattga agattacagc cactgaactg    1020
tgcaaattac aaattgcaga tggtgttata cctgagccac ttggtggtgc acatgcagat    1080
ccagagtgga cctctcaaca gataaaaaag gctatcaaag aaaccatgga tgagctcacg    1140
aagatgaaca cagaagaact gttaaaacat cgcatgctta agttcagaaa gattggtggg    1200
ttccaggaag gtattcctat agatcctaag agaaaagcca acatgaagaa gagggatcta    1260
tctattgcta agattcctga tgctgaacta gaagttgagg ttgagaaact gaagcaacag    1320
gttttggaag ctaaggaatc ttctcctgtt cctccaaaac tagatctgga tgagatgcta    1380
aagcaactgg caagggaggt cgatctagaa tactctgagg cagttaaagc cacgggcttg    1440
acagacagtt tgttgaaact aagggaggaa gtttcgaaag caaatgcaga taatcaaatt    1500
gttgatccat tgctgagggg taagatagaa aagctaaggg tggagtttga acagcaattg    1560
cgtgcagctc ccaattatgg taggctgcag aataagctta actatctgag cgaattatgt    1620
aaagttaagc ttctgtcaga tggaaagaag aacaatgagg ctgtcacatt taagcaagag    1680
ttgaagaaaa aaattgatga tgccttgagt gatccgaaaa taagggagac atttgaagca    1740
```

-continued

```
ttaaaggctg aaattaaagg tgttggtgca tcctcagcaa gtgatttgga tgacgagttg    1800
aagaagaaaa tcattgagtt tatcaaagaa gtaaaagaag taaagaagt aaaagaggta     1860 atagaaaatc aaattgaaag tttggtaaac tcgtcggatg atattaagag caagatactg    1920
caattgaaat tggaggttcc taaggctgga gagacgcctg attcagaacc aaagaataga    1980
attggtgctt tggtgcaact aattaagccg agcctagtgg aggccgttga ctcgtctggc    2040
ttaaaagatc tgtttgaaaa tctggtgtct aatgatggaa gtttgacaca tggagatcca   2100
gctagagaca gtctcaccga tgaccagtag                                     2130
```

<210> SEQ ID NO 169
<211> LENGTH: 709
<212> TYPE: PRT
<213> ORGANISM: Glycine max

<400> SEQUENCE: 169

```
Met Ala Ala Ser Ser Ala Ser Leu Ser Gly Ala Ser Ala Ser Asp Leu
1               5                   10                  15

Leu Arg Ser Ser Thr Ser Gly Phe Asn Gly Val Pro Leu Arg Thr Met
            20                  25                  30

Gly Lys Gly Lys Leu Val Leu Lys Arg Arg Asn Phe Thr Val Ala Ala
        35                  40                  45

Arg Leu Arg Lys Val Lys Lys His Glu Tyr Pro Trp Pro Pro Asn Pro
    50                  55                  60

Asp Pro Asn Val Lys Gly Gly Val Leu Ser His Leu Ser Leu Phe Lys
65                  70                  75                  80

Pro Leu Lys Glu Lys Pro Lys Pro Val Thr Leu Asp Phe Glu Arg Pro
                85                  90                  95

Leu Val Asp Leu Gln Lys Lys Ile Ile Asp Val Gln Lys Met Ala Asn
            100                 105                 110

Glu Thr Gly Leu Asp Phe Ser Asp Gln Ile Leu Ser Leu Glu Thr Lys
        115                 120                 125

Tyr His Gln Ala Leu Lys Asp Leu Tyr Thr His Leu Thr Pro Ile Gln
    130                 135                 140

Arg Val Asn Ile Ala Arg His Pro Asn Arg Pro Thr Phe Leu Asp His
145                 150                 155                 160

Val Phe Asn Ile Thr Glu Lys Phe Val Glu Leu His Gly Asp Arg Ala
                165                 170                 175

Gly Tyr Asp Asp Pro Ala Ile Val Thr Gly Leu Gly Thr Ile Asp Gly
            180                 185                 190

Arg Ser Tyr Met Phe Ile Gly His Gln Lys Gly Arg Asn Thr Lys Glu
        195                 200                 205

Asn Ile Gln Arg Asn Phe Gly Met Pro Thr Pro His Gly Tyr Arg Lys
    210                 215                 220

Ala Leu Arg Leu Met Glu Tyr Ala Asp His His Gly Phe Pro Ile Val
225                 230                 235                 240

Thr Phe Ile Asp Thr Pro Gly Ala Tyr Ala Asp Leu Lys Ser Glu Glu
                245                 250                 255

Leu Gly Gln Gly Glu Ala Ile Ala His Asn Leu Arg Ser Met Phe Gly
            260                 265                 270

Leu Lys Val Pro Val Ile Ser Ile Val Ile Gly Glu Gly Gly Ser Gly
        275                 280                 285

Gly Ala Leu Ala Ile Gly Cys Ala Asn Lys Leu Leu Met Leu Glu Asn
    290                 295                 300
```

```
Ala Val Phe Tyr Val Ala Ser Pro Glu Ala Cys Ala Ala Ile Leu Trp
305                 310                 315                 320

Lys Thr Ala Lys Ala Ser Pro Lys Ala Ala Glu Lys Leu Lys Ile Thr
            325                 330                 335

Ala Thr Glu Leu Cys Lys Leu Gln Ile Ala Asp Gly Val Ile Pro Glu
                340                 345                 350

Pro Leu Gly Gly Ala His Ala Asp Pro Glu Trp Thr Ser Gln Gln Ile
            355                 360                 365

Lys Lys Ala Ile Lys Glu Thr Met Asp Glu Leu Thr Lys Met Asn Thr
370                 375                 380

Glu Glu Leu Leu Lys His Arg Met Leu Lys Phe Arg Lys Ile Gly Gly
385                 390                 395                 400

Phe Gln Glu Gly Ile Pro Ile Asp Pro Lys Arg Lys Ala Asn Met Lys
                405                 410                 415

Lys Arg Asp Leu Ser Ile Ala Lys Ile Pro Asp Ala Glu Leu Glu Val
                420                 425                 430

Glu Val Glu Lys Leu Lys Gln Gln Val Leu Glu Ala Lys Glu Ser Ser
            435                 440                 445

Pro Val Pro Pro Lys Leu Asp Leu Asp Glu Met Leu Lys Gln Leu Ala
450                 455                 460

Arg Glu Val Asp Leu Glu Tyr Ser Glu Ala Val Lys Ala Thr Gly Leu
465                 470                 475                 480

Thr Asp Ser Leu Leu Lys Leu Arg Glu Glu Val Ser Lys Ala Asn Ala
                485                 490                 495

Asp Asn Gln Ile Val Asp Pro Leu Leu Glu Gly Lys Ile Glu Lys Leu
            500                 505                 510

Arg Val Glu Phe Glu Gln Gln Leu Arg Ala Ala Pro Asn Tyr Gly Arg
            515                 520                 525

Leu Gln Asn Lys Leu Asn Tyr Leu Ser Glu Leu Cys Lys Val Lys Leu
            530                 535                 540

Leu Ser Asp Gly Lys Lys Asp Asn Glu Ala Val Thr Phe Lys Gln Glu
545                 550                 555                 560

Leu Lys Lys Lys Ile Asp Asn Ala Leu Ser Asp Pro Lys Ile Arg Glu
                565                 570                 575

Thr Phe Glu Ala Leu Lys Ala Glu Ile Lys Gly Val Gly Ala Ser Ser
                580                 585                 590

Ala Ser Asp Leu Asp Asp Glu Leu Lys Lys Ile Ile Glu Phe Ile
            595                 600                 605

Lys Glu Val Lys Glu Val Lys Glu Val Lys Glu Val Ile Glu Asn Gln
610                 615                 620

Ile Glu Ser Leu Val Asn Ser Ser Asp Ile Lys Ser Lys Ile Leu
625                 630                 635                 640

Gln Leu Lys Leu Glu Val Pro Lys Ala Gly Glu Thr Pro Asp Ser Glu
            645                 650                 655

Pro Lys Asn Arg Ile Gly Ala Leu Val Gln Leu Ile Lys Pro Ser Leu
            660                 665                 670

Val Glu Ala Val Asp Ser Ser Gly Leu Lys Asp Leu Phe Glu Asn Leu
            675                 680                 685

Val Ser Asn Asp Gly Ser Leu Thr His Gly Asp Pro Ala Arg Asp Ser
            690                 695                 700

Leu Thr Asp Asp Gln
705
```

<210> SEQ ID NO 170
<211> LENGTH: 2070
<212> TYPE: DNA
<213> ORGANISM: Glycine max

<400> SEQUENCE: 170

| | |
|---|---:|
| atggctgctt cttctgcatc tctttctggt gcttctgctt cggatcttct gaggagttca | 60 |
| accagcggtt tcaatggtgt tcctttgaga accttgggga agggaaagtt ggttttgaag | 120 |
| aggagggact ttacagttgc tgctaaactg aggaaggtga agaagcatga atatccttgg | 180 |
| cctcctaacc ctgatcccaa tgtgaaaggt ggagtgctga gccacctttc catgttcaag | 240 |
| ccactcaagg agaaaccaaa gcctgtcact ttggattttg aaaagcctct tgttgatctg | 300 |
| caaaagaaga tcattgatgt acaaaagatg gcgaacgaaa ctggactgga cttcagtgat | 360 |
| cagattctct cattggagac caagtaccag caggctttaa aggatctgta tacgcatctg | 420 |
| actcctattc agcgggtcaa catcgctcgg caccctaaca ggccaacttt ccttgatcat | 480 |
| gtctttaaca taactgaaaa gtttgttgaa ctccatggtg atcgggcagg ttatgatgat | 540 |
| cctgctattg ttactggtct agggactata gatggtagaa gctacatgtt catcggtcac | 600 |
| caaaagggta gaaatactaa agaaaacatt cagcgtaact ttgggatgcc aactcctcat | 660 |
| ggttacagga aggcccttcg cttgatggaa tatgcagatc atcatggggtt ccccatagtt | 720 |
| actttcattg acacgcctgg ggcatatgct gaccttaaat cagaggaact aggacagggt | 780 |
| gaagcgattg ctcacaattt gagatccatg tttggtctga aggtgccagt tatatctata | 840 |
| gttattggag aaggtggttc aggtggcgcc ctagccattg gatgtgctaa taaattactc | 900 |
| atgcttgaaa atgctgtttt ttatgttgcc agtccagagg catgtgcagc aatcttgtgg | 960 |
| aagacagcta agcttctcc aaaggctgct gagaaattga agattacagc cactgaactg | 1020 |
| tgcaaattac aaattgcaga tggtgttata cctgagccac ttggtggtgc acatgcagat | 1080 |
| ccagagtgga cctctcaaca gataaaaaag gctatcaaag aaaccatgga tgagctcatg | 1140 |
| aagatgaaca cagaagaact gttaaaacat cgcatgctta agttcagaaa gattggtgga | 1200 |
| ttccaggaag gtattcctat agatcctaag agaaaagcca acatgaagaa gagggatcta | 1260 |
| tctattgcta agatttctga tgctgaacta gaagttgagg ttgagaaact gaagcaacag | 1320 |
| gttttggaag ctaaggaatc ttctcctgtt cctccaaaac tagatctgga tgagatgcta | 1380 |
| aagcaactga caagggaggt tgatctagaa tactctgagg cagttaaagc cacgggcttg | 1440 |
| acagacagtt tgttgaaact aagggaggaa gtttcaaaag caaatgcaga taatcaaatt | 1500 |
| gttgatccat tgctgaagga taagatagaa aagctaaggg tggagtttga acagcaactg | 1560 |
| cgtgcagctc ccaattatgg aaggctgcag aataagttta cctatctgag cgaattatgt | 1620 |
| aaagttaagc ttctgtcaga tgcaaacaag gacaatgagg ctgtcacatt taagcaagag | 1680 |
| ttggagaaaa aagttgataa tgccttgagt aatccaaaaa taagggaaac atttgaagca | 1740 |
| ttaaaggctg aaattaaagg tgctggtgca tcctcagcaa gtgatttgga tgacgagttg | 1800 |
| aagaagaaaa tcgttgagtt tatgatagaa ctaaagaag taaagaagt aaaagaggta | 1860 |
| atagaaaatc aaattgaaag tttggttaac tcatcggatg atattaagaa caaggtactg | 1920 |
| caattgaaat tggaggttcc taaggctgga gagacgcctg attcagaatc aaagagtaga | 1980 |
| attggtgatt ttatatttag aacatcatct agaattatta tggccatact tcttagagac | 2040 |
| atgtttggta atttaagga gataccgtgt | 2070 |

<210> SEQ ID NO 171

```
<211> LENGTH: 690
<212> TYPE: PRT
<213> ORGANISM: Glycine max

<400> SEQUENCE: 171
```

| | | | | | | | | | | | | | | |
|---|---|---|---|---|---|---|---|---|---|---|---|---|---|---|
Met Ala Ala Ser Ser Ala Ser Leu Ser Gly Ala Ser Ala Ser Asp Leu
1               5                   10                  15

Leu Arg Ser Ser Thr Ser Gly Phe Asn Gly Val Pro Leu Arg Thr Leu
            20                  25                  30

Gly Lys Gly Lys Leu Val Leu Lys Arg Arg Asp Phe Thr Val Ala Ala
        35                  40                  45

Lys Leu Arg Lys Val Lys His Glu Tyr Pro Trp Pro Pro Asn Pro
50                  55                  60

Asp Pro Asn Val Lys Gly Gly Val Leu Ser His Leu Ser Met Phe Lys
65                  70                  75                  80

Pro Leu Lys Glu Lys Pro Lys Pro Val Thr Leu Asp Phe Glu Lys Pro
                85                  90                  95

Leu Val Asp Leu Gln Lys Lys Ile Ile Asp Val Gln Lys Met Ala Asn
            100                 105                 110

Glu Thr Gly Leu Asp Phe Ser Asp Gln Ile Leu Ser Leu Glu Thr Lys
        115                 120                 125

Tyr Gln Gln Ala Leu Lys Asp Leu Tyr Thr His Leu Thr Pro Ile Gln
130                 135                 140

Arg Val Asn Ile Ala Arg His Pro Asn Arg Pro Thr Phe Leu Asp His
145                 150                 155                 160

Val Phe Asn Ile Thr Glu Lys Phe Val Glu Leu His Gly Asp Arg Ala
                165                 170                 175

Gly Tyr Asp Asp Pro Ala Ile Val Thr Gly Leu Gly Thr Ile Asp Gly
            180                 185                 190

Arg Ser Tyr Met Phe Ile Gly His Gln Lys Gly Arg Asn Thr Lys Glu
        195                 200                 205

Asn Ile Gln Arg Asn Phe Gly Met Pro Thr Pro His Gly Tyr Arg Lys
    210                 215                 220

Ala Leu Arg Leu Met Glu Tyr Ala Asp His His Gly Phe Pro Ile Val
225                 230                 235                 240

Thr Phe Ile Asp Thr Pro Gly Ala Tyr Ala Asp Leu Lys Ser Glu Glu
                245                 250                 255

Leu Gly Gln Gly Glu Ala Ile Ala His Asn Leu Arg Ser Met Phe Gly
            260                 265                 270

Leu Lys Val Pro Val Ile Ser Ile Val Ile Gly Glu Gly Gly Ser Gly
        275                 280                 285

Gly Ala Leu Ala Ile Gly Cys Ala Asn Lys Leu Leu Met Leu Glu Asn
    290                 295                 300

Ala Val Phe Tyr Val Ala Ser Pro Glu Ala Cys Ala Ala Ile Leu Trp
305                 310                 315                 320

Lys Thr Ala Lys Ala Ser Pro Lys Ala Ala Glu Lys Leu Lys Ile Thr
                325                 330                 335

Ala Thr Glu Leu Cys Lys Leu Gln Ile Ala Asp Gly Val Ile Pro Glu
            340                 345                 350

Pro Leu Gly Gly Ala His Ala Asp Pro Glu Trp Thr Ser Gln Gln Ile
        355                 360                 365

Lys Lys Ala Ile Lys Glu Thr Met Asp Glu Leu Met Lys Met Asn Thr
    370                 375                 380

Glu Glu Leu Leu Lys His Arg Met Leu Lys Phe Arg Lys Ile Gly Gly

```
                385                 390                 395                 400
        Phe Gln Glu Gly Ile Pro Ile Asp Pro Lys Arg Lys Ala Asn Met Lys
                        405                 410                 415

Lys Arg Asp Leu Ser Ile Ala Lys Ile Ser Asp Ala Glu Leu Glu Val
                        420                 425                 430

Glu Val Glu Lys Leu Lys Gln Val Leu Glu Ala Lys Glu Ser Ser
                    435                 440                 445

Pro Val Pro Pro Lys Leu Asp Leu Asp Glu Met Leu Lys Gln Leu Thr
                450                 455                 460

Arg Glu Val Asp Leu Glu Tyr Ser Glu Ala Val Lys Ala Thr Gly Leu
        465                 470                 475                 480

Thr Asp Ser Leu Leu Lys Leu Arg Glu Glu Val Ser Lys Ala Asn Ala
                        485                 490                 495

Asp Asn Gln Ile Val Asp Pro Leu Leu Lys Asp Lys Ile Glu Lys Leu
                    500                 505                 510

Arg Val Glu Phe Glu Gln Gln Leu Arg Ala Ala Pro Asn Tyr Gly Arg
                    515                 520                 525

Leu Gln Asn Lys Phe Thr Tyr Leu Ser Glu Leu Cys Lys Val Lys Leu
                530                 535                 540

Leu Ser Asp Ala Asn Lys Asp Asn Glu Ala Val Thr Phe Lys Gln Glu
        545                 550                 555                 560

Leu Glu Lys Lys Val Asp Asn Ala Leu Ser Asn Pro Lys Ile Arg Glu
                        565                 570                 575

Thr Phe Glu Ala Leu Lys Ala Glu Ile Lys Gly Ala Gly Ala Ser Ser
                        580                 585                 590

Ala Ser Asp Leu Asp Asp Glu Leu Lys Lys Ile Val Glu Phe Met
                    595                 600                 605

Ile Glu Leu Lys Glu Val Lys Glu Val Lys Glu Val Ile Glu Asn Gln
                    610                 615                 620

Ile Glu Ser Leu Val Asn Ser Ser Asp Asp Ile Lys Asn Lys Val Leu
        625                 630                 635                 640

Gln Leu Lys Leu Glu Val Pro Lys Ala Gly Glu Thr Pro Asp Ser Glu
                        645                 650                 655

Ser Lys Ser Arg Ile Gly Asp Phe Ile Phe Arg Thr Ser Arg Ile
                    660                 665                 670

Ile Met Ala Ile Leu Leu Arg Asp Met Phe Gly Asn Phe Lys Glu Ile
                    675                 680                 685

Pro Cys
            690

<210> SEQ ID NO 172
<211> LENGTH: 2070
<212> TYPE: DNA
<213> ORGANISM: Glycine max

<400> SEQUENCE: 172
atggctgctt cttctgcatc tctttctggt gcttctgctt cggatcttct gaggagttca      60
accagcggtt tcaatggtgt tcctttgaga accttgggga agggaaagtt ggttttgaag     120
aggagggact ttacagttgc tgctaagctg aggaaggtga agaagcatga atatccttgg     180
cctgctaacc ctgatcccaa tgtgaaaggt gggtgctga gccacctttc cttgttcaag     240
ccactcaagg agaagccaaa gcctgtcact ttggattttg aaaagcctct tgttgatctg     300
caaaagaaga tcattgatgt acagaagatg gcgaacgaaa ctggactgga cttcagtgat     360
```

```
cagattctct cattggagaa caagtaccag caggctttaa aggatctgta tacgcatctg    420
actcctattc agcgggtcaa catcgcacgg caccctaaca ggccaacttt ccttgatcat    480
gtctttaaca taactgaaaa gtttgttgaa ctccatggtg atcgggcagg ttatgatgat    540
cctgctattg ttactggtct agggactata gatggtagaa gctacatgtt catcggtcac    600
caaaagggta gaaatactaa agaaaacatt cagcgtaact ttgggatgcc aactcctcat    660
ggttacagga aggcccttcg cttgatggaa tatgcagatc atcatgggtt ccccatagtt    720
actttcattg acacgcctgg ggcatatgct gaccttaaat cagaggaact aggacagggt    780
gaagcgattc tcacaatttt gagatccatg tttggtctga aggtgccagt tatatctata    840
gttattggag aaggtggttc gggtggtgcc ctagccattg gatgtgctaa taaattactc    900
atgcttgaaa atgctgtttt ttatgttgcc agtccagagg catgtgcagc aatcttgtgg    960
aagaccgcca agcttctcc aaaggctgct gagaaattga agattactgc cactgaattg   1020
tgcaaattac aaattgcaga cggtgttata cctgagccac ttggtggtgc acatgcagat   1080
ccagagtgga cctctcaaca gataaaaaag gctatcaaag aaaccatgga tgaactcacg   1140
aagatgaaca cagaagaact gttaaaacat cgcatgctta agttcagaaa gattggtgga   1200
ttccaggaag gtattcctat agatcccaag agaaaagcca acatgaagaa gagggatcta   1260
tctattgcta agattcctga tgctgaacta gaagttgagg ttgagaaact gaagcaacag   1320
gttttggaag ctaaggaatc ttctcctgtt cctccaaaac tagatctgga tgagatgcta   1380
aagcaactgg caagggaggt cggtctagaa tactctgagg cagttaaagc cacgggcttg   1440
acagacagtt tgctgaaact aagggaggaa gtttcaaaag caaatgcaga tagtcaaatt   1500
gttgatccat tgctgaagga taagatagaa aagctaaggg tggagtttga acagcaattg   1560
cgtgcagctc ccaattatgg taggctgcag aataagtttta agtatctgag cgaattatgt   1620
aaagtaaagc ttctttcaga tgcaaacaag gacaatcagg ctgtcacctt taagcaagag   1680
ttggagaaaa aagttgataa tgccttgaat gatccaaaaa taagggaaac atttgaagca   1740
ttaaaggctg aaattaaagg tgctggtgca tcctcggcaa gtgatttgga tgacgagttg   1800
aagaagaaaa tcgttggggtt tatgatgaaa ctaaaagaag taaagaagt aaaagaagta   1860
atagaaaatc aaattgaaag tttggtaaac tcatcggatg atattaagag caagatactg   1920
caattgaaat tggagcttcc taaggctgga gagacgcctg attcagaatc aaataataga   1980
attggtgatt ttatatttaa aaaatcatct aaaattatta tggccatact tcttagagac   2040
atgtttggta attttaagga gataccgtgt                                    2070
```

<210> SEQ ID NO 173
<211> LENGTH: 690
<212> TYPE: PRT
<213> ORGANISM: Glycine max

<400> SEQUENCE: 173

Met Ala Ala Ser Ser Ala Ser Leu Ser Gly Ala Ser Ala Ser Asp Leu
1               5                   10                  15

Leu Arg Ser Ser Thr Ser Gly Phe Asn Gly Val Pro Leu Arg Thr Leu
            20                  25                  30

Gly Lys Gly Lys Leu Val Leu Lys Arg Arg Asp Phe Thr Val Ala Ala
        35                  40                  45

Lys Leu Arg Lys Val Lys Lys His Glu Tyr Pro Trp Pro Ala Asn Pro
    50                  55                  60

Asp Pro Asn Val Lys Gly Gly Val Leu Ser His Leu Ser Leu Phe Lys

```
                65                  70                  75                  80
        Pro Leu Lys Glu Lys Pro Lys Pro Val Thr Leu Asp Phe Glu Lys Pro
                        85                  90                  95

Leu Val Asp Leu Gln Lys Lys Ile Ile Asp Val Gln Lys Met Ala Asn
                       100                 105                 110

Glu Thr Gly Leu Asp Phe Ser Asp Gln Ile Leu Ser Leu Glu Asn Lys
                       115                 120                 125

Tyr Gln Gln Ala Leu Lys Asp Leu Tyr Thr His Leu Thr Pro Ile Gln
                       130                 135                 140

Arg Val Asn Ile Ala Arg His Pro Asn Arg Pro Thr Phe Leu Asp His
        145                 150                 155                 160

Val Phe Asn Ile Thr Glu Lys Phe Val Glu Leu His Gly Asp Arg Ala
                       165                 170                 175

Gly Tyr Asp Asp Pro Ala Ile Val Thr Gly Leu Gly Thr Ile Asp Gly
                       180                 185                 190

Arg Ser Tyr Met Phe Ile Gly His Gln Lys Gly Arg Asn Thr Lys Glu
                       195                 200                 205

Asn Ile Gln Arg Asn Phe Gly Met Pro Thr Pro His Gly Tyr Arg Lys
                       210                 215                 220

Ala Leu Arg Leu Met Glu Tyr Ala Asp His His Gly Phe Pro Ile Val
        225                 230                 235                 240

Thr Phe Ile Asp Thr Pro Gly Ala Tyr Ala Asp Leu Lys Ser Glu Glu
                       245                 250                 255

Leu Gly Gln Gly Glu Ala Ile Ala His Asn Leu Arg Ser Met Phe Gly
                       260                 265                 270

Leu Lys Val Pro Val Ile Ser Ile Val Ile Gly Glu Gly Gly Ser Gly
                       275                 280                 285

Gly Ala Leu Ala Ile Gly Cys Ala Asn Lys Leu Leu Met Leu Glu Asn
                       290                 295                 300

Ala Val Phe Tyr Val Ala Ser Pro Glu Ala Cys Ala Ala Ile Leu Trp
        305                 310                 315                 320

Lys Thr Ala Lys Ala Ser Pro Lys Ala Ala Glu Lys Leu Lys Ile Thr
                       325                 330                 335

Ala Thr Glu Leu Cys Lys Leu Gln Ile Ala Asp Gly Val Ile Pro Glu
                       340                 345                 350

Pro Leu Gly Gly Ala His Ala Asp Pro Glu Trp Thr Ser Gln Gln Ile
                       355                 360                 365

Lys Lys Ala Ile Lys Glu Thr Met Asp Glu Leu Thr Lys Met Asn Thr
                       370                 375                 380

Glu Glu Leu Leu Lys His Arg Met Leu Lys Phe Arg Lys Ile Gly Gly
        385                 390                 395                 400

Phe Gln Glu Gly Ile Pro Ile Asp Pro Lys Arg Lys Ala Asn Met Lys
                       405                 410                 415

Lys Arg Asp Leu Ser Ile Ala Lys Ile Pro Asp Ala Glu Leu Glu Val
                       420                 425                 430

Glu Val Glu Lys Leu Lys Gln Gln Val Leu Glu Ala Lys Glu Ser Ser
                       435                 440                 445

Pro Val Pro Pro Lys Leu Asp Leu Asp Glu Met Leu Lys Gln Leu Ala
                       450                 455                 460

Arg Glu Val Gly Leu Glu Tyr Ser Glu Ala Val Lys Ala Thr Gly Leu
        465                 470                 475                 480

Thr Asp Ser Leu Leu Lys Leu Arg Glu Glu Val Ser Lys Ala Asn Ala
                       485                 490                 495
```

```
Asp Ser Gln Ile Val Asp Pro Leu Leu Lys Asp Lys Ile Glu Lys Leu
                500                 505                 510

Arg Val Glu Phe Glu Gln Gln Leu Arg Ala Ala Pro Asn Tyr Gly Arg
            515                 520                 525

Leu Gln Asn Lys Phe Lys Tyr Leu Ser Glu Leu Cys Lys Val Lys Leu
        530                 535                 540

Leu Ser Asp Ala Asn Lys Asp Asn Gln Ala Val Thr Phe Lys Gln Glu
545                 550                 555                 560

Leu Glu Lys Lys Val Asp Asn Ala Leu Asn Asp Pro Lys Ile Arg Glu
                565                 570                 575

Thr Phe Glu Ala Leu Lys Ala Glu Ile Lys Gly Ala Gly Ala Ser Ser
            580                 585                 590

Ala Ser Asp Leu Asp Asp Glu Leu Lys Lys Lys Ile Val Gly Phe Met
        595                 600                 605

Ile Glu Leu Lys Glu Val Lys Glu Val Lys Glu Val Ile Glu Asn Gln
        610                 615                 620

Ile Glu Ser Leu Val Asn Ser Ser Asp Asp Ile Lys Ser Lys Ile Leu
625                 630                 635                 640

Gln Leu Lys Leu Glu Leu Pro Lys Ala Gly Glu Thr Pro Asp Ser Glu
                645                 650                 655

Ser Asn Asn Arg Ile Gly Asp Phe Ile Phe Lys Lys Ser Ser Lys Ile
            660                 665                 670

Ile Met Ala Ile Leu Leu Arg Asp Met Phe Gly Asn Phe Lys Glu Ile
        675                 680                 685

Pro Cys
    690

<210> SEQ ID NO 174
<211> LENGTH: 764
<212> TYPE: PRT
<213> ORGANISM: Brassica napus

<400> SEQUENCE: 174

Met Ala Ser Met Ser His Ser Ser Ile Ala Leu Cys Gly Ala Ser Ala
1               5                   10                  15

Ser Ala Ser Ala Ser Asp His Leu Arg Ser Ser Thr Asn Gly Val Ser
            20                  25                  30

Leu Arg Thr Leu Gly Arg Ala Met Val Ala Ser Thr Lys Arg Asn Asn
        35                  40                  45

Leu Tyr Val Thr Ala Arg Leu Lys Lys Gly Lys Lys Phe Asp His Pro
    50                  55                  60

Trp Pro Ser Asn Pro Asp Pro Asn Val Lys Gly Gly Val Leu Ser Tyr
65                  70                  75                  80

Leu Ser Thr Phe Lys Pro Leu Gly Asp Thr Gln Lys Pro Val Thr Leu
                85                  90                  95

Asp Phe Glu Lys Pro Leu Val Glu Leu Glu Lys Ile Val Asp Val
            100                 105                 110

Arg Lys Met Ala Ala Glu Thr Gly Leu Asp Phe Thr Asp Gln Ile Ile
        115                 120                 125

Thr Leu Glu Thr Lys Tyr Arg Gln Ala Leu Lys Asp Leu Tyr Thr His
    130                 135                 140

Leu Thr Pro Ile Gln Arg Val Asn Ile Ala Arg His Pro Asn Arg Pro
145                 150                 155                 160

Thr Phe Leu Asp His Ile His Asn Ile Thr Asp Lys Phe Met Glu Leu
```

```
              165                 170                 175
His Gly Asp Arg Ala Gly Tyr Asp Asp Pro Ala Ile Val Thr Gly Ile
            180                 185                 190

Gly Thr Ile Asp Gly Lys Arg Tyr Met Phe Ile Gly His Gln Lys Gly
            195                 200                 205

Arg Asn Thr Lys Glu Asn Ile Met Arg Asn Phe Gly Met Pro Thr Pro
            210                 215                 220

His Gly Tyr Arg Lys Ala Leu Arg Met Met Tyr Tyr Ala Asp His His
225                 230                 235                 240

Gly Phe Pro Ile Val Thr Phe Ile Asp Thr Pro Gly Ala Tyr Ala Asp
                245                 250                 255

Leu Lys Ser Glu Glu Leu Gly Gln Gly Glu Ala Ile Ala Asn Asn Leu
            260                 265                 270

Arg Thr Met Phe Gly Leu Lys Val Pro Ile Leu Ser Ile Val Ile Gly
            275                 280                 285

Glu Gly Gly Ser Gly Gly Ala Leu Ala Ile Gly Cys Ala Asn Lys Met
            290                 295                 300

Leu Met Leu Glu Asn Ala Val Phe Tyr Val Ala Ser Pro Glu Ala Cys
305                 310                 315                 320

Ala Ala Ile Leu Trp Asn Ser Ser Lys Ala Ala Pro Glu Ala Ala Glu
                325                 330                 335

Lys Leu Arg Ile Thr Ser Arg Glu Leu Val Lys Leu Asn Val Ala Asp
            340                 345                 350

Gly Ile Ile Pro Glu Pro Leu Gly Gly Ala His Ala Asp Pro Ser Trp
            355                 360                 365

Thr Ser Gln Gln Ile Lys Ile Ala Ile Asn Glu Asn Met Asn Glu Phe
            370                 375                 380

Gly Lys Met Ser Gly Glu Leu Leu Lys His Arg Met Ala Lys Tyr
385                 390                 395                 400

Arg Lys Ile Gly Val Phe Ile Glu Asn Ala Pro Val Glu Pro Glu Ile
                405                 410                 415

Lys Val Asn Met Lys Arg Arg Asp Ala Val Val Ser Asn Ser Arg Lys
            420                 425                 430

Leu Glu Gly Glu Val Glu Lys Leu Lys Glu Gln Ile Leu Lys Ala Lys
            435                 440                 445

Glu Thr Ser Ser Glu Asp Gln Pro Ser Ser Glu Val Leu Asn Glu
            450                 455                 460

Met Ile Lys Lys Leu Lys Ser Glu Ile Asp Asp Glu Tyr Thr Glu Ala
465                 470                 475                 480

Ala Arg Ala Met Gly Leu Glu Glu Arg Leu Thr Ala Met Arg Gly Glu
                485                 490                 495

Phe Ser Lys Ala Ser Glu Glu Glu His Leu Val His Pro Ile Leu Ile
            500                 505                 510

Glu Lys Ile Glu Lys Leu Lys Glu Glu Phe Asn Thr Arg Leu Ser Glu
            515                 520                 525

Ala Pro Asn Tyr Glu Ser Leu Lys Ser Lys Leu Asp Met Leu Arg Asp
            530                 535                 540

Phe Ser Arg Ala Lys Ala Ala Ser Glu Ala Ala Ser Val Lys Asn Glu
545                 550                 555                 560

Ile Asn Lys Arg Phe Gln Glu Ala Val Asp Arg Pro Glu Val Arg Glu
                565                 570                 575

Lys Val Glu Ala Ile Lys Ala Glu Val Ala Ser Ser Gly Ala Ser Ser
            580                 585                 590
```

-continued

```
Phe Glu Glu Leu Ser Asp Glu Leu Lys Glu Val Leu Lys Thr Lys
            595                 600                 605

Gly Glu Val Glu Ala Glu Met Ala Gly Val Leu Lys Ser Met Gly Leu
        610                 615                 620

Glu Leu Glu Ala Val Lys Pro Asn Val Ala Glu Gln Ile Phe Val Pro
625                 630                 635                 640

Ser Glu Asn Ile Gln Glu Lys Val Glu Lys Leu Asn Arg Glu Ile Ser
                645                 650                 655

Glu Lys Ile Glu Glu Val Val Arg Ala Pro Glu Ile Lys Ser Met Val
            660                 665                 670

Glu Leu Leu Lys Val Glu Asn Ala Lys Ala Ser Gln Thr Pro Gly Asp
        675                 680                 685

Thr Lys Val Ser Gln Lys Ile Glu Thr Leu Glu Gln Gln Ile Lys Gln
    690                 695                 700

Lys Ile Ala Asp Ala Leu Ser Met Ser Gly Leu Gln Glu Lys Gln Glu
705                 710                 715                 720

Glu Leu Glu Lys Glu Leu Ala Val Ala Arg Glu Val Ala Ala Val Lys
                725                 730                 735

Ser Glu Glu Ser Leu Lys Glu Asp Asp Asp Asp Asp Gly Ser Glu
            740                 745                 750

Ser Glu Lys Pro Glu Ile Ile Asn Pro His Phe Ala
        755                 760

<210> SEQ ID NO 175
<211> LENGTH: 769
<212> TYPE: PRT
<213> ORGANISM: Brassica napus

<400> SEQUENCE: 175

Met Ala Ser Met Ser His Ser Ser Ile Ala Leu Gly Gly Ala Ser Ala
1               5                   10                  15

Ser Ala Ser Asp Tyr Leu Arg Ser Ala Asn Gly Val Thr Gly Val
            20                  25                  30

Ser Leu Arg Ala Leu Gly Arg Arg Thr Met Val Thr Ala Thr Thr Arg
        35                  40                  45

Ser Ser Asn Asn Leu Tyr Val Thr Ala Arg Leu Lys Lys Gly Lys Lys
    50                  55                  60

Phe Asp His Pro Trp Pro Ala Asn Pro Asp Pro Asn Val Lys Gly Gly
65                  70                  75                  80

Val Leu Ser Tyr Leu Ser Asp Phe Lys Pro Leu Gly Asn Ala Gln Lys
                85                  90                  95

Pro Val Thr Leu Asp Phe Glu Arg Pro Leu Val Glu Leu Glu Lys Lys
            100                 105                 110

Ile Val Asp Val Arg Lys Met Ala Glu Glu Thr Gly Leu Asp Phe Thr
        115                 120                 125

Glu Gln Ile Ile Thr Leu Glu Thr Lys Tyr Arg Gln Ala Leu Lys Asp
    130                 135                 140

Leu Tyr Thr His Leu Thr Pro Ile Gln Arg Val Asn Ile Ala Arg His
145                 150                 155                 160

Pro Asn Arg Pro Thr Phe Leu Asp His Ile His Asn Ile Thr Asp Lys
                165                 170                 175

Phe Met Glu Leu His Gly Asp Arg Ala Gly Tyr Asp Asp Pro Ala Ile
            180                 185                 190

Val Thr Gly Ile Gly Thr Ile Asp Gly Lys Arg Tyr Met Phe Ile Gly
```

-continued

```
            195                 200                 205
His Gln Lys Gly Arg Asn Thr Lys Glu Asn Ile Met Arg Asn Phe Gly
210                 215                 220
Met Pro Thr Pro His Gly Tyr Arg Lys Ala Leu Arg Met Met Tyr Tyr
225                 230                 235                 240
Ala Asp His His Gly Phe Pro Ile Val Thr Phe Ile Asp Thr Pro Gly
            245                 250                 255
Ala Tyr Ala Asp Leu Lys Ser Glu Glu Lys Gly Gln Gly Glu Ala Ile
            260                 265                 270
Ala Asn Asn Leu Arg Thr Met Leu Gly Leu Lys Val Pro Ile Leu Ser
            275                 280                 285
Ile Val Ile Gly Glu Gly Gly Ser Gly Gly Ala Leu Ala Ile Gly Arg
290                 295                 300
Ala Asn Lys Met Leu Met Leu Glu Asn Ala Val Phe Tyr Val Ala Ser
305                 310                 315                 320
Pro Glu Ala Cys Ala Ala Ile Leu Trp Gln Thr Ser Lys Ala Ala Pro
            325                 330                 335
Glu Ala Ala Glu Lys Leu Arg Ile Thr Ser Lys Glu Leu Val Asn Leu
            340                 345                 350
Asn Val Ala Asp Gly Ile Ile Pro Glu Pro Leu Gly Gly Ala His Ala
            355                 360                 365
Asp Pro Ser Trp Thr Ser Gln Gln Ile Lys Ile Ala Ile Asn Glu Asn
370                 375                 380
Met Asn Glu Phe Gly Lys Met Ser Gly Glu Glu Leu Leu Lys His Arg
385                 390                 395                 400
Met Ala Lys Tyr Arg Lys Ile Gly Ala Phe Ile Glu Gly Glu Pro Val
            405                 410                 415
Glu Pro Glu Lys Lys Ile Asn Met Lys Arg Arg Asp Ala Val Ala Ser
            420                 425                 430
Thr Ser Arg Asn Leu Glu Gly Glu Val Glu Lys Leu Arg Glu Gln Ile
            435                 440                 445
Leu Lys Ala Lys Glu Ala Ser Pro Glu Ser Glu Val Glu Leu Ser Ser
450                 455                 460
Glu Val Leu Asn Glu Met Ile Glu Lys Leu Lys Ser Asp Ile Asp Glu
465                 470                 475                 480
Glu Tyr Thr Lys Ala Ala Lys Ala Met Gly Leu Glu Glu Arg Leu Ala
            485                 490                 495
Ala Thr Arg Glu Glu Phe Ser Lys Ala Asn Ala Glu Glu His Leu Met
            500                 505                 510
His Pro Val Leu Ile Glu Arg Ile Glu Lys Leu Lys Glu Glu Phe Asn
            515                 520                 525
Ala Arg Leu Ser Glu Ala Pro Asn Tyr Glu Ser Leu Lys Ala Lys Leu
            530                 535                 540
Asp Met Leu Lys Asp Phe Ser Arg Ala Lys Ala Ala Ser Glu Ala Ala
545                 550                 555                 560
Ser Val Lys Lys Glu Ile Asp Lys Arg Phe Arg Glu Ala Val Glu Arg
            565                 570                 575
Pro Glu Val Arg Glu Lys Val Glu Ala Val Lys Ala Glu Val Ala Ser
            580                 585                 590
Ser Gly Ala Ser Ser Phe Glu Glu Leu Ser Asp Glu Leu Lys Glu Lys
            595                 600                 605
Val Leu Lys Thr Lys Arg Glu Ala Glu Ala Glu Met Ala Val Val Leu
            610                 615                 620
```

```
Lys Ser Met Gly Leu Gly Leu Glu Ala Val Lys Pro Asn Leu Lys Glu
625                 630                 635                 640

Val Val Ala Glu Ser Pro Asn Glu Asn Ile Gln Glu Lys Leu Glu Lys
                645                 650                 655

Leu Asn Arg Glu Ile Asn Glu Lys Ile Glu Glu Val Val Arg Thr Pro
                660                 665                 670

Glu Ile Lys Ser Met Val Glu Leu Leu Lys Val Glu Thr Ala Lys Ala
                675                 680                 685

Ser Arg Met Pro Asp Gln Gly Ser Gln Lys Ile Glu Ala Leu Glu Met
                690                 695                 700

Gln Ile Lys Gln Lys Ile Ala Asp Ala Leu Ser Met Ser Gly Leu Gln
705                 710                 715                 720

Glu Lys Gln Glu Glu Leu Glu Lys Glu Leu Ala Ala Ala Arg Glu Leu
                725                 730                 735

Ala Gly Glu Glu Ser Asp Glu Ser Val Lys Glu Asp Asp Asp Asp Asp
                740                 745                 750

Glu Asp Gly Ser Gly Ser Gly Arg Ser Glu Ile Ile Asn Pro His Phe
                755                 760                 765

Ala

<210> SEQ ID NO 176
<211> LENGTH: 769
<212> TYPE: PRT
<213> ORGANISM: Brassica napus

<400> SEQUENCE: 176

Met Ala Ser Met Ser His Ser Ser Ile Ala Leu Gly Gly Ala Ser Ala
1               5                   10                  15

Ser Ala Ser Asp Tyr Leu Arg Ser Ala Asn Gly Val Thr Gly Val
                20                  25                  30

Ser Leu Arg Ala Leu Gly Arg Arg Thr Met Val Thr Ala Thr Thr Arg
            35                  40                  45

Ser Ser Asn Leu Tyr Val Thr Ala Arg Leu Lys Lys Gly Lys Lys Phe
        50                  55                  60

Asp His Pro Trp Pro Ala Asn Pro Asp Pro Asn Val Lys Gly Gly Val
65                  70                  75                  80

Leu Ser Tyr Leu Ser Glu Phe Lys Pro Leu Gly Asn Ala Gln Lys Pro
                85                  90                  95

Val Thr Leu Asp Phe Glu Arg Pro Leu Val Glu Leu Lys Lys Ile
                100                 105                 110

Val Asp Val Arg Lys Met Ala Glu Glu Thr Gly Leu Asp Phe Thr Glu
            115                 120                 125

Gln Ile Ile Thr Leu Glu Thr Lys Tyr Arg Gln Ala Leu Lys Asp Leu
        130                 135                 140

Tyr Thr His Leu Thr Pro Ile Gln Arg Val Asn Ile Ala Arg His Pro
145                 150                 155                 160

Asn Arg Pro Thr Phe Leu Asp His Ile His Asn Ile Thr Asp Lys Phe
                165                 170                 175

Met Glu Leu His Gly Asp Arg Ala Gly Tyr Asp Asp Pro Ala Ile Val
            180                 185                 190

Thr Gly Ile Gly Thr Ile Asp Gly Lys Arg Tyr Met Phe Ile Gly His
        195                 200                 205

Gln Lys Gly Arg Asn Thr Lys Glu Asn Ile Met Arg Asn Phe Gly Met
210                 215                 220
```

```
Pro Thr Pro His Gly Tyr Arg Lys Ala Leu Arg Met Tyr Tyr Ala
225                 230                 235                 240

Asp His His Gly Phe Pro Ile Val Thr Phe Ile Asp Thr Pro Gly Ala
            245                 250                 255

Tyr Ala Asp Leu Lys Ser Glu Glu Lys Gly Gln Gly Glu Ala Ile Ala
        260                 265                 270

Asn Asn Leu Arg Thr Met Phe Gly Leu Lys Val Pro Ile Leu Ser Ile
    275                 280                 285

Val Ile Gly Glu Gly Gly Ser Gly Gly Ala Leu Ala Ile Gly Cys Ala
290                 295                 300

Asn Lys Met Leu Met Leu Glu Asn Ala Val Phe Tyr Val Ala Ser Pro
305                 310                 315                 320

Glu Ala Cys Ala Ala Ile Leu Trp Gln Thr Ser Lys Ala Ala Pro Glu
            325                 330                 335

Ala Ala Glu Lys Leu Arg Ile Ala Ser Lys Glu Leu Val Asn Leu Asn
        340                 345                 350

Val Ala Asp Gly Ile Ile Pro Glu Pro Leu Gly Gly Ala His Ala Asp
    355                 360                 365

Pro Ser Trp Thr Ser Gln Gln Ile Lys Ile Ala Ile Asn Glu Asn Met
370                 375                 380

Asn Glu Phe Gly Lys Met Ser Gly Glu Glu Leu Leu Lys His Arg Met
385                 390                 395                 400

Ala Lys Tyr Arg Lys Ile Gly Val Phe Ile Glu Gly Glu Pro Val Glu
            405                 410                 415

Pro Glu Lys Lys Ile Asn Met Lys Arg Arg Asp Ala Val Ala Ser Thr
        420                 425                 430

Ser Arg Asn Leu Glu Gly Glu Val Glu Lys Leu Arg Glu Gln Ile Leu
    435                 440                 445

Lys Ala Lys Glu Ala Ser Pro Glu Ser Asp Glu Gly Glu Glu Leu Ser
450                 455                 460

Ser Gln Val Leu Lys Glu Met Ile Glu Lys Leu Lys Ser Asp Ile Asp
465                 470                 475                 480

Glu Glu Tyr Thr Lys Ala Ala Lys Ala Met Gly Leu Glu Glu Arg Leu
            485                 490                 495

Ala Ala Thr Arg Glu Glu Phe Ser Lys Ala Asn Ala Glu Glu His Leu
        500                 505                 510

Met His Pro Val Leu Ile Glu Arg Ile Glu Lys Leu Lys Glu Glu Phe
    515                 520                 525

Asn Ala Arg Leu Ser Glu Ala Pro Asn Tyr Glu Ser Leu Lys Ala Lys
530                 535                 540

Leu Asp Met Leu Lys Asp Phe Ser Arg Ala Lys Ala Ala Ser Asp Ala
545                 550                 555                 560

Ala Ser Val Lys Lys Glu Ile Asn Lys Arg Phe Gln Glu Ala Val Glu
            565                 570                 575

Arg Pro Glu Val Arg Glu Lys Val Glu Ala Lys Ala Glu Val Ala
        580                 585                 590

Ser Ser Gly Ala Ser Ser Phe Glu Glu Leu Ser Asp Glu Leu Lys Glu
    595                 600                 605

Lys Val Leu Lys Thr Lys Arg Glu Val Glu Ala Glu Met Ala Val Val
610                 615                 620

Leu Lys Ser Met Gly Leu Glu Leu Glu Ala Val Lys Pro Asn Leu Lys
625                 630                 635                 640
```

```
Glu Val Val Ala Glu Ser Pro Asn Glu Asn Ile Gln Glu Lys Ile Glu
                645                 650                 655

Lys Leu Asn Arg Glu Ile Thr Glu Lys Ile Glu Val Val Arg Thr
            660                 665                 670

Pro Glu Ile Lys Ser Met Val Glu Leu Leu Lys Val Glu Thr Ala Lys
            675                 680                 685

Ala Ser Gln Met Pro Asp Gln Gly Ser Gln Lys Ile Glu Ala Leu Glu
            690                 695                 700

Met Gln Ile Lys Gln Lys Ile Ala Asp Ala Leu Ser Met Ser Gly Leu
705                 710                 715                 720

Gln Glu Lys Gln Glu Glu Leu Gly Lys Glu Leu Ala Ala Arg Glu
                725                 730                 735

Leu Ala Gly Glu Glu Ser Asp Glu Ser Val Lys Asp Asp Asp Asp
            740                 745                 750

Glu Asp Gly Ser Gly Ser Gly Arg Ser Glu Ile Ile Asn Pro His Phe
            755                 760                 765

Ala

<210> SEQ ID NO 177
<211> LENGTH: 765
<212> TYPE: PRT
<213> ORGANISM: Brassica napus

<400> SEQUENCE: 177

Met Ala Ser Met Ser His Ser Ser Ile Ala Leu Cys Gly Ala Ser Ala
1               5                   10                  15

Ser Ala Ser Ala Ser Val Leu Leu Ser Thr Thr Gly Val Ser Leu Arg
            20                  25                  30

Thr Leu Gly Arg Ala Met Val Ala Ser Thr Lys Arg Ser Asn Leu Tyr
        35                  40                  45

Val Thr Ala Arg Leu Lys Lys Gly Lys Lys Phe Asp His Pro Trp Pro
    50                  55                  60

Ser Asn Pro Asp Pro Asn Val Lys Gly Gly Val Leu Ser Tyr Leu Ser
65                  70                  75                  80

Thr Phe Lys Pro Leu Gly Asp Thr Gln Lys Pro Val Thr Leu Asp Phe
                85                  90                  95

Glu Lys Pro Leu Val Glu Leu Gly Lys Lys Ile Val Asp Val Arg Lys
            100                 105                 110

Met Ala Ala Glu Thr Gly Leu Asp Phe Thr Asp Gln Ile Ile Thr Leu
        115                 120                 125

Glu Thr Lys Tyr Arg Gln Ala Leu Lys Asp Leu Tyr Thr His Leu Thr
    130                 135                 140

Pro Ile Gln Arg Val Asn Ile Ala Arg His Pro Asn Arg Pro Thr Phe
145                 150                 155                 160

Leu Asp His Ile His Asn Ile Thr Asp Lys Phe Met Glu Leu His Gly
                165                 170                 175

Asp Arg Ala Gly Tyr Asp Asp Pro Ala Ile Val Thr Gly Ile Gly Thr
            180                 185                 190

Ile Asp Gly Lys Arg Tyr Met Phe Ile Gly His Gln Lys Gly Arg Asn
        195                 200                 205

Thr Lys Glu Asn Ile Met Arg Asn Phe Gly Met Pro Thr Pro His Gly
    210                 215                 220

Tyr Arg Lys Ala Leu Arg Met Met Tyr Tyr Ala Asp His His Gly Phe
225                 230                 235                 240
```

-continued

```
Pro Ile Val Thr Phe Ile Asp Thr Pro Gly Ala Tyr Ala Asp Leu Lys
                245                 250                 255

Ser Glu Glu Leu Gly Gln Gly Glu Ala Ile Ala Asn Asn Leu Arg Thr
            260                 265                 270

Met Phe Gly Leu Lys Val Pro Ile Leu Ser Ile Val Ile Gly Glu Gly
        275                 280                 285

Gly Ser Gly Gly Ala Leu Ala Ile Gly Cys Ala Asn Lys Met Leu Met
    290                 295                 300

Leu Glu Asn Ala Val Phe Tyr Val Ala Ser Pro Glu Ala Cys Ala Ala
305                 310                 315                 320

Ile Leu Trp Asn Ser Ser Lys Ala Ala Pro Glu Ala Ala Glu Lys Leu
                325                 330                 335

Arg Ile Thr Ser Arg Glu Leu Val Lys Leu Asn Val Ala Asp Gly Ile
            340                 345                 350

Ile Pro Glu Pro Leu Gly Gly Ala His Ala Asp Pro Ser Trp Thr Ser
        355                 360                 365

Gln Gln Ile Lys Ile Ala Ile Asn Glu Asn Met Asn Glu Phe Gly Lys
    370                 375                 380

Met Ser Gly Glu Glu Leu Leu Lys His Arg Met Ala Lys Tyr Arg Lys
385                 390                 395                 400

Ile Gly Val Phe Ile Glu Asp Ala Pro Val Glu Pro Glu Ile Lys Val
                405                 410                 415

Asn Met Lys Arg Arg Asp Ala Val Ile Ser Asn Ser Arg Lys Leu Glu
            420                 425                 430

Gly Glu Val Glu Lys Leu Arg Asp Gln Ile Leu Lys Ala Lys Glu Thr
        435                 440                 445

Ser Ser Glu Glu Ala Pro Ser Ser Glu Val Leu Asn Glu Met Ile Lys
    450                 455                 460

Lys Leu Lys Ser Glu Ile Asp Asp Glu Tyr Thr Glu Ala Ala Arg Ala
465                 470                 475                 480

Met Gly Leu Glu Glu Arg Leu Thr Ala Met Arg Gly Glu Phe Ser Lys
                485                 490                 495

Ala Ser Ala Glu Glu His Leu Met His Pro Ile Leu Ile Glu Lys Ile
            500                 505                 510

Glu Lys Leu Lys Glu Glu Phe Asn Thr Arg Leu Ser Glu Ala Pro Asn
        515                 520                 525

Tyr Glu Ser Leu Lys Ser Lys Leu Asp Met Leu Arg Asp Phe Ser Arg
    530                 535                 540

Ala Lys Ala Ala Ser Glu Ala Ser Val Arg Asn Glu Ile Asn Lys
545                 550                 555                 560

Arg Phe Gln Glu Ala Val Asp Arg Pro Glu Val Arg Glu Lys Val Glu
                565                 570                 575

Ala Ile Lys Ala Glu Val Ala Ser Ser Gly Ala Ser Ser Phe Glu Glu
            580                 585                 590

Leu Ser Asp Glu Leu Lys Glu Lys Val Leu Lys Thr Lys Gly Glu Val
        595                 600                 605

Glu Ala Glu Met Ala Gly Val Leu Lys Ser Met Gly Leu Glu Leu Glu
    610                 615                 620

Ala Val Lys Pro Tyr Val Ala Glu Gln Ile Phe Val Pro Ser Glu Asn
625                 630                 635                 640

Ile Gln Glu Lys Val Glu Lys Leu Asn Arg Glu Ile Ser Glu Lys Ile
                645                 650                 655

Glu Glu Val Val Arg Thr Pro Glu Ile Lys Ser Met Val Glu Leu Leu
```

```
                    660                 665                 670
Lys Val Glu Asn Ala Lys Ala Ser Gln Thr Pro Gly Asp Thr Lys Val
                675                 680                 685

Ser Gln Lys Ile Glu Thr Leu Glu Gln Gln Ile Lys Gln Lys Ile Ala
            690                 695                 700

Asp Ala Leu Ser Met Ser Gly Leu Gln Glu Lys Gln Glu Glu Leu Glu
705                 710                 715                 720

Lys Glu Leu Ala Val Ala Arg Glu Leu Ala Ala Glu Lys Ser Gln Glu
                725                 730                 735

Ser Leu Lys Glu Asp Asp Asp Asp Asp Asp Asp Glu Asp Gly Ser
            740                 745                 750

Glu Ser Glu Lys Pro Glu Ile Ile Asn Pro His Phe Ala
        755                 760                 765
```

<210> SEQ ID NO 178
<211> LENGTH: 768
<212> TYPE: PRT
<213> ORGANISM: Brassica rapa

<400> SEQUENCE: 178

```
Met Ala Ser Met Ser His Ser Ser Ile Ala Leu Gly Gly Ala Ser Ala
1               5                   10                  15

Ser Ala Ser Asp Tyr Leu Arg Ser Ser Ala Asn Gly Val Thr Gly Val
                20                  25                  30

Ser Leu Arg Ala Leu Gly Arg Arg Thr Met Val Thr Ala Thr Thr Arg
            35                  40                  45

Ser Ser Asn Asn Leu Tyr Val Thr Ser Arg Leu Lys Lys Gly Lys Lys
        50                  55                  60

Phe Asp His Pro Trp Pro Ala Asn Pro Asp Pro Asn Val Lys Gly Gly
65                  70                  75                  80

Val Leu Ser Tyr Leu Ser Glu Phe Lys Pro Leu Gly Asn Ala Gln Lys
                85                  90                  95

Pro Val Thr Leu Asp Phe Glu Arg Pro Leu Val Glu Leu Glu Lys Lys
            100                 105                 110

Ile Val Asp Val Arg Lys Met Ala Glu Glu Thr Gly Leu Asp Phe Thr
        115                 120                 125

Glu Gln Ile Ile Thr Leu Glu Thr Lys Tyr Arg Gln Ala Leu Lys Asp
    130                 135                 140

Leu Tyr Thr His Leu Thr Pro Ile Gln Arg Val Asn Ile Ala Arg His
145                 150                 155                 160

Pro Asn Arg Pro Thr Phe Leu Asp His Ile His Asn Ile Thr Asp Lys
                165                 170                 175

Phe Met Glu Leu His Gly Asp Arg Ala Gly Tyr Asp Asp Pro Ala Ile
            180                 185                 190

Val Thr Gly Ile Gly Thr Ile Asp Gly Lys Arg Tyr Met Phe Ile Gly
        195                 200                 205

His Gln Lys Gly Arg Asn Thr Lys Glu Asn Ile Met Arg Asn Phe Gly
    210                 215                 220

Met Pro Thr Pro His Gly Tyr Arg Lys Ala Leu Arg Met Met Tyr Tyr
225                 230                 235                 240

Ala Asp His His Gly Phe Pro Ile Val Thr Phe Ile Asp Thr Pro Gly
                245                 250                 255

Ala Tyr Ala Asp Leu Lys Ser Glu Glu Lys Gly Gln Gly Glu Ala Ile
            260                 265                 270
```

```
Ala Asn Asn Leu Arg Thr Met Phe Gly Leu Lys Val Pro Ile Leu Ser
            275                 280                 285

Ile Val Ile Gly Glu Gly Gly Ser Gly Ala Leu Ala Ile Gly Cys
        290                 295                 300

Ala Asn Lys Met Leu Met Leu Glu Asn Ala Val Phe Tyr Val Ala Ser
305                 310                 315                 320

Pro Glu Ala Cys Ala Ala Ile Leu Trp Gln Thr Ser Lys Ala Ala Pro
                325                 330                 335

Glu Ala Ala Glu Lys Leu Arg Ile Thr Ser Lys Glu Leu Val Asn Leu
                340                 345                 350

Asn Val Ala Asp Gly Ile Ile Pro Glu Pro Leu Gly Gly Ala His Ala
                355                 360                 365

Asp Pro Ser Trp Thr Ser Gln Gln Ile Lys Ile Ala Ile Asn Glu Asn
    370                 375                 380

Met Asn Glu Phe Gly Lys Met Ser Gly Glu Glu Leu Leu Lys His Arg
385                 390                 395                 400

Met Ala Lys Tyr Arg Lys Ile Gly Val Phe Ile Glu Gly Glu Pro Val
                405                 410                 415

Glu Pro Glu Lys Lys Ile Asn Met Lys Arg Arg Asp Ala Val Ala Ser
                420                 425                 430

Thr Ser Arg Asn Leu Glu Gly Glu Val Glu Lys Leu Arg Glu Gln Ile
        435                 440                 445

Leu Lys Ala Lys Glu Ala Ser Pro Glu Ser Glu Val Glu Leu Ser Ser
        450                 455                 460

Glu Val Leu Asn Glu Met Ile Glu Lys Leu Lys Ser Asp Ile Asp Glu
465                 470                 475                 480

Glu Tyr Thr Lys Ala Ala Lys Ala Met Gly Leu Glu Glu Arg Leu Ala
                485                 490                 495

Ala Thr Arg Glu Glu Phe Ser Lys Ala Asn Ala Glu Glu His Leu Met
            500                 505                 510

His Pro Val Leu Ile Glu Arg Ile Glu Lys Leu Lys Glu Glu Phe Asn
            515                 520                 525

Ala Arg Leu Ser Glu Ala Pro Asn Tyr Glu Ser Val Lys Ala Lys Leu
        530                 535                 540

Asp Met Leu Lys Asp Phe Ser Arg Ala Lys Ala Ala Ser Glu Ala Ala
545                 550                 555                 560

Ser Val Lys Lys Glu Ile Asn Lys Arg Phe Gln Glu Ala Val Glu Arg
                565                 570                 575

Pro Glu Val Arg Glu Lys Val Glu Ala Val Lys Ala Glu Val Ala Ser
            580                 585                 590

Ser Gly Thr Ser Ser Phe Glu Glu Leu Ser Asp Glu Leu Lys Glu Lys
        595                 600                 605

Val Leu Lys Thr Lys Arg Glu Val Glu Ala Glu Met Ala Val Val Leu
610                 615                 620

Lys Ser Met Gly Leu Glu Leu Glu Ala Val Lys Pro Asn Leu Lys Glu
625                 630                 635                 640

Val Val Ala Glu Ser Pro Asn Glu Asn Ile Gln Glu Lys Leu Glu Lys
                645                 650                 655

Pro Asn Arg Glu Ile Asn Glu Lys Ile Glu Glu Val Val Arg Thr Pro
            660                 665                 670

Glu Ile Lys Ser Met Val Glu Leu Leu Lys Val Glu Thr Ala Lys Ala
            675                 680                 685

Ser Arg Met Pro Asp Gln Gly Ser Gln Lys Ile Glu Ala Leu Glu Met
```

```
                690             695             700
Gln Ile Lys Gln Lys Ile Ala Asp Ala Leu Ser Met Ser Gly Leu Gln
705             710             715             720

Glu Lys Gln Glu Glu Leu Glu Lys Glu Leu Ala Ala Arg Glu Leu
            725             730             735

Ala Gly Glu Glu Ser Asp Glu Ser Val Lys Asp Asp Asp Asp Glu
            740             745             750

Asp Gly Ser Gly Ser Gly Arg Ser Glu Ile Ile Asn Pro His Phe Ala
            755             760             765
```

<210> SEQ ID NO 179
<211> LENGTH: 770
<212> TYPE: PRT
<213> ORGANISM: Brassica rapa

<400> SEQUENCE: 179

```
Met Ala Ser Met Ser His Ser Ser Ile Ala Leu Cys Gly Ala Ser Ala
1               5                   10                  15

Ser Ala Ser Asp His Leu Arg Ser Ser Thr Asn Gly Val Thr Gly Val
            20                  25                  30

Ser Leu Arg Thr Leu Gly Arg Ala Met Val Ala Ser Thr Lys Arg Ser
        35                  40                  45

Asn Leu Tyr Val Thr Ala Arg Leu Lys Lys Gly Lys Lys Phe Asp His
50                  55                  60

Pro Trp Pro Ser Asn Pro Asp Pro Asn Val Lys Gly Val Leu Ser
65                  70                  75                  80

Tyr Leu Ser Thr Phe Lys Pro Leu Gly Asp Thr Gln Lys Pro Val Thr
                85                  90                  95

Leu Asp Phe Glu Lys Pro Leu Val Glu Leu Glu Lys Lys Ile Val Asp
            100                 105                 110

Val Arg Lys Met Ala Ala Glu Thr Gly Leu Asp Phe Thr Asp Gln Ile
            115                 120                 125

Ile Thr Leu Glu Thr Lys Tyr Arg Gln Ala Leu Lys Asp Leu Tyr Thr
130                 135                 140

His Leu Thr Pro Ile Gln Arg Val Asn Ile Ala Arg His Pro Asn Arg
145                 150                 155                 160

Pro Thr Phe Leu Asp His Ile His Asn Ile Thr Asp Lys Phe Met Glu
                165                 170                 175

Leu His Gly Asp Arg Ala Gly Tyr Asp Asp Pro Ala Ile Val Thr Gly
            180                 185                 190

Ile Gly Thr Ile Asp Gly Lys Arg Tyr Met Phe Ile Gly His Gln Lys
        195                 200                 205

Gly Arg Asn Thr Lys Glu Asn Ile Met Arg Asn Phe Gly Met Pro Thr
    210                 215                 220

Pro His Gly Tyr Arg Lys Ala Leu Arg Met Met Tyr Tyr Ala Asp His
225                 230                 235                 240

His Gly Phe Pro Ile Val Thr Phe Ile Asp Thr Pro Gly Ala Tyr Ala
                245                 250                 255

Asp Leu Lys Ser Glu Glu Leu Gly Gln Gly Glu Ala Ile Ala Asn Asn
            260                 265                 270

Leu Arg Thr Met Phe Gly Leu Lys Val Pro Ile Leu Ser Ile Val Ile
        275                 280                 285

Gly Glu Gly Gly Ser Gly Gly Ala Leu Ala Ile Gly Cys Ala Asn Lys
    290                 295                 300
```

-continued

```
Met Leu Met Leu Glu Asn Ala Val Phe Tyr Val Ala Ser Pro Glu Ala
305                 310                 315                 320

Cys Ala Ala Ile Leu Trp Asn Ser Ser Lys Ala Pro Glu Ala Ala
            325                 330                 335

Glu Lys Leu Arg Ile Thr Ser Arg Glu Leu Val Lys Leu Asn Val Ala
            340                 345                 350

Asp Gly Ile Ile Pro Glu Pro Leu Gly Gly Ala His Ala Asp Pro Ser
            355                 360                 365

Trp Thr Ser Gln Gln Ile Lys Ile Ala Ile Asn Glu Asn Met Asn Glu
    370                 375                 380

Phe Gly Lys Thr Ser Gly Asp Glu Leu Leu Lys His Arg Met Ala Lys
385                 390                 395                 400

Tyr Arg Lys Ile Gly Val Phe Ile Glu Asn Ala Pro Val Glu Pro Glu
                405                 410                 415

Ile Lys Val Asn Leu Lys Arg Arg Asp Ala Val Val Ser Thr Ser Arg
            420                 425                 430

Lys Leu Glu Gly Glu Val Glu Lys Leu Lys Glu Gln Ile Leu Lys Ala
            435                 440                 445

Lys Glu Thr Ser Ser Ser Glu Asp Gln Pro Ser Ser Glu Val Leu Asn
450                 455                 460

Glu Met Ile Lys Lys Leu Lys Ser Glu Ile Asp Asp Glu Tyr Thr Glu
465                 470                 475                 480

Ala Ala Arg Ala Met Gly Leu Gln Glu Arg Leu Thr Ala Met Arg Gly
                485                 490                 495

Glu Phe Ser Lys Ala Ser Ala Gly Glu His Leu Met His Pro Ile Leu
            500                 505                 510

Ile Glu Lys Ile Glu Lys Leu Lys Glu Phe Asn Thr Arg Leu Ser
    515                 520                 525

Glu Ala Pro Asn Tyr Glu Ser Leu Lys Ser Lys Leu Asp Met Leu Ser
530                 535                 540

Asp Phe Ser Arg Ala Lys Ala Ser Glu Ala Ala Ser Val Lys Asn
545                 550                 555                 560

Glu Ile Asn Lys Arg Phe Gln Glu Ala Val Asp Arg Pro Glu Val Arg
                565                 570                 575

Glu Lys Val Glu Ala Ile Lys Ala Glu Val Ala Ser Ser Gly Ala Ser
            580                 585                 590

Ser Phe Lys Glu Leu Ser Asp Glu Leu Lys Glu Lys Val Leu Lys Thr
    595                 600                 605

Lys Gly Glu Val Glu Ala Glu Met Ala Val Val Leu Lys Ser Met Gly
610                 615                 620

Leu Glu Leu Glu Ala Val Lys Pro Asn Val Ala Glu Gln Ile Phe Val
625                 630                 635                 640

Pro Ser Glu Asn Ile Gln Glu Lys Val Glu Lys Leu Asn Gln Glu Ile
                645                 650                 655

Ser Glu Lys Ile Glu Glu Val Val Arg Thr Pro Glu Ile Lys Ser Met
            660                 665                 670

Val Glu Leu Leu Lys Val Glu Asn Ala Lys Ala Ser Gln Thr Pro Gly
            675                 680                 685

Asp Thr Lys Val Ser Gln Lys Ile Glu Thr Leu Glu Gln Gln Ile Lys
            690                 695                 700

Gln Lys Ile Ala Asp Ala Leu Ser Met Ser Gly Leu Gln Glu Lys Gln
705                 710                 715                 720

Glu Glu Leu Glu Lys Glu Leu Ala Val Ala Arg Glu Leu Ala Ala Glu
```

```
            725                 730                 735
Lys Ser Gln Glu Ser Leu Lys Glu Asp Asp Asp Asp Asp Asp
            740                 745                 750

Asp Glu Asp Gly Ser Glu Ser Glu Lys Pro Glu Ile Ile Asn Pro His
        755                 760                 765

Phe Ala
    770

<210> SEQ ID NO 180
<211> LENGTH: 1336
<212> TYPE: DNA
<213> ORGANISM: Artificial sequence
<220> FEATURE:
<223> OTHER INFORMATION: BADC CRISPR Guide Cassette

<400> SEQUENCE: 180
ggggacaagt ttgtacaaaa aagcaggctt cattcaacaa gaaaagaata tgtgtaactg      60
acgaaagttc ttaggctaac aaaaatgtat tatagtgaac atagaaataa cagaatgctt    120
ttttactcgt aaacacatga tcacaaaatt cacaatcaaa gtcggtttag atgtaccgtc    180
cggtttaaag caaataagtt gggaatgggt tttacaaata aacaagtggg ctttggcccg    240
tatcacctac tattacaagg gaactcaact cacattacaa tttacaagag tacaaacatc    300
ccacatcgct cgcctaggaa acatagctgt tgtatatata acgttagagag agcaacgttg    360 gtcatggcgt cttctgcagc tctgttttag agctagaaat agcaagttaa ataaggcta      420 gtccgttatc aacttgaaaa agtggcaccg agtcggtgct ttttttgtcc tcgaggttta    480
agttataatt cccccatagg ttctcgctaa atcagatacc agtaacattt agcaacatcc    540
catagtcttt tttttttta atcaaacttt aaaccacaag tcattagctt taacaaattt    600
aaagctaacg ttacaaaacc aacggcgtcg tttcactcaa tctctaagaa taataatcag    660
aaagaggact tttaattacc ttaaataggc ctttttatca aacgagcccct tttaagcttt    720 aaccgataac aaatatacca catcgcatag aacagaggac aaaagctgcg tttaaataat    780
gttagagtcg agtaagtgat tgctcattcc caagtcctct ggttttagag ctagaaatag    840
caagttaaaa taaggctagt ccgttatcaa cttgaaaaag tggcaccgag tcggtgcttt    900
ttttgtccat tcggagtttt tgtatcttgt ttcatagttt gtcccaggat tagaatgatt    960
aggcatcgaa ccttcaagaa tttgattgaa taaaacatct tcattcttaa gatatgaaga   1020
taatcttcaa aaggcccctg ggaatctgaa agaagagaag caggcccatt tatatgggaa   1080
agaacaatag tatttcttat ataggcccat ttaagttgaa aacaatcttc aaaagtccca   1140
catcgcttag ataagaaaac gaagctgagt ttatatacag ctagagtcga agtagtgatt   1200
gaccttagta gagtaagttc gttttagagc tagaaatagc aagttaaaat aaggctagtc   1260
cgttatcaac ttgaaaaagt ggcaccgagt cggtgctttt tttgtcgacc cagctttctt   1320
gtacaaagtg gtcccc                                                    1336
```

INCREASING PLANT OIL CONTENT BY IMPROVING ACTIVITY OF ACETYL-COA CARBOXYLASE

CROSS REFERENCE TO RELATED APPLICATIONS

This application is a 371 National Stage application of International Application No. PCT/US2017/040851, filed Jul. 6, 2017, which claims benefit of U.S. provisional application No. 62/359,635, filed Jul. 7, 2016, each of which is herein incorporated by reference in its entirety.

STATEMENT REGARDING FEDERALLY SPONSORED RESEARCH

This invention was made with Government support under contract No. 1339385 awarded by the National Science Foundation (NSF). The Government has certain rights in the invention.

INCORPORATION OF SEQUENCE LISTING

The sequence listing that is contained in the file named "UVMO116WO_ST25.txt," which is 423 kilobytes as measured in Microsoft Windows operating system and was created on Jul. 5, 2017, is filed electronically herewith and incorporated herein by reference.

FIELD OF THE INVENTION

The present invention relates to methods and systems for increasing plant and seed oil content, and more particularly to constructs and methods to increase activity of acetyl-coenzyme A carboxylase (ACCase) in order to increase fatty acid and ultimately triacylglycerol production in plants and algae.

BACKGROUND OF THE INVENTION

Vegetable oils are an important renewable source of hydrocarbons for food, energy, and industrial feedstocks. As demand for this commodity increases, discovering ways to enhance oil production in crops will be an agronomic priority. Oil production begins with the de novo fatty acid synthesis (FAS) pathway to generate the acyl chains that are eventually esterified to glycerol to produce triacylglycerol, the major storage lipid in the seed. The committed step of de novo FAS is catalyzed by acetyl-coenzyme A carboxylase (ACCase) which carboxylates acetyl-CoA to form malonyl-CoA in a two-step reaction requiring ATP, bicarbonate, and biotin cofactor. In prokaryotes, and in plastids of most plants, ACCase is a heteromeric complex requiring four distinct subunits: biotin carboxylase (BC), biotin carboxyl carrier protein (BCCP), and α- and β-carboxyltransferases (CT). Graminaceous monocots possess a homomeric form of plastid ACCase where the catalytic components are adjoined in tandem as a single polypeptide. Structural models for the heteromeric ACCase are primarily based on studies in *Escherichia coli*. The *E. coli* ACCase is composed of two subcomplexes: an α/β-CT heterotetramer and a BC/BCCP heterotetramer. The components of the two subcomplexes form stable associations, while the subcomplexes themselves show a relatively weak interaction with one another. This property has contributed to the difficulties in biochemical and structural characterization of heteromeric ACCase from plants. Plastidial ACCase is regulated by light, feedback inhibition, and a 2-oxoglutarate-binding protein PII. It remains unknown if such regulation is mediated by additional proteins, or if other factors are involved, as the plant heteromeric ACCase has never been fully characterized. A comprehensive study of ACCase protein interactions is needed.

Therefore, there is a need to provide a better understanding of protein structure and regulation of ACCase to leverage the potential for manipulating flux through this committed and irreversible step for de novo FAS. There is also a need to develop a novel method to efficiently increase ACCase activity to consequently increase fatty acid and, ultimately, triacylglycerol production in plants and algae.

SUMMARY OF THE INVENTION

In one aspect, the present invention provides methods/systems to modulate or alter fatty acid and protein production in plants and algae. Such methods comprise the step of altering the activity level of ACCase, the committed step for de novo fatty acid biosynthesis. In one embodiment, the altering step may comprise increasing the activity level of ACCase by increasing expression of α-CT or a portion thereof. In other embodiments, the altering step comprises overexpression of an endogenous α-CT, such as a *Camelina sativa*, *Glycine max*, *Brassica napus*, or a *Brassica rapa* α-CT, or expression or overexpression of a heterologous α-CT, such as a *Pisum sativum* α-CT (SEQ ID NO:162). In another embodiment, the altering step comprises overexpression of a catalytic portion of an α-CT. In certain embodiments, the altering step comprises overexpression of a catalytic portion of a endogenous α-CT, or expression or overexpression of a heterologous α-CT, such as the catalytic portion of a *Pisum sativum* α-CT (SEQ ID NO:164). In further embodiments, the altering step may comprise altering the expression of a gene family of negative regulators, biotin/lipoyl attachment domain containing (BADC or BLADC) proteins, which bind to the multi-subunit ACCase found in the plastids of dicotyledon and non-graminaceous monocot plants, as well as algae. Such methods may enable higher oil content in algae and/or land plants, in either vegetative or reproductive tissues including, but not limited to, leaves and seeds.

In another embodiment, a method of the invention comprises total or partial silencing of one or more BADC gene. In some embodiments, said BADC gene comprises genes and gene orthologs of BADC1, BADC2, and BADC3, or artificial genes containing essential BADC motifs, either alone or in combination with increasing expression of an α-CT or a portion thereof, such as the catalytic portion. In other embodiments, the one or more BADC gene comprises from about 34%, 40%, 50%, 60%, 62% or 70% to about 100% sequence identity to a nucleotide sequence selected from the group consisting of SEQ ID NOs: 2, 4, 6, 7, and 138, or a complement thereof. In still further embodiments, the one or more BADC gene encodes a polypeptide comprising from about 34%, 40%, 50%, 60%, 62% or 70% to about 100% sequence identity to a polypeptide sequence selected from the group consisting of SEQ ID NOs: 1, 3, 5, 8-137, and 139-143. In another embodiment, said silencing comprises expression of an RNAi cassette comprising SEQ ID NOs:7 or 138. In another embodiment, the invention provides a plant or part thereof produced by such a method, wherein the plant produces seed comprising increased seed oil content. In another embodiment, the seed comprises increased seed oil content. In some embodiments, such methods may be carried out in organisms that contain orthologs to the *Arabidopsis thaliana* BADC genes, such as *Amborella trichopoda, Arabidopsis lyrata, Arabidopsis alpine, Arachis hypogaea, Auxenochlorella protothecoides, Brassica napus, Brassica rapa, Camelina sativa, Capsella rubella, Cathamus tinctorius, Chlamydomonas reinhardtii, Chlorella variabilis, Cicer arietinum, Citrus clementina, Citrus sinensis, Coccomyxa subellipsoideas* C-169, *Coffea canephora, Cucumis melo, Cucumis sativus, Elaeis guineensis, Erythranthe guttata, Eucalyptus grandis, Eutrema salsugineum, Fragaria vesca, Genlisea aurea, Glycine max, Helianthus annuus, Helicosporidium* ATCC 50920, *Jatropha curcas, Lotus japonicas, Medicago truncatula, Morus notabilis, Musa acuminate, Nelumbo nucifera, Nicotiana sylvestris, Nicotiana tomentosiformis, Phaseolus vulgaris, Pheonix dactylifera, Physcomitrella patens, Picea sitchensis, Polytomella parva, Populus trichocarpa, Prunus mume, Prunes persica, Pyrus×bretschneideri, Ricinus communis, Selaginella moellendorffii, Sesamum indicum, Solanum lycopersicum, Solanum tuberosum, Theobroma cacao, Thlaspi arvense, Vitis vinifera,* or *Volvox carteri*.

In an additional embodiment, the method comprises increasing the activity level of ACCase by increasing expression of α-CT or a portion thereof and total or partial silencing of one or more BADC gene. In another embodiment, the invention provides a plant or part thereof produced by a method described herein, wherein the plant comprises increased seed oil content, or a seed that produces the plant or part thereof, wherein the seed comprises increased seed oil content, such as *Amborella trichopoda, Arabidopsis lyrata, Arabidopsis alpine, Arachis hypogaea, Auxenochlorella protothecoides, Brassica napus, Brassica rapa, Camelina sativa, Capsella rubella, Cathamus tinctorius, Chlamydomonas reinhardtii, Chlorella variabilis, Cicer arietinum, Citrus clementina, Citrus sinensis, Coccomyxa subellipsoideas* C-169, *Coffea canephora, Cucumis melo, Cucumis sativus, Elaeis guineensis, Erythranthe guttata, Eucalyptus grandis, Eutrema salsugineum, Fragaria vesca, Genlisea aurea, Glycine max, Helianthus annuus, Helicosporidium* ATCC 50920, *Jatropha curcas, Lotus japonicas, Medicago truncatula, Morus notabilis, Musa acuminate, Nelumbo nucifera, Nicotiana sylvestris, Nicotiana tomentosiformis, Phaseolus vulgaris, Pheonix dactylifera, Physcomitrella patens, Picea sitchensis, Polytomella parva, Populus trichocarpa, Prunus mume, Prunes persica, Pyrus×bretschneideri, Ricinus communis, Selaginella moellendorffii, Sesamum indicum, Solanum lycopersicum, Solanum tuberosum, Theobroma cacao, Thlaspi arvense, Vitis vinifera,* or *Volvox carteri*. In certain embodiments, the plant part is a leaf, pollen, ovule, fruit, rootstock, flower, scion or a cell. Another embodiment of the present invention is a tissue culture of regenerable cells of a plant produced by the presently disclosed methods. The present invention further provides a seed that produces a plant produced by the presently disclosed methods.

In another embodiment of the invention, a method described herein may comprises the step of reducing plastid ACCase activity by up-regulating BADC genes through biotechnology or selective breeding approaches in an organism that contains an ortholog to the *Arabidopsis thaliana* BADC genes. In one embodiment, such up-regulation of one or more BADC genes may comprise altering expression of one or more BADC genes in either seed or vegetative tissue of a plant or alga, such as genes and gene orthologs of BADC1, BADC2, and/or BADC3 or artificial genes containing essential BADC motifs. In one embodiment, the one or more BADC genes may comprise from about 34%, 40%, 50%, 60%, 62% or 70% to about 100% sequence identity to a nucleotide sequence selected from the group consisting of SEQ ID NOs: 2, 4, 6, 7, and 138, or a complement thereof. In another embodiment, the one or more BADC genes may encode a polypeptide comprising from about 34%, 40%, 50%, 60%, 62% or 70% to about 100% sequence identity to a polypeptide sequence selected from the group consisting of SEQ ID NOs: 1, 3, 5, 8-137, and 139-143.

Further areas of applicability of the present disclosure will become apparent from the description provided herein. It should be understood that the description and specific examples are intended for purposes of illustration only and are not intended to limit the scope of the present teachings.

BRIEF DESCRIPTION OF THE DRAWINGS

For a more complete understanding of the features and advantages of the present invention, reference is now made to the detailed description of the invention along with the accompanying figures. The drawings described herein are for illustration purposes only and are not intended to limit the scope of the present teachings in any way.

FIG. 2—Shows primer design for yeast two-hybrid and recombinant expression cloning studies. (A) Primers used to amplify the genes shown were ordered from Sigma-Aldrich and include: BCCP1 (accession no. AT5G16390) sense and antisense primers (SEQ ID NOs:144 and 145, respectively); BCCP2 (accession no. AT5G15530) sense and antisense primers (SEQ ID NOs:146 and 147, respectively); BADC1 (accession no. AT3G56130) sense and antisense primers (SEQ ID NOs:148 and 149, respectively); BADC2 (accession no. AT1G52670) sense and antisense primers (SEQ ID NOs:150 and 151, respectively); BADC3 (accession no. AT3G15690) sense and antisense primers (SEQ ID NOs:152 and 153, respectively), and apo-BCCP1 (accession no. AT5G16390) mutant sense and antisense primers (SEQ ID NOs:160 and 161, respectively). Underlined segments indicate a restriction endonuclease site. (B) Transit peptide lengths were predicted using TargetP. Primers were designed to omit the bases coding for these peptides from the gene of interest to allow for proper protein folding.

FIG. 4—Shows that BADC proteins share substantial sequence identity with BCCP subunits of ACCase in *Arabidopsis thaliana*. Protein sequences from *Arabidopsis thaliana* were aligned and percent amino acid identity was calculated using Clustal-W.

FIG. 5—Shows an alignment of the C-termini of the *Arabidopsis thaliana* BCCP and BADC proteins demonstrating that the BADC proteins resemble BCCP isoforms but lack the conserved biotinylation motif and biotinyl lysine residue. BCCP1 (SEQ ID NO:1), BCCP2 (SEQ ID NO:2), BADC1 (SEQ ID NO:3), BADC2 (SEQ ID NO:4), and BADC3 (SEQ ID NO:5).

FIG. 10—Seed specific RNAi silencing of BADC1 increases seed oil content in *A. thaliana*. (A) Bar graph shows total seed oil content in WT and basta-resistant T2 *A. thaliana* lines containing a construct that silences BADC1 expression in the seed. Each bar represents the average of four plants. Error bars denote SD. (B) RT-PCR analysis of BADC1 RNAi silencing lines. BADC1 transcript level was quantified relative to Actin transcript level and normalized to WT. RNA used for analysis was extracted from four biological replicates of ten day old siliques. Error bars denote SEM. In both graphs, statistical significance was determined by Student's t-test (*, P<0.05).

FIG. 11A—Shows a scatter plot demonstrating the expression profiles of ACCase and BADC genes in developing seed of *Arabidopsis thaliana* using publicly available transcriptomics data.

FIG. 11B—Shows a scatter plot demonstrating the expression profiles of ACCase and BADC genes in developing seed of *Glycine max*.

FIG. 12—Shows a table showing dose-dependent inhibition of ACCase activity by BADC1. ACCase activity was measured in 20-day-old *A. thaliana* leaf extracts, average of four biological replicates.

FIG. 15—Shows ACCase and BADC absolute protein abundance during *Arabidopsis thaliana* silique development.

BRIEF DESCRIPTION OF THE SEQUENCES

Figure 1A:
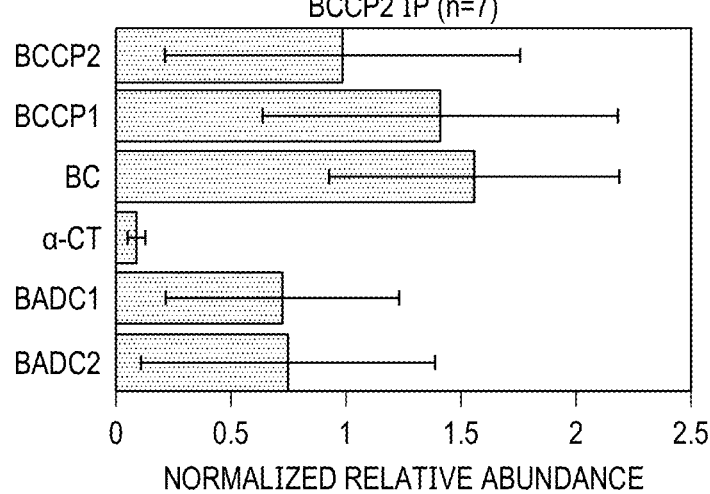
FIG. 1—Shows co-immunoprecipitation of ACCase and BADC proteins from *Arabidopsis thaliana* seedlings. (A and B) Proteins were precipitated from *Arabidopsis thaliana* crude chloroplast lysate using antibodies specific for ACCase subunits BCCP2 (A) or α-CT (B) and identified by LC-MS/MS. Control precipitations were performed with uncoated Protein A Sepharose beads. For both sets of studies, n=7. Error bars represent standard deviation. Semi-quantitative normalized relative abundance values were determined by dividing total spectral matches for each protein by protein size and normalizing to the antibody-specific protein.

SEQ ID NO:1—BADC1 polypeptide sequence, AT3G56130, biotin/lipoyl attachment domain-containing protein.

SEQ ID NO:2—BADC1 full genomic nucleic acid sequence, AT3G56130, biotin/lipoyl attachment domain-containing protein.

SEQ ID NO:3—BADC2 polypeptide, AT1G52670, Single hybrid motif protein.

SEQ ID NO:4—BADC2 full genomic nucleic acid, AT1G52670, Single hybrid motif protein.

SEQ ID NO:5—BADC3 polypeptide, AT3G15690, Single hybrid motif protein.

SEQ ID NO:6—BADC3 full genomic nucleic acid, AT3G15690, Single hybrid motif protein.

SEQ ID NO:7—Nucleic acid, RNAi cassette for BADC1 silencing in *Arabidopsis thaliana*.

SEQ ID NOs:8-134—Polypeptide sequences of each BADC ortholog across various organisms. Orthologous proteins were identified by performing a PSI-BLAST search using the protein sequence of each BADC from *Arabidopsis thaliana* as the query against known plant and algae proteomes. Orthologs were confirmed by reciprocal BLAST search against the *Arabidopsis thaliana* proteome. Sequences show GenBank ID, reference number, protein annotation, and name of the genus and species.

SEQ ID NOs:135-137—Show the consensus sequence identified by multiple sequence alignment of all identified BADC orthologs and the three BADC isoforms in *Arabidopsis thaliana*. This consensus sequence identifies a protein as a BADC ortholog.

SEQ ID NO:135—Polypeptide sequence of internal 44 amino acids of *Arabidopsis thaliana* BADC1 protein, accession AT3G56130. The 44 amino acids are conserved among the BADC protein family.

SEQ ID:136—Internal 44 amino acids of BADC consensus motif 1, with identical amino acid residues at positions 1, 2, 11, 12, 28, 29, 36, 38, and 42.

SEQ ID NO:137—Internal 44 amino acids of BADC consensus motif 1, with variable amino acid residues at positions 1, 2, 11, 12, 28, 29, 36, 38, and 42, and providing variable residues.

SEQ ID NO:138—Nucleic acid, RNAi cassette to target BADC1 and BADC3 genes in *Glycine max*.

SEQ ID NO:139—BCCP1 protein sequence.
SEQ ID NO:140—BCCP2 protein sequence.
SEQ ID NO:141—BADC1 protein sequence.
SEQ ID NO:142—BADC2 protein sequence.
SEQ ID NO:143—BADC3 protein sequence.
SEQ ID NOs:144 and 145—Sequences of BCCP1 (accession no. AT5G16390) sense and antisense primers, respectively.
SEQ ID NOs: 146 and 147—Sequences of BCCP2 (accession no. AT5G15530) sense and antisense primers, respectively.
SEQ ID NOs:148 and 149—Sequences of BADC1 (accession no. AT3G56130) sense and antisense primers, respectively.

SEQ ID NOs:150 and 151—Sequences of BADC2 (accession no. AT1G52670) sense and antisense primers, respectively.

SEQ ID NOs:152 and 153—Sequences of BADC3 (accession no. AT3G15690) sense and antisense primers, respectively.

SEQ ID NO:154 and 155—Primer Sequences used to amplify AtBADC1.

SEQ ID NOs:156—Sequence of sense primer used to amplify BADC1.

SEQ ID NOs:157—Sequence of antisense primer used to amplify BADC1.

SEQ ID NOs:158—Sequence of sense primer used to amplify Actin 8.

SEQ ID NOs:159—Sequence of antisense primer used to amplify Actin 8.

SEQ ID NOs:160 and 161—Sequences of apo-BCCP1 (accession no. AT5G16390) mutant sense and antisense primers, respectively.

SEQ ID NO:162—α-CT DNA sequence from *P. sativum*.

SEQ ID NO:163—α-CT protein sequence from *P. sativum*.

SEQ ID NO:164—α-CT ΔBAM (catalytic fragment) DNA sequence from *P. sativum*.

SEQ ID NO:165—α-CT ΔBAM (catalytic fragment) protein sequence from *P. sativum*.

SEQ ID NO:166—α-CT DNA sequence from A, *thaliana*.

SEQ ID NO:167—α-CT protein sequence from *A. thaliana*.

SEQ ID NO:168—α-CT DNA sequence (isoform 1) from *Glycine max*.

SEQ ID NO:169—α-CT protein sequence (isoform 1) from *Glycine max*.

SEQ ID NO:170—α-CT DNA sequence (isoform 2) from *Glycine max*.

SEQ ID NO:171—α-CT protein sequence (isoform 2) from *Glycine max*.

SEQ ID NO:172—α-CT DNA sequence (isoform 3) from *Glycine max*.

SEQ ID NO:173—α-CT protein sequence (isoform 3) from *Glycine max*.

SEQ ID NO:174—α-CT protein sequence (isoform 1) from *Brassica napus*.

SEQ ID NO:175—α-CT protein sequence (isoform 1-2) from *Brassica napus*.

SEQ ID NO:176—α-CT protein sequence (isoform 2) from *Brassica napus*.

SEQ ID NO:177—α-CT protein sequence (isoform 2-2) from *Brassica napus*.

SEQ ID NO:178—α-CT protein sequence (isoform 1) from *Brassica rapa*.

SEQ ID NO:179—α-CT protein sequence (isoform 2) from *Brassica rapa*.

SEQ ID NO:180—BADC CRISPR guide cassette sequence

DETAILED DESCRIPTION OF THE INVENTION

The present invention provides methods and means to modulate fatty acid, and ultimately triacylglycerol, production, as well as protein production, in plants and algae. Such methods comprise altering the activity levels of the committed step for de novo fatty acid biosynthesis, catalyzed by acetyl-CoA carboxylases (ACCase). In accordance with the invention, a method described herein may increase or decrease ACCase activity levels by expressing or overexpressing an α-CT, or a portion thereof, such as the catalytic domain or portion, in a plant such that ACCase activity is increased thereby increasing seed oil content. In another embodiment, alteration of ACCase expression may comprise down- or up-regulating the biotin/lipoyl attachment domain containing (BADC) genes, respectively. In some embodiments, the invention provides a method wherein an endogenous or heterologous α-CT, or a catalytic portion thereof, is expressed or overexpressed in a plant, and expression of one or more BADC gene is reduced or eliminated in the same plant. The invention also provides plants, plant parts, and seeds produced by such methods, wherein such plants and seeds exhibit increased seed oil content.

The BADC proteins are a family of three proteins in *Arabidopsis thaliana* and resemble the biotin carboxyl carrier protein (BCCP) subunit to ACCase. BADC protein expression has a negative effect on ACCase activity, which in turn affects oil production in plants and algae. The activity of ACCase in catalyzing the committed step of de novo fatty acid synthesis and regulation of flux through this central metabolic pathway is known in the art. In dicot and non-graminaceous monocot plants and algae, plastid ACCase is a heteromeric complex comprised of four catalytic subunits: biotin carboxylase (BC), biotin carboxyl carrier protein (BCCP), and α- and β-carboxyltransferase (α-CT, β-CT). The plant complex is recalcitrant to conventional purification schemes and hence the structure and composition of the full assembly is unknown.

As described in detail below, in vivo co-immunoprecipitation with subunit-specific antibodies was used to identify a novel family of BADC proteins, provided herein as SEQ ID NOs:1-6, in *Arabidopsis thaliana*. It was determined that BADC proteins resemble BCCP (subunits of ACCase complex) but cannot be biotinylated, and based on the results from orthogonal techniques, all three BADC proteins interact with the two *A. thaliana* BCCP isoforms and the biotin carboxylase subunit of ACCase, based on yeast two-hybrid and heterologous co-expression analyses. None of the BADC proteins were biotinylated in planta or when expressed in *Escherichia coli*, unlike BCCP controls. Gene orthologs to BADC were found only in plant and green algae species that contain a heteromeric ACCase suggesting BADC genes co-evolved with this form of ACCase. It was further discovered that expression of BADC proteins inhibited ACCase activity when co-expressed with a functional BCCP in a temperature-sensitive *Escherichia coli* BCCP mutant. Thus, BADC proteins regulate ACCase by competing with BCCP to form less active complexes. Down-regulating BADC genes (i.e., silencing the expression of BADC protein) promotes the formation of active ACCase complexes, which in turn increases ACCase activity levels and thus oil production in plants and/or algae. Down-regulating one or more BADC genes may be achieved via various biotechnology or selective breeding approaches as described herein and/or known in the art.

The invention also provides methods of reducing fatty acid synthesis in plants and/or algae by overexpression of BADC genes. Such methods would reduce the amount of triacylglycerol stored in the seed and concomitantly increase the amount of protein stored in the seed. Overexpression of BADC genes may therefore reduce ACCase activity and in turn reduce fatty acid biosynthesis.

The present disclosure provides a method of marker-assisted selection as a screening tool for plant and/or algae species that contain higher oil content. The BADC genes are traits that can be monitored to select for specific organisms that may have the potential to produce more triacylglycerol. The expression level of BADC genes may be the marker used to assist in such selection, wherein organisms with naturally reduced expression of BADC genes may be selected.

Plant oils are an important renewable source of hydrocarbons for food, energy, and industrial feedstocks. Acyl chains stored as triacylglycerol are produced by the de novo fatty acid synthesis (FAS) pathway. The committed step of de novo FAS is catalyzed by the heteromeric acetyl-coenzyme A carboxylase (hetACCase) which carboxylates acetyl-CoA to form malonyl-CoA in a two-step reaction requiring ATP, bicarbonate, and biotin cofactor. In prokaryotes, and in plastids of dicots and non-graminaceous monocots, hetACCase is a heteromeric complex requiring four distinct subunits: biotin carboxylase (BC), biotin carboxyl carrier protein (BCCP), and α- and β-carboxyltransferase (CT). Graminaceous monocots possess a homomeric form of plastid ACCase wherein the catalytic components are fused in tandem as a single polypeptide. Structural models for hetACCase are based on studies of the *Escherichia coli* homolog. The *E. coli* hetACCase is composed of two enzymatic subcomplexes: an α/β-CT heterotetramer and a BC/BCCP heterooctamer. The components of each subcomplex form stable associations while the two subcomplexes themselves show a relatively weak interaction with one another. This property has contributed to the difficulties in biochemical and structural characterization of hetACCase from plants.

Without being limited to a particular theory, a plant useful for the present invention may be include, but is not limited to, plant or algal apecies, such as *Amborella trichopoda, Arabidopsis lyrata, Arabidopsis alpine, Auxenochlorella protothecoides, Brassica napus, Brassica rapa, Capsella rubella, Chlamydomonas reinhardtii, Chlorella variabilis, Cicer arietinum, Citrus clementina, Citrus sinensis, Coccomyxa subellipsoideas* C-169, *Coffea canephora, Cucumis melo, Cucumis sativus, Elaeis guineensis, Erythranthe guttata, Eucalyptus grandis, Eutrema salsugineum, Fragaria vesca, Genlisea aurea, Glycine max, Helianthus annuus, Helicosporidium* ATCC 50920, *Jatropha curcas, Lotus japonicas, Medicago truncatula, Morus notabilis, Musa acuminate, Nelumbo nucifera, Nicotiana sylvestris, Nicotiana tomentosiformis, Phaseolus vulgaris, Pheonix dactylifera, Physcomitrella patens, Picea sitchensis, Polytomella parva, Populus trichocarpa, Prunus mume, Prunes persica, Pyrus×bretschneideri, Ricinus communis, Selaginella moellendorffii, Solanum lycopersicum, Solanum tuberosum, Theobroma cacao, Vitis vinifera,* or *Volvox carteri.*

I. Nucleic Acids, Polypeptides and Plant Transformation Constructs

Certain embodiments of the current invention concern isolated nucleic acid sequences and the corresponding polypeptide sequences for a novel family of BADC proteins, provided herein as SEQ ID NOs:1-6, in *Arabidopsis thaliana*. Additional embodiments of the present invention concern nucleic acid sequences encoding α-CT proteins, or portions thereof, such as the catalytic portion. Complements to any nucleic acid or protein sequences described herein are also provided.

"Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. "Identity" can be readily calculated by known methods including, but not limited to, those described in Lesk, ed., (1988); Smith, ed., (1993); Griffin, and Griffin, eds., (1994); von Heinje, (1987); Gribskov and Devereux, eds., (1991); and Carillo and Lipman, (1988). Computer programs can be used to determine "identity" between two sequences these programs include but are not limited to, GCG (Devereux, 1984); suite of five BLAST programs, three designed for nucleotide sequences queries (BLASTN, BLASTX, and TBLASTX) and two designed for protein sequence queries (BLASTP and TBLASTN) (Coulson, 1994; Birren, et al., 1997). The BLASTX program is publicly available from NCBI and other sources (BLAST Manual, Altschul, et al., NCBI NLM NIH, Bethesda, Md. 20894; Altschul, et al., 1990). The well known Smith Waterman algorithm can also be used to determine identity.

In accordance with the invention, a polynucleotide or polypeptide sequence as described herein may exhibit at least from about 34%, 40%, 50%, 60%, 62% or 70% to about 100% sequence identity to at least one of the sequences set forth herein. For example, in one embodiment, a BADC gene as described herein may comprise, for example, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a sequence selected from SEQ ID NO:2, 4, 6, 7, or 138, or a complement thereof. In other embodiments, a BADC protein as described herein may comprise for example, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a sequence selected from SEQ ID NO:1, 3, or 5, or a complement thereof.

Parameters for polypeptide sequence comparison include the following: Algorithm: Needleman and Wunsch (1970); Comparison matrix: BLOSUM62 from Hentikoff and Hentikoff, (1992); Gap Penalty: 12; and Gap Length Penalty: 4. A program which can be used with these parameters is publicly available as the "gap" program from Genetics Computer Group, Madison Wis. The above parameters along with no penalty for end gap may serve as default parameters for peptide comparisons.

Parameters for nucleic acid sequence comparison include the following: Algorithm: Needleman and Wunsch (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

As used herein, "hybridization," "hybridizes," or "capable of hybridizing" is understood to mean the forming of a double- or triple-stranded molecule or a molecule with partial double- or triple-stranded nature. Such hybridization may take place under relatively high-stringency conditions, including low salt and/or high temperature conditions, such as provided by a wash in about 0.02 M to about 0.15 M NaCl at temperatures of about 50° C. to about 70° C. for 10 min. In one embodiment of the invention, the conditions are 0.15 M NaCl and 70° C. Stringent conditions tolerate little mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like. Also included may be a protein or polypeptide, or fragment thereof, such as any of those set forth herein.

The nucleic acids provided herein as SEQ ID NOs:1-6 may be from any source, e.g., identified as naturally occurring in a plant, or synthesized, e.g., by mutagenesis of SEQ ID NOs:1-6. In an embodiment, the naturally occurring sequence may be from any plant or algal species, such as *Amborella trichopoda, Arabidopsis lyrata, Arabidopsis alpine, Auxenochlorella prototheocoides, Brassica napus, Brassica rapa, Capsella rubella, Chlamydomonas reinhardtii, Chlorella variabilis, Cicer arietinum, Citrus clementina, Citrus sinensis, Coccomyxa subellipsoideas* C-169, *Coffea canephora, Cucumis melo, Cucumis sativus, Elaeis guineensis, Erythranthe guttata, Eucalyptus grandis, Eutrema salsugineum, Fragaria vesca, Genlisea aurea, Glycine max, Helianthus annuus, Helicosporidium* ATCC 50920, *Jatropha curcas, Lotus japonicas, Medicago truncatula, Morus notabilis, Musa acuminate, Nelumbo nucifera, Nicotiana sylvestris, Nicotiana tomentosiformis, Phaseolus vulgaris, Pheonix dactylifera, Physcomitrella patens, Picea sitchensis, Polytomella parva, Populus trichocarpa, Prunus mume, Prunes persica, Pyrus× bretschneideri, Ricinus communis, Selaginella moellendorffii, Solanum lycopersicum, Solanum tuberosum, Theobroma cacao, Vitis vinifera,* or *Volvox carteri.*

Coding sequences may be provided in a recombinant vector operably linked to a heterologous promoter functional in plants, in either sense or antisense orientation. Expression constructs may also be provided comprising these sequences, including antisense oligonucleotides thereof. In other embodiments, plants and plant cells transformed with the sequences may be provided. The construction of vectors which may be employed in conjunction with plant transformation techniques using these or other sequences according to the invention will be known to those of skill of the art in light of the present disclosure (see, for example, Sambrook, et al., 1989; Gelvin, et al., 1990). The techniques of the current invention are thus not limited to any particular nucleic acid sequences.

The choice of any additional elements used in conjunction with a coding sequences or corresponding encoded product may depend on the purpose of the transformation. One of the major purposes of transformation of crop plants is to add commercially desirable, agronomically important traits to the plant, as described herein.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to, e.g., an entire biosynthetic pathway, into a plant.

Particularly useful for transformation are expression cassettes which have been isolated from such vectors. DNA segments used for transforming plant cells will generally comprise the cDNA, gene, or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. Preferred components likely to be included with vectors used in the current invention are as follows.

Additional embodiments of the present invention concern nucleic acid sequences encoding α-CT proteins, or portions thereof, such as the catalytic portion. Complements to any nucleic acid or protein sequences described herein are also provided. Among the α-CT nucleic acid and polypeptide or protein sequences useful in the practice of certain embodiments of the present invention are those provided in SEQ ID NOs:162-179, and nucleic acid sequences from *Brassica napus* or *Brassica rapa* that encode α-CT proteins (see, for example, GenBank Accession Numbers GQ341625.1, GQ341624.1, FJ719766.1, FJ719765.1, AY538675.1, FJ719762.1 and FJ719761.1).

Additional α-CT sequences for use in various embodiments of the present invention are known to the skilled artisan, and may be from any plant or algal species, including, but not lim ited to, *Amborella trichopoda, Arabidopsis lyrata, Arabidopsis alpine, Auxenochlorella prototheocoides, Brassica napus, Brassica rapa, Capsella rubella, Chlamydomonas reinhardtii, Chlorella variabilis, Cicer arietinum, Citrus clementina, Citrus sinensis, Coccomyxa subellipsoideas* C-169, *Coffea canephora, Cucumis melo, Cucumis sativus, Elaeis guineensis, Erythranthe guttata, Eucalyptus grandis, Eutrema salsugineum, Fragaria vesca, Genlisea aurea, Glycine max, Helianthus annuus, Helicosporidium* ATCC 50920, *Jatropha curcas, Lotus japonicas, Medicago truncatula, Morus notabilis, Musa acuminate, Nelumbo nucifera, Nicotiana sylvestris, Nicotiana tomentosiformis, Phaseolus vulgaris, Pheonix dactylifera, Physcomitrella patens, Picea sitchensis, Polytomella parva, Populus trichocarpa, Prunus mume, Prunes persica, Pyrus× bretschneideri, Ricinus communis, Selaginella moellendorffii, Solanum lycopersicum, Solanum tuberosum, Theobroma cacao, Vitis vinifera,* or *Volvox carteri.*

A. Regulatory Elements

Exemplary promoters for expression of a nucleic acid sequence include plant promoters such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), α-tubulin, actin (Wang et al., 1992), cab (Sullivan et al., 1989), PEPCase (Hudspeth and Grula, 1989) or those promoters associated with the R gene complex (Chandler, et al., 1989). Tissue-specific promoters such as leaf specific promoters, or tissue selective promoters (e.g., promoters that direct greater expression in leaf primordia than in other tissues), and tissue-specific enhancers (Fromm et al., 1986) are also contemplated to be useful, as are inducible promoters such as ABA- and turgor-inducible promoters. Any suitable promoters known in the art may be used to express coding sequences in a plant.

The DNA sequence between the transcription initiation site and the start of the coding sequence, i.e., the untranslated leader sequence, can also influence gene expression. One may thus wish to employ a particular leader sequence with a transformation construct of the invention. In an embodiment, leader sequences are contemplated to include those which comprise sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure.

It is envisioned that a sequence useful for altering activity levels of ACCase as described herein may comprise any sequence set forth herein, for example SEQ ID NOs:1-6. In certain embodiments, a gene useful for altering ACCase levels may comprise altering expression of a BADC gene, such as BADC1, BADC2, BADC3, set forth herein as SEQ ID NOs:2, 4, and 6, respectively, or orthologs or homologs thereof. Such an ortholog or homolog may be from any species useful in accordance with the invention. Such a sequence may be introduced into a plant under the control of novel promoters, enhancers, etc., or homologous or tissue-specific or tissue-selective promoters or control elements. Vectors for use in tissue-specific targeting of genes in transgenic plants will typically include tissue-specific or tissue-selective promoters and may also include other tissue-specific or tissue-selective control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters, which have higher activity in roots; or napin and glycinin promoters, which have higher activity in developing seed.

B. Terminators

Transformation constructs prepared in accordance with the invention may include a 3' end DNA sequence that acts as a signal to terminate transcription and allow for the polyadenylation of the mRNA produced by coding sequences operably linked to a promoter. In one embodiment of the invention, the native terminator of a BADC coding sequence may be used. Alternatively, a heterologous 3' end may enhance the expression of sense or antisense BADC coding sequences. Examples of terminators that may be used in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II gene from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, Golgi apparatus, and outside of the cellular membrane). By facilitating the transport of the protein into compartments inside and outside the cell, these sequences may increase the accumulation of gene products by protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed.

D. Marker Genes

By employing a selectable or screenable marker, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

One beneficial use of the sequences provided by the invention may be in the alteration of plant phenotypes such as fatty acid or triacylglycerol production, as well as protein production, in plants and/or algae by genetic transformation with a coding sequence set forth herein, such as a BADC coding sequence. A BADC coding sequence such as described herein may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

II. Genetic Transformation

Additionally provided herein are transgenic plants transformed with the above-identified recombinant vector encoding a BADC, an α-CT, or a sequence modulating expression thereof.

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by Agrobacterium-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species may be stably transformed, and these cells developed into transgenic plants.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

Agrobacterium-mediated transformation is most efficient in dicotyledonous plants and is the preferable method for transformation of dicots, including Arabidopsis, tobacco, tomato, alfalfa and potato. Indeed, while Agrobacterium-mediated transformation has been routinely used with dicotyledonous plants for a number of years, including alfalfa (Thomas et al., 1990), it has only recently become applicable to monocotyledonous plants. Advances in Agrobacterium-mediated transformation techniques have now made the technique applicable to nearly all monocotyledonous plants. For example, Agrobacterium-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998) and maize (Ishidia et al., 1996).

Modern Agrobacterium transformation vectors are capable of replication in E. coli as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. Gateway™ and other recombination-based cloning technology is also available in vectors useful for plant transformation. In addition, Agrobacterium containing both armed and disarmed Ti genes can be used for the transformations. In those plant strains where Agrobacterium-mediated transformation is efficient, it is the method of choice because of the facile and defined nature of the gene transfer.

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Another method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

The transgenic plants of the present invention expressing heterologous BADC, or homologous or heterologous α-CT, can be of any plant or algal apecies, such as *Amborella trichopoda, Arabidopsis lyrata, Arabidopsis alpine, Auxenochlorella protothecoides, Brassica napus, Brassica rapa, Capsella rubella, Chlamydomonas reinhardtii, Chlorella variabilis, Cicer arietinum, Citrus clementina, Citrus sinensis, Coccomyxa subellipsoideas* C-169, *Coffea canephora, Cucumis melo, Cucumis sativus, Elaeis guineensis, Erythranthe guttata, Eucalyptus grandis, Eutrema salsugineum, Fragaria vesca, Genlisea aurea, Glycine max, Helianthus annuus, Helicosporidium* ATCC 50920, *Jatropha curcas, Lotus japonicas, Medicago truncatula, Morus notabilis, Musa acuminate, Nelumbo nucifera, Nicotiana sylvestris, Nicotiana tomentosiformis, Phaseolus vulgaris, Pheonix dactylifera, Physcomitrella patens, Picea sitchensis, Polytomella parva, Populus trichocarpa, Prunus mume, Prunus persica, Pyrus×bretschneideri, Ricinus communis, Selaginella moellendorffii, Solanum lycopersicum, Solanum tuberosum, Theobroma cacao, Vitis vinifera,* or *Volvox carteri*. The plant can be an $R_0$ transgenic plant (i.e., a plant derived from the original transformed tissue). The plant can also be a progeny plant of any generation of an $R_0$ transgenic plant, wherein the transgenic plant has the nucleic acid sequence from the $R_0$ transgenic plant.

Seeds of the any above-described transgenic plants may also be provided, particularly where the seed comprises the nucleic acid sequence. Additionally contemplated are host cells transformed with the above-identified recombinant vector. In some embodiments, the host cell is a plant cell.

Also contemplated herein is a plant genetically engineered to increase expression of a BADC, where the BADC comprises a protein product of SEQ ID NOs: 2, 4, 6, 7, or 138, where the protein product (e.g. a polypeptide) alters plant morphology as described herein. Such a protein product may comprise SEQ ID NOs:1, 3, or 5, or any other sequence described herein that is appropriate for use with the present invention. In an embodiment, the altered plant morphology may be increased or decreased fatty acid content. Such altered morphology may be accomplished by increasing or decreasing ACCase activity levels by down- or up-regulating a BADC gene described herein. Additionally contemplated are plants genetically engineered to increase expression of an α-CT sequence. Such plants are described in the Examples, and may be useful, e.g., as commercial plants.

The plants of these embodiments having altered expression of ACCase or one or more BADC genes may be of any species. The species may be any monocotyledonous or dicotyledonous plant, such as those described herein. One of skill in the art will recognize that the present invention may be applied to plants of other species by employing methods described herein and others known in the art.

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. A medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. The rate of cell growth also will vary among cultures initiated with the array of media that permit growth of that cell type.

Tissue that can be grown in a culture includes meristem cells, Type I, Type II, and Type III callus, immature embryos and gametic cells such as microspores, pollen, sperm, and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

A. Altering Gene Expression in a Plant

In accordance with the invention, alteration of expression of a gene as described herein may comprise increasing expression of a gene relative to a wildtype, or decreasing expression of a gene relative to a wildtype. As described herein, the present invention may comprise altering expression of a BADC gene. In some embodiments, methods are provided comprising completely silencing or down-regulating expression of a gene. In other embodiments, partial or incomplete silencing or down-regulation of a gene may be sufficient to achieve the desired effect. In other embodiments, ACCase activity may be altered (i.e., increased) by increasing expression or overexpressing an α-CT in a plant. An α-CT useful in accordance with the invention for increasing activity of ACCase and therefore increasing seed oil content, may be an endogenous α-CT, or may be a heterologous α-CT expressed in a plant. Such a heterologous α-CT may be from any plant described herein, including, but not limited to, *Pisum sativum*. In other embodiments, an α-CT useful for the present invention may comprise a catalytic portion or domain from a plant described herein. Methods of effecting increased expression or overexpression are known in the art.

Alteration of gene expression in a plant may be accomplished by a variety of methods known in the art. In accordance with the invention, any method useful for altering expression of a gene or gene product may be used, including, but not limited to, antisense, RNAi, CRISPR, TALON, nanobodies, EMS, T-DNA or transposon-mediated gene knockout, or conventional mutagenesis/targeted breeding. Such methods are known in the art. As used herein the words "gene suppression" are intended to refer to any of the well-known methods for reducing the levels of protein produced as a result of gene transcription to mRNA and subsequent translation of the mRNA.

Gene suppression is also intended to mean the reduction of protein expression from a gene or a coding sequence including post-transcriptional gene suppression and transcriptional suppression. Post-transcriptional gene suppression is mediated by the homology between of all or a part of a mRNA transcribed from a gene or coding sequence targeted for suppression and the corresponding double stranded RNA used for suppression, and refers to the substantial and measurable reduction of the amount of available mRNA available in the cell for binding by ribosomes. The transcribed RNA may be in the sense orientation to effect what is called co-suppression, in the anti-sense orientation to effect what is called anti-sense suppression, or in both orientations, in which case a dsRNA may be produced to achieve RNA interference (RNAi). Such methods may be useful in accordance with the invention for down-regulating or silencing a BADC gene as described herein. Transcriptional suppression is mediated by the presence in the cell of a dsRNA, a gene suppression agent, exhibiting substantial sequence identity to a DNA sequence or the complement thereof to result in promoter trans-suppression. Gene suppression may be effective against a native gene associated with a trait, e.g., to produce a plant with reduced levels of a protein encoded by the native gene or with enhanced or reduced levels of an affected gene product. A gene product may include an RNA molecule, including, but not limited to, mRNA, rRNA, tRNA, siRNA, shRNA, or the like. A gene product may also include a protein or polypeptide, or a fragment thereof.

Post-transcriptional gene suppression by anti-sense or sense-oriented RNA to regulate gene expression in plant cells is known in the art, as is the use of dsRNA to suppress genes in plants. Post-transcriptional gene suppression in plants may employ both sense-oriented and anti-sense-oriented, transcribed RNA that is stabilized, e.g., as a hairpin or stem-and-loop structure.

As used herein, the term "expression" refers to the transcription and stable accumulation of sense or anti-sense RNA derived from a nucleic acid. "Expression" may also refer to translation of mRNA into a polypeptide or protein. As used herein, the term "antisense RNA" refers to an RNA transcript that is complementary to all or a part of a mRNA that is normally produced in a cell. The complementarity of an antisense RNA may be with any part of the specific gene transcript, i.e., at the 5' non-coding sequence, 3' non-translated sequence, introns, or the coding sequence. As used herein, the term "RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from post-transcriptional processing of the primary transcript and is referred to as the mature RNA.

As used herein, the phrase "inhibition of gene expression" or "inhibiting expression of a target gene" refers to the absence (or observable decrease) in the level of protein and/or mRNA product from the target gene. Specificity refers to the ability to inhibit the target gene without manifest effects on other genes of the cell and without any effects on any gene within the cell that is producing the dsRNA molecule. The inhibition of gene expression of a target gene as described herein may result in novel phenotypic traits in the plant.

III. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce, into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad-spectrum herbicide bialaphos. Another example of a herbicide which is useful for selection of transformed cell lines in the practice of the invention is the broad-spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived therefrom. U.S. Pat. No. 4,535,060 describes the isolation of EPSPS mutations which confer glyphosate resistance on the EPSPS of *Salmonella typhimurium*, encoded by the gene aroA. The EPSPS gene from *Zea mays* was cloned and mutations similar to those found in a glyphosate resistant aroA gene were introduced in vitro. Mutant genes encoding glyphosate resistant EPSPS enzymes are described in, for example, International Patent WO 97/4103.

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 weeks, then transferred to media conducive to maturation of embryoids. Cultures are transferred every 2 weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2} s^{-1}$ of light. Plants may be matured in a growth chamber or greenhouse. Plants can be regenerated in from about 6 weeks to 10 months after a transformant is identified, depending on the initial tissue. During regeneration, cells are grown on solid media in tissue culture vessels. Illustrative embodiments of such vessels are Petri dishes and Plant Cons. Regenerating plants can be grown at about 19 to 28° C. After the regenerating plants have reached the stage of shoot and root development, they may be transferred to a greenhouse for further growth and testing.

To confirm the presence of the exogenous DNA or "transgene(s)" in the regenerating plants, a variety of assays may be performed. Such assays include, for example, "molecular biological" assays, such as Southern and northern blotting and PCR™; "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

The expression of a gene product is often determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes that change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IV. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected BADC coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein, the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a plant of a starting line with a plant of a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

V. Definitions

As used herein, accessions AT3G56130, AT1G52670, and AT3G15690 are intended to refer to BADC1, BADC2, and BADC3, respectively.

As used herein, $\alpha$-CT refers to AT2G38040; $\beta$-CT refers to ATCG00500; BC refers to AT5G35360; BCCP1 refers to AT5G16390; BCCP2 refers to AT5G15530; BADC1 refers to AT3G56130; BADC2 refers to AT1G52670; and BADC3 refers to AT3G15690.

Catalytic Portion or Domain of $\alpha$-CT: The catalytic portion of $\alpha$-CT can be identified by amino acid alignment with bacterial and some algae $\alpha$-CT subunits, as they possess the heteromeric form of ACCase. The large C-terminal non-catalytic region is only found in plants containing heteromeric ACCases.

Endogenous: A sequence natively found in a host cell or a cell of the same species. In one embodiment, an endogenous sequence may be overexpressed or expressed at a higher level compared to wildtype and still be considered endogenous.

Expression: The combination of intracellular processes, including transcription and translation, undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found. In this respect, the sequence may be native to the host genome, but be rearranged with respect to other genetic sequences within the host sequence. For example, a regulatory sequence may be heterologous in that it is linked to a different coding sequence relative to the native regulatory sequence. In addition, a particular sequence can be "heterologous" with respect to a cell or organism into which it is introduced (for example, a sequence that does not naturally occur in that particular cell or organism).

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus, or explant).

Selected DNA: A DNA segment which one desires to introduce or has introduced into a plant genome by genetic transformation.

Transformation construct: A chimeric DNA molecule designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell in which the DNA complement has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

The description herein is merely exemplary in nature and, thus, variations that do not depart from the gist of that which is described are intended to be within the scope of the teachings. Such variations are not to be regarded as a departure from the spirit and scope of the teachings.

EXAMPLES

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments, which are disclosed and still obtain a like or similar result without departing from the spirit and scope of the invention.

Example 1

Two Novel Proteins, BADC1 and BADC2, Co-Immunoprecipitate with hetACCase

To discover unknown protein interactors with the hetAC-Case, quantitative co-innmunoprecipitation (co-IP) analyses were performed. Wild type *A. thaliana* (ecotype-Columbia-0) were grown in a growth chamber with long-day (16 h, 23° C., 50% humidity, 50 pmol m$^{-2}$ s$^{-1}$) and short-night (8 h, 20° C., 50% humidity) conditions. For co-immunoprecipitation studies, 8.5 cm×8.5 cm pots were filled with moist soil (Sunshine Mix #6, Sun Gro Horticulture), covered with screen (1 mm$^2$ pore size), and coated with seeds.

For co-innmunoprecipitation of hetACCase from *Arabidopsis* seedlings, crude chloroplasts were isolated from approximately 10 g 14-d-old *A. thaliana* seedlings after 1 h light exposure. Fresh leaves were homogenized in ice-cold grinding buffer (50 mM HEPES-KOH pH 8.0, 330 mM sorbitol, 1.5 mM MnCl$_2$, 2 mM MgCl$_2$, 2 mM EDTA, 0.1% (w/v) BSA) using a Waring blender. Homogenate was filtered through two layers of Miracloth and centrifuged at 2,600 g at 4° C. for 20 min. Chloroplasts were lysed for 30 min in ice-cold lysis buffer (50 mM HEPES-KOH pH 8.0, 10% (v/v) glycerol, 0.5% (v/v) Triton X-100). Lysates were homogenized ten times in a Dounce homogenizer on ice and then centrifuged at 30 k g for 20 min at 4° C. Then, 1 mL of the 30 k g supernatant was added to 25 μL Protein A-Sepharose beads (Sigma Aldrich) either uncoated (control) or coated with antibody specific for α-CT, BCCP, BADC1, or BADC2. Co-immunoprecipations (co-IP) were carried out at 4° C. for 3 h with gentle mixing. The beads were washed twice with 1 mL ice-cold lysis buffer and precipitated protein was eluted by adding 30 μL 6×SDS sample buffer (350 mM Tris-HCl, pH 6.8, 350 mM SDS, 30% (v/v) glycerol, 100 mM dithiothreitol, 2.5 mM bromophenol blue) and heating at 65° C. for 10 min. Eluted proteins were resolved on 10% SDS-PAGE gels for western and mass spectrometry analysis.

As described in detail above, clarified chloroplast lysates from 14-d-old *A. thaliana* seedlings were incubated with Protein A-Sepharose beads coated with polyclonal antibodies to either BCCP2 or α-CT. Control precipitations were performed using uncoated beads. Precipitated proteins were identified by LC-MS/MS analysis of trypsin-digested peptides.

For mass spectrometry, sample preparation and analysis was as follows. Precipitated proteins from co-IPs were resolved by 10% SDS-PAGE and stained with colloidal Coomassie Brilliant Blue (CBB) G-250. Each lane was separated into 0.5 cm segments and subsequently diced into approximately 1 mm$^3$ gel pieces. Gel pieces were digested with sequencing-grade trypsin and peptides were extracted according to methods known in the art. Tryptic peptides were lyophilized and stored at −20° C. until analysis by liquid chromatography-tandem mass spectrometry (LC-MS/MS). Lyophilized peptides were prepared for mass spectrometry analysis as described previously. Samples were analyzed on a LTQ Orbitrap XL ETD (Thermo Fisher Scientific) according to Swatek et al., (*Biochem J* 459(1): 15-25, 2014), with the exception that peptides were eluted using a 30 min acetonitrile gradient (5-43% acetonitrile), the top 8 masses from the precursor scan were selected for data-dependent acquisition, and precursor ions were fragmented using CID (collision-induced dissociation). Dynamic exclusion was enabled with the following settings: repeat count, 3; repeat duration, 30 s; exclusion list, 50; and exclusion list duration, 30 s.

Acquired spectra were searched against the TAIR10 protein database (70,773 entries, downloaded on Jun. 11, 2012), concatenated to a randomized TAIR10 database as a decoy. Search parameter settings of SEQUEST were static modification of cysteine-carboxyamidomethylation and variable modification of methionine-oxidation. Other search parameter settings of SEQUEST included two missed tryptic cleavage sites, absolute threshold: 1000, minimum ion count: 10, mass range: 650-3500, and a parent and fragment ion tolerance of 1 Da and 1000 ppm, respectively. Search result files were loaded into Proteome Discoverer 1.3 (Thermo Fisher Scientific). Identified peptides were filtered to <1% false discovery rate using the following criteria: 10 ppm peptide mass deviation, 'Xcorr versus charge state', and 2 and 1 peptide minimum for co-IPs and 2D BN-SDS PAGE, respectively. Protein grouping was also enabled. False discovery rate was calculated manually using spectral counting. Files generated for each biological replicate by Proteome Discoverer 1.3 were exported into Microsoft Excel for further analysis.

Proteins identified from SEQUEST searches were compared against uncoated Sepharose bead controls that had been treated in an identical manner to the hetACCase subunit co-IPs. Proteins that were only identified in the hetACCase subunit co-IPs were considered as putative interacting clients. All other proteins were disregarded. The hetACCase subunits were never identified in controls.

Figure 1B:
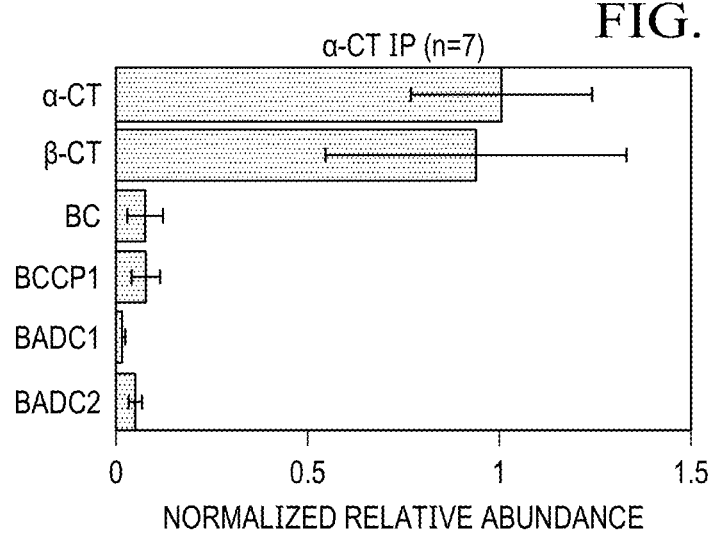

Quantitative mass spectrometry of these co-IPs revealed all four known subunits to ACCase and two unknown proteins annotated as 'biotin/lipoyl attachment domain containing' (BADC) proteins. From seven biological replicates of the α-CT co-IPs, the entire hetACCase complex was identified. Likewise, all subunits, except β-CT, were identified from co-IPs with antibodies to BCCP2 (FIGS. 1A and 1B). As expected, the BC/BCCP and α/β-CT subcomplexes were relatively higher in abundance in the BCCP2 and α-CT co-IPs, respectively. Additionally, two unknown proteins with a "biotin attachment domain-containing" region, hereafter termed BADC1 (AT3G56130) and BADC2 (AT1G52670), were identified from both co-IPs. The BADC1 protein was present in seven and one replicate of the BCCP2 and α-CT co-IPs, respectively, while BADC2 was present in six and two replicates of the BCCP2 and α-CT co-IPs, respectively. The normalized, relative abundance of these proteins was more commensurate with BC and BCCP abundance than α- and β-CT from both co-IP analyses. Reciprocal co-IPs using antibodies specific to BADC1 and BADC2 precipitated both BCCP isoforms. Thus, BADC1 and BADC2 appear to interact with the BC/BCCP components of hetACCase.

Example 2

Recombinant Protein Expression and Purification and Immunoblotting

The ORFs of BCCP1, BCCP2, BADC1, BADC2, and BADC3 were amplified via PCR from a cDNA clone (ABRC). The primer pairs for these amplifications were the same as those used in the yeast two-hybrid construct formation (FIG. 2A). These primers were designed to remove the transit peptide, as predicted by TargetP (FIG. 2B). The amplified ORF of all five genes were cloned into either the expression vector pET28a or pET11a producing an N-terminal His-tagged fusion protein or an untagged recombinant protein, respectively. All constructs were sequence confirmed via DNA sequencing. Constructs were then transformed into *E. coli* strain BL21 (B2685: Sigma). Recombinant protein was expressed and purified from transformed BL21 cells as described in Swatek et al., *J Proteome Res* 10(9):4076-4087, 2011). For co-expression studies, ~200 ng of each plasmid was used to transform BL21 cells.

Proteins resolved by SDS-PAGE were transferred to PVDF membrane and stained with the appropriate primary antibody overnight at 4° C. for western blot analysis. All antibodies were used at 1:5000 dilution in PBS-T (10 mM $NaH_2PO_4$—NaOH pH 7.2, 150 mM NaCl, 0.3% (v/v) Tween 20). hetACCase antibodies used in this study were derived from rabbits immunized with recombinant *P. sativum* α-CT, recombinant *A. thaliana* BCCP2, or recombinant *A. thaliana* BADC1. Blots were rinsed twice in PBS-T and probed in secondary antibody for 1 h at room temperature and developed. Goat anti-rabbit IgG secondary antibody conjugated to alkaline phosphatase was obtained from Sigma-Aldrich (St. Louis, Mo.).

Example 3

Orthogonal Approaches Confirm a Direct Interaction Between Three BADC and Two BCCP Isoforms from *Arabidopsis*

Yeast two-hybrid construct design. The ORF of genes of interest were inserted into bait and prey vectors PGBKT7 and pGADT7. Primers were designed to exclude the transit peptide from the coding region, as predicted by TargetP (FIG. 2B). Genes were amplified from cDNA clones obtained from the *Arabidopsis* Biological Resource Center. Amplicons were first inserted into Zero Blunt TOPO vector (Life Technologies) and checked for errors by DNA sequencing. Error-free amplicons were then subcloned into either pGBKT7 or pGADT7 vector. Completed constructs were transformed into competent DH5a cells. Cells transformed with pGBKT7 and pGADT7 were grown on LB media agar plates containing 50 pg/mL kanamycin (Kan) and 100 pg/mL ampicillin (Amp), respectively. Plasmids were purified from 5 mL culture of positive colonies using QlAprep Spin Miniprep kit (Qiagen).

To confirm the co-IP results and determine which hetACCase subunit directly interacts with BADC1 and BADC2, targeted yeast two-hybrid analysis was employed using an adaptation of the lithium acetate method. Strain AH109 yeast were transformed with 100 ng of bait and prey vector. Pelleted transformed cells were resuspended in 300 μL sterile water. Aliquots of 100 μL cell suspension were plated on synthetic dropout (SD) media lacking leucine, tryptophan, and histidine. Plates were incubated at 30° C. for 4 d and then imaged. Images shown are representative of at least three replicate studies.

In addition to the two experimentally-identified BADCs a third, putative BADC isoform was also tested, termed BADC3 (AT3G15690), identified by BLAST interrogation of the *A. thaliana* genome. This protein shares 61% amino acid identity with BADC2, suggesting it might have similar function. Based upon yeast two hybrid analyses, each of the three BADC proteins interacted with each BCCP isoform.

Figure 3:
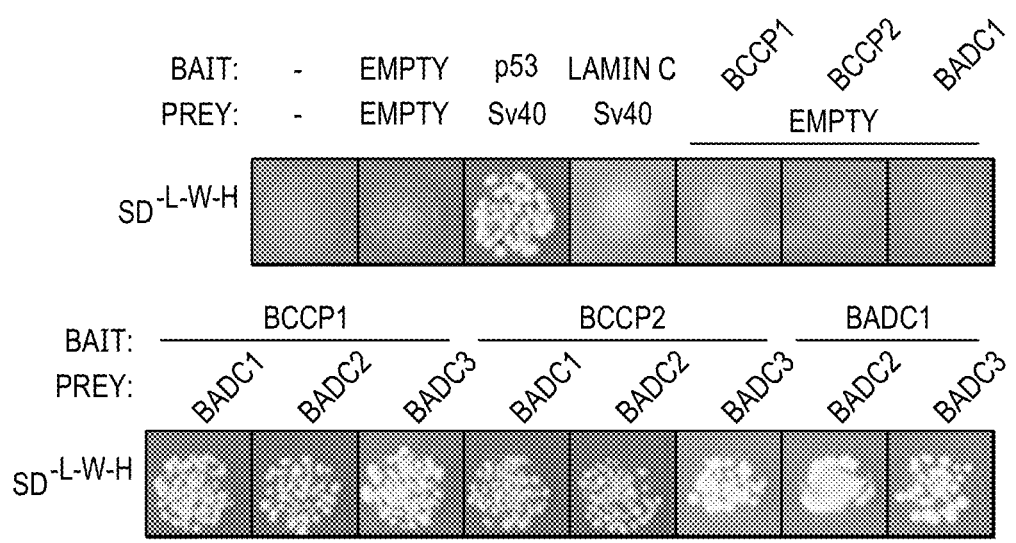
FIG. 3—Shows the direct interaction of BADC proteins with BCCP subunits of ACCase. Strain AH109 yeast was transformed with bait and prey constructs containing the genes shown. Negative controls showed minimal or no growth. Sv40 and p53 were used as positive controls. Lamin C was used as a negative control. Transformed yeast were plated on media lacking Trp, Leu, and His. Results shown are representative of three biological replicates.

As shown in FIG. 3, strain AH109 yeast was transformed with bait and prey constructs containing the genes shown. Negative controls showed minimal or no growth. Sv40 and p53 were used as positive controls. Transformed yeast were plated on media lacking Trp, Leu, and His. Results shown are representative of three biological replicates. Additionally, each of the BADC isoforms interacts with one another.

To further evaluate the interaction between BADC and BCCP, *A. thaliana* BCCP1 was co-expressed with each of the three *A. thaliana* BADC proteins in *E. coli*. In these studies, either the BADC or BCCP1 protein was expressed with a $His_6$-tag, while the other contained no affinity tag. When the $His_6$-tagged protein was purified by $Ni^{2+}$-NTA affinity chromatography, the respective "untagged" protein was present in the same elution fractions. Coomassie-stained gels showed the elution fractions of $Ni^{2+}$-NTA-purified protein from *E. coli* when a native protein was co-expressed with a His6-tagged protein, and when the native protein was expressed alone. The native proteins were present strongly in the elution fractions only when co-expressed with the His6-tagged protein. Protein identities were confirmed by LC-MS/MS. These studies were performed to test if the BADC proteins can interact directly with ACCase. The results confirm the BADC proteins associate with ACCase via a direct interaction with the BCCP and BC subunits. As a control, it was verified that untagged proteins were unable to bind to the affinity column. Using this system, it was observed that *A. thaliana* BC and BADC3 also co-purified, suggesting that BADC3, and likely BADC1 and 2, may also interact with BC. These studies confirm BADC isoforms directly interact with the BCCP and BC subunits of hetACCase.

Example 4

Biotin is not Required for BADC-BCCP Interaction

To determine if the BCCP-BADC interaction involves the biotin cofactor, as previously reported for PII interaction with hetACCase, the biotinyl Lys245 residue on BCCP1 was mutated to Arg by site-directed mutagenesis. This mutation prevents biotinylation of BCCP1. Using this 'apo-BCCP1', the yeast two-hybrid and co-expression analysis was repeated with BADCs. All BADC isoforms were shown to interact with apo-BCCP1.

Example 5

Recombinant AtBADC1 and AtBADC3 Form Homodimers Through a Disulfide Bond

Previous analysis of *E. coli* BCCP suggested that this subunit forms functional homodimers in vivo. Through intact mass analysis of purified recombinant BCCP2, it was observed that plant BCCP can also form homodimers. In addition, analysis of recombinant BADCs showed that BADC1 and BADC3, but not BADC2, can form homodimers. The observed monomer size for each BADC was in agreement with the predicted mass, suggesting these proteins are unmodified. In the absence of DTT, purified recombinant BCCP2, BADC1, and BADC3 show a monomer and dimer band when denatured and resolved by SDS-PAGE. Recombinant BADC2 shows only a monomer band. Increasing DTT concentration led to the disappearance of the dimer band, suggesting a disulfide bond is involved in dimer formation of BADCs and plant BCCPs.

Example 6

BADCs Resemble BCCPs but are not Biotinylated

The three BADC isoforms share many characteristics with the two BCCP isoforms from *A. thaliana*. First, these proteins contain a canonical plastid target peptide and are plastid localized based upon bioinformatic predictions, co-IP, and western blot studies. Secondly, the BADC isoforms share 24 to 29% amino acid identity with the BCCP isoforms (FIG. 4). Last, structural predictions of the BADC and BCCP proteins show similar β-sheet secondary structure with a characteristic "thumb motif" as previously observed for the *E. coli* BCCP. Intact mass analysis showed that BADC proteins are able to form homodimers.

Despite these similarities, the BADC proteins lack the canonical biotinylation motif. As shown in FIG. 5, the alignment of the C-termini of the *Arabidopsis thaliana* BCCP1 and BCCP2 and BADC proteins (BADC1, BADC2, and BADC3) shows multiple conserved residues (shown in bold). The canonical biotinylation motif containing the biotinyl Lys in BCCP1/2 is shown boxed in on lines 1 and 2 of the sequence alignment. The alignment comparison indicates the BADC proteins resemble BCCP isoforms but lack a canonical biotinylation motif. The tetrapeptide (Ala-Nal)-Met-Lys-(Met/Leu) is the known biotinylation motif and is usually located 34 or 35 residues from the C-terminus. The BADC proteins do, however, possess a conserved Lys residue in a similar (Val/Ile)-(LeuNal)-Lys-(Leu/Ile) motif located near the C-terminus suggesting the possibility of a non-canonical biotinylation motif.

To test this possibility, recombinant BADC proteins expressed in *E. coli* and the native BADC1 protein from *A. thaliana* seedlings were purified and probed for biotinylation using a biotin-specific antibody. Based on the western blotting analysis of recombinant *Arabidopsis* proteins using a biotin-specific antibody, BCCP2 is observed to be biotinylated, while the BADCs are not. In the protein blot analysis of immunoprecipitated in vivo BADC1 from *Arabidopsis* seedlings, blotting precipitate with BADC1-specific antibody shows the presence BADC1 in the sample, while blotting with biotin-specific antibody shows no recognition of BADC1. Results of these studies confirmed that the BADC proteins are not biotinylated in vivo, although BCCP controls clearly were.

Example 7

BADC Orthologs are Present in Green Algae and Land Plants but not Bacteria

Identification of BADC orthologs and co-occurrence analysis suggests BADCs first appeared in red algae. The evidence of a direct BADC-BCCP interaction suggests that BADC function is linked to hetACCase. If true, orthologs to *A. thaliana* BADCs (AtBADC) would be expected to reside only in organisms that contain hetACCase, not the homomeric form that predominates in eukaryotes. To search for the presence of AtBADC orthologous proteins, the primary sequence of each AtBADC was used to search against the KEGG Sequence Similarity database. Putative orthologs were confirmed by reciprocal BLAST searches against the *A. thaliana* proteome. All AtBADC orthologs lacked the conserved biotinyl Lys found in BCCPs. Orthologous proteins were identified for AtBADCs across 78 different species of land plants and algae (Table 1). The full-length protein sequences of identified AtBADC orthologs were used to generate a maximum-likelihood phylogenetic tree. All of the species that harbor a putative AtBADC ortholog also contain the heteromeric form of ACCase. No orthologs were detected in organisms that contain only the homomeric ACCase. Additionally, no AtBADC orthologs were detected in prokaryotes, which also contain a hetACCase. The presence of orthologs in algae but not prokaryotes suggests that BADCs first appeared in algae.

TABLE 1

Orthologous proteins identified for AtBADC1, AtBADC2, and AtBADC3.

| Species | Category | BCCP1 | BCCP2 | BADC1 | BADC2 | BADC3 |
|---|---|---|---|---|---|---|
| *Amborella trichopoda* | Flowering Plants | XP_011621081.1 | N/A | XP_011627066.1 | N/A | XP_011622803.1 |
| *Arabidopsis lyrata* subsp. *lyrata* | Eudicots | XP_002873773.1 | XP_002871669.1 | XP_002876350.1 | XP_002894393.1 | XP_002882958.1 |
| *Arabidopsis thaliana* | Eudicots | NP_197143.1 | NP_568316.1 | NP_567035.1 | NP_564612.1 | NP_188190.1 |
| *Arabis alpina* | Eudicots | KFK25879.1 | KFK25777.1 | KFK34856.1 | N/A | KFK38917.1 |
| *Arachis duranensis* | Eudicots | XP_015962701.1 | XP_015946097.1 | XP_015944188.1 | N/A | XP_015933506.1 |
| *Arachis ipaensis* | Eudicots | XP_016194346.1 | XP_016181644.1 | XP_016181047.1 | N/A | XP_016170604.1 |
| *Auxenochlorella protothecoides* | Green Algae | XP_011398894.1 | N/A | N/A | N/A | XP_011395766.1 |
| *Beta vulgaris* subsp. *vulgaris* | Eudicots | XP_010679318.1 | N/A | XP_010692910.1 | N/A | XP_010691182.1 |
| *Brachypodium distachyon* | Monocots | N/A | N/A | N/A | N/A | N/A |
| *Brassica napus* | Eudicots | XP_013663621.1 | XP_013728269.1 | XP_013663447.1 | N/A | XP_013645085.1 |
| *Brassica oleracea* var. *oleracea* | Eudicots | XP_013625183.1 | XP_013621850.1 | XP_013605292.1 | N/A | XP_013585896.1 |
| *Brassica rapa* | Eudicots | XP_009131537.1 | XP_009131471.1 | XP_009116310.1 | N/A | XP_009115305.1 |
| *Cajanus cajan* | Eudicots | KYP60383.1 | N/A | KYP44948.1 | N/A | KYP59593.1 |
| *Camelina sativa* | Eudicots | XP_010453799.1 | XP_010453692.1 | XP_010504497.1 | XP_010479781.1 | XP_010465548.1 |
| *Capsella rubella* | Eudicots | XP_006286538.1 | XP_006288243.1 | N/A | XP_006305526.1 | XP_006298142.1 |
| *Capsicum annuum* | Eudicots | XP_016573862.1 | N/A | XP_016575440.1 | N/A | XP_016578500.1 |
| *Chlamydomonas reinhardtii* | Green Algae | N/A | XP_001700442.1 | N/A | N/A | XP_001690119.1 |
| *Chlorella variabilis* | Green Algae | N/A | XP_005850451.1 | N/A | N/A | XP_005845403.1 |
| *Cicer arietinum* | Eudicots | XP_012569122.1 | N/A | XP_004500525.1 | N/A | XP_004486692.1 |
| *Citrus clementina* | Eudicots | N/A | XP_006431277.1 | XP_006435833.1 | N/A | XP_006427204.1 |
| *Citrus sinensis* | Eudicots | N/A | XP_006482733.1 | XP_006486239.1 | N/A | XP_006465373.1 |
| *Coccomyxa subellipsoidea* C-169 | Green Algae | N/A | XP_005649768.1 | N/A | N/A | XP_005646014.1 |
| *Cucumis melo* | Eudicots | N/A | XP_008456473.1 | XP_008441486.1 | N/A | XP_008461084.2 |
| *Cucumis sativus* | Eudicots | N/A | XP_004137199.1 | XP_011656420.1 | N/A | XP_004135840.1 |
| *Daucus carota* subsp. *sativus* | Eudicots | KZM82431.1 | N/A | KZM80059.1 | N/A | KZM88409.1 |
| *Dorcoceras hygrometricum* | Eudicots | KZV23283.1 | N/A | KZV16809.1 | N/A | N/A |
| *Elaeis guineensis* | Monocots | XP_010936329.1 | N/A | XP_010938420.1 | N/A | XP_010921048.1 |

TABLE 1-continued

Orthologous proteins identified for AtBADC1, AtBADC2, and AtBADC3.

| Species | Category | BCCP1 | BCCP2 | BADC1 | BADC2 | BADC3 |
|---|---|---|---|---|---|---|
| *Erythranthe guttata* | Eudicots | XP_012834625.1 | XP_012844390.1 | XP_012858601.1 | N/A | XP_012856758.1 |
| *Eucalyptus grandis* | Eudicots | XP_010038361.1 | XP_010032526.1 | XP_010067567.1 | N/A | XP_010033940.1 |
| *Eutrema salsugineum* | Eudicots | XP_006400177.1 | XP_006400073.1 | XP_006403020.1 | XP_006392894.1 | XP_006406933.1 |
| *Fragaria vesca* subsp. *vesca* | Eudicots | N/A | XP_004304236.1 | XP_004307696.1 | N/A | XP_004302964.1 |
| *Genlisea aurea* | Eudicots | EPS63946.1 | N/A | N/A | EPS63437.1 | N/A |
| *Glycine max* | Eudicots | N/A | XP_003543944.1 | XP_006590336.1 | N/A | XP_003543673.1 |
| *Glycine soja* | Eudicots | KHN13569.1 | N/A | KHN04794.1 | N/A | KHN44161.1 |
| *Gonium pectorale* | Green Algae | N/A | KXZ51015.1 | N/A | N/A | KXZ55249.1 |
| *Gossypium arboreum* | Eudicots | KHG03380.1 | KHG02691.1 | N/A | KHG02291.1 | N/A |
| *Gossypium hirsutum* | Eudicots | XP_016683408.1 | XP_016752201.1 | XP_016724217.1 | N/A | N/A |
| *Gossypium raimondii* | Eudicots | XP_012451021.1 | N/A | XP_012462883.1 | N/A | XP_012454990.1 |
| *Helicosporidium* sp. ATCC 50920 | Green Algae | KDD76354.1 | N/A | N/A | N/A | KDD73528.1 |
| *Jatropha curcas* | Eudicots | XP_012085783.1 | XP_012084810.1 | XP_012086589.1 | N/A | XP_012073227.1 |
| *Klebsormidium flaccidum* | Green Plants | N/A | GAQ84037.1 | N/A | N/A | GAQ80014.1 |
| *Malus domestica* | Eudicots | N/A | XP_008379410.1 | XP_008374383.1 | N/A | N/A |
| *Marchantia polymorpha* subsp. *polymorpha* | Liverworts | OAE20385.1 | N/A | N/A | N/A | OAE28621.1 |
| *Medicago truncatula* | Eudicots | XP_003624197.1 | N/A | XP_003616717.1 | N/A | XP_003597852.2 |
| *Morus notabilis* | Eudicots | N/A | XP_010089617.1 | XP_010087032.1 | XP_010097264.1 | N/A |
| *Musa acuminata* subsp. *malaccensis* | Monocots | XP_009394324.1 | N/A | XP_009418932.1 | N/A | N/A |
| *Nelumbo nucifera* | Eudicots | XP_010259375.1 | N/A | XP_010250846.1 | N/A | XP_010254348.1 |
| *Nicotiana sylvestris* | Eudicots | XP_009759359.1 | N/A | XP_009785832.1 | XP_009787427.1 | N/A |
| *Nicotiana tabacum* | Eudicots | XP_016465895.1 | XP_016481002.1 | XP_016473105.1 | N/A | XP_016514334.1 |
| *Nicotiana tomentosiformis* | Eudicots | XP_009588294.1 | XP_009616596.1 | XP_009618778.1 | N/A | XP_009628995.1 |
| *Phaseolus vulgaris* | Eudicots | XP_007139713.1 | N/A | XP_007163588.1 | N/A | XP_007150717.1 |
| *Phoenix dactylifera* | Monocots | XP_008805110.1 | N/A | XP_008789922.1 | N/A | XP_008809725.1 |
| *Physcomitrella patens* | Mosses | N/A | XP_001754932.1 | N/A | N/A | XP_001775667.1 |
| *Populus euphratica* | Eudicots | XP_011013398.1 | XP_011013434.1 | XP_011004753.1 | N/A | XP_011040023.1 |
| *Populus trichocarpa* | Eudicots | N/A | XP_002305399.1 | XP_002311250.1 | N/A | XP_002299605.2 |
| *Prunus mume* | Eudicots | XP_008240458.1 | N/A | XP_008233825.1 | XP_008228653.1 | N/A |
| *Prunus persica* | Eudicots | XP_007204703.1 | XP_007215770.1 | XP_007218764.1 | XP_007215787.1 | N/A |
| *Pyrus* × *bretschneideri* | Eudicots | N/A | XP_009360536.1 | XP_009369234.1 | XP_009349124.1 | XP_009348645.1 |
| *Ricinus communis* | Eudicots | XP_015572257.1 | XP_002526099.1 | XP_002520803.1 | N/A | XP_015573743.1 |
| *Selaginella moellendorffii* | Club-Mosses | XP_002963883.1 | N/A | N/A | N/A | XP_002963889.1 |
| *Sesamum indicum* | Eudicots | N/A | XP_011072842.1 | XP_011084859.1 | N/A | XP_011072247.1 |
| *Setaria italica* | Monocots | N/A | N/A | N/A | N/A | N/A |
| *Solanum lycopersicum* | Eudicots | NP_001234322.1 | N/A | XP_004240889.1 | N/A | XP_004241703.1 |
| *Solanum pennellii* | Eudicots | XP_015076155.1 | N/A | XP_015080112.1 | N/A | XP_015079819.1 |
| *Solanum tuberosum* | Eudicots | XP_006345777.1 | N/A | XP_006353414.1 | N/A | XP_006356200.1 |
| *Sorghum bicolor* | Monocots | N/A | N/A | N/A | N/A | N/A |
| *Spinacia oleracea* | Eudicots | KNA11791.1 | N/A | KNA11168.1 | N/A | KNA24821.1 |
| *Tarenaya hassleriana* | Eudicots | XP_010558581.1 | XP_010551815.1 | XP_010534633.1 | XP_010535127.1 | N/A |
| *Theobroma cacao* | Eudicots | N/A | XP_007029252.1 | XP_007008844.1 | N/A | XP_007023903.1 |
| *Triticum urartu* | Monocots | N/A | N/A | N/A | N/A | N/A |
| *Vigna angularis* | Eudicots | N/A | KOM56589.1 | KOM39631.1 | N/A | KOM44575.1 |
| *Vigna radiata* var. *radiata* | Eudicots | N/A | XP_014523207.1 | XP_014494474.1 | N/A | XP_014498647.1 |
| *Vitis vinifera* | Eudicots | XP_010649227.1 | XP_002284374.1 | XP_002278151.2 | N/A | XP_002285378.1 |
| *Volvox carteri* f. *nagariensis* | Green Algae | N/A | XP_002952670.1 | N/A | N/A | XP_002954026.1 |
| *Zea mays* | Monocots | N/A | N/A | N/A | N/A | N/A |
| *Ziziphus jujuba* | Eudicots | XP_015875754.1 | XP_015879793.1 | XP_015877502.1 | N/A | XP_015868335.1 |
| *Zostera marina* | Monocots | N/A | KMZ60645.1 | KMZ56653.1 | KMZ55983.1 | N/A |
| *Galdieria sulphuraria* | Red Algae | N/A | YP_009051081.1 | XP_005708748.1 | N/A | N/A |

To determine if BADCs arose from a previously functional BCCP in algae, co-occurrence analysis was performed. With the exception of two red algae and *Cyanophora paradoxa* all species contained AtBCCP and AtBADC orthologs. In red algae, only one putative AtBADC1 ortholog (GenBank ID: XP_005708748.1) was identified in the species *Galdieria sulphuraria*. This protein shares the same number of identical (31) and similar (46) amino acid residues with both AtBADC1 and AtBADC2, as well as 30 identical and 44 similar amino acid residues with AtBADC3. However, the BLAST search attributed the highest score to AtBADC1. In addition, two putative BCCP proteins were identified in the red algae species *Chondrus crispus* and *Cyanidioschyzon merolae* to lack the biotin motif residue but shared higher sequence similarity to AtBCCP2 than AtBADCs (GenBank ID XP_005715802.1 and XP_005535248.1, respectively), suggesting that BADCs originated from a BCCP gene duplication and loss-of-function mutation in red algae. From this observation, it appears not only that BADCs and BCCPs are related, but that the branch point between these proteins occurred in red algae, particularly since the more primitive glaucophytes contain no AtBADC orthologs.

Figure 6:
FIG. 6—Shows species containing orthologs of the *Arabidopsis thaliana* BADC proteins. Phylogenetic trees showing all species that were identified to contain an ortholog to one or more of the BADC proteins in *A. thaliana*. Ortholog candidates were identified by performing PSI-BLAST on the primary sequence of each BADC protein. Results were filtered by performing a reciprocal BLAST against the *A. thaliana* proteome. Species classification is indicated by color. All species identified contain heteromeric ACCase.
Figure 6:
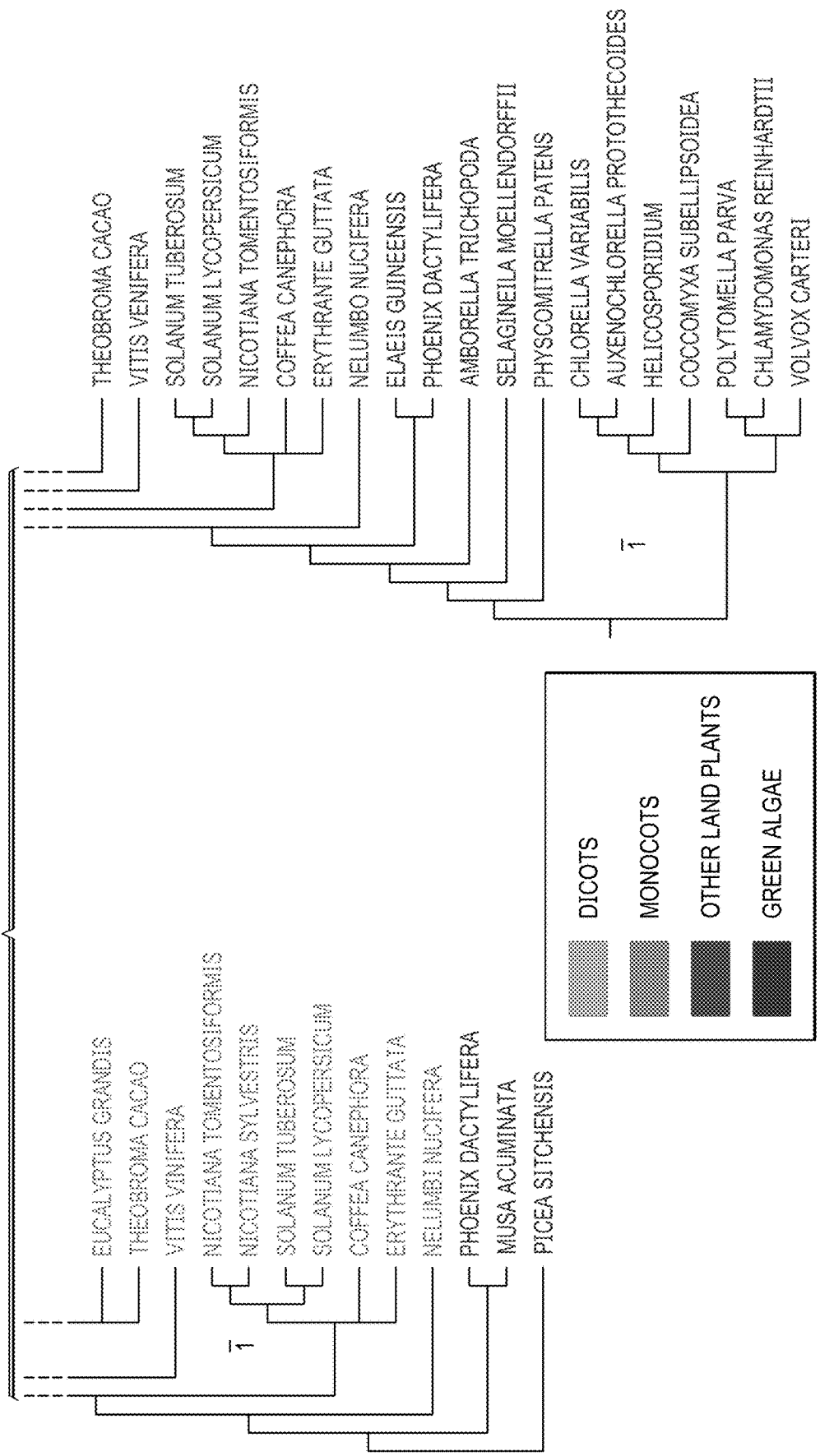

If BADC proteins are exclusive to acetyl-CoA carboxylases and not other acyl-CoA carboxylases, BADC protein orthologs would be found only in plant clades that contain hetACCase. To search for BADC ortholog-containing species, PSI-BLAST was performed using the primary sequence of each BADC from *A. thaliana*. Putative orthologs were confirmed by reciprocal BLAST searches against the *A. thaliana* proteome and all putative BADCs were manually confirmed to lack a conserved biotinyl Lys. FIG. 6 shows the phylogenetic tree of species containing an ortholog to all three BADCs. Orthologs to the *A. thaliana* BADCs were only observed in dicots, non-graminaceous monocots, and green algae. The founding member of the family, BADC3, dates back to green algae. All of these plant clades contain a hetACCase. No BADC ortholog was detected in prokaryotes or graminaceous monocots, the latter containing only the homomeric form of ACCase.

Example 8

BADC3 Expression Reduces hetACCase Activity in a Temperature-Sensitive *E. coli* Mutant Due to their similarity with BCCPs but lack of a conserved biotinylation motif, BADCs may be negative regulators of hetACCase activity. As *E. coli* contain hetACCase but lack BADC orthologs, this system was appropriate to test this theory. In vivo growth assays in *E. coli* accb strain L8 were performed to evaluate the potential the effect of the BADC proteins on hetACCase activity. This strain contains temperature-sensitive (Ts) mutations in the BCCP gene (accB) that prevent de novo FAS. Thus, cell growth at 37° C. is directly correlated to hetACCase activity when lacking an exogenous source of fatty acids. Experiments were performed in minimal media containing only glucose and glycerol as carbon sources. In brief, the temperature-sensitive (Ts) L8 strain *E. coli* was obtained from the *Coli* Genetic Stock Center (Yale, New Haven, Conn.) and transformed with the vectors in the text using the heat shock method. Transformants were selected by antibiotic resistance and confirmed by PCR. Prior to the growth experiment, cultures were grown overnight in LB media at 30° C. Overnight cultures were centrifuged at 3,000 g and resuspended in 5 mL sterile deionized water. Cultures were centrifuged again and resuspended in M63 minimal media to make OD600=3.75. Then 200 µL cell suspension was added to 7 mL M63 media plus antibiotics in 15 mL sterile culture tubes. Cultures contained Kan, and Amp if necessary, at 50 µm/mL each as well as 1 µM isopropyl β-D-1-thiogalactopyranoside at T=0.

To complement the Ts phenotype, the native *E. coli* BCCP (EcBCCP) gene was cloned into L8 cells in the inducible pET28a vector. Induced expression of EcBCCP rescued cell growth at 37° C. in media lacking fatty acids, while empty vector controls showed minimal growth. Cultures of transformed L8 cells were grown in M63 liquid culture at 37° C. in the absence of fatty acids. Transformed cells contained the following vectors: empty pET28a (EV28a), pET28a containing the *E. coli* BCCP gene (EcBCCP), empty pET11a (EV11a), and/or pET11a containing the AtBADC3 gene (BADC3). At T=0 h, the optical density was 0.15 and protein expression was induced with 1 µM IPTG. The EV control cells show minimal growth at 37° C., while re-introduction of native EcBCCP complemented the temperature-sensitive phenotype. BADC3 expression alone showed no statistical difference from EV control except at T=10 h, while co-expression of BADC3 with EcBCCP showed an approximate 75% reduction in growth compared to EcBCCP alone across multiple studies.

In the same way, the *A. thaliana* BADC3 gene was cloned into L8 cells and was unable to complement the Ts phenotype. Co-expression of BADC3 with EcBCCP reduced the complementing effect of EcBCCP expression by 71 to 74% over multiple replicates. Affinity pull-down assays with tagged BADC3 confirmed the inhibition was mediated by interaction with EcBCCP. Protein blot shows that EcBCCP protein co-purifies with $His_6$-BADC3, indicating its direct effect on ACCase activity. The experiment demonstrated that BADC protein expression has a negative effect on *E. coli* growth. Co-association of BADC3 with EcBCCP in vivo verified that this growth phenotype is due to a direct inhibition of hetACCase activity by BADC3.

Example 9

Recombinant BADC Inhibits Plant hetACCase Activity

To test if the BADCs can also inhibit plant hetACCase, enzyme activity assays were performed on ten-day-old *A. thaliana* silique extracts. The activity of hetACCase was monitored in vitro in ten-d-old siliques by measuring the incorporation of $H^{14}CO_3$ into acid-stable products. *A. thaliana* WT Col-0 10-d-old siliques were harvested after six hours of light exposure. In each trial, four biological replicates of three siliques were assayed. Siliques were pulverized in homogenization buffer (20 mM TES, pH 7.5, 10% glycerol, 5 mM EDTA, 2 mM DTT, 2 mM benzamidine, 2 mM PMSF, 1% Triton X-100), centrifuged at 10 k g for 15 s, and assayed within 5 minutes of harvest to minimize loss of hetACCase activity. Assays were performed in the presence of 10 µM haloxyfop to inhibit homomeric ACCase activity. Enzyme activity values for (−)acetyl-CoA controls were subtracted from (+)acetyl-CoA trials to determine the true hetACCase activity levels. Purified recombinant protein was added to assay tubes prior to addition of silique lysate.

Figure 7:
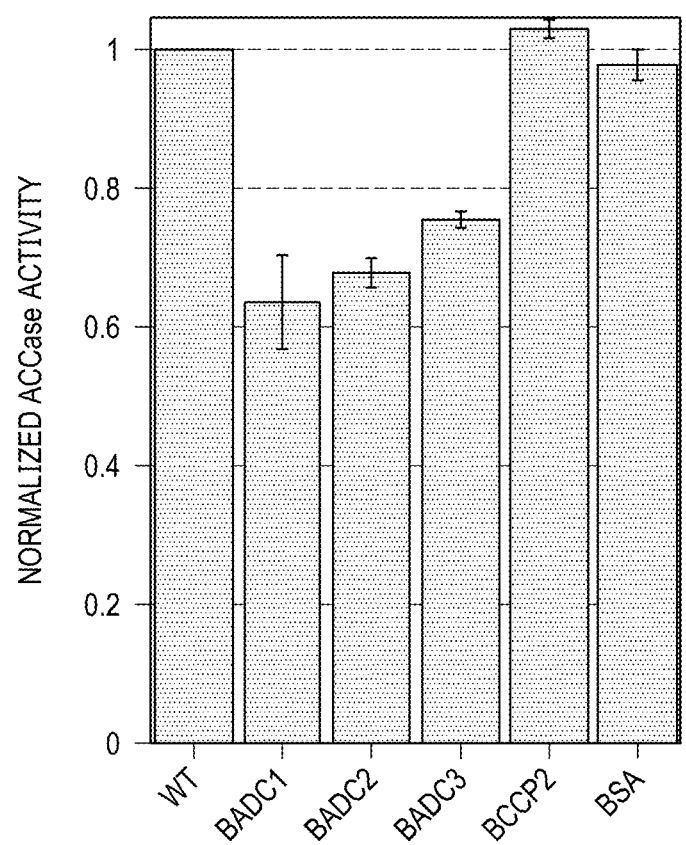
FIG. 7—BADCs reduce ACCase activity in *A. thaliana*. Protein extracted from 10-d-old *A. thaliana* siliques was assayed for ACCase activity by incorporation of radiolabelled sodium bicarbonate into acid-stable products. Assays were performed in the absence (WT) or presence of 10 μM recombinant BADC1, BADC2, BADC3, BCCP2, or BSA. Specific activities were calculated for each assay and then normalized to WT control. Four biological replicates were performed for each trial. Error bars denote SEM.

Assays were performed in the presence of 10 µM purified recombinant BADC1, BADC2, BADC3, BCCP2, or BSA and compared to buffer control (WT). The average of four biological replicates showed that all three BADCs inhibited hetACCase activity by 25 to 37%, while BCCP2 and BSA showed no effect (FIG. 7). These results, in addition to the *E. coli* expression results, confirm the BADCs can negatively affect hetACCase activity.

Example 10

Expression Profiles of BADC and hetACCase Subunits Respond Differently to Light

Figure 8A:
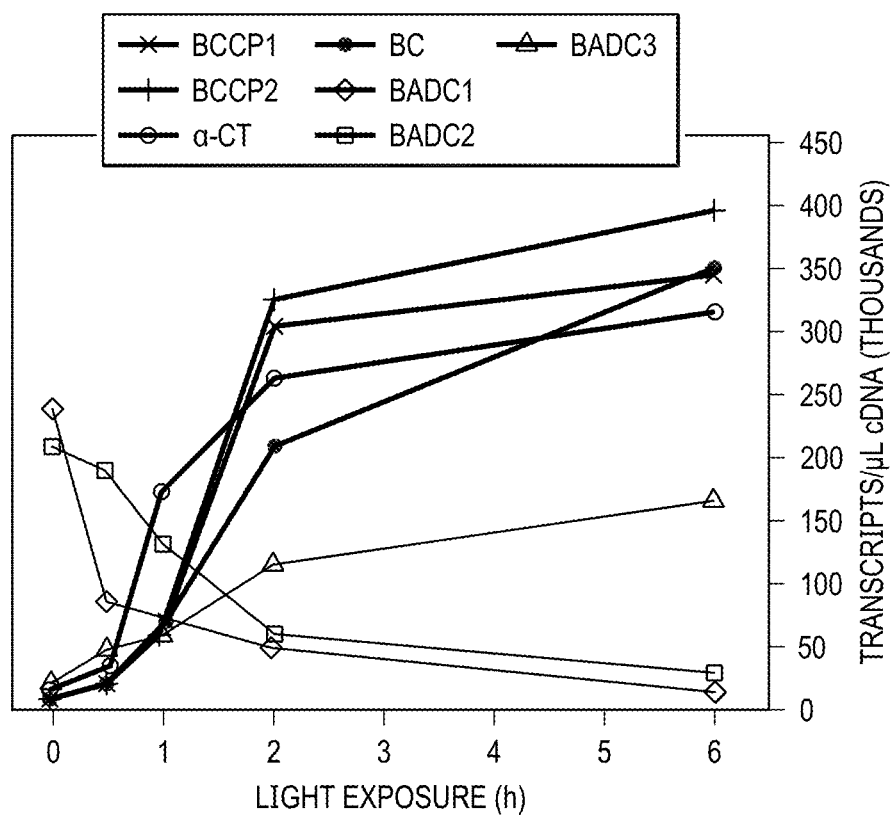
FIG. 8—Shows light-dependent changes in gene expression of BADC and hetACCase in *A. thaliana* siliques. (A) Graph shows the absolute expression level of the given genes obtained by qPCR. Ten d old *A. thaliana* siliques were collected after various amounts of light exposure. RNA extracted from these tissues was used to create cDNA for this analysis. Average values of four biological replicates are shown. Standard error was approximately 5 to 10 percent for all data points. (B) Graph depicts the shift in BADC and BCCP total transcript level in response to light. The sum of transcript levels from BCCPs and BADCs in (A) for each time point were normalized to the sum of BCCP transcripts at six hours light exposure. At T=0, the ratio of BADC:BCCP transcript is 9:1. At T=6, the ratio shifts to 1:4.
Figure 8B:
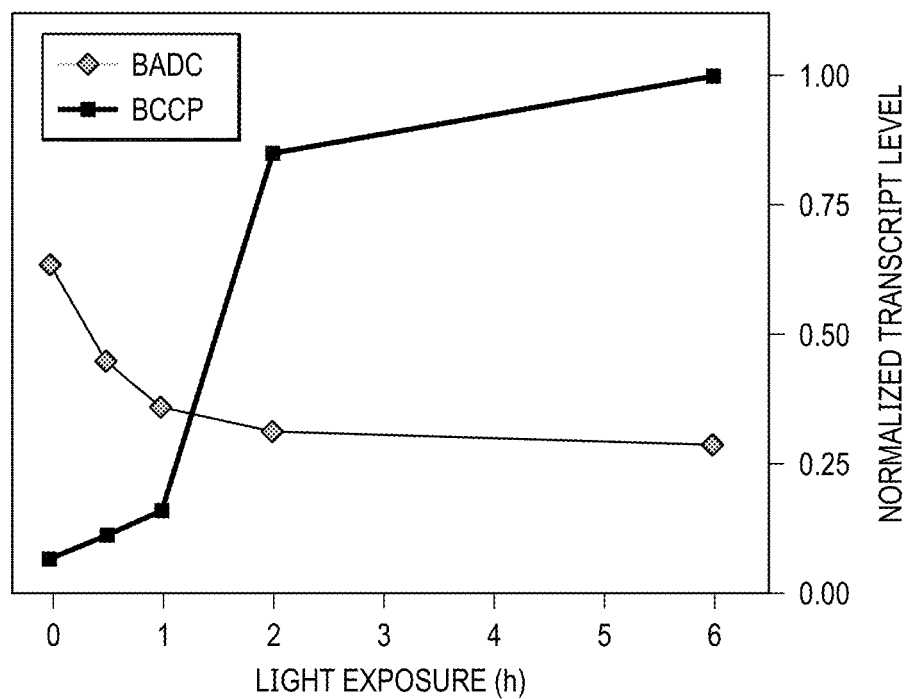

HetACCase activity is enhanced upon light exposure in photosynthetic cells. Absolute transcript levels of the BADCs and nuclear-encoded hetACCase subunits were monitored in ten-d-old *A. thaliana* siliques to determine the effect of light on gene expression. Siliques were harvested after dark-adaption or exposure to various lengths of light. Quantitative PCR analysis of RNA extracts from these samples showed that gene expression for each nuclear-encoded catalytic subunit to hetACCase increases significantly in response to light. After six hours, expression of BCCP1, BCCP2, and α-CT increased approximately 15-fold, while BC expression increased 35-fold (FIG. 8A). In contrast, BADC1 and BADC2 expression was reduced approximately ten-fold, while BADC3 expression increased eight-fold. Despite the conflicting changes in BADC isoforms, total BADC transcript level was reduced by half after six hours light exposure (FIG. 8B). The total BADC:BCCP transcript ratio is approximately 9:1 prior to light exposure, and then shifts to almost 1:4 after six hours light exposure (FIG. 8B), suggesting that BADC protein levels are relatively greater than BCCP protein levels in the dark, and vice versa in the light. These data further support the premise that BADC genes are negative regulators of ACCase.

Example 11

Oil Production in *Arabidopsis thaliana* Seed Increases in Response to Silencing BADC1 Gene The inventors further designed an in planta experiment to confirm that silencing BADC protein expression has a positive effect on ACCase activity in *Arabidopsis thaliana*, and results in increased fatty acid production. An RNAi cassette (SEQ ID NO:7) was produced and transformed into wild type plants in order to silence BADC1 expression in *A. thaliana*. Inverted repeats targeting AtBADC1 were inserted into the pMU103 vector. The repeats coded for bases 774 to 1034 of the cDNA sequence (accession AT3G56130.1). Primers used to amplify the sequence were 5'-GTGTTAGT-CACATCTCCCGCAGT-3' (SEQ ID NO:154) and 5'-GATGTTGATGTCGTGGAAAGATGGC-3' (SEQ ID NO:155). A sequence confirmed construct was transformed into *A. thaliana* ecotype Col-0 using the floral dip method. Basta herbicide screening was used to identify independent lines. Expression of the RNAi cassette was driven by the glycinin promoter. For monitoring seed oil content, T2 plants from each independent line were grown to maturity alongside wild type plants. Dry seed was harvested for analysis.

Figure 9:
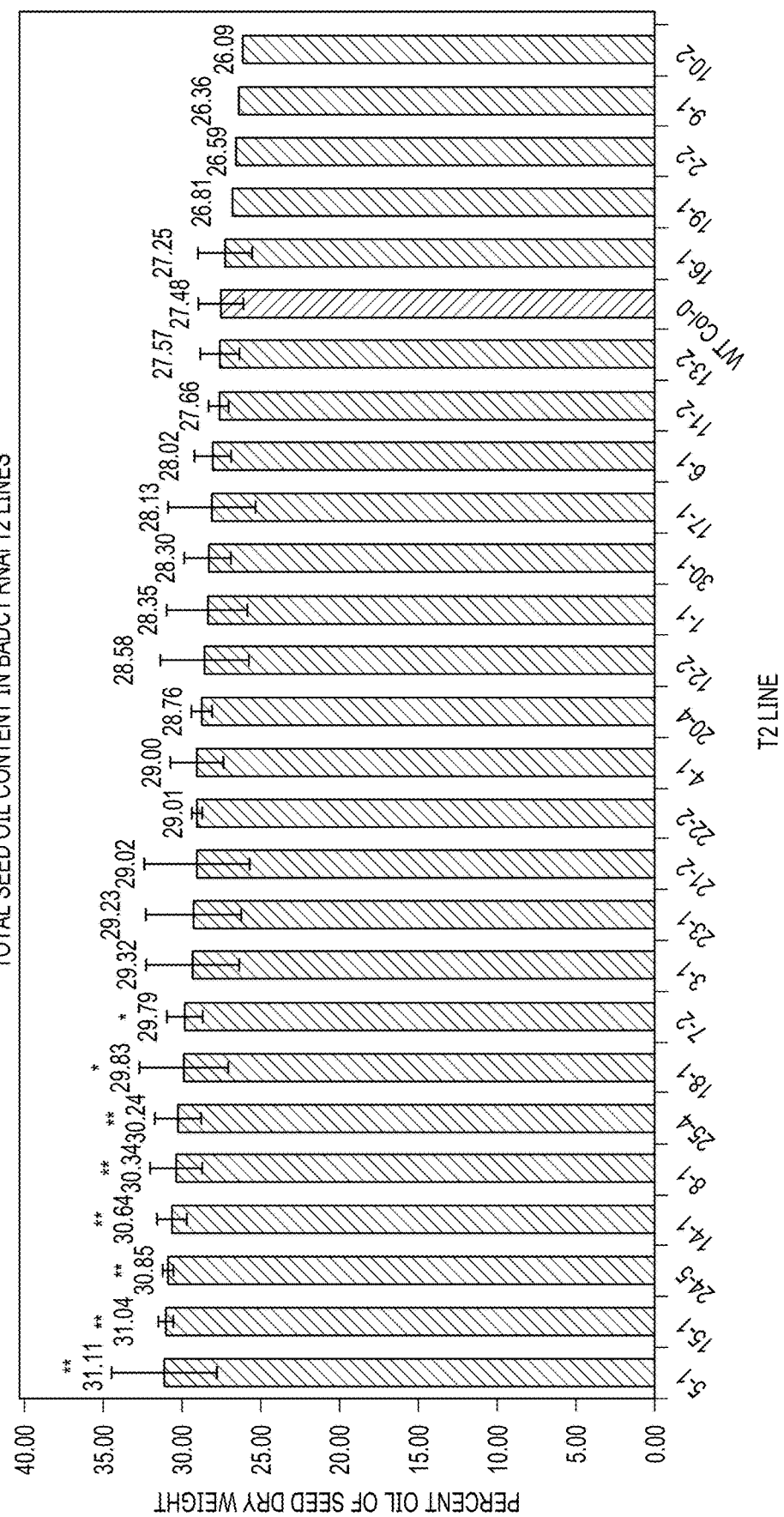
FIG. 9—Shows a bar graph illustrating seed oil content of 26 mutant BADC1 RNAi lines and one wild type. Statistical significance was determined by Student's t-test (*, P<0.05).

The fatty acid content in the T3 generation were collected and analyzed to show increased oil production. Seed oil was derivatized as described by Li et al., *Phytochemistry* 67, 904-915, 2006). Heptadecanoic acid was used as an internal standard. FAMEs were analyzed by a Hewlett Packard 6890 gas chromatography system. For WT and each independent line, 5 mg seed from thirteen and four plants, respectively, were analyzed. Seeds were dried over desiccant for one week prior to analysis FIG. 9 illustrates that the oil production (in *Arabidopsis thaliana* seed) increases in response to silencing of the BADC1 gene. Total seed oil content of 26 independent *A. thaliana* lines containing the BADC1 RNAi cassette has been analyzed along with wild type. The bar graph shows 22 of the 27 lines higher contained higher seed oil content on average. Asterisks signify statistical significance (*, $P<0.05$, **, $P<0.01$). Among the 26 lines, eight lines showed statistically higher seed oil content with increases of 7.7 to 11.7%, which is listed in Table 2.

TABLE 2

T3 lines with statistically higher seed oil content

| Plant line | P value | Percent change from wild type |
|---|---|---|
| 5-1 | 0.006 | 11.7 |
| 15-1 | 0.000 | 11.5 |
| 24-5 | 0.008 | 10.9 |
| 14-1 | 0.001 | 10.3 |
| 8-1 | 0.005 | 9.4 |
| 25-4 | 0.005 | 9.1 |
| 18-1 | 0.040 | 7.9 |
| 7-2 | 0.023 | 7.7 |

Seed oil content analysis showed a significant increase in oil in three of six independent T2 lines (FIG. 10A). Additionally, RT-PCR analysis of whole silique tissue showed a significant reduction in BADC1 transcript level of approximately 22% on average in the three lines containing significantly higher seed oil (FIG. 10B). RNA for RT-PCR and qPCR analysis was extracted from 10-d-old siliques using the RNeasy Plant Mini Kit (Qiagen). cDNA was synthesized from 500 ng RNA of four biological replicates. Primers used in analysis were: BADC1 sense, 5'-GCTCCTAGCCCATCT-CAAGC-3' (SEQ ID NO:156); BADC1 antisense, 5'-TCCAGATGCCTCCAAAGCAG-3' (SEQ ID NO:157); Actin 8 sense, 5'-CCAGATCTTCATCGTCGTGGT-3' (SEQ ID NO:158); Actin 8 antisense, 5'-ATCCAGCCTTAAC-CATTCCAGT-3' (SEQ ID NO:159). qPCR assays were performed on an ABI 7500 system (Applied Biosystems). Reaction volumes were 20 μL and contained SYBR Green PCR Master Mix (Applied Biosystems). Control reactions contained no template and were performed in triplicate. Amplicon identity was confirmed through melting curve analysis. For qPCR analysis, absolute transcript quantities were calculated using a standard curve of serially diluted amplicons of known concentrations. The fractional silencing is partly due to the use of whole silique tissue instead of isolated seed for RT-PCR analysis. These results demonstrate that BADC proteins are negative regulators of het-ACCase.

Example 12

Gene Expression Levels of BADC and ACCase Genes During Seed Development in *A. thaliana*

FIG. 11A shows the gene expression levels of BADC and ACCase genes during seed development in *Arabidopsis thaliana* (Comprehensive Systems Biology project, csbdb.mpimp-golm.mpg.de). Although all three BADC proteins are expressed during seed filling, BADC2 showed the highest expression over these time points. FIG. 11B shows the gene expression levels of BADC and ACCase genes in *Glycine max* during seed development (Soybase Database, soybase.org). In this species, the BADC1 ortholog is the most highly expressed in the seed, while BADC3 is relatively lower in expression and BADC2 is not present. Therefore RNAi silencing of BADC1 is the most likely to increase ACCase activity in the seed of *Glycine max*. Nevertheless, the presence of multiple BADC genes in most plants suggests targeted gene silencing (i.e. specific promoter) of multiple copies may be necessary to obtain maximal increases in ACCase activity and thus oil yield, due to the potential for gene compensation.

Example 13

Dose-Dependent Inhibition of ACCase Activity by BADC1

ACCase activity was monitored in vitro in 20-day-old *A. thaliana* leaf extracts with increasing concentrations of recombinant BADC1. Specific activity was determined for each experiment and 0 μM controls were normalized to 1. Specific activity values for controls ranged from 0.84-2.00 nmol/min/mg. Each data point represented the average of four biological replicates, with each biological replicate comprised of four light-adapted leaves. The data fit to a polynomial curve where $R2=0.987$. The Ki for BADC1 was determined to be approximately 4.3 μM under these conditions. FIG. 12 shows a table with the inhibition results. SDS-PAGE analysis was also performed to demonstrate purity of recombinant BADC1 protein used in the assays.

A model was developed of negative regulation of ACCase by BADC. The BC-BCCP subcomplex of ACCase consists of two dimers of BC and four BCCP proteins. A model was proposed in which BADC proteins compete with BCCP for binding to BC. Binding of BADC prevents binding of the essential BCCP subunit. The pool of BC/BCCP and BC/BCCP/BADC subcomplexes then compete for interaction with the CT subcomplex, leading to variable reductions in ACCase activity. While a transient association of the two ACCase half reactions is known, it is unclear whether BADC can displace BCCP from an assembled BC/BCCP subcomplex.

Example 14

Stacking Reduced or Eliminated Expression of BADC and Overexpression of α-CT in a Plant Creates Synergistic or Additive Effects on Seed Oil Content FIG. 15 shows absolute protein abundance for ACCase subunits α-CT, β-CT, BC, BCCP1, and BCCP2, as well as negative regulators of ACCase, BADC1, BADC2, and BADC3 in *Arabidopsis thaliana* during silique development. Since α-CT and β-CT subunits to ACCase associate at 1:1 ratios, the near 10-fold lower abundance of α-CT protein in vivo suggested the ACCase complex could be improved by overexpressing only the α-CT subunit.

Overexpressing α-CT or the catalytic domain thereof, and/or overexpressing a heterologous or semi-conserved form of α-CT in an oilseed crop plant that contains a multi subunit ACCase would result in increased seed oil content in the plant. In addition, as described in detail above, reducing or eliminating expression of one or more BADC genes, which negatively regulate ACCase, would also result in increased seed oil content in the plant. Such reduction or elimination in BADC gene expression may be accomplished with the use of antisense, RNAi, CRISPR, TALON, nanobodies, EMS, T-DNA or transposon-mediated gene knockout, or conventional mutagenesis/targeted breeding. Stacking these two traits in a single plant, or crossing individual plants, each having one of these traits, would result in an additive or syngergistic effect on seed oil content due to the complementary nature of these traits on ACCase activity.

High oil *Camelina* lines that are homozygous for the α-CT transgene are used for transformation with a CRISPR-Cas9 construct targeting all *Camelina* BADC genes. This construct is a triple-sequence BADC CRISPR guide cassette (SEQ ID NO:180). The triple-sequence BADC CRISPR guide cassette comprises an attB1 sequence, a *Camelina* U3 promoter, a *Camelina* U6 promoter, an *Arabidopsis* U6 promoter, and an attB2 sequence. Seed oil content is measured in the transformants.

Example 15

Figure 13:
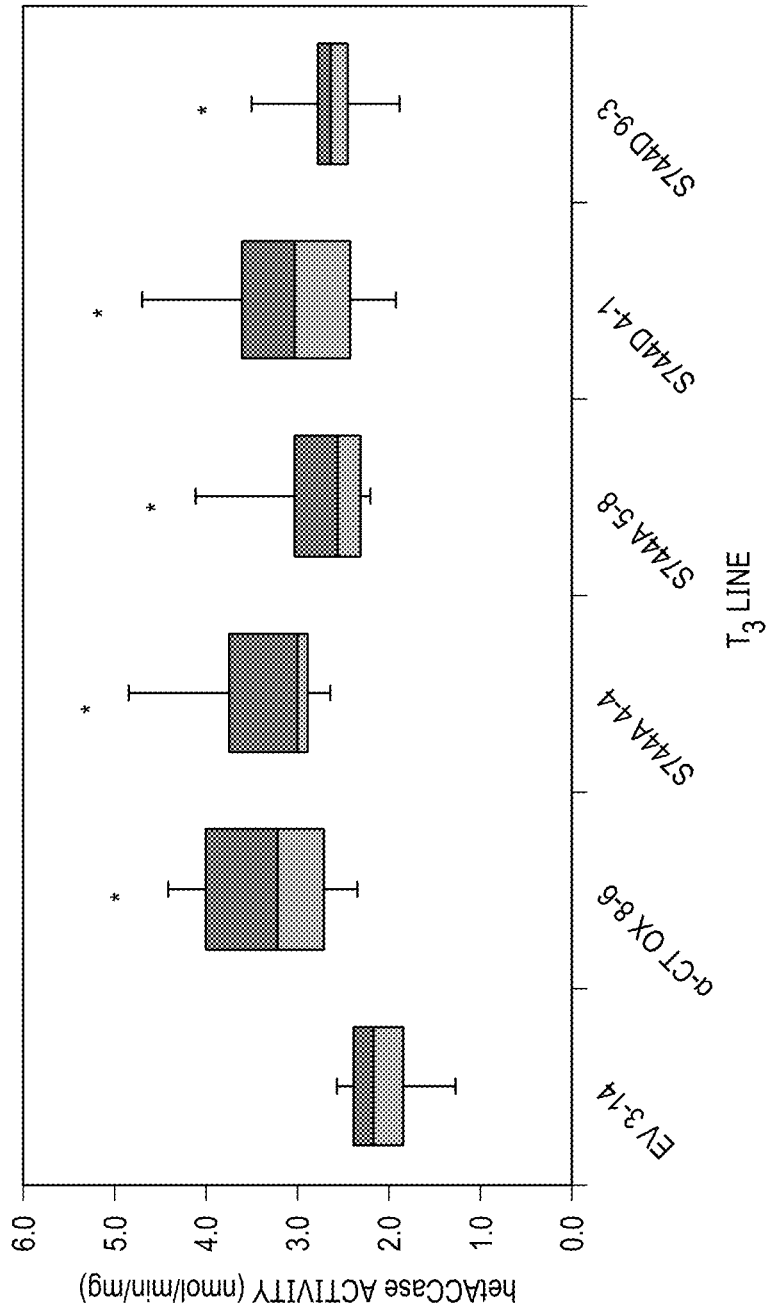
FIG. 13—Shows increased ACCase activity in α-CT overexpression lines regardless of mutation.

Transgenic Lines Overexpressing *Arabidopsis thaliana* α-CT Show Higher ACCase-Specific Activity In Vitro ACCase activity increases in α-CT overexpression lines regardless of mutation. FIG. 13 shows the specific activity of hetACCase in 21-d-old *A. thaliana* leaves of each T4 homozygous line. Specific activity was calculated by dividing the total 14C incorporated into acid-stable products per min per mg of leaf protein extract. Eight biological replicate containing three leaves were each assayed for each independent line. All overexpression lines showed statistically higher hetACCase activity that the EV control according to Student's t-test (*, Pvalue<0.05). The results demonstrated that S744A and S744D mutant lines were not statistically different from α-CT OX 8-6.

Example 16

Overexpressing α-CT from *Pisum sativum* Increases Seed Oil Content in *Arabidopsis*

The α-CT subunit of ACCase, one of the largest and key subunits to the ACCase complex, was shown to be expressed at sub-stoichiometric levels in vivo during *Arabidopsis thaliana* seed development using a multiplexed absolute quantitative tandem mass spectrometry assay. This subunit also contains a large (>40 kDa) non-catalytic domain of unknown function that is predicted to have a coiled coil structure, typically involved in protein-protein interactions.

Figure 14A:
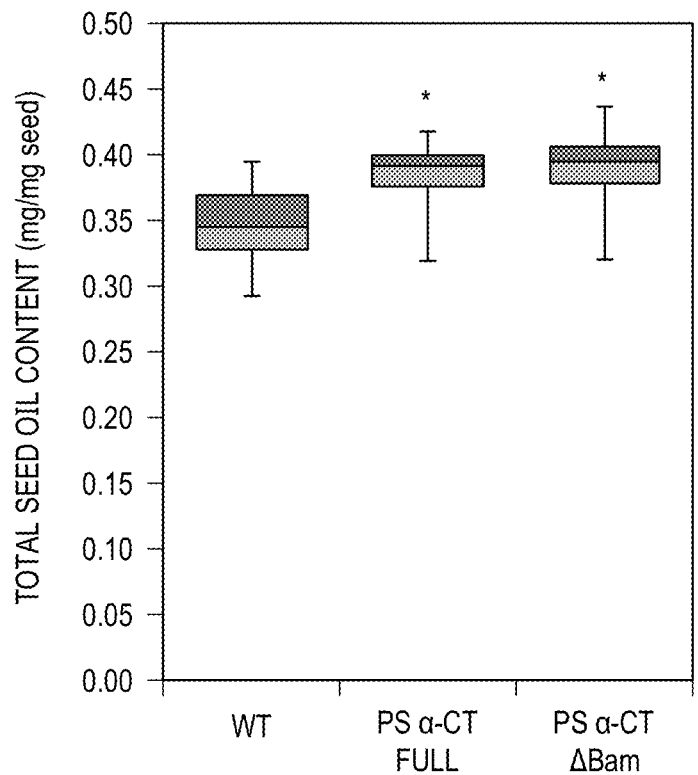
FIG. 14—Shows *Arabidopsis thaliana* lines overexpressing full-length α-CT from *Pisum sativum* and lines expressing only the catalytic region (D409-875, BamHI site). (A) Shows total seed oil content. (B) Shows seed setting.
Figure 14B:
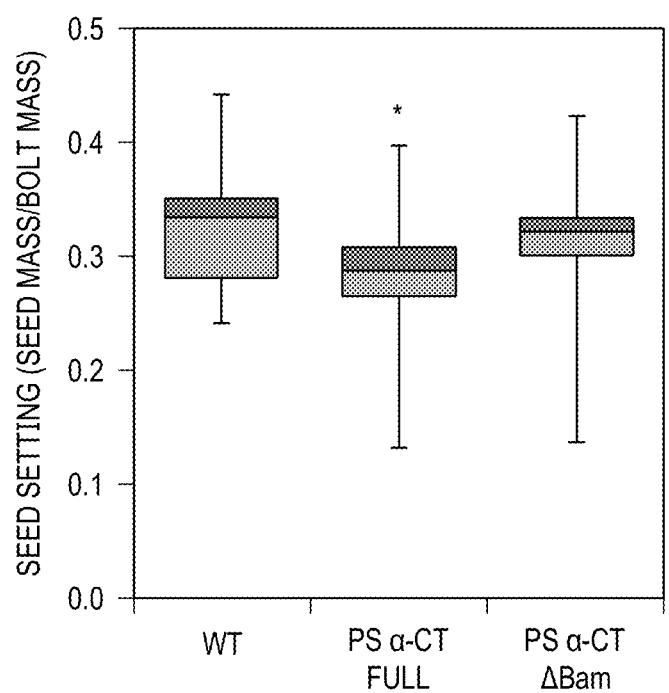

Both full-length α-CT and the catalytic portion of α-CT (4409-875, corresponding to a BamHI site) from pea (*Pisum sativum*) were individually overexpressed in *A. thaliana* using transgenic technology, and the total seed oil content (FIG. 14A) and seed setting (FIG. 14B) were measured. Experiments were performed in replicates, using 21 wild-type plants, 25 plants expressing full-length α-CT, and 47 plants expressing only the catalytic portion of α-CT (P-value <0.05). *A. thaliana* lines expressing full-length α-CT showed an average increase in total seed oil content of 10.9%, and lines expressing the catalytic portion only showed an average increase of 12.4%. The results demonstrated that seed oil content was increased in both *Arabidopsis* lines expressing full-length pea α-CT and lines expressing only the catalytic portion, showing an increase in the specific activity of ACCase up to 40% and seed oil content 10-15% compared to wild type.

The pea α-CT was shown to interact with endogenous *Arabidopsis* ACCase, but did not exhibit the plastid envelope association typically observed with this CT component enzyme. Overexpression of the *Arabidopsis* α-CT produced up to 50% higher specific activity for ACCase, but no reproducible increase in seed oil content. These results indicated that pea α-CT not only increased activity of the multienzyme ACCase complex, but also abrogated envelope membrane association involved in feedback inhibition to produced a de-regulated ACCase.

Example 17

Overexpressing α-CT Full Length or Catalytic Region from *Pisum sativum* Increases Seed Oil Content in *Camelina*

Both full-length α-CT and the catalytic portion of α-CT (4409-875, corresponding to a BamHI restriction site; also referenced as ΔBAM) from pea (*Pisum sativum*) were individually overexpressed in *Camelina* using transgenic technology (Lu and Kang, Plant Cell Rep. 27:273-278, 2008), and the total seed oil content was measured. *Camelina* is a cover crop oilseed, whereby the oil is used primarily for fuel and chemical feedstocks rather than food. Except where noted, ten individual seeds for wild-type and each of 11 transgenic lines were analyzed: wild-type (WT), full length 1 (FL1), full length 2 (FL2), full length 3 (FL3), ΔBAM A (15 seeds were analyzed), ΔBAM B (15 seeds were analyzed), ΔBAM C, ΔBAM D, ΔBAM E, ΔBAM F, ΔBAM G, and ΔBAM H. For oil content determination single seed GC-MS analysis was performed, as *Camelina* seed are about 100× larger than *Arabidopsis*. The results are shown in Tables 3-14.

TABLE 3

WT

| Weight (mg) | % Oil Content (Dry Weight) | μg FAME/seed |
|---|---|---|
| 1.07 | 29.60 | 316.69 |
| 1.00 | 31.89 | 362.13 |
| 1.15 | 31.51 | 362.31 |
| 1.13 | 32.58 | 368.14 |
| 1.15 | 31.71 | 364.61 |
| 1.07 | 31.88 | 341.10 |
| 1.28 | 27.48 | 351.79 |
| 1.17 | 33.00 | 386.10 |
| 1.15 | 31.28 | 359.69 |
| 1.00 | 33.20 | 331.98 |
| Average 1.12 + 0.03 | 31.58 + 0.42 | 318.98 + 6.53 |

TABLE 4

FL1

| Weight (mg) | % Oil Content (Dry Weight) | μg FAME/seed |
|---|---|---|
| 1.59 | 21.4 | 340.20 |
| 1.00 | 32.69 | 326.92 |
| 1.53 | 30.56 | 467.60 |
| 1.47 | 24.42 | 352.03 |
| 1.79 | 22.92 | 410.23 |
| 1.59 | 25.89 | 411.66 |
| 1.63 | 26.79 | 436.70 |
| 1.34 | 26.19 | 350.99 |
| 1.37 | 29.61 | 405.63 |
| 1.12 | 32.23 | 361.01 |
| Average 1.44 + 0.08 | 27.27 + 1.23 | 386.30 + 14.70 |

TABLE 5

FL2

| Weight (mg) | % Oil Content (Dry Weight) | μg FAME/seed |
|---|---|---|
| 1.15 | 31.76 | 365.21 |
| 0.89 | 32.20 | 286.54 |
| 1.27 | 28.70 | 307.10 |
| 1.04 | 46.66 | 485.27 |
| 1.12 | 36.67 | 410.69 |
| 1.09 | 31.35 | 341.71 |
| 1.14 | 38.51 | 439.05 |
| 1.08 | 34.12 | 368.51 |
| 1.14 | 30.73 | 350.33 |
| 0.94 | 47.33 | 444.84 |
| Average 1.09 + 0.04 | 35.80 + 2.07 | 379.93 + 20.13 |

TABLE 6

FL3

| Weight (mg) | % Oil Content (Dry Weight) | μg FAME/seed |
|---|---|---|
| 1.26 | 40.31 | 507.91 |
| 1.41 | 37.98 | 535.49 |
| 0.95 | 39.48 | 375.06 |
| 1.04 | 43.62 | 453.69 |
| 1.25 | 44.69 | 558.67 |
| 1.08 | 42.37 | 457.60 |

TABLE 6-continued

FL3

| Weight (mg) | % Oil Content (Dry Weight) | μg FAME/seed |
|---|---|---|
| 1.13 | 37.02 | 418.29 |
| 1.06 | 41.34 | 438.22 |
| 1.17 | 44.25 | 517.73 |
| 1.15 | 46.12 | 530.36 |
| Average 1.15 + 0.04 | 41.72 + 0.95 | 479.30 + 18.79 |

TABLE 7

ΔBAM A

| Weight (mg) | % Oil Content (Dry Weight) | μg FAME/seed |
|---|---|---|
| 1.14 | 37.76 | 430.48 |
| 1.07 | 38.84 | 415.60 |
| 1.22 | 29.01 | 353.97 |
| 0.97 | 38.89 | 377.27 |
| 0.97 | 24.28 | 235.52 |
| 1.21 | 36.94 | 447.02 |
| 1.09 | 36.56 | 398.48 |
| 1.06 | 33.10 | 350.84 |
| 1.12 | 29.32 | 328.33 |
| 0.97 | 35.33 | 342.65 |
| 1.20 | 39.96 | 479.48 |
| 1.04 | 44.92 | 467.19 |
| 1.09 | 43.93 | 478.88 |
| 1.12 | 44.03 | 493.08 |
| 1.23 | 35.98 | 442.63 |
| Average 1.10 + 0.02 | 36.59 + 1.51 | 402.76 + 18.43 |

TABLE 8

ΔBAM B

| Weight (mg) | % Oil Content (Dry Weight) | μg FAME/seed |
|---|---|---|
| 1.03 | 38.27 | 394.17 |
| 0.84 | 40.15 | 337.26 |
| 1.15 | 43.67 | 502.17 |
| 0.81 | 38.52 | 312.00 |
| 1.18 | 40.28 | 435.03 |
| 1.08 | 36.75 | 418.92 |
| 1.14 | 38.81 | 481.26 |
| 1.24 | 33.43 | 374.36 |
| 1.12 | 46.89 | 422.04 |
| 0.90 | 33.71 | 467.23 |
| 1.34 | 43.09 | 577.49 |
| 1.44 | 44.50 | 640.83 |
| 1.08 | 46.65 | 503.79 |
| 1.14 | 38.37 | 437.40 |
| 1.22 | 44.06 | 537.50 |
| Average 1.11 + 0.05 | 40.48 + 1.09 | 456.10 + 22.82 |

TABLE 9

ΔBAM C

| Weight (mg) | % Oil Content (Dry Weight) | μg FAME/seed |
|---|---|---|
| 1.00 | 36.34 | 363.38 |
| 1.01 | 36.98 | 373.48 |
| 1.08 | 28.13 | 303.75 |
| 1.16 | 36.23 | 420.24 |
| 1.10 | 35.46 | 392.49 |
| 1.04 | 42.37 | 357.20 |
| 1.14 | 33.76 | 384.82 |

TABLE 9-continued

ΔBAM C

|  | Weight (mg) | % Oil Content (Dry Weight) | μg FAME/seed |
|---|---|---|---|
|  | 0.98 | 33.95 | 332.72 |
|  | 1.23 | 34.86 | 428.83 |
|  | 1.02 | 36.11 | 330.43 |
| Average | 1.08 + 0.03 | 35.42 + 1.11 | 368.73 + 12.59 |

TABLE 10

ΔBAM D

|  | Weight (mg) | % Oil Content (Dry Weight) | μg FAME/seed |
|---|---|---|---|
|  | 0.82 | 33.62 | 275.66 |
|  | 1.15 | 22.45 | 258.21 |
|  | 1.12 | 40.41 | 452.54 |
|  | 1.07 | 38.68 | 413.82 |
|  | 1.03 | 29.06 | 299.27 |
|  | 1.05 | 42.05 | 441.55 |
|  | 1.05 | 37.24 | 390.98 |
|  | 0.94 | 38.02 | 357.39 |
|  | 1.17 | 44.58 | 521.55 |
|  | 1.02 | 31.86 | 324.95 |
| Average | 1.04 + 0.03 | 35.78 + 2.10 | 373.59 + 27.02 |

TABLE 11

ΔBAM E

|  | Weight (mg) | % Oil Content (Dry Weight) | μg FAME/seed |
|---|---|---|---|
|  | 1.01 | 30.32 | 306.26 |
|  | 1.01 | 40.05 | 404.52 |
|  | 1.32 | 40.41 | 452.54 |
|  | 1.09 | 38.68 | 413.82 |
|  | 1.16 | 36.10 | 418.80 |
|  | 0.83 | 26.42 | 219.24 |
|  | 1.01 | 33.52 | 338.56 |
|  | 1.03 | 34.10 | 351.21 |
|  | 1.14 | 29.29 | 333.89 |
|  | 1.09 | 42.50 | 463.22 |
| Average | 1.07 + 0.04 | 35.14 + 1.69 | 370.21 + 23.67 |

TABLE 12

ΔBAM F

|  | Weight (mg) | % Oil Content (Dry Weight) | μg FAME/seed |
|---|---|---|---|
|  | 0.91 | 30.06 | 273.50 |
|  | 1.00 | 33.75 | 337.47 |
|  | 0.98 | 34.13 | 334.48 |
|  | 0.96 | 34.26 | 328.89 |

TABLE 12-continued

ΔBAM F

|  | Weight (mg) | % Oil Content (Dry Weight) | μg FAME/seed |
|---|---|---|---|
|  | 0.93 | 32.90 | 305.94 |
|  | 0.99 | 23.99 | 237.49 |
|  | 1.30 | 28.87 | 375.28 |
|  | 1.25 | 21.83 | 272.93 |
|  | 0.96 | 36.73 | 352.57 |
|  | 0.91 | 37.07 | 337.32 |
| Average | 1.02 + 0.04 | 31.36 + 1.63 | 315.59 + 13.42 |

TABLE 13

ΔBAM G

|  | Weight (mg) | % Oil Content (Dry Weight) | μg FAME/seed |
|---|---|---|---|
|  | 0.99 | 29.44 | 291.50 |
|  | 0.88 | 51.59 | 454.02 |
|  | 1.11 | 25.83 | 286.71 |
|  | 1.07 | 33.34 | 356.72 |
|  | 0.94 | 31.01 | 291.53 |
|  | 0.93 | 41.13 | 382.50 |
|  | 0.96 | 28.44 | 273.03 |
|  | 0.96 | 41.14 | 394.97 |
|  | 1.20 | 34.58 | 414.92 |
|  | 0.88 | 35.68 | 313.97 |
| Average | 0.99 + 0.03 | 35.22 + 2.42 | 345.99 + 20.02 |

TABLE 14

ΔBAM H

|  | Weight (mg) | % Oil Content (Dry Weight) | μg FAME/seed |
|---|---|---|---|
|  | 1.14 | 31.03 | 353.70 |
|  | 1.14 | 31.12 | 354.77 |
|  | 0.99 | 32.67 | 323.45 |
|  | 0.83 | 36.63 | 304.03 |
|  | 1.08 | 40.46 | 436.95 |
|  | 1.18 | 40.94 | 483.12 |
|  | 1.19 | 41.35 | 492.04 |
|  | 1.34 | 32.46 | 435.05 |
|  | 1.38 | 30.26 | 417.52 |
|  | 1.40 | 36.67 | 513.44 |
| Average | 1.17 + 0.06 | 35.34 + 1.39 | 411.41 + 23.36 |

Since these were T2 seed, Mendelian segregation of the single transgene was observed. Thus 25% of the seed are wild-type and should be around 28-32% oil content (dry weight)—which is exactly what was found. The remaining seed are transgenic and higher in oil content. All independent lines had higher oil except for the FL1 and BamF transgenic events which may not express the α-CT protein very well.

What is claimed is:

1. A method of altering fatty acid and/or triacylglycerol production in plants and/or algae, comprising the step of altering activity levels of the committed step for de novo fatty acid biosynthesis, acetyl-CoA carboxylase (ACCase), wherein said altering step comprises increasing the activity level of ACCase by increasing expression of α-carboxyltransferase (α-CT) or a catalytic portion thereof, and total or partial silencing of one or more biotin/lipoyl attachment domain containing (BADC) gene, wherein said BADC gene comprises from about 90% to 100% sequence identity to a nucleotide sequence selected from the group consisting of SEQ ID NOs: 2, 4, or 6, or a complement thereof, in said plant and/or algae, and wherein said increased activity level of ACCase and said increased expression of α-CT is compared to a control plant and/or algae prior to altering activity levels of ACCase.

2. The method of claim 1, wherein said altering step comprises overexpression of an α-CT gene already present in said plant.

3. The method of claim 1, wherein said altering step comprises expression or overexpression of a heterologous α-CT.

4. The method of claim 3, wherein said heterologous α-CT comprises a *Pisum sativum* α-CT.

5. The method of claim 1, wherein said altering step comprises overexpression of a catalytic portion of an α-CT.

6. The method of claim 1, wherein said BADC gene comprises genes of BADC1, BADC2, and BADC3, or artificial genes that lack the conserved biotinylation motif and biotinyl lysine residue present in biotin carboxyl carrier proteins (BCCPs).

7. The method of claim 6, wherein said one or more BADC gene encodes a polypeptide comprising from about 90% to 100% sequence identity to a polypeptide sequence selected from the group consisting of SEQ ID NOs: 1, 3, and 5.

8. The method of claim 1, wherein said silencing comprises expression of an RNAi cassette comprising SEQ ID NO:7 or 138.

* * * * *